United States Patent [19]
Ohki et al.

[11] Patent Number: 6,107,458
[45] Date of Patent: *Aug. 22, 2000

[54] CYCLIC HEXAPEPTIDES HAVING ANTIBIOTIC ACTIVITY

[75] Inventors: Hidenori Ohki, Takarazuka; Masaki Tomishima, Minoo; Akira Yamada, Fujiidera; Hisashi Takasugi, Sakai, all of Japan

[73] Assignee: Fujisawa Pharmaceutical Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,723

[22] PCT Filed: Sep. 29, 1995

[86] PCT No.: PCT/JP95/01983

§ 371 Date: May 21, 1997

§ 102(e) Date: May 21, 1997

[87] PCT Pub. No.: WO96/11210

PCT Pub. Date: Apr. 18, 1996

[30]    Foreign Application Priority Data

Oct. 17, 1994 [GB] United Kingdom .................. 9420425
Apr. 28, 1995 [GB] United Kingdom .................. 9508745

[51] Int. Cl.[7] ...................... A61K 38/00; A61K 38/12; C07K 5/00; C07K 7/00
[52] U.S. Cl. ............................... 530/317; 514/9; 514/11
[58] Field of Search ....................... 530/317; 514/11, 514/9

[56]    References Cited

U.S. PATENT DOCUMENTS 5,376,634   12/1994   Iwamoto et al. ..................... 530/317

FOREIGN PATENT DOCUMENTS 0462531   12/1991   European Pat. Off. .

Primary Examiner—Avis M. Davenport
Attorney, Agent, or Firm—Oblon, Spivak, McClelland, Maier & Neustadt, P.C.

[57]    ABSTRACT

This invention relates to new polypeptide compounds represented by the following formula (I):

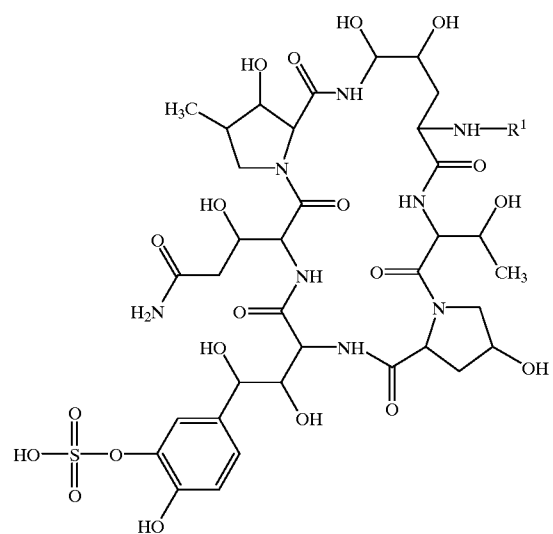

wherein $R^1$ is as defined in the description and pharmaceutically acceptable salt thereof which have antimicrobial activities (especially, antifungal activities), inhibitory activity on $\beta$-1,3-glucan synthase, to process for preparation thereof, to a pharmaceutical composition comprising the same, and to a method for the prophylactic and/or therapeutic treatment of infectious diseases including *Pneumocystis carinii* infection (e.g. *Pneumocystis carinii* pneumonia) in a human being or an animal.

5 Claims, No Drawings

CYCLIC HEXAPEPTIDES HAVING ANTIBIOTIC ACTIVITY

TECHNICAL FIELD

The present invention relates to new polypeptide compound and a pharmaceutically acceptable salt thereof which are useful as a medicament.

BACKGROUND ART

In U.S. Pat. No. 5,376,634, there are disclosed the polypeptide compound and a pharmaceutically acceptable salt thereof, which have antimicrobial activities (especially antifungal activity).

DISCLOSURE OF INVENTION

The present invention relates to new polypeptide compound and a pharmaceutically acceptable salt thereof.

More particularly, it relates to new polypeptide compound and a pharmaceutically acceptable salt thereof, which have antimicrobial activities [especially, antifungal activities, in which the fungi may include Aspergillus, Cryptococcus, Candida, Mucor, Actinomyces, Histoplasma, Dermatophyte, Malassezia, Fusarium and the like.], inhibitory activity on β-1,3-glucan synthase, and further which are expected to be useful for the prophylactic and/or therapeutic treatment of *Pneumocystis carinii* infection (e.g. *Pneumocystis carinii* pneumonia) in a human being or an animal, to a process for preparation thereof, to a pharmaceutical composition comprising the same, and to a method for the prophylactic and/or therapeutic treatment of infection diseases including *Pneumocystis carinii* infection (e.g. *Pneumocystis carinii* pneumonia) in a human being or an animal.

The object polypeptide compound used in the present invention are new and can be represented by the following general formula [I]:

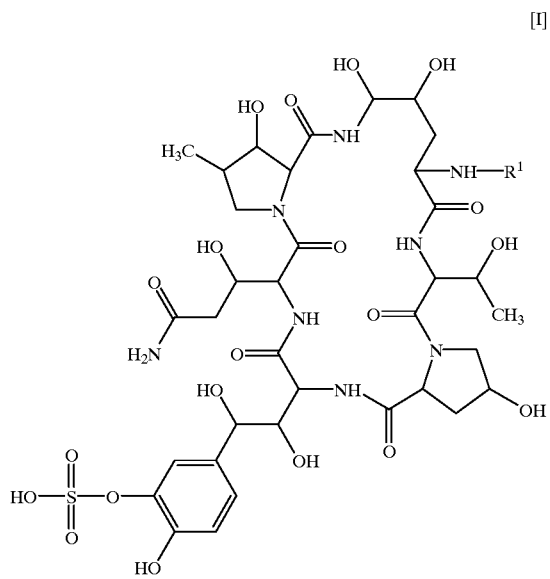

[I]

wherein $R^1$ is a lower alkanoyl substituted with unsaturated 6-membered heteromonocyclic group containing at least one nitrogen atom which may have one or more suitable substituent(s);

lower alkanoyl substituted with 1,2,3,4-tetrahydroisoquinoline which may have one or more suitable substituent(s);

lower alkanoyl substituted with unsaturated condensed heterocyclic group containing at least one oxygen atom which may have one or more suitable substituent(s);

lower alkanoyl substituted with unsaturated condensed heterocyclic group containing 1 to 3 sulfur atom(s) which may have one or more suitable substituent(s);

lower alkanoyl substituted with unsaturated condensed heterocyclic group containing 2 or more nitrogen atom(s) which may have one or more suitable substituent(s);

lower alkanoyl substituted with saturated 3 to 8 membered heteromonocyclic group containing at least one nitrogen atom which may have one or more suitable substituent(s);

ar(lower)alkenoyl substituted with aryl which may have one or more suitable substituent(s);

naphthyl(lower)alkenoyl which may have one or more higher alkoxy;

lower alkynoyl which may have one or more suitable substituent(s);

$(C_2\text{--}C_6)$ alkanoyl substituted with naphthyl having higher alkoxy;

ar$(C_2\text{--}C_6)$ alkanoyl substituted with aryl having one or more suitable substituent(s), in which ar$(C_2\text{--}C_6)$ alkanoyl may have one or more suitable substituent(s);

aroyl substituted with heterocyclic group which may have one or more suitable substituent(s), in which aroyl may have one or more suitable substituent(s);

aroyl substituted with aryl having heterocyclic(higher) alkoxy, in which heterocyclic group may have one or more suitable substituent(s);

aroyl substituted with aryl having lower alkoxy(higher) alkoxy;

aroyl substituted with aryl having lower alkenyl(lower) alkoxy;

aroyl substituted with 2 lower alkoxy;

aroyl substituted with aryl having lower alkyl;

aroyl substituted with aryl having higher alkyl;

aryloxy(lower)alkanoyl which may have one or more suitable substituent(s);

ar(lower)alkoxy(lower)alkanoyl which may have one or more suitable substituent(s);

arylamino(lower)alkanoyl which may have one or more suitable substituent(s);

lower alkanoyl substituted with pyrazolyl which has lower alkyl and aryl having higher alkoxy;

lower alkoxy(higher)alkanoyl, in which higher alkanoyl may have one or more suitable substituent(s);

aroyl substituted with aryl having heterocyclicoxy, in which heterocyclicoxy may have one or more suitable substituent(s);

aroyl substituted with cyclo(lower)alkyl having lower alkyl;

indolylcarbonyl having higher alkyl;

naphthoyl having lower alkyl;

naphthoyl having higher alkyl;

naphthoyl having lower alkoxy(higher)alkoxy;

aroyl substituted with aryl having lower alkoxy(lower) alkoxy(higher)alkoxy;

aroyl substituted with aryl having lower alkoxy(lower) alkoxy;

aroyl substituted with aryl which has aryl having lower alkoxy;

aroyl substituted with aryl which has aryl having lower alkoxy(lower)alkoxy;

aroyl substituted with aryl having heterocyclicoxy (higher)alkoxy;

aroyl substituted with aryl having aryloxy(lower)alkoxy;

aroyl substituted with aryl having heterocycliccarbonyl (higher)alkoxy;

lower alkanoyl substituted with oxazolyl which has aryl having higher alkoxy;

lower alkanoyl substituted with furyl which has aryl substituted with aryl having lower alkoxy;

lower alkanoyl substituted with triazolyl which has oxo and aryl having higher alkyl;

higher alkanoyl having hydroxy;

higher alkanoyl having ar(lower)alkyl and hydroxy;

3-methyl-tridecenoyl; or ($C_2$–$C_6$) alkanoyl substituted with aryl having higher alkoxy, in which ($C_2$–$C_6$) alkanoyl may have amino or protected amino.

The new polypeptide compound [I] and a pharmaceutically acceptable salt thereof can be prepared by the process as illustrated in the following reaction scheme or can be prepared by elimination reaction of amino protective group in $R^1$.

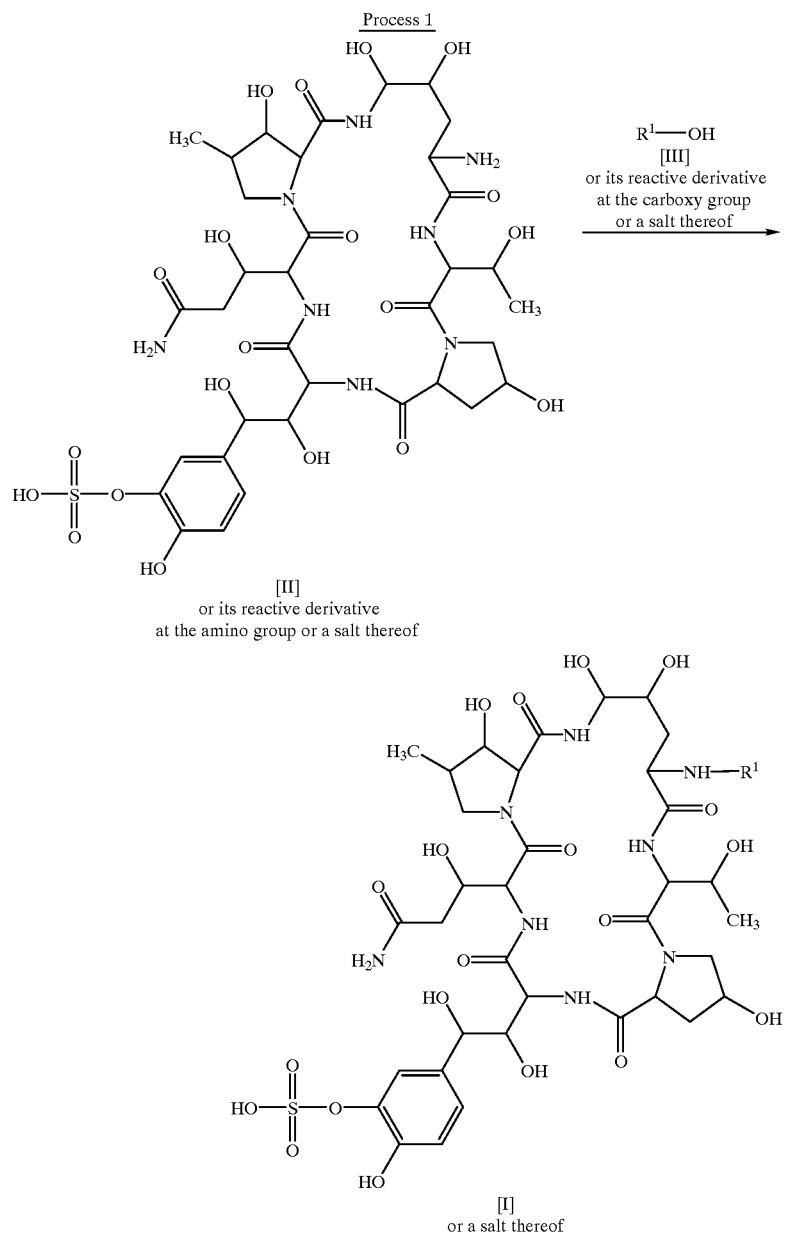

wherein $R^1$ is as defined above.

Suitable pharmaceutically acceptable salts of the object polypeptide compound [I] are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dichclohexylamine salt, N,N'-dibenzylethylenediamine salt, etc.); and inorganic acid addition salt (e.g., hydrochloride, hydrobromide, sulfate, phosphate, etc.); an organic carboxylic sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6 carbon atom(s), unless otherwise provided.

The term "higher" is used to intend a group having 7 to 20 carbon atoms, unless otherwise provided.

Suitable example of "one or more" may be the number of 1 to 6, in which the preferred one may be the number of 1 to 3.

Suitable example of "lower alkanoyl" may include straight or branched one such as formyl, acetyl, 2-methylacetyl, 2,2-dimethylacetyl, propionyl, butyryl, isobutyryl, pentanoyl, 2,2-dimethylpropionyl, hexanoyl, and the like.

Suitable example of "suitable substituent(s)" in the groups such as "lower alkanoyl substituted with unsaturated 6-membered heteromonocyclic group containing at least one nitrogen atom which may have one or more suitable substituent(s)", "lower alkanoyl substituted with 1,2,3,4-tetrahydroisoquinoline which may have one or more suitable substituent(s)", etc. may include lower alkoxy as mentioned below, higher alkoxy as mentioned below, lower alkyl as mentioned below, higher alkyl as mentioned below, higher alkoxy(lower)alkyl, lower alkoxycarbonyl, oxo, aryl which may have one or more lower alkoxy, aryl which may have one or more higher alkoxy, aryl which may have one or more lower alkyl, aryl which may have one or more higher alkyl, aryl substituted with aryl which may have one or more lower alkoxy, aryl substituted with aryl which may have one or more higher alkoxy, aryl substituted with aryl which may have one or more lower alkyl, aryl substituted with aryl which may have one or more higher alkyl, aroyl which may have one or more lower alkoxy, aroyl which may have one or more higher alkoxy, aroyl which may have one or more lower alkyl, aroyl which may have one or more higher alkyl, heterocyclic group which may have one or more lower alkoxy, heterocyclic group which may have one or more higher alkoxy, aryl having heterocyclic(higher)alkoxy, heterocyclic group which may have aryl having higher alkoxy, heterocyclic group which may have aryl having lower alkoxy(higher)alkoxy, heterocyclic group which may have aryl having lower alkoxy, lower alkoxy(lower)alkyl, halo (lower)alkoxy, lower alkenyloxy, halo(higher)alkoxy, lower alkoxy(higher)alkoxy, aryl which may have one or more lower alkoxy(lower)alkoxy, heterocyclic group, aryl which may have one or more lower alkoxy(higher)alkoxy, aryl which may have one or more higher alkenyloxy, cyclo (lower)alkyl which may have aryl, aryl substituted with heterocyclic group which may have lower alkyl and oxo, cyclo(lower)alkyl which may have one or more lower alkyl, aryl which may have cyclo(lower)alkyl, aryl which may have heterocyclic group, and the like.

Suitable example of "lower alkoxy" may include straight or branched one such as methoxy, ethoxy, propoxy, isopropoxy, butoxy, isobutoxy, tert-butoxy, pentyloxy, tert-pentyloxy, neo-pentyloxy, hexyloxy, isohexyloxy and the like,
in which the preferred one may be methoxy, ethoxy, propoxy, butoxy, pentyloxy, hexyloxy and isohexyloxy.

Suitable example of "higher alkoxy" may include straight or branched one such as heptyloxy, octyloxy, 3,5-dimethyloxtyloxy, 3,7-dimethyloctyloxy, nonyloxy, decyloxy, undecyloxy, dodecylocy, tridecyloxy, tetradecyloxy, hexadecyloxy, heptadecyloxy, octadecyloxy, nonadecyloxy, icosyloxy, and the like,
in which the preferred one may be ($C_7$–$C_{14}$) alkoxy, and the more preferred one may be heptyloxy and octyloxy.

Suitable example of "lower alkyl" may include straight or branched one having 1 to 6 carbon atom(s), such as methyl, ethyl, propyl, isopropyl, butyl, isobutyl, sec-butyl, tert-butyl, pentyl, tert-pentyl, neo-pentyl, hexyl, isohexyl and the like,
in which the preferred one may be methyl, pentyl, hexyl and isohexyl.

Suitable example of "higher alkyl" may include straight or branched one having 7 to 20 carbon atoms, such as heptyl, octyl, 3,5-dimethyloctyl, 3,7-dimethyloctyl, nonyl, decyl, undecyl, dodecyl, tridecyl, tetradecyl, pentadecyl, hexadecyl, heptadecyl, octadecyl, nonadecyl, icosyl, and the like,
in which the preferred one may be ($C_7$–$C_{14}$) alkyl, and the more preferred one may be heptyl, octyl, nonyl and decyl.

Suitable example of "aryl" and "ar" moiety may include phenyl which may have lower alkyl (e.g., phenyl, mesityl, tolyl, etc.), naphthyl, anthryl, and the like,
in which the preferred one may be phenyl and naphthyl.

Suitable example of "aroyl" may include benzoyl, toluoyl, naphthoyl, anthrylcarbonyl, and the like,
in which the preferred one may be benzoyl and naphthoyl.

Suitable example of "heterocyclic group" and "heterocyclic" moiety may include unsaturated 3 to 8-membered (more preferably 5 to 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1, 2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 to 6-membered heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 to 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzotriazolyl, benzothiadiazolyl, etc.;

unsaturated 3 to 8-membered (more preferably 5 or 6-membered) heteromonocyclic group containing an oxygen atom, for example, furyl, etc.;

saturated 3 to 8-membered (more preferably 5 or 6-membered) heteromonocyclic group containing an oxygen atom, for example, tetrahydrofuran, tetrahydropyran, etc.;

unsaturated 3 to 8-membered (more preferably 5 to 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

Suitable example of "halo" may include fluoro, chloro, bromo and iodo.

Suitable example of "lower alkenyloxy" may include vinyloxy, 1-(or 2-)propenyloxy, 1-(or 2- or 3-)butenyloxy, 1-(or 2- or 3- or 4-)pentenyloxy, 1-(or 2- or 3- or 4- or 5-)hexenyloxy, and the like, in which the preferred one may be ($C_2$–$C_6$)alkenyloxy, and the most preferred one may be 5-hexenyloxy.

Suitable example of "higher alkenyloxy" may include ($C_7$–$C_{20}$)alkenyloxy, in which the preferred one may be 6-heptenyloxy and 7-octenyloxy.

Suitable example of "cyclo(lower)alkyl" may include cyclopropyl, cyclobutyl, cyclopentyl, cyclohexyl, and the like, in which the preferred one may be cyclo($C_4$–$C_6$)alkyl, and the most preferred one may be cyclohexyl.

Suitable example of "higher alkanoyl" may include heptanoyl, octanoyl, nonanoyl, decanoyl, undecanoyl, lauroyl, tridecanoyl, tetradecanoyl, pentadecanoyl, hexadecanoyl, heptadecanoyl, octadecanoyl, nonadecanoyl, icosanoyl, and the like, in which the preferred one may be ($C_7$–$C_{20}$)alkanoyl, and the most preferred one may be hexadecanoyl.

Suitable example of "ar(lower)alkyl" may include benzyl, phenethyl, phenylpropyl, phenylbutyl, phenylpentyl, phenylhexyl, naphthylmethyl, naphthylethyl, naphthylpropyl, naphthylbutyl, naphthylpentyl, naphthylhexyl, and the like, in which the preferred on may be phenyl($C_1$–$C_4$)alkyl, and the most preferred one may be benzyl.

Suitable example of "protected amino" may include lower or higher alkoxycarbonylamino (e.g., methoxycarbonylamino, ethoxycarbonylamino, t-butoxycarbonylamino, t-pentyloxycarbonylamino, heptyloxycarbonylamino, etc.), ar(lower) alkoxycarbonylamino [e.g., phenyl(lower)alkoxycarbonylamino (e.g., benzyloxycarbonylamino, etc.), etc.], an amino group substituted with a conventional protecting group such as ar(lower)alkyl which may have suitable substituent(s) (e.g., benzyl, trityl, etc.) and the like, in which the preferred one may be phenyl(lower)alkoxycarbonylamino, and the most preferred one may be benzyloxycarbonylamino.

Suitable example of "lower alkonyl" in the term of "lower alkanoyl substituted with unsaturated 6-membered heteromonocyclic group containing at least one nitrogen atom which may have one or more suitable substituent(s)" can be referred to aforementioned "lower alkanoyl",
in which the preferred one may be ($C_1$–$C_4$) alkanoyl, and the more preferred one may be formyl.

Suitable example of "unsaturated 6-membered heteromonocyclic group containing at least one nitrogen atom" in the term of "lower alkanoyl substituted with unsaturated 6-membered heteromonocyclic group containing at least one nitrogen atom which may have one or more suitable substituent(s)" may include pyridyl, dihydropyridyl, pyrimidyl, pyrazinyl, pyridazinyl, triazinyl (e.g., 4H-1,2,4,5-tetrazinyl, 1,2,3,4-tetrazinyl, etc.), and the like,
in which the preferred one may be unsaturated 6-membered heteromonocyclic group containing 1 to 3 nitrogen atom(s), and the most preferred one may be pyridyl and pyridazinyl.

Suitable example of "suitable substituent(s)" in the term of "lower alkanoyl substituted with unsaturated 6-membered heteromonocyclic groups containing at least one nitrogen atom which may have one or more suitable substituent(s)" can be referred to aforementioned "suitable substituent(s)",
in which the preferred one may be higher alkoxy, higher alkoxy(lower)alkyl, heterocyclic group which may have aryl having higher alkoxy, aryl which may have one or more higher alkoxy, aryl substituted with aryl which may have lower alkoxy, heterocyclic group which may have aryl having lower alkoxy(higher)alkoxy, and heterocyclic group which may have aryl having lower alkoxy, and the more preferred one may be ($C_7$–$C_{14}$)alkoxy, ($C_7$–$C_{14}$)alkoxy-($C_1$–$C_4$)alkyl, 3 to 8-membered saturated heteromonocyclic group containing at least one nitrogen atom which may have phenyl having 1 to 3 ($C_7$–$C_{14}$)alkoxy, phenyl which may have 1 to 3 ($C_7$–$C_{14}$)alkoxy, phenyl substituted with phenyl which may have 1 to 3 ($C_3$–$C_6$)alkoxy, 3 to 8-membered saturated heteromonocyclic group containing at least one nitrogen atom which may have phenyl having ($C_1$–$C_4$)-alkoxy($C_7$–$C_{14}$)alkoxy, and 3 to 8-membered saturated heteromonocyclic group containing at least one nitrogen atom which may have phenyl having 1 to 3 ($C_3$–$C_6$)alkoxy, and the most preferred one may be octyloxy, octyloxymethyl, piperazinyl which has phenyl having heptyloxy or octyloxy, phenyl having heptyloxy, phenyl substituted with phenyl having butoxy, piperazinyl which has phenyl having methoxyoctyloxy, and piperazinyl which has phenyl having hexyloxy.

Suitable example of "lower alkanoyl" in the term of "lower alkanoyl substituted with 1,2,3,4-tetrahydroisoquinoline which may have one or more suitable substituent(s)" can be referred to aforementioned "lower alkanoyl",
in which the preferred one may be ($C_1$–$C_4$)-alkanoyl, and the more preferred one may be formyl.

Suitable example of "suitable substituent(s)" in the term of "lower alkanoyl substituted with 1,2,3,4-tetrahydroisoquinoline which may have one or more suitable substituent(s)" can be referred to aforementioned "suitable substituent(s)", in which the preferred one may be lower alkoxy, higher alkoxy, lower alkyl, higher alkyl and lower alkoxycarbonyl, and the more preferred one may be $(C_7$–$C_{14})$alkoxy and $(C_1$–$C_4)$alkoxycarbonyl, and the most preferred one may be octyloxy and tert-butoxycarbonyl.

Suitable example of "lower alkanoyl" in the term of "lower alkanoyl substituted with unsaturated condensed heterocyclic group containing at least one oxygen atom which may have one or more suitable substituent(s)" can be referred to aforementioned "lower alkanoyl",
in which the preferred one may be $(C_1$–$C_4)$alkanoyl, and the more preferred one may be formyl.

Suitable example of "unsaturated condensed heterocyclic group containing at least one oxygen atom" in the term of "lower alkanoyl substituted with unsaturated condensed heterocyclic group containing at least one oxygen atom which may have one or more suitable substituent(s)" may include unsaturated condensed heterocyclic group containing one or more oxygen atom(s) and, optionally, another hetero atom(s) except oxygen atom,
in which the preferred one may be unsaturated condensed heterocyclic group containing 1 to 3 oxygen atom(s), unsaturated condensed heterocyclic group containing 1 to 2 oxygen atom(s) and 1 to 2 sulfur atom(s) and unsaturated condensed heterocyclic group 1 to 3 oxygen atom(s) and 1 to 3 nitrogen atom(s), and the more preferred one may be benzo[b]furanyl, isobenzofuranyl, chromenyl, xanthenyl, benzoxazoyly, benzoxadiazolyl, dihydrooxathiinyl, phenoxathiinyl, and the like, and the most preferred one may be benzo[b]furanyl, chromenyl and benzoxazolyl.

Suitable example of "suitable substituent(s)" in the term of "lower alkanoyl substituted with unsaturated condensed heterocyclic group containing at least one oxygen atom which may have one or more suitable substituent(s)" can be referred to aforementioned "suitable substituent(s)",
in which the preferred one may be lower alkoxy, higher alkoxy, lower alkyl, higher alkyl, oxo, aryl which may have one or more lower alkoxy, heterocyclic group which may have one or more higher alkoxy, and aryl substituted with aryl which may have one or more lower alkyl, and the more preferred one may be $(C_7$–$C_{14})$alkoxy, $(C_1$–$C_4)$alkyl, $(C_7$–$C_{14})$alkyl, oxo, phenyl which may have 1 to 3 $(C_3$–$C_6)$ alkoxy, unsaturated 6-membered heteromonochclic group containing at least one nitrogen atom which may have 1 to 3 $(C_7$–$C_{14})$alkoxy, and phenyl substituted with phenyl which may have 1 to 3 $(C_3$–$C_6)$alkyl, and the most preferred one may be octyloxy, methyl, nonyl, oxo, phenyl having hexyloxy, pyridyl having octyloxy, and phenyl substituted with phenyl having hexyl.

Suitable example of "lower alkanoyl" in the term of "lower alkanoyl substituted with unsaturated condensed heterocyclic group containing 1 to 3 sulfur atom(s) which may have one or more suitable substituent(s)" can be referred to aforementioned "lower alkanoyl",
in which the preferred one may be $(C_1$–$C_4)$alkanoyl, and the more preferred one may be formyl.

Suitable example of "unsaturated condensed heterocyclic group containing 1 to 3 sulfur atom(s)" in the term of "lower alkanoyl substituted with unsaturated condensed heterocyclic group containing 1 to 3 sulfur atom(s) which may have one or more suitable substituent(s)" may include unsaturated condensed heterocyclic group containing only 1 to 3 sulfur atom(s),
in which the preferred one may be benzothienyl and benzodithiinyl, and the most preferred one may be benzothienyl.

Suitable example of "suitable substituent(s)" in the term of "lower alkanoyl substituted with unsaturated condensed heterocyclic group containing 1 to 3 sulfur atom(s) which may have one or more suitable substituent(s)" can be referred to aforementioned "suitable substituent(s)",
in which the preferred one may be lower alkoxy, higher alkoxy, lower alkyl and higher alkyl, and more preferred one may be $(C_7$–$C_{14})$alkoxy, and the most preferred one may be octyloxy.

Suitable example of "lower alkanoyl" in the term of "lower alkanoyl substituted with unsaturated condensed heterocyclic group containing 2 or more nitrogen atom(s) which may have one or more suitable substituent(s)" can be referred to aforementioned "lower alkanoyl",
in which the preferred one may be $(C_1$–$C_4)$alkanoyl, and the most preferred one may be formyl.

Suitable example of "unsaturated condensed heterocyclic group containing 2 or more nitrogen atom(s)" in the term of "lower alkanoyl substituted with unsaturated condensed heterocyclic group containing 2 or more nitrogen atom(s) which may have one or more suitable substituent(s)" may include 1H-indazolyl, purinyl, phthalazinyl, benzoimidazolyl, naphthyridinyl, quinoxalinyl, quinazolyl, cinnolinyl, peteridinyl, and the like,
in which the most preferred one may be benzoimidazolyl.

Suitable example of "suitable substituent(s)" in the term of "lower alkanoyl substituted with unsaturated condensed heterocyclic group containing 2 or more nitrogen atom(s) which may have one or more suitable substituent(s)" can be referred to aforementioned "suitable substituent(s)",
in which the preferred one may be lower alkoxy, higher alkoxy, lower alkyl, higher alkyl, aryl which may have one or more lower alkoxy and aryl which may have one or more higher alkoxy, and the more preferred one may be $(C_7$–$C_{14})$ alkyl and phenyl which may have 1 to 3 $(C_1$–$C_6)$alkoxy, and the most preferred one may be nonyl and phenyl which may have hexyloxy.

Suitable example of "lower alkanoyl" in the term of "lower alkanoyl substituted with saturated 3 to 8-membered heteromonocyclic group containing at least one nitrogen atom which may have one or more suitable substituent(s)" can be referred to aforementioned "lower alkanoyl",
in which the preferred one may be $(C_1$–$C_4)$alkanoyl, and the more preferred one may be formyl.

Suitable example of "saturated 3 to 8-membered heteromonocyclic group containing at least one nitrogen atom" in the term of "lower alkanoyl substituted with saturated 3 to 8-membered heteromonocyclic group containing at least one nitrogen atom which may have one or more suitable substituent(s)" may include pyrrolidinyl, imidazolidinyl, piperidyl, piperazinyl, pyrazolidinyl, morpholinyl, thiomorpholinyl, and the like,
in which the preferred one may be piperidyl and piperazinyl.

Suitable example of "suitable substituent(s)" in the term of "lower alkanoyl substituted with saturated 3 to 8-membered heteromonocyclic group containing at least one nitrogen atom which may have one or more suitable substituent(s)" may include lower alkoxy, higher alkoxy, higher alkoxy(lower)alkyl, lower alkyl, higher alkyl, oxo, aryl which may have one or more lower alkoxy, aryl which may have one or more higher alkoxy, aryl which may have one or more lower alkyl, aryl which may have one or more higher alkyl, aroyl which may have one or more lower alkoxy, aroyl which may have one or more higher alkoxy, aroyl which may have one or more lower alkyl, aroyl which may have one or more higher alkyl, and the like,
in which the preferred one may be aryl which may have one or more lower alkoxy, aryl which may have one or more higher alkoxy, aroyl which may have one or more lower alkoxy and aroyl which may have one or more higher alkoxy, and the more preferred one may be aryl which may have 1 to 3 higher alkoxy and aroyl which may have 1 to 3 higher alkoxy, and the much more preferred one may be phenyl which may have 1 to 3 ($C_7$–$C_{14}$)alkoxy and naphthoyl which may have 1 to 3 ($C_7$–$C_{14}$)alkoxy, and the most preferred one may be phenyl which may have octyloxy and naphthoyl which may have heptyloxy.

Suitable example of "ar(lower)alkenoyl" in the term of "ar(lower)alkenoyl substituted with aryl which may have one or more suitable substituent(s)" may include phenyl (lower)alkenoyl (e.g., 3-phenylacryloyl, (2- or 3- or 4-)phenyl-(2- or 3-)butenoyl, 3-phenylmethacryloyl, (2- or 3- or 4- or 5-)phenyl-(2- or 3- or 4-)pentanoyl, (2- or 3- or 4- or 5- or 6-)phenyl-(2- or 3- or 4- or 5-)-hexanoyl, etc.), naphthyl(lower)alkenoyl (e.g., 3-naphthylacryloyl, (2- or 3- or 4-)naphthyl-(2- or 3-)butenoyl, (2- or 3- or 4- or 5-)naphthyl-(2- or 3- or 4-)pentanoyl, (2- or 3- or 4- or 5- or 6-)naphthyl-(2- or 3- or 4- or 5-)hexanoyl, etc.), and the like, in which the preferred one may be 3-phenylacryloyl and 3-methyl-3-phenylacryloyl.

Suitable example of "suitable substituent(s)" in the term of "ar(lower)alkenoyl substituted with aryl which may have one or more suitable substituent(s)" can be referred to aforementioned "suitable substituent(s)", in which the preferred one may be lower alkoxy, lower alkyl, higher alkyl, lower alkoxy(lower)alkyl, halo(lower)alkoxy, lower alkenyloxy, halo(higher)alkoxy, and lower alkoxy (higher)alkoxy and the much more preferred one may be ($C_1$–$C_6$)alkoxy, ($C_1$–$C_6$)alkyl, ($C_7$–$C_{14}$)alkyl, ($C_1$–$C_4$)alkoxy($C_3$–$C_6$)alkyl, halo($C_3$–$C_6$)alkoxy, ($C_3$–$C_6$) alkenyloxy, halo($C_7$–$C_{14}$)alkoxy, and ($C_1$–$C_4$)alkoxy ($C_7$–$C_{14}$)alkoxy and the most preferred one may be pentyloxy, heptyl, pentyl, methoxyhexyl, fluorohexyloxy, isohexyloxy, 5-hexenyloxy, haloheptyloxy, methoxyheptyloxy, methoxyoctyloxy, and butyloxy.

Suitable example of "naphthyl(lower)alkenoyl" in the term of "naphthyl(lower)alkenoyl which may have one or more higher alkoxy" may include 3-naphthylacryloyl, (2- or 3- or 4-)naphthyl-(2- or 3-)butenoyl, (2- or 3- or 4- or 5-)naphthyl-(2- or 3- or 4-)pentanoyl, (2- or 3- or 4- or 5- or 6-)naphthyl-(2- or 3- or 4- or 5-)hexanoyl, and the like, in which the preferred one may be 3-naphthylacryloyl.

Suitable example of "lower alkynoyl" in the term of "lower alkynoyl which may have one or more suitable substituent(s)" may include 2-propynoyl, (2- or 3-)butynoyl, (2- or 3- or 4-)pentynoyl, (2- or 3- or 4- or 5-)hexynoyl, and the like, in which the preferred one may be 2-propynoyl.

Suitable example of "suitable substituent(s)" in the term of "lower alkynoyl which may have one or more suitable substituent(s)" can be referred to aforementioned "suitable substituent(s)", in which the preferred one may be aryl which may have one or more lower alkoxy, aryl which may have one or more higher alkoxy, aryl substituted with aryl which may have one or more lower alkyl and aryl substituted with aryl which may have one or more higher alkyl, and the more preferred one may be aryl substituted with aryl which may have 1 to 3 lower alkyl and aryl which may have 1 to 3 higher alkoxy, and the much more preferred one may be phenyl substituted with phenyl which may have 1 to 3 ($C_1$–$C_6$)alkyl and phenyl which may have 1 to 3 ($C_7$–$C_{14}$)alkoxy, and the most preferred one may be phenyl substituted with phenyl which may have pentyl and naphthyl which may have heptyloxy.

Suitable example of "ar($C_2$–$C_6$)alkanoyl" in the term of "ar($C_2$–$C_6$)alkanoyl substituted with aryl having one or more suitable substituent(s), in which ar($C_2$–$C_6$)alkanoyl may have one or more suitable substituent(s)" may include phenyl($C_2$–$C_6$)alkanoyl [e.g., phenylacetyl, (2- or 3-)-phenylpropanoyl, (2- or 3- or 4-)phenylbutanoyl, (2- or 3- or 4- or 5-)phenylpentanoyl, (2- or 3- or 4- or 5- or 6-)-phenylhexanoyl, etc.], naphthyl($C_2$–$C_6$)alkanoyl [e.g. naphthylacetyl, (2- or 3-)naphthylpropanoyl, (2- or 3- or 4-)naphthylbutanoyl, (2- or 3- or 4- or 5-)-naphthylpentanoyl, (2- or 3- or 4- or 5- or 6-)-naphthylhexanoyl, etc.], and the like, in which the preferred one may be 2-phenylacetyl and 3-phenylpropanoyl.

Suitable example of "suitable substituent(s)" in the term of "ar($C_2$–$C_6$)alkanoyl substituted with aryl having one or more suitable substituent(s), in which ar($C_2$–$C_6$)-alkanoyl may have one or more suitable substituent(s)" may include lower alkoxy, higher alkoxy, lower alkyl, higher alkyl, higher alkoxy(lower)alkyl, oxo, aryl having one or more lower alkoxy, aryl having one or more higher alkoxy, aryl having one or more lower alkyl, aryl having one or more higher alkyl, aryl substituted with aryl having one or more lower alkoxy, aryl substituted with aryl having one or more higher alkoxy, aryl substituted with aryl having one or more lower alkyl, aryl substituted with aryl having one or more higher alkyl, aryl having one or more lower alkoxy(lower) alkoxy and the like, in which the preferred one may be lower alkoxy, higher alkoxy, lower alkyl, higher alkyl, and phenyl having 1 to 3 lower alkoxy(lower)alkoxy and the much more preferred one may be ($C_1$–$C_6$)alkoxy, ($C_1$–$C_6$)alkyl, ($C_7$–$C_{14}$)alkyl and phenyl having ($C_1$–$C_4$)alkoxy($C_3$–$C_6$)alkoxy and the most preferred one may be pentyloxy, pentyl, heptyl and phenyl having methoxypentyloxy.

Suitable example of "suitable substituent(s)" in the term of "in which ar($C_2$–$C_6$)alkanoyl may have one or more suitable substituent(s)" may be hydroxy, oxo, amino and aforementioned "protected amino".

Suitable example of "($C_2$–$C_6$)alkanoyl" in the term of "($C_2$–$C_6$)alkanoyl substituted with naphthyl having higher alkoxy" may include acetyl, propanoyl, butanoyl, pentanoyl, hexanoyl, and the like, in which the preferred one may be propanoyl.

Suitable example of "higher alkoxy" in the term of "($C_2$–$C_6$)alkanoyl substituted with naphthyl having higher alkoxy" may include acetyl, propanoyl, butanoyl, pentanoyl, hexanoyl, and the like, in which the preferred one may be propanoyl.

Suitable example of "higher alkoxy" in the term of "($C_2$–$C_6$)alkanoyl substituted with naphthyl having higher alkoxy" can be referred to aforementioned "higher alkoxy", in which the preferred one may be ($C_7$–$C_{14}$)alkoxy, and the most preferred one may be heptyloxy.

Suitable example of "aroyl" in the term of "aroyl substituted with heterocyclic group which may have one or more suitable substituent(s), in which aroyl may have one or more suitable substituent(s)" may include benzoyl, toluoyl, naphthoyl, and the like, in which the preferred one may be benzoyl.

Suitable example of "heterocyclic group" in the term of "aroyl substituted with heterocyclic group which may have one or more suitable substituent(s), in which aroyl may have one or more suitable substituent(s)" may include unsaturated 3 to 8-membered (more preferably 5 or 6-membered) heteromonocyclic group containing 1 to 4 nitrogen atom(s), for example, pyrrolyl, pyrrolinyl, imidaxolyl, pyraxolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1, 2,3-triazolyl, etc.), tetrazolyl (e.g., 1H-tetrazolyl, 2H-tetrazolyl, etc.), etc.;

saturated 3 to 8-membered (more preferably 5 to 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 to 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 to 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 to 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 to 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 to 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered) heteromonocyclic group containing an oxygen atom, for example, furyl, etc.;

saturated 3 to 8-membered (more preferably 5 to 6-membered) heteromonocyclic group containing an oxygen atom, for example, tetrahydrofuran, tetrahydropyran, etc.;

unsaturated 3 to 8-membered (more preferably 5 to 6membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like, in which the preferred one may be saturated 3 to 8-membered heteromonocyclic group containing 1 to 4 nitrogen atom(s), unsaturated 3 to 8-membered heteromonocyclic group containing 1 to 2 oxygen atom(s) and 1 to 3 nitrogen atom(s), unsaturated 3 to 8-membered heteromonocyclic group containing 1 to 4 nitrogen atom(s), and unsaturated 3 to 8-membered heteromonocyclic group containing 1 to 2 sulfur atom(s) and 1 to 3 nitrogen atoms(s), and the most preferred one may be piperazinyl, isoxazolyl, oxadiazolyl, thiadiazolyl, pyrazolyl, piperidyl, oxazolyl and pyrimidyl.

Suitable example of "suitable substituent(s)" in the term of "aroyl substituted with heterocyclic group which may have one or more suitable substituents(s), in which aroyl may have one or more suitable substituent(s)", in which the preferred one may be aryl which may have 1 to 3 higher alkoxy, aryl which may have 1 to 3 lower alkoxy, higher alkyl, heterocyclic group, aryl which may have 1 to 3 lower alkoxy(higher)alkoxy, aryl which may have higher alkenyloxy, heterocyclic group which may have aryl having lower alkoxy, cyclo(lower)alkyl which may have aryl, aryl which may have 1 to 3 lower alkyl, aryl which may have cyclo(lower)alkyl, aryl which may have higher alkenyloxy, aryl substituted with heterocyclic group which may have lower alkyl and oxo, cyclo(lower)alkyl which may have lower alkyl, aryl substituted with aryl which may have 1 to 3 lower alkoxy, and aryl which may have heterocyclic group, and the more preferred one may be phenyl which may have 1 to 3 ($C_7$–$C_{14}$)alkoxy, phenyl which may have 1 to 3 ($C_3$–$C_6$)alkoxy, ($C_7$–$C_{14}$)alkyl, saturated 3 to 8-membered heteromonocyclic group containing 1 to 4 nitrogen atom(s), phenyl which may have 1 to 3 ($C_1$–$C_4$)alkoxy ($C_7$–$C_{14}$) alkoxy, phenyl which may have ($C_7$–$C_{14}$)alkenyloxy, saturated 3 to 8-membered heteromonocyclic group containing 1 to 4 nitrogen atom(s) substituted with phenyl having ($C_3$–$C_6$)alkoxy, cyclo($C_3$–$C_6$)alkyl which may have phenyl, phenyl which may have 1 to 3 ($C_3$–$C_6$)alkyl, phenyl which may have cyclo($C_3$–$C_6$)alkyl, phenyl which may have ($C_7$–$C_{14}$)alkenyloxy, phenyl substituted with heterocyclic group which may have ($C_3$–$C_6$)alkyl and oxo, cyclo($C_3$–$C_6$) alkyl which may have ($C_3$–$C_6$)alkyl, phenyl substituted with phenyl which may have 1 to 3 ($C_1$–$C_4$)alkoxy, and phenyl which may have 3 to 8-membered heteromonocyclic group containing 1 to 4 nitrogen atom(s), and the most preferred one may be phenyl having octyloxy, phenyl having pentyloxy, phenyl having hexyloxy, heptyl, piperidyl, phenyl having isohexyloxy, phenyl having heptyloxy, phenyl having methoxyheptyloxy, phenyl having methoxyoctyloxy, phenyl having 6-heptenyloxy, piperidyl substituted with phenyl having hexyloxy, cyclohexyl having phenyl, phenyl having hexyl, phenyl having cyclohexyl, phenyl having 7-octenyloxy, phenyl substituted with triazolyl having lower alkyl and oxo, cyclohexyl having pentyl, phenyl having methoxyoctyloxy, nonyl, phenyl substituted with phenyl having propoxy, and phenyl having piperidine.

Suitable example of "suitable substituents(s)" in the term of "in which aroyl may have one or more suitable substituent (s)" may be halogen, in which the preferred one may be fluoro and chloro.

Suitable example of "aroyl" in the term of "aroyl substituted with aryl having heterocyclic(higher)alkoxy, in which heterocyclic group may have one or more suitable substituent(s)" may include benzoyl, toluoyl, naphthoyl, anthrylcarbonyl and the like, in which the preferred one may be benzoyl.

Suitable example of "heterocyclic" moiety in the term of "aroyl substituted with aryl having heterocyclic)higher) alkoxy, in which heterocyclic group may have one or more suitable substituent(s)" can be referred to the ones as exemplified before for "heterocyclic group" in the term of "aroyl substituted with heterocyclic group which may have one or more suitable substituent(s)", in which the preferred one may be unsaturated 3 to 8-membered heteromonocyclic group containing 1 to 4 nitrogen atom(s) and saturated 3 to 8-membered heteromonocyclic group containing 1 to 2 oxygen atom(s) and 1 to 3 nitrogen atom(s), and the most preferred one may be triazolyl, tetrazolyl and morpholinyl.

Suitable example of "(higher)alkoxy" moiety in the term of "aroyl substituted with aryl having heterocyclic(higher) alkoxy, in which heterocyclic group may have one or more suitable substituent(s)" can be referred to aforementioned "higher alkoxy", in which the preferred one may be ($C_7$–$C_{14}$)alkoxy, and the most preferred one may be octyloxy.

Suitable example of "aryl" in the term of "aroyl substituted with aryl having heterocyclic(higher)alkoxy, in which heterocyclic group may have one or more suitable substituent(s)" can be referred to aforementioned "aryl", in which the preferred one may be phenyl.

Suitable example of "suitable substituent(s)" in the term of "in which heterocyclic group may have one or more suitable substituent(s)" may be lower alkyl, in which the preferred one may be methyl.

Suitable example of "aroyl" in the term of "aroyl substituted with aryl having lower alkoxy(higher)alkoxy" may include benzoyl, toluoyl, naphthoyl, anthrylcarbonyl and the like, in which the preferred one may be benzoyl.

Suitable example of "aryl" in the term of "aroyl substituted with aryl having lower alkoxy(higher)alkoxy" can be referred to aforementioned "aryl", in which the preferred one may be phenyl.

Suitable example of "lower alkoxy(higher)alkoxy" in the term of "aroyl substituted with aryl having lower alkoxy (higher)alkoxy" may be methoxyheptyloxy, methoxyoctyloxy, methoxynonyloxy, methoxydecyloxy, ethoxyheptyloxy, ethoxyoctyloxy, ethoxynonyloxy, ethoxydecyloxy, ethoxyundecylocy, propoxyundecyloxy, butoxydodecyloxy, pentyloxytridecyloxy, hexyloxytetradecyloxy, propoxyheptyloxy, propoxyoctyloxy, propoxynonyloxy, butoxydecyloxy, or the like, in which the preferred one may be ($C_1$–$C_6$)alkoxy ($C_7$–$C_{14}$)alkoxy, and the more preferred one may be methoxyoctyloxy.

Suitable example of "aroyl" in the term of "aroyl substituted with aryl having lower alkenyl(lower)alkoxy" may include benzoyl, toluoyl, naphthoyl, anthrylcarbonyl and the like, in which the preferred one may be benzoyl.

Suitable example of "aryl" in the term of "aroyl substituted with aryl having lower alkenyl(lower)alkoxy" can be referred to aforementioned "aryl", in which the preferred one may be phenyl.

Suitable example of "lower alkenyl(lower)alkoxy" in the term of "aroyl substituted with aryl having lower alkenyl (lower)alkoxy" may be vinylmethoxy, vinylethoxy, vinylpropoxy, vinylbutoxy, vinylpentyloxy, vinylhexyloxy, 1-(or 2-)propenylmethoxy, 1-(or 2-)propenylethoxy, 1-(or 2-)propenylpropoxy, 1-(or 2-)propenylbutoxy, 1-(or 2-)propenylpentyloxy, 1-(or 2-propenylhexyloxy, 1-(or 2- or 3-(butenylbutoxy, 1-(or 2- or 3-)butenylhexyloxy, 1-(or 2- or 3- or 4-)pentenylpentyloxy, 1-(or 2- or 3- or 4-)pentenylhexyloxy, 1-(or 2- or 3- or 4- or 5-)hexenylbutoxy, 1-(or 2- or 3- or 4- or 5-)hexenylhexyloxy, or the like, in which the preferred one may be ($C_2$–$C_6$)alkenyl ($C_1$–$C_6$) alkoxy, and the more preferred one may be vinylhexyloxy.

Suitable example of "aroyl substituted with 2 lower alkoxy" may include benzoyl substituted with 2 lower alkoxy and naphthoxyl substituted with 2 lower alkoxy, in which the preferred one may be benzoyl substituted with 2 ($C_1$–$C_6$)alkoxy, and the most preferred one may be benzoyl substituted with 2 pentyloxy.

Suitable example of "aroyl substituted with aryl having lower alkyl" may include benzoyl substituted with phenyl having lower alkyl, benzoyl substituted with naphthyl having lower alkyl, naphthoyl substituted with phenyl having lower alkyl, naphthoyl substituted with naphthyl having lower alkyl, and the like, in which the preferred one may be benzoyl substituted with phenyl having ($C_1$–$C_6$)alkyl, and the most preferred one may be benzoyl substituted with phenyl having hexyl and benzoyl substituted with phenyl having pentyl.

Suitable example of "aroyl substituted with aryl having higher alkyl" may include benzoyl substituted with phenyl having higher alkyl, benzoyl substituted with naphthyl having higher alkyl, naphthoyl substituted with phenyl having higher alkyl, naphthoyl substituted with naphthyl having higher alkyl, and the like, in which the preferred one may be benzoyl substituted with phenyl having ($C_7$–$C_{14}$)alkyl, and the most preferred one may be benzoyl substituted with phenyl having heptyl.

Suitable example of "aryloxy" moiety in the term of "aryloxy(lower)alkanoyl which may have one or more suitable substituent(s)" may include phenoxy, mesityloxy, tolyloxy, naphthyloxy, anthryloxy, and the like, in which the preferred one may be phenoxy.

Suitable example of "lower alkanoyl" moiety in the term of "aryloxy(lower)alkanoyl which may have one or more suitable substituent(s)" can be referred to aforementioned "lower alkanoyl", in which the preferred one may be formyl, acetyl, 2,2-dimethylacetyl, propionyl, butyryl, isobutyryl and pentanoyl, hexanoyl, and the more preferred one may be ($C_1$–$C_6$)alkanoyl, and the much more preferred one may be formyl, acetyl, propionyl and 2,2-dimethylacetyl.

Suitable example of "suitable substituent(s)" in the term of "aryloxy(lower)alkanoyl which may have one or more suitable substituent(s)" can be referred to aforementioned "suitable substituent(s)", in which the preferred one may be ($C_7$–$C_{14}$)alkoxy, and the more preferred one may be octyloxy.

Suitable example of "ar(lower)alkoxy" moiety in the term of "ar(lower)alkoxy(lower)alkanoyl which may have one or more suitable substituent(s)" may include phenyl(lower) alkoxy [e.g., phenylmethoxy, (1- or 2-)phenylethoxy, phenylpropoxy, 2-phenyl-1-methylpropoxy, 3-phenyl-2,2-dimethylpropoxy,
[1- or 2- or 3- or 4-)phenylbutoxy, (1- or 2- or 3- or 4- or 5-)phenylpentyloxy, (1- or 2- or 3- or 4- or 5- or 6-)phenylhexyloxy, etc.], naphthyl(lower)alkoxy [e.g. naphthylmethoxy, (1- or 2-)naphtylethoxy, 1-naphthylpropoxy, 2-naphthyl-1-methylpropoxy, 3-naphthyl-2,2-dimethylpropoxy, (1- or 2- or 3- or 4-)naphthylbutoxy, (1- or 2- or 3- or 4- or 5-)naphthylpentyloxy, (1- or 2- or 3- or 4- or 5- or 6-)naphthylhexyloxy, etc.], and the like, in which the preferred one may be naphthyl($C_1$–$C_4$) alkoxy, and the more preferred one may be naphthylmethoxy.

Suitable example of "(lower)alkanoyl" moiety in the term of "ar(lower)alkoxy(lower)alkanoyl which may have one or more suitable substituent(s)" can be referred to aforementioned "lower alkanoyl", in which the preferred one may be ($C_1$–$C_4$)alkanoyl, and the more preferred one may be formyl.

Suitable example of "suitable substituent(s)" in the term of "ar(lower)alkoxy(lower)alkanoyl which may have one or more suitable substituent(s)" can be referred to aforementioned "suitable substituent(s)", in which the preferred one may be lower alkoxy, higher alkoxy, lower alkyl and higher alkyl, and the more preferred one may be higher alkoxy, and the much more preferred one may be $(C_7-C_{14})$alkoxy, and the most preferred one may be heptyloxy.

Suitable example of "arylamino" moiety in the term of "arylamino(lower)alkanoyl which may have one or more suitable substituent(s)" may include phenylamino, mesitylamino, tolylamino, naphthylamino, anthrylamino and the like, in which the preferred one may be phenylamino and naphthylamino.

Suitable example of "lower alkanoyl" moiety in the term of "arylamino(lower)alkanoyl which may have one or more suitable substituent(s)" can be referred to aforementioned "lower alkanoyl", in which the preferred one may be $(C_1-C_4)$alkanoyl, and the more preferred one may be formyl.

Suitable example of "suitable substituent(s)" in the term of "arylamino(lower)alkanoyl which may have one or more suitable substituent(s)" can be referred to aforementioned "suitable substituent(s)", in which the preferred one may be lower alkoxy, higher alkoxy, lower alkyl, higher alkyl, aryl which may have 1 to 3 lower alkoxy and aryl which may have 1 to 3 higher alkoxy, and the more preferred one may be $(C_7-C_{14})$alkoxy, and phenyl which may have 1 to 3 $(C_7-C_{14})$alkoxy, and the most preferred one may be heptyloxy and phenyl which may have heptyloxy.

Suitable example of "lower alkanoyl" in the term of "lower alkanoyl substituted with pyrazolyl which has lower alkyl and aryl having higher alkoxy" can be referred to aforementioned "lower alkanoyl", in which the preferred one may be $(C_1-C_4)$alkanoyl, and the most preferred one may be formyl.

Suitable example of "lower alkyl" in the term of "lower alkanoyl substituted with pyrazolyl which has lower alkyl and aryl having higher alkoxy" can be referred to aforementioned "lower alkyl", in which the preferred one may be $(C_1-C_4)$alkyl, and the most preferred one may be methyl.

Suitable example of "aryl" in the term of "lower alkanoyl substituted with pyrazolyl which has lower alkyl and aryl having higher alkoxy" can be referred to aforementioned "aryl", in which the preferred one may be phenyl.

Suitable example of "higher alkoxy" in the term of "lower alkanoyl substituted with pyrazolyl which has lower alkyl and aryl having higher alkoxy" can be referred to aforementioned "higher alkoxy", in which the preferred one may be $(C_7-C_{14})$alkoxy, and the most preferred one may be octyloxy.

Suitable example of "lower alkoxy(higher)alkanoyl" in the term of "lower alkoxy(higher)alkanoyl, in which higher alkanoyl may have one or more suitable substituent(s)" may be $(C_1-C_4)$alkoxy$(C_7-C_{20})$alkanoyl, in which the preferred one may be methoxyoctadecanoyl.

Suitable example of "suitable substituent(s)" in the term of "lower alkoxy(higher)alkanoyl, in which higher alkanoyl may have one or more suitable substituent(s)" may be amino and aforementioned "protected amino", in which the preferred one may be amino and ar(lower)alkoxycarbonylamino, and the most preferred one may be amino and benzyloxycarbonylamino.

Suitable example of "aroyl" in the term of "aroyl substituted with aryl having heterocyclicoxy, in which heterocyclicoxy may have one or more suitable substituent(s)" can be referred to aforementioned "aroyl", in which the preferred one may be benzoyl.

Suitable example of "aryl" in the term of "aroyl substituted with aryl having heterocyclicoxy, in which heterocyclicoxy may have one or more suitable substituent(s)" can be referred to aforementioned "aryl", in which the preferred one may be phenyl.

Suitable example of "heterocyclic" moiety in the term of "aroyl substituted with aryl having heterocyclicoxy, in which heterocyclicoxy may have one or more suitable substituent(s)" can be referred to aforementioned "heterocyclic" moiety, in which the preferred one may be unsaturated 3 to 8-membered heteromonocyclic group containing 1 to 4 nitrogen atom(s), and the most preferred one may be pyridazinyl.

Suitable example of "suitable substituent(s)" in the term of "aroyl substituted with aryl having heterocyclicoxy, in which heterocyclicoxy may have one or more suitable substituent(s)" may be aryl, in which the preferred one may be phenyl.

Suitable example of "aroyl" in the term of "aroyl substituted with cyclo(lower)alkyl having lower alkyl" can be referred to aforementioned "aroyl", in which the preferred one may be benzoyl.

Suitable example of "cyclo(lower)alkyl" in the term of "aroyl substituted with cyclo(lower)alkyl having lower alkyl" can be referred to aforementioned "cyclo(lower)alkyl", in which the preferred one may be cyclohexyl.

Suitable example of "lower alkyl" in the term of "aroyl substituted with cyclo(lower)alkyl having lower alkyl" can be referred to aforementioned "lower alkyl", in which the preferred one may be pentyl.

Suitable example of "higher alkyl" in the term of "indolylcarbonyl having higher alkyl" can be referred to aforementioned "higher alkyl", in which the preferred one may be decyl.

Suitable example of "lower alkyl" in the term of "naphthoyl having lower alkyl" can be referred to aforementioned "lower alkyl", in which the preferred one may be hexyl.

Suitable example of "higher alkyl" in the term of "naphthoyl having higher alkyl" can be referred to aforementioned "higher alkyl", in which the preferred one may be heptyl.

Suitable example of "lower alkoxy(higher)alkoxy" in the term of "naphthoyl having lower alkoxy(higher)alkoxy" may be $(C_1-C_4)$alkoxy$(C_7-C_{14})$alkoxy, in which the preferred one may be methoxyoctyloxy.

Suitable example of "aroyl" in the term of "aroyl substituted with aryl having lower alkoxy(lower)alkoxy(higher) alkoxy", "aroyl substituted with aryl having lower alkoxy (lower)alkoxy", "aroyl substituted with aryl which has aryl having lower alkoxy", "aroyl substituted with aryl which has aryl having lower alkoxy(lower)alkoxy", "aroyl substituted with aryl having heterocyclicoxy(higher)alkoxy", "aroyl substituted with aryl having aryloxy(lower)alkoxy" and "aroyl substituted with aryl having heterocycliccarbonyl (higher)alkoxy" can be referred to aforementioned "aroyl", in which the preferred one may be benzoyl.

Suitable example of "aryl" in abovementioned terms can be referred to aforementioned "aryl", in which the preferred one may be phenyl.

Suitable example of "lower alkoxy(lower)alkoxy(higher) alkoxy" in the term of "aroyl substituted with aryl having lower alkoxy(lower)alkoxy(higher)alkoxy" may be $(C_1-C_4)$alkoxy$(C_1-C_4)$alkoxy$(C_7-C_{14})$alkoxy, in which the preferred one may be ethoxyethoxyoctyloxy.

Suitable example of "lower alkoxy(lower)alkoxy" in the term of "aroyl substituted with aryl having lower alkoxy (lower)alkoxy" may be $(C_1-C_4)$alkoxy$(C_3-C_6)$alkoxy, in which the preferred one may be propoxyhexyloxy.

Suitable example of "lower alkoxy" in the term of "aroyl substituted with aryl which has phenyl having lower alkoxy" may be $(C_3-C_6)$alkoxy, in which the preferred one may be butoxy.

Suitable example of "lower alkoxy(lower)alkoxy" in the term of "aroyl substituted with aryl which has phenyl having lower alkoxy(lower)alkoxy" may be $(C_1-C_4)$alkoxy$(C_3-C_6)$alkoxy, in which the preferred one may be methoxypentyloxy and methoxyhexyloxy.

Suitable example of "heterocyclic" moiety in the term of "aroyl substituted with aryl having heterocyclicoxy(higher)alkoxy" can be referred to aforementioned "heterocyclic" moiety, in which the preferred one may be saturated 3 to 8-membered heteromonocyclic group containing an oxygen atom, and the most preferred one may be tetrahydropyranyl.

Suitable example of "higher alkoxy" moiety in the term of "aroyl substituted with aryl having heterocyclicoxy(higher)alkoxy" may be $(C_7-C_{14})$alkoxy, in which the preferred one may be octyloxy.

Suitable example of "aryloxy(lower)alkoxy" in the term of "aroyl substituted with aryl having aryloxy(lower)alkoxy" may be phenoxy$(C_3-C_6)$alkoxy, in which the preferred one may be phenoxypentyloxy.

Suitable example of "heterocyclic" moiety in the term of "aroyl substituted with aryl having heterocycliccarbonyl(higher)alkoxy" can be referred to aforementioned "heterocyclic" moiety, in which the preferred one may be saturated 3 to 8-membered heteromonocyclic group containing 1 to 4 nitrogen atom(s), and the most preferred one may be piperidyl.

Suitable example of "higher alkoxy" moiety in the term of "aroyl substituted with aryl having heterocycliccarbonyl(higher)alkoxy" can be referred to aforementioned "higher alkoxy", in which the preferred one may be $(C_7-C_{14})$alkoxy, and the most preferred one may be heptyloxy.

Suitable example of "lower alkanoyl" in the term of "lower alkanoyl substituted with oxazolyl which has aryl having higher alkoxy" can be referred to aforementioned "lower alkanoyl", in which the preferred one may be $(C_1-C_4)$alkanoyl, and the most preferred one may be formyl.

Suitable example of "aryl" in the term of "lower alkanoyl substituted with oxazolyl which has aryl having higher alkoxy" can be referred to aforementioned "aryl", in which the preferred one may be phenyl.

Suitable example of "higher alkoxy" in the term of "lower alkanoyl substituted with oxazolyl which has aryl having higher alkoxy" can be referred to aforementioned "higher alkoxy", in which the preferred one may be $(C_7-C_{14})$alkoxy, and the most preferred one may be octyloxy.

Suitable example of "lower alkanoyl" in the term of "lower alkanoyl substituted with furyl which has aryl substituted with aryl having lower alkoxy" can be referred to aforementioned "lower alkanoyl", in which the preferred one may be $(C_1-C_4)$alkanoyl, and the most preferred one may be formyl.

Suitable example of "aryl" in the term of "lower alkanoyl substituted with furyl which has aryl substituted with aryl having lower alkoxy" can be referred to aforementioned "aryl", in which the preferred one may be phenyl.

Suitable example of "lower alkoxy" in the term of "lower alkanoyl substituted with furyl which has aryl substituted with aryl having lower alkoxy" can be referred to aforementioned "lower alkoxy", in which the preferred one may be $(C_1-C_4)$alkoxy, and the most preferred one may be butoxy.

Suitable example of "lower alkanoyl" in the term of "lower alkanoyl substituted with triazolyl which has oxo and aryl having higher alkyl" can be referred to aforementioned "lower alkanoyl", in which the preferred one may be $(C_1-C_4)$alkanoyl, and the most preferred one may be formyl.

Suitable example of "higher alkyl" in the term of "lower alkanoyl substituted with triazolyl which has oxo and aryl having higher alkyl" can be referred to aforementioned "higher alkyl", in which the preferred one may be $(C_7-C_{14})$alkyl, and the most preferred one may be octyl.

Suitable example of "aryl" in the term of "lower alkanoyl substituted with triazolyl which has oxo and aryl having higher alkyl" can be referred to aforementioned "aryl", in which the preferred one may be phenyl.

Suitable example of "higher alkanoyl" in the term of "higher alkanoyl having hydroxy" can be referred to aforementioned "higher alkanoyl", in which the preferred one may be $(C_7-C_{20})$alkanoyl, and the most preferred one may be hexadecanoyl.

Suitable example of "higher alkanoyl" in the term of "higher alkanoyl having ar(lower)alkyl and hydroxy" can be referred to aforementioned "higher alkanoyl", in which the preferred one may be $(C_7-C_{20})$alkanoyl, and the most preferred one may be hexadecanoyl.

Suitable example of "ar(lower)alkyl" in the term of "higher alkanoyl having ar(lower)alkyl and hydroxy" can be referred to aforementioned "ar(lower)alkyl", in which the preferred one may be phenyl$(C_1-C_4)$alkyl, and the most preferred one may be benzyl.

Suitable example of "$(C_2-C_6)$alkanoyl" in the terms of "$C_2-C_6$)alkanoyl substituted with aryl having higher alkoxy, in which $(C_2-C_6)$alkanoyl may have amino or protected amino" may include acetyl, propanoyl, butanoyl, pentanoyl, hexanoyl, and the like, in which the preferred one may be acetyl and propanoyl.

Suitable example of "aryl" in the term of "$(C_2-C_6)$alkanoyl substituted with aryl having higher alkoxy, in which $(C_2-C_6)$alkanoyl may have amino or protected amino" can be referred to aforementioned "aryl", in which the preferred one may be phenyl.

Suitable example of "higher alkoxy" in the term of "$(C_2-C_6)$alkanoyl substituted with aryl having higher alkoxy, in which $(C_2-C_6)$alkanoyl may have amino or protected amino" can be referred to aforementioned "higher alkoxy", in which the preferred one may be $(C_7-C_{14})$alkoxy, and the most preferred one may be octyloxy.

Suitable example of "protected amino" in the term of "$(C_2-C_6)$alkanoyl substituted with aryl having higher alkoxy, in which $(C_2-C_6)$alkanoyl may have amino or protected amino" can be referred to aforementioned "protected amino", in which the preferred one may be ar(lower)alkoxycarbonylamino, and the most preferred one may be benzyloxycarbonylamino.

The process for preparing the object polypeptide compound [I] or a salt thereof of the present invention are explained in detail in the following.

Process 1

The object polypeptide compound [I] or a salt thereof can be prepared by reacting the compound [II] or its reactive derivative at the amino group or a salt thereof with the compound [III] or its reactive derivative at the carboxy group or a salt thereof.

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g., benzoic acid, etc.]p; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [(CH$_3$)$_2$N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the mind of the compound [III] to be used.

Suitable salts of the compound [III] and its reactive derivative can be referred to the ones as exemplified for the object polypeptide compound [I].

The reaction is usually carried out in a conventional solvent such as water, alcohol (e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide, N,N-carbonylbis-(2-methylimidazole); pentamethyleneketene-N-cyclohexylimine; diphenylketene-N-cyclohexylimine; ethoxyacetylene; 1-alkoxy-2-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorous oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction is usually carried out under cooling to warming.

The starting compound [II] is a known compound. It can be prepared by fermentation and synthetic processes disclosed in EP 0462531 A2.

A culture of Coleophoma sp. F-11899, which is used in said fermentation process, has been deposited with National Institute of Bioscience and Human-Technology Agency of Industrial Science and Technology (former name: Fermentation Research Instituted Agency of Industrial Science and Technology) (1–3, Higashi 1-chome, Tsukubashi, IBARAKI 305, JAPAN) on Oct. 26, 1989 under the number of FERM BP-2635.

The compounds obtained by the above Process 1 can be isolated and purified by a conventional method such as pulverization, recrystallization, column-chromatography, high-performance liquid chromatography (HPLC), reprecipitation, or the like.

The compounds obtained by the above Process 1 may be obtained as its hydrate, and its hydrate is included within the scope of this invention.

It is to be noted that each of the object compound (I) may include one or more stereoisomer such as optical isomer(s) and geometrical isomer(s) due to asymmetric carbon atom(s) and double bond(s) and all such isomers and mixture thereof are included within the scope of this invention.

Biological property of the polypeptide compound [I] of the present invention

In order to show the usefulness of the polypeptide compound [I] of the present invention, the biological data of the representative compound is explained in the following.

Test 1 (Antimicrobial activity)

In vitro antimicrobial activity of the compound of Example 17 disclosed later was determined by the two-fold agar-plate dilution method as described below.

Test Method

One loopful of an overnight culture of each test microorganism in Sabouraud broth containing 2% Glucose ($10^5$ viable cells per ml) was streaked on yeast nitrogen base dextrose agar (YNBDA) containing graded concentrations of the object polypeptide compound [I], and the minimal inhibitory concentration (MIC) was expressed in terms of ug/ml after incubation at 30° C. for 24 hours.

| Test organism | Test Result MIC (μg/ml) Test compound The compound of Example 17 |
|---|---|
| *candida albicans* FP-633 | 0.2 |

From the test result, it is realized that the object polypeptide compound [I] of the present invention has an antimicrobial activity (especially, antifungal activity).

The pharmaceutical composition of the present invention can be used in the form of a pharmaceutical preparation, for example, in solid, semisolid or liquid from, which contains the object polypeptide compound (I) or a pharmaceutically acceptable salt thereof, as an active ingredient in admixture with an organic or inorganic carrier or excipient which is suitable for rectal; pulmonary (nasal or buccal inhalation); ocular; external (topical); oral administration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams, ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The object polypeptide compound [I] or a pharmaceutically acceptable salt thereof is/are included in the pharmaceutical composition in an amount sufficient to produce the desired antimicrobial effect upon the process or condition of diseases.

For applying the composition to human, it is preferable to apply it by intravenous, intramuscular, pulmonary, oral administration, or insufflation. While the dosage of therapeutically effective amount of the object polypeptide compound [I] varies from and also depends upon the age and condition of each individual patient to be treated, in the case of intravenous administration, a daily dose of 0.01–20 mg of the object polypeptide compound [I] per kg weight of human being in the case of intramuscular administration, a daily dose of 0.1–20 mg of the object polypeptide compound [I] per kg weight of human being, in case of oral administration, a daily dose of 0.5–50 mg of the object polypeptide compound [I] per kg weight of human being is generally given for treating or preventing infectious diseases.

Especially in case of the treatment of prevention of *Pneumocystis carinii* infection, the followings are to be noted.

For administration by inhalation, the compounds of the present invention are conveniently delivered in the form of an aerosol spray presentation from pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

The following Preparations and Examples are given for the purpose of illustrating the present invention in more detail.

Preparation 1

To a suspension of 1-(4-Hydroxyphenyl)-4-tert-butoxycarbonylpiperazine (3 g) and potassium carbonate (0.82 g) in N,N-dimethylformamide (15 ml) was added octyl bromide (1.87 ml). The mixture was stirred for 10 hours at 70° C. The reaction mixture was added to a mixture of water and ethyl acetate. The organic layer was taken, and dried over magnesium sulfate. The magnesium sulfate was filtered off, and the filtrate was evaporated under reduced pressure. The residue was subjected to column chromatography on silica gel, and eluted with (hexane : ethyl acetate=9:1). The fractions containing the object compound were combined, and evaporated under reduced pressure to give 1-(4-n-Octyloxyphenyl)-4-tert-butoxycarbonylpiperazine (2.71 g).

IR (KBr) : 1687, 1513, 1241 cm$^{-1}$

NMR (CDCl$_3$, δ) : 0.88 (3H, t, J=6.2 Hz), 1.2–1.4 (10 H, m), 1.48 (9H, s), 1.65–1.85 (2H, m), 3.00 (4H, t, J=5.2 Hz), 3.57 (4H, t, J=5.2 Hz), 3.90 (2H, t, J=6.5 Hz), 6.83 (2H, dd, J=6.4 and 2.1 Hz), 6.89 (2H, dd, J=6.4 and 2.1 Hz)

Preparation 2

A solution of 1-(4-n-Octyloxyphenyl)-4-tert-butoxycarbonylpiperazine (2.61 g) in trifluoroacetic acid (20 ml) was stirred for 4 hours at ambient temperature. The reaction mixture was evaporated under reduced pressure, and to the residue was added a mixture of 1N NaOH aqueous solution and ethyl acetate. The organic layer was taken, and dried over magnesium sulfate. The magnesium sulfate was filtered off, and the filtrate was evaporated under reduced pressure to give 1-(4-n-Octyloxyphenyl)piperazine (0.86 g).

IR (KBr) : 2923, 1513, 1259, 831 cm$^{-1}$

NMR (CDCl$_3$, δ) : 0.88 (3H, t, J=6.4 Hz), 1.2–1.53 (10H, m), 1.65–1.85 (2H, m), 3.03 (4H, s), 3.90 (2H, t, J=6.5 Hz), 6.83 (2H, dd, J=6.4 and 2.9 Hz), 6.90 (2H, dd, J=6.4 and 2.9 Hz)

APCI-MASS : m/z=291 (M$^+$+1)

Preparation 3

To a suspension of 1-(4-n-Octyloxyphenyl)piperazine (1 g)and potassium carbonate (0.476 g) in N,N-dimethylformamide (1 ml) was added p-fluorobenzonitrile (0.347 g), and stirred for 5 hours at 160° C. The reaction mixture was added to a mixture of water and ethyl acetate. The organic layer was taken, and dried over magnesium sulfate. The magnesium sulfate was filtered off, and the filtrate was evaporated under reduced pressure to give 4-[4-(4-n-Octyloxyphenyl)piperazine-1-yl]benzonitrile (0.93 g).

IR (KBr) : 2848, 2217, 1604, 1511, 1241 cm$^{-1}$

NMR (CDCl$_3$, δ) : 0.89 (3H, t, J=6.8 Hz), 1.2–1.53 (10 H, m), 1.65–1.85 (2H, m), 3.20 (4H, t, J=5.4 Hz), 3.48 (4H, t, J=5.4 Hz), 3.91 (2H, t, J=6.5 Hz), 6.8–7.0 (6H, m), 7.52 (2H, d, J=8.9 Hz)

APCI-MASS : m/z=392 (M$^+$+1)

Preparation 4

A mixture of 2,4-Dihydroxybenzaldehyde (5.52 g), potassium carbonate (6.08 g) and octyl bromide (7.73 g) in acetonitrile (55 ml) was stirred for 16 hours at 60° C. The solvent of reaction mixture was removed under reduced pressure, and the residue was dissolved in ethyl acetate, and washed with water and brine. The separated organic layer was dried over magnesium sulfate. The magnesium sulfate was filtered off, and the filtrate was evaporated under reduced pressure. The residue was subjected to column chromatography on silica gel and eluted with (hexane : ethyl acetate=9:1) to give 2-Hydroxy-4-octyloxybenzaldehyde (6.73 g).

NMR (CDCl$_3$, δ) : 0.89 (3H, t, J=8.8 Hz), 1.2–1.5 (10H, m), 1.8–2.0 (2H, m), 4.0–4.2 (2H, m), 6.42 (1H, s), 6.52 (1H, d, J=8.7Hz), 7.79 (1H, d, J=8.7 Hz), 10.33 (1H, s)

APCI-Mass : m/z=257 (M$^+$+1)

The following compound was obtained according to a similar manner to that of Preparation 4.

Preparation 5

Methyl 3,4-dipentyloxybenzoate

NMR (CDCl$_3$, δ) : 0.93 (6H, t, J=6.0 and 9.0 Hz), 1.3–2.0 (12H, m), 3.88 (3H, s), 4.04 (4H, m), 6.86(1H, d, J=8.4 Hz), 7.53 (1H, d, J=2.0 Hz), 7.63 (1H, dd, J=8.4 and 2.0 Hz)

APCI-MASS : m/z=309 (M$^+$+1)

Preparation 6

A mixture of 4-bromo-4'-pentylbiphenyl (5.04 g), trimethylsilylacetylene (2.4 ml), tetrakis(triphenylphosphine) palladium (0.96 g), triphenylphosphine (0.22 g) and cuproous iodide (95 mg) in piperidine (10 ml) was heated for an hour under atmospheric pressure of nitrogen at 90° C. The reaction mixture was poured into a mixture of cold water and ethyl acetate, and adjusted to about pH 1 with 6N hydrochloric acid. The separated organic layer was washed with water and brine, and dried over magnesium sulfate. The magnesium sulfate was filtered off, and the filtrate was evaporated under reduced pressure to give crude (2-[4-(4-pentylphenyl)phenyl]-1-trimethylsilylacetylene, which was used for the next reaction without further purification. Crude mixture was dissolved in a mixture of dichloromethane (10 ml) and methanol (10 ml), and to the solution was added potassium carbonate (2.75 g) at 0° C. The mixture was allowed to warm to ambient temperature, and stirred for another 2 hours. The reaction mixture was poured into a mixture of cold water and ethyl acetate, and the resultant precipitate was filtered off. The filtrate was adjusted to about pH 7 with 1N hydrochloric acid, and washed with brine, and dried over magnesium sulfate. The magnesium sulfate was filtered off, and the filtrate was evaporated under reduced pressure to give a crude powder, which was subjected to column chromatography on silica gel (300 ml), and eluted with a mixture of (n-hexane : ethyl acetate=99:1–97:3, V/V) to give 4-(4-Pentylphenyl)phenylacetylene (2.09 g).

IR (Nujol) : 3274, 1490 cm$^{-1}$

NMR (CDCl$_3$, δ) : 0.90 (3H, t, J=6.4 Hz), 1.30–1.50 (4H, ), 1.50–1.80 (2H, m), 2.64 (2H, t, J=7.6 Hz), 7.20–7.30 (2H, m), 7.45–7.60 (6H, m)

APCI-MASS : m/z=281 (M$^+$+1+MeOH)

The following compound was obtained according to a similar manner to that of Preparation 6.

Preparation 7

6-Heptyloxynaphthalen-2-yl-acetylene

NMR (CDCl$_3$, δ) : 0.90 (3H, t, J=6.5 Hz), 1.20–1.60 (8H, m), 1.70–1.90 (2H, m), 3.10 (1H, s), 4.07 (2H, t, J=6.5 Hz), 7.08 (1H, d, J=2.5 Hz), 7.15 (1H, dd, J=2.5 and 8.9 Hz), &.47 (1H, dd, J=1.6 and 8.5 Hz), 7.64 (1H, d, J=7.3 Hz), 7.68 (1H, d, J=8.5 Hz), 7.94 (1H, d, J=1.6 Hz)

APCI-MASS : m/z=267 (M$^+$+1)

Preparation 8

To a solution of 4-(4-Pentylphenyl)phenylacetylene (2.09 g) in tetrahydrofuran (30 ml) was added dropwise a solution of lithium diisobutylamide in a mixture of tetrahydrofuran and n-hexane (1.60 M, 5.6 ml) at −75° C., and the resultant mixture was stirred for an hour at −78° C. To the mixture was added methyl chloroformate (0.72 ml), and the reaction mixture was allowed to warm to ambient temperature. The solution was diluted with ethyl acetate, and washed in turn with water and brine, and dried over magnesium sulfate. The magnesium sulfate was filtered off, and the filtrate was evaporated under reduced pressure to give a crude product, which was subjected to column chromatography on silica gel (150 ml), and eluted with a mixture of (n-hexane:ethyl acetate=100:0–9:1, V/V) to give Methyl 3-[4-(4-pentylphenyl)phenyl]propionate (2.20 g).

IR (Nujol): 2225, 1712 cm$^{-1}$

NMR (CDCl$_3$, δ): 0.90 (3H, t, J=6.5Hz), 1.25–1.50 (4H, m), 1.52–1.80 (2H, m), 2.64 (2H, t, J=7.6Hz), 3.85 (3H, s), 7.20–7.35 (2H, m), 7.40–7.70 (6H, m)

APCI-MASS: m/z=307 (M$^+$+1)

The following compound was obtained according to a similar manner to that of Preparation 8.

Preparation 9

Methyl 3-(6-heptyloxynaphthalen-2-yl)propionate

IR (Nujol): 2219, 1704, 1621 cm$^{-1}$

NMR (CDCl$_3$, δ): 0.90 (3H, t, J=6.5Hz), 1.20–1.60 (8H, m), 1.70–2.00 (2H, m), 3.86 (3H, s), 4.08 (2H, t, J=6.5Hz), 7.10 (1H, d, J=2.5Hz), 7.17 (1H, dd, J=2.5 and 8.9Hz), 7.52 (1H, dd, J=1.6 and 8.5Hz), 7.68 (1H, d, J=7.3Hz), 7.72 (1H, d, J=8.5Hz), 8.06 (1H, d, J=1.6Hz)

APCI-MASS: m/z=325 (M$^+$+1)

Preparation 10

A mixture of 4-bromo-4'-pentylbiphenyl (5.0 g), methyl acrylate (2.2 ml), palladium acetate (0.11 g) and tris(o-tolyl) phosphine (0.60 g) in triethylamine (16 ml) was refluxed for 15 hours under nitrogen atmosphere. The reaction mixture was poured into a mixture of cold water and ethyl acetate, and adjusted to about pH 1.5 with 6N hydrochloric acid. The separated organic layer was washed in turn with water and brine, and dried over magnesium sulfate. The magnesium sulfate was filtered off, and the filtrate was evaporated under reduced pressure to give a crude powder, which was subjected to column chromatography on silica gel (200 ml), and eluted with a mixture of (n-hexane:ethyl acetate=100:0–93:6, V/V) to give Methyl 3-[4-(4-pentylphenyl)phenyl]acrylate (4.48 g).

IR (Nujol): 1718, 1637 cm$^{-1}$

NMR (CDCl$_3$, δ): 0.91 (3H, t, J=6.7Hz), 1.20–1.50 (4H, m), 1.50–1.80 (2H, m), 2.65 (2H, t, J=7.4Hz), 3.82 (3H, s), 6.47 (1H, d, J=16.0Hz), 7.20–7.35 (2H, m), 7.45–7.68 (6H, m), 7.73 (1H, d, J=16.0Hz)

APCI-MASS: m/z=309 (M$^+$+1)

The following compounds (Preparations 11 to 13) were obtained according to a similar manner to that of Preparation 10

Preparation 11

Methyl 3-(6-heptyloxynaphthalen-2-yl)acrylate

IR (Nujol): 1716, 1625, 1459 cm$^{-1}$

NMR (CDCl$_3$, δ): 0.90 (3H, t, J=6.5Hz), 1.20–1.65 (8H, m), 1.76–1.93 (2H, m), 3.82 (3H, s), 4.07 (2H, t, J=6.5Hz), 6.49 (1H, d, J=16.0Hz), 7.05–7.20 (2H, m), 7.55–7.90 (5H, m)

APCI-MS: m/z=327 (M$^+$+1)

Preparation 12

Methyl 3-[4-(4-heptylphenyl)phenyl]acrylate

NMR (CDCl$_3$, δ): 0.88 (3H, t, J=6.5Hz), 1.15–1.50 (8H, m), 1.50–1.75 (2H, m), 2.64 (2H, t, J=7.6Hz), 3.81 (3H, s), 6.46 (1H, d, J=16.0Hz), 7.26 (2H, d, J=8.2Hz), 7.52 (2H, d, J=8.2Hz), 7.59 (6H, s), 7.73 (1H, d, J=16.0Hz)

APCI-MASS: m/z=337 (M$^+$+1)

Preparation 13

Methyl 3-[4-(4-pentyloxyphenyl)phenyl]acrylate

NMR (CDCl$_3$, δ): 0.94 (3H, t, J=7.0Hz), 1.30–1.60 (4H, m), 1.70–1.93 (2H, m), 3.82 (3H, s), 4.00 (2H, t, J=6.7Hz), 6.45 (1H, d, J=16.0Hz), 6.90–7.05 (2H, m), 7.48–8.65 (6H, m), 7.72 (1H, d, J=16.0Hz)

APCI-MASS: m/z=325 (M$^+$+1)

Preparation 14

A mixture of 6-Heptyloxynaphthalen-2-carboxylic acid (1.00 g) and thionyl chloride (5 ml) was stirredn for 18 hours at ambient temparature, and concentrated under reduced pressure to give crude 6-hepthyloxy-2-naphthoyl chloride. To a mixture of ethyl isonipecotinate (605 mg), triethylamine (425 mg) and N,N-dimethylaminopyridine (10 mg) in dichloromethane (10 ml) was added crude 6-heptyloxy-2-naphthoyl chloride, and the mixture was stirred for 2 hours at ambient temperature, and diluted with dichloromethane. The mixture was washed with water, 1N hydrochloric acid and brine, and dried over magnesium sulfate. The magnesium sulfate was filtered off, and filtrate was evaporated under reduced pressure. The residue was subjected to column chromatography on silica gel, and eluted with (n-hexane:ethyl acetate=3:1) to give 4-Ethoxycarbonyl-1-(6-heptyloxy-2-naphthoyl)piperidine (1.20 g).

NMR (CDCl$_3$, δ): 0.90 (3H, t, J=6.6Hz), 1.2–2.0 (19H, m), 2.5–2.7 (1H, m), 3.0–3.2 (2H, m), 4.1–4.3 (4H, m), 7.1–7.2 (2H, m), 7.44 (1H, dd, J=8.4 and 1.7Hz), 7.72 (1H, d, J=3.9Hz), 7.77 (1H, d, J=3.9Hz), 7.82 (1H, s)

APCI-MASS: m/z=426 (M$^+$+1)

Preparation 15

To a mixture of Methyl 3,4-diaminobenzoate (1.91 g) and triethylamine (0.56 g) in N,N-dimethylformamide (20 ml) was added decanoyl chloride (2.31 g), and the mixture was stirred for an hour at 0° C. The reaction mixture was diluted with ethyl acetate, and washed with water and brine. The separated organic layer was dried over magnesium sulfate. The magnesium sulfate was filtered off, and filtrate was evaporated under reduced pressure. The residue was dissolved in methanol (20 ml), and conc. sulfuric acid (0.05 ml) was added, and the mixture was stirred for 6 hours at 60° C. After cooling, the reaction mixture was evaporated under reduced pressure. The residue was diluted with ethyl acetate, and washed with water and brine. The separated organic layer was dried over magnesium sulfate. The magnesium sulfate was filtered off, and filtrate was evaporated under reduced pressure. Purification of the residue by column chromatography on silica gel eluted with (n-hexane:ethyl acetate=3:1) gave 5-methoxycarbonyl-2-nonylbenzimidazole (1.40 g).

IR (KBr pelet): 2923, 1718, 1623, 1544, 1438, 1413, 1288, 1213, 1085, 750 cm$^{-1}$ NMR (DMSO-d$_6$, δ): 0.84 (3H, t, J=6.7Hz), 1.1–1.4 (12H, m), 1.7–1.9 (2H, m), 2.83 (2H, t, J=7.4Hz), 7.56 (1H, d, J=8.4Hz), 7.78 (1H, d, J=8.4Hz), 8.07 (1H, s)

APIC-MASS: m/z=303 (M$^+$+1)

Preparation 16

To a mixture of dimethylmalonate (4 ml), 2-hydroxy-4-octyloxybenzaldehyde (2.50 g) and piperidine (0.1 ml) in methanol (10 ml) was added acetic acid (0.01 ml), and the mixture was stirred for 3 hours at 70° C. The solvents were removed under reduced pressure, and the residue was dissolved in ethyl acetate, and washed with 0.5N hydrochloric acid, water and brine, and dried over magnesium sulfate. The magnesium sulfate was filtered off, and filtrate was evaporated under reduced pressure, and the precipitate was collected by filtration, and washed with n-hexane, and dried to give Methyl 7-octyloxycoumarin-3-carboxylate (0.94 g).

NMR (DMSO-d$_6$, δ): 0.86 (3H, m), 1.2–1.6 (10H, m), 1.7–1.8 (2H, m), 3.81 (3H, s), 4.11 (2H, t, J=6.4Hz), 6.9–7.1 (2H, m), 7.83 (1H, d, J=9.0Hz), 8.75 (1H, s)

APCI-MASS: m/z=333 (M$^+$+1)

Preparation 17

To a mixture of sodium hydride (423 mg) and 4-octylphenol (2.06 g) in tetrahydrofuran (16 ml) was added dropwise ethyl 2-chloroacetoacetate at ambient temperature. The mixture was stirred for 6 hours at 70° C. under nitrogen atmosphere, and poured into saturated ammonium chloride aqueous solution. The solution was extracted with ethyl acetate, and the organic layer was washed with water and brine, and dried over magnesium sulfate. The magnesium sulfate was filtered off, and the filtrate was evaporated under reduced pressure. The residue was added to conc. H$_2$SO$_4$ (10 ml) at 0° C., and mixture was stirred for 10 minutes. The reaction mixture was poured into ice-water, and adjusted to pH 7.0 with 1N NaOH aqueous solution, and extracted with ethyl acetate. The organic layer was washed with water and brine, and dried over magnesium sulfate. The magnesium sulfate was filtered off, and the filtrate was evaporated under reduced pressure. The residue was subjected to column-chromatography on silica gel, and eluted with (hexane:ethyl acetate=95.5). The fractions containing the object compound were combined, and evaporated under reduced pressure to give Ethyl 3-methyl 5-octylbenzo[b]furan-2-carboxylate (1.44 g).

IR (Neat): 2925, 2854, 1712, 1596, 1463, 1292, 1149, 1089 cm$^{-1}$

NMR (CDCl$_2$, δ): 0.88 (3H, t, J=6.7Hz), 1.2–1.5 (10H, m), 1.44 (3H, t, J=7.1Hz), 1.6–1.8 (2H, m), 2.58 (3H, s), 2.71 (2H, t, J=8.0Hz), 4.45 (2H, t, J=7.1Hz), 7.2–7.5 (3H, m)

APCI-MASS: m/z=317 (M$^+$+1)

Preparation 18

To a solution of Ethyl 3-amino-4-hydroxybenzoate (1.81 g) and triethylamine (1.53 ml) in dichloromethane (20 ml) was dropwise added decanoyl chloride (2.01 ml) at 0° C. The reaction mixture was stirred for 48 hours at ambient temperature, and washed with water, 0.5N hydrochloric acid, water and brine. The separated organic layer was dried over magnesium sulfate. The magnesium sulfate was filtered off, and the filtrate was evaporated under reduced pressure. To the residue dissolved in xylene (30 ml) was added p-tolune sulfonic acid monohydrate (0.5 g), and the mixture was stirred for 4 hours at 130° C. Ethyl acetate was added to the mixture, and washed with water and brine. The separated organic layer was dried over magnesium sulfate. The magnesium sulfate was filtered off, and the filtrate was evaporated under reduced pressure. Purification of the residue by column chromatography on silica gel elluted with (n-hexane:ethyl acetate=9.1, V/V) gave Ethyl 2-nonyl benzo [b]oxazole-6-carboxylate (2.36 g).

IR (KBr pelet): 2914, 1722, 1621, 1575, 1470, 1429, 1365, 1290, 1203, 1151, 1115, 1081, 1022 cm$^{-1}$ NMR (CDCl$_3$, δ): 0.88 (3H, t, J=6.7Hz), 1.2–1.4 (12H, m), 1.42 (3H, t, J=7.2Hz), 1.90 (2H, m), 2.95 (2H, t, J=7.4Hz), 4.40 (2H, q, J=7.0Hz), 7.50 (1H, d, J=8.5Hz), 8.06 (1H, d, J=8.5Hz), 8.37 (1H, s)

APCI-MASS: m/z=318 (M$^+$+1)

Preparation 19

A mixture of Methyl 3,4-diaminobenzoate (1.84 g) and 4-hexyloxy benzaldehyde (2.30 g) in nitrobenzene (40 ml) was stirred for 48 hours at 145° C. After cooling, the mixture was evaporated under reduced pressure. Purification of the residue by column chromatography on silica gel eluted with (n-hexane:ethyl acetate=2:1) gave 5-Methoxycarbonyl-2-(4-hexyloxyphenyl)benzimidazole (1.19 g).

NMR (CDCl$_3$, δ): 0.90 (3H, t, J=6.4Hz), 1.2–1.9 (8H, m), 3.92 (3H, s), 3.90–4.1 (2H, m), 6.93 (2H, d, J=8.9Hz), 7.5–7.8 (1H, br), 7.94 (1H, dd, J=8.5 and 1.5Hz), 8.03 (1H, d, J=8.9Hz), 8.2–8.4 (1H, br)

APCI-MASS: m/z=353 (M$^+$+1)

Preparation 20

A mixture of Methyl 3-[4-(4-pentylphenyl)phenyl]acrylate (2.0 g) and 10% palladium on carbon (50% wet, 0.2 g) in tetrahydrofuran (20 ml) was stirred for 8 hours under atmospheric pressure of hydrogen at ambient temparature. The catalyst was filtered off, and the filtrate was evaporated under reduced pressure to give Methyl 3-[4-(4-pentylphenyl)phenyl]propionate (1.93 g).

NMR (CDCl$_3$, δ): 0.90 (3H, t, J=6.8Hz), 1.25–1.50 (4H, m), 1.50–1.75 (2H, m), 2.55–2.75 (4H, m), 2.99 (2H, t, J=8.0Hz), 3.68 (3H, s), 7.10–7.30 (4H, m), 7.40–7.60 (4H, m)

APCI-MASS: m/z=311 (M$^+$+1)

Preparation 21

A mixture of Methyl 3-[4-(4-pentyloxyphenyl)phenyl]acrylate (2.70 g) and platinum oxide (0.41 g) in tetrahydrofuran (40 ml) was stirred for 8 hours under 3 atom of hydrogen at ambient temperature. The catalyst was filtered off, and the filtrate was evaporated under reduced pressure to give Methyl 3-[4-(4-pentyloxyphenyl)phenyl]propionate (2.70 g).

NMR (CDCl$_3$, δ): 0.94 (3H, t, J=7.0Hz), 1.28–1.60 (4H, m), 1.60–1.95 (2H, m), 2.55–2.78 (2H, m), 2.98 (2H, t, J=7.8Hz), 3.98 (2H, t, J=6.5Hz), 6.85–7.05 (2H, m), 7.05–7.30 (2H, m), 7.40–7.55 (4H, m)

APCI-MASS: m/z=327 (M$^+$+1)

The following compound was obtained according to a similar manner to that of Preparation 21.

Preparation 22

Methyl 3-(6-heptyloxynaphthalen-2-yl)propionate

NMR (CDCl$_3$, δ): 0.90 (3H, t, J=6.5Hz), 1.20–1.70 (8H, m), 1.70–1.93 (2H, m), 2.70 (2H, t, J=7.7Hz), 3.07 (2H, t, J=7.7Hz), 3.67 (3H, s), 4.05 (2H, t, J=6.5Hz), 7.02–7.20 (2H, m), 7.20–7.38 (2H, m), 7.55 (1H, s), 7.66 (1H, dd, J=3.0 and 8.5Hz)

APCI-MASS: m/z=329 (M$^+$+1)

Preparation 23

To a mixture of Methyl 3-[4-(4-pentylphenyl)phenyl]acrylate (0.41 g) in tetrahydrofuran (5ml) was added 3N NaOH aqueous solution (1.3 ml), and the resultant mixture was heated to 85° C. for 10 hours. The reaction mixture was poured into a mixture of cold water and ethyl acetate, and adjusted to about pH 2 with 6N hydrochloric acid. The separated organic layer was washed in turn with water and brine, and dried over magnesium sulfate. The magnesium sulfate was filtered off, and the filtrate was evaporated under reduced pressure to give 3-[4-(4-Pentylphenyl)phenyl]acrylic acid (0.41 g).

NMR (DMSO-d$_6$, δ): 0.87 (3H, t, J=7.5Hz), 1.15–1.46 (4H, m), 1.48–1.70 (2H, m), 2.61 (2H, t, J=7.4Hz), 6.56 (1H, d, J=16.0Hz), 7.29 (2H, d, J=8.2Hz), 7.60 (2H, d, J=4.0Hz), 7.66 (2H, d, J=4.0Hz), 7.68–7.85 (3H, m)

APCI-MASS: m/z=295 (M$^+$+1)

The following compounds (Preparations 24 to 31) were obtained according to a similar manner to that of Preparation 23.

Preparation 24

3-[4-(4-Pentyloxyphenyl)phenyl]propionic acid

IR (Nujol): 1697, 1606, 1500 cm$^{-1}$

NMR (CDCl$_3$, δ): 0.94 (3H, t, J=7.1Hz), 1.25–1.60 (4H, m), 1.70–1.95 (2H, m), 2.72 (2H, t, J=7.5Hz), 3.00 (2H, t, J=7.5Hz), 3.99 (2H, t, J=6.5Hz), 6.95 (2H, dd, J=2.1 and 6.7Hz), 7.25 (2H, d, J=8.2Hz), 7.40–7.60 (4H, m)

APCI-MASS: m/z=313 (M$^+$+1)

Preparation 25

3-[4-(4-Heptylphenyl)phenyl]propionic acid

NMR (CDCl$_3$, δ): 0.88 (3H, t, J=6.8Hz), 1.15–1.50 (8H, m), 1.50–1.78 (2H, m), 2.65 (2H, t, J=7.6Hz), 6.48 (1H, d, J=16.0Hz), 7.27 (2H, d, J=8.2Hz), 7.53 (2H, d, J=8.2Hz), 7.63 (4H, m), 7.83 (1H, d, J=16.0Hz)

APCI-MASS: m/z=323 (M$^+$+1)

Preparation 26

3-[4-(4-Pentylphenyl)phenyl]propionic acid

NMR (CDCl$_3$, δ): 0.90 (3H, t, J=6.4Hz), 1.20–1.50 (4H, m), 1.50–1.75 (2H, m), 2.64 (2H, t, J=8.0Hz), 2.67 (2H, t, J=9.6Hz), 3.00 (2H, t, J=8.0Hz), 7.15–7.38 (4H, m), 7.38–7.60 (4H, m)

APCI-MASS: m/z=297 (M$^+$+1)

Preparation 27

3-(6-Heptyloxynaphthalen-2-yl)propionic acid

NMR (CDCl$_3$, δ): 0.90 (3H, t, J=6.5Hz), 1.20–1.65 (8H, m), 1.75–2.00 (2H, m), 2.75 (2H, t, J=7.7Hz), 3.09 (2H, t, J=7.7Hz), 4.06 (2H, t, J=6.5Hz), 7.05–7.15 (2H, m), 7.15–7.35 (2H, m), 7.50–7.73 (2H, m)

APCI-MASS: m/z=315 (M$^+$+1)

Preparation 28

3-(6-Heptyloxynaphthalen-2-yl)acrylic acid

NMR (CDCl$_3$, δ): 0.90 (3H, t, J=6.5Hz), 1.15–1.60 (8H, m), 1.75–1.95 (2H, m), 4.09 (2H, t, J=6.5Hz), 6.51 (1H, d, J=16.0Hz), 7.09–7.30 (2H, m), 7.65–8.00 (5H, m)

Preparation 29

3-[4-(4-Pentylphenyl)phenyl]propionic acid

NMR (CDCl$_3$, δ): 0.91 (3H, t, J=6.5Hz), 1.23–1.50 (4H, m), 1.50–1.80 (2H, m), 2.65 (2H, t, J=7.6Hz), 7.27 (2H, d, J=8.2Hz), 7.51 (2H, d, J=8.2Hz), 7.58–7.80 (4H, m)

APCI-MASS: m/z=325 (M$^+$+1+MeOH)

Preparation 30

3-(6-Heptyloxynaphthalen-2-yl)propionic acid

IR (Nujol): 2645, 2198, 1670, 1627 cm$^{-1}$

NMR (DMSO-d$_6$, δ): 0.85 (3H, t, J=6.5Hz), 1.10–1.60 (8H, m), 1.65–1.90 (2H, m), 4.10 (2H, t, J=6.5Hz), 7.24 (1H, dd, J=2.4 and 8.9Hz), 7.39 (1H, d, J=2.5Hz), 7.55 (1H, dd, J=1.6 and 8.5Hz), 7.8–8.0 (2H, m), 8.22 (1H, d, J=1.6Hz)

APCI-MASS: m/z=343 (M$^+$+1+MeOH)

Preparation 31

4-[5-(4-Pentyloxyphenyl)isoxazolyl-3-yl]benzoic acid

IR (KBr): 2939, 2867, 1681, 1614, 1429, 1255, 1178, 821 cm$^{-1}$

NMR (DMSO-d$_6$, δ): 0.91 (3H, t, J=7.1Hz), 1.3–1.5 (4H, m), 1.6–1.8 (2H, m), 4.04 (2H, t, J=6.5Hz), 7.11 (2H, d, J=8.9Hz), 7.54 (1H, s), 7.85 (2H, d, J=8.9Hz), 7.98 (2H, d, J=8.6Hz), 8.11 (2H, d, J=8.6Hz)

APCI-MASS: m/z=352 (M+H)$^+$

Preparation 32

To a solution of Ethyl 3-methyl-5-octylbenzo[b]furan-2-carboxylate (1.44 g) in ethanol (20 ml) was added 10% NaOH aqueous solution (2.2 ml), and stirred for 2 hours at ambient temperature, and evaporated under reduced pressure. The residue was adjusted to pH 3.0 with 1N hydrochloric acid, and extracted with ethyl acetate. The organic layer was washed with brine, and dried over magnesium sulfate. The magnesium sulfate was filtered off, and the filtrate was evaporated under reduced pressure to give 3-Methyl-5-octylbenzo[b]furan-2-carboxylic acid (1.00 g).

IR (KBr pelet): 2923, 1689, 1664, 1581, 1456, 1319, 1159, 933 cm$^{-1}$

NMR (DMSO-d$_6$, δ): 0.85 (3H, t, J=6.7Hz), 1.2–1.5 (10H, m), 1.5–1.8 (2H, m), 2.49 (3H, s), 2.69 (2H, t, J=7.9Hz), 7.32 (1H, dd, J=8.5 and 1.7Hz), 7.52 (1H, d, J=8.5Hz), 7.54 (1H, d, J=1.7Hz), 13.2–13.5 (1H, br)

APCI-MASS: m/z=289 (M$^+$+1)

The following compounds (Preparations 33 to 39) were obtained according to a similar manner to that of Preparation 32.

Preparation 33

3,4-Dipentyloxybenzoic acid

NMR (DMSO-d$_6$, δ): 0.89 (6H, t, J=6.8Hz), 1.2–1.5 (8H, m), 1.6–1.8 (4H, m), 3.9–4.1 (4H, m), 7.02 (1H, d, J=8.4Hz), 7.43 (1H, d, J=1.7Hz), 7.53 (1H, dd, J=8.4 and 1.7Hz)

APCI-MASS: m/z=295 (M$^+$+1)

Preparation 34

1-(6-Heptyloxy-2-naphthoyl)piperidine-4-carboxylic acid

NMR (DMSO-d$_6$, δ): 0.88 (3H, t, J=6.7Hz), 1.2–2.0 (14H, m), 2.5–2.6 (1H, m), 2.9–3.2 (2H, br), 3.25 (2H, s), 4.09 (2H, t, J=6.5Hz), 7.20 (1H, dd, J=8.9 and 2.4Hz), 7.36 (1H, d, J=2.3Hz), 7.43 (1H, dd, J=8.4 and 1.5Hz), 7.8–8.0 (3H, m), 12.30 (1H, br)

APCI-MASS: m/z=398 (M$^+$+1)

Preparation 35

7-Octyloxycoumarin-3-carboxylic acid

IR (KBr): 1748, 1625, 1558, 1467, 1430, 1386, 1360, 1257, 1217, 1120 cm$^{-1}$

NMR (DMSO-d$_6$, δ): 0.86 (3H, t, J=6.8Hz), 1.2–1.5 (10H, m), 1.6–1.8 (2H, m), 4.11 (2H, t, J=6.4Hz), 6.9–7.1 (2H, m), 7.82 (1H, d, J=8.9Hz), 8.72 (1H, s), 12.98 (1H, br)

APCI-MASS: m/z=319 (M$^+$+1)

Preparation 36

4-(4-Pentyloxyphenyl)cinnamic acid

IR (Nujol): 2923, 1675, 1500, 1290, 1223, 985, 821 cm$^{-1}$

NMR (DMSO-d$_6$, δ): 0.90 (3H, t, J=7.0Hz), 1.3–1.5 (4H, m), 1.6–1.8 (2H, m), 4.01 (2H, t, J=6.5Hz), 6.54 (1H, d, J=16.0Hz), 7.02 (2H, d, J=8.8Hz), 7.5–7.8 (7H, m)

APCI-MASS: m/z=311 (M$^+$+1)

Preparation 37

2-Nonylbenzoxazole-6-carboxylic acid

NMR (DMSO-d$_6$, δ): 0.84 (3H, t, J=6.7Hz), 1.2–1.5 (12H, m), 1.7–1.9 (2H, m), 2.96 (2H, t, J=7.4Hz), 7.76 (1H, d, J=8.4Hz), 7.98 (1H, d, J=8.4Hz), 8.19 (1H, s)

APCI-MASS: m/z=290 (M$^+$+1)

Preparation 38

2-(4-Hexyloxyphenyl)benzimidazole-5-carboxylic acid

NMR (DMSO-d$_6$, δ): 0.8–1.0 (3H, m), 1.3–1.6 (6H, m), 1.7–1.8 (2H, m), 4.06 (2H, t, J=6.4Hz), 7.12 (2H, d, J=8.8Hz), 7.6–7.9 (2H, m), 8.1–8.2 (3H, m), 13.00 (1H, br)

APCI-MASS: m/z=339 (M$^+$+1)

Preparation 39

2-Nonylbenzimidazole-5-carboxylic acid

NMR (DMSO-d$_6$, δ): 0.85 (3H, t, J=6.7Hz), 1.1–1.4 (12H, m), 2.7–2.9 (2H, m), 2.96 (2H, t, J=7.6Hz), 3.6–5.2 (1H, br), 7.66 (1H, d, J=8.4Hz), 7.90 (1H, d, J=8.4Hz), 8.15 (1H, s)

APCI-MASS: m/z=289 (M$^+$+1)

Preparation 40

A solution of 4-[4-(4-Octyloxyphenyl)piperazin-1-yl]benzonitrile (0.5 g) in 20% H$_2$SO$_4$ aqueous solution (30 ml) and acetic acid (20 ml) was refluxed for 9 hours. The reaction mixture was pulverized with water. The precipitate was collected by filtration, and added to a mixture of water, tetrahydrofuran and ethyl acetate, and adjusted to pH 2.5 with 1N NaOH aqueous solution. The organic layer was taken, and dried over magnesium sulfate. The magnesium sulfate was filtered off, and the filtrate was evaporated under reduced pressure to give 4-[4-(4-Octyloxyphenyl)piperazin-1-yl]benzoic acid (388 mg).

IR (KBr): 2929, 1664, 1600, 1510, 1240 cm$^{-1}$

NMR (DMSO-d$_6$, δ): 0.86 (3H, t, J=6.6Hz), 1.2–1.5 (10H, m), 1.5–1.8 (2H, m), 3.13 (4H, t, J=5.3Hz), 3.44 (4H, t, J=5.3Hz), 3.88 (2H, t, J=6.5Hz), 6.83 (2H, d, J=9.2Hz), 6.94 (2H, d, J=9.2Hz), 7.02 (2H, d, J=9.0Hz), 7.79 (2H, d, J=9.0Hz)

APCI-MASS: m/z=411 (M$^+$+1)

Preparation 41

To a suspension of sodium hydride (60% suspension in mineral oil) (0.296 g) in N,N-dimethylformamide (14 ml) was added 1,2,4-triazole (0.511 g) and 4-[4-(8-bromooctyloxy)phenyl]benzoic acid (1 g), and was stirred for 5 hours at 120° C. The reaction mixture was added to a mixture of water and ethyl acetate, and adjusted to pH 2.5 with conc. hydrochloric acid. The organic layer was taken and dried over magnesium sulfate. The magnesium sulfate was filtered off, and the filtrate was evaporated under reduced pressure to give 4-[4-[8-(1,2,4-Triazol-1-yl)octyloxy]phenyl]benzoic acid (0.81 g).

IR (KBr): 2940, 1689, 1604, 1297, 1189 cm$^{-1}$

NMR (DMSO-d$_6$, δ): 1.1–1.53 (8H, m), 1.6–1.9 (4H, m), 4.00 (2, t, J=6.3Hz), 4.16 (2H, t, J=7.0Hz), 7.03 (2H, d, J=8.7Hz), 7.67 (2H, d, J=8.7Hz), 7.75 (2H, d, J=8.4Hz), 7.95 (1H, s), 7.99 (2H, d, J=8.4Hz), 8.51 (1H, s), 12.9 (1H, s)

APCI-MASS: m/z=394 (M$^+$+1)

Preparation 42

A mixture of 2-Carbamoyl-5-methoxybenzo[b]thiophene (2.0 g), acetic acid (5 ml) and 48% hydrobromic acid (20 ml) was stirred for 16 hours at 110° C., and the mixture was poured into the ice-water. The resulting precipitate was collected by filtration, and dried to give 5-Hydroxybenzo[b]thiophene-2-carboxylic acid (1.66 g).

NMR (DMSO-d$_6$, δ): 7.03 (1H, dd, J=8.8 and 0.6Hz), 7.31 (1H, d, J=0.6Hz), 7.81 (1H, d, J=8.8Hz), 7.96 (1H, s), 9.64 (1H, s), 13.32 (1H, s)

APCI-MASS: m/z=195 (M$^+$+1)

Preparation 43

A solution of (S)-2-Tert-butoxycarbonyl-1,2,3,4-tetrahydro-7-hydroxyisoquinoline-3-carboxylic acid (1 g) in a mixture of 10% NaOH aqueous solution (2.73 ml) and dimethylsulfoxide (11 ml) was stirred for half an hour at 80° C. Then, octyl bromide (0.589 ml) was added thereto, and stirred for 4 hours at 60° C. The reaction mixture was added to a mixture of water and ethyl acetate, and adjusted to pH 2.5 with conc. hydrochloric acid. The organic layer was taken, and dried over magnesium sulfate. The magnesium sulfate was filtered off, and the filtrate was evaporated under reduced pressure to give (S)-2-Tert-butoxycarbonyl-1,2,3,4-tetrahydro-7-octyloxyisoquinoline-3-carboxylic acid (1.30 g).

IR (Neat): 2929, 1743, 1704, 1164 cm$^{-1}$

NMR (CDCl$_3$, δ): 0.89 (3H, t, J=6.1Hz), 1.1–1.6 (10H, m), 1.41+1.51 (9H, s, cit+trans), 1.75 (2H, quint, J=6.5Hz), 3.10 (2H, m), 3.90 (2H, t, J=3.9Hz), 4.42 (1H, d, J=16.8Hz), 4.65 (1H, d, J=16.8Hz), 4.74+5.09 (1H, m, cis+trans), 6.5–6.8 (2H, m), 7.03 (1H, d, J=8.3Hz)

APCI-MASS: m/z=306 (M$^+$+1-Boc)

The following compounds (Preparations 44 to 45) were obtained according to a similar manner to that of Preparation 43.

Preparation 44

5-Octyloxybenzo[b]thiophene-2-carboxylic acid

IR (Kbr): 1673, 1666, 1600, 1517, 1409, 1267, 1214, 1153, 865 cm$^{-1}$

NMR (DMSO-d$_6$, δ): 0.86 (3H, t, J=6.7Hz), 1.2–1.5 (10H, m), 1.7–1.9 (2H, m), 4.02 (2H, t, J=6.4Hz), 7.13 (1H, dd, J=8.9 and 0.6Hz), 7.51 (1H, d, J=0.6Hz), 7.90 (1H, d, J=9.0Hz), 7.99 (1H, s)

APCI-MASS: m/z=307 (M$^+$+1)

Preparation 45

4-[4-(4-Hexyloxyphenyl)piperazin-1-yl]benzoic acid dihydrochloride

IR (KBr): 1668, 1600, 1510, 1228 cm$^{-1}$

NMR (DMSO-d$_6$, δ): 0.88 (3H, t, J=6.9Hz), 1.2–1.5 (6H, m), 1.6–1.9 (2H, m), 3.0–3.2 (4H, m), 3.3–3.5 (4H, m), 3.88 (2H, t, J=6.3Hz), 6.83 (2H, d, J=9Hz), 6.9–7.1 (4H, m), 7.79 (2H, d, J=8.8Hz), 12.32 (1H, s)

APCI-MASS: m/z=383 (M+H$^+$)

Preparation 46

To a suspension of dimethyl terephthalate (1.94 g) and potassium t-butoxide (2.24 g) in tetrahydrofuran (30 ml) was added 4-pentyloxyacetophenone (1.59 g) in tetrahydrofuran (10 ml) at 70° C. dropwise. The mixture was refluxed for 30 minutes and poured into 1N HCl (50 ml). The mixture was extracted with ethyl acetate (100 ml) and the organic layer was washed with H$_2$O (100 ml), brine (100 ml) and evaporated under reduced pressure. The residue was triturated with acetonitrile (20 ml), collected by filtration and dried under reduced pressure to give 1-(4-Methoxycarbonylphenyl)-3-(4-pentyloxyphenyl)propane-1,3-dione (2.41 g) as yellow solid.

IR (KBr): 3475, 2956, 2923, 1720, 1606, 1508, 1284, 1176, 1108, 769 cm$^{-1}$

NMR (CDCl$_3$, δ): 0.95 (3H, t, J=7.0Hz), 1.3–1.5 (4H, m), 1.7–2.0 (2H, m), 3.96 (3H, s), 4.04 (2H, t, J=6.5Hz), 6.82 (1H, s), 6.96 (2H, d, J=8.9Hz), 8.0–8.1 (4H, m), 8.14 (2H, m, J=8.7Hz), 12–13 (1H, br)

APCI-MASS: m/z=369 (M+H$^+$)

Preparation 47

The solution of 1-(4-Methoxycarbonylphenyl)-3-(4-pentyloxyphenyl)propane-1,3-dione (1.00 g) and hydroxylamine hydrochloride (567 mg) in methanol (10 ml) was refluxed for 10 hours. The reaction mixture was diluted with ethyl acetate (50 ml) and washed with water (50 ml×2), brine (50 ml). The organic layer was dried over magnesium sulfate and the solvents were removed under reduced pressure. The residue was triturated with acetonitrile (10 ml), collected by filtration, and dried under reduced pressure to give Methyl 4-[5-(4-pentyloxyphenyl)isoxazol-3-yl]benzoate (0.74 g).

IR (KBr): 2942, 2873, 1716, 1616, 1508, 1280, 1108 cm$^{-1}$

NMR (CDCl$_3$, δ): 0.95 (3H, t, J=6.9 Hz), 1.3–1.6 (4H, m), 1.8–2.0 (2H, m), 3.95 (3H, s), 4.02 (2H, t, J=6.5Hz), 6.74 (1H, s), 6.99 (2H, d, J=8.8Hz), 7.76 (2H, d, J=8.8Hz), 7.93 (2H, d, J=8.5Hz), 8.14 (2H, d, J=8.5Hz)

APCI-MASS: m/z=366 (M+H)$^+$

Preparation 48

A solution of 4-[4-(8-Bromooctyloxy)phenyl]benzoic acid (1 g) in a mixture of sodium methylate (28% solution in metanol) (10 ml) and N,N-dimethylformamide (5 ml) was refluxed for 5 hours. The reaction mixture was added to a mixture of water and ethyl acetate and adjusted to pH 2.0 with conc. HCl. The organic layer was taken and dried over magnesium sulfate. The magnesium sulfate was filtered off, and the filtrate was evaporated under reduced pressure to give 4-[4-(8-Methoxyoctyloxy)phenyl]benzoic acid (0.77 g).

IR (KBr): 2935, 1685, 835, 773 cm$^{-1}$

NMR (CDCl$_3$, δ): 1.27–1.7 (10H, m), 1.7–1.95 (2H, m), 3.34 (3H, s), 3.38 (2H, t, J=6.4Hz), 4.01 (2H, t, J=6.5Hz), 6.99 (2H, d, J=8.7Hz), 7.58 (2H, d, J=8.7Hz), 7.66 (2H, d, J=8.4Hz), 8.15 (2H, d, J=8.4Hz)

APCI-MASS: m/z=339 (M$^+$+H—H$_2$O)

Preparation 49

To a suspension of 1-Hydroxybenzotriazole (0.283 g) and 6-octyloxymethylpicolinic acid (0.505 g) in dichloromethane (15 ml) was added 1-ethyl-3-(3'-dimethylaminopropyl)carbodiimide hydrochloride (WSCD.HCl) (0.473 g), and stirred for 3 hours at ambient temperature. The reaction mixture was poured into water. The organic layer was taken, and dried over magnesium sulfate. The magnesium sulfate was filtered off, and the filtrate was evaporated under reduced pressure to give 1-(6-Octyloxymethylpicolinyl)benzotriazole 3-oxide (737 mg).

IR (Neat): 1793, 1654, 1591, 1039 cm$^{-1}$

The following compounds [Preparations 50 to 66) were obtained according to a similar manner to that of Preparation 49.

Preparation 50

1-[4-(4-Octyloxyphenyl)piperazin-1-yl)benzoyl] benzotriazole 3-oxide

IR (KBr): 1783, 1600, 1511, 1232, 1184 cm$^{-1}$

NMR (CDCl$_3$, δ): 0.89 (3H, t, J=6.6Hz), 1.2–1.65 (10H, m), 1.65–1.9 (2H, m), 3.24 (4H, t, J=5.3Hz), 3.62 (4H, t, J=5.3Hz), 3.93 (2H, t, J=6.5Hz), 6.8–7.1 (6H, m), 7.35–7.63 (3H, m), 8.0–8.25 (3H, m)

Preparation 51

1-[4-[4-[8-(1,2,4-Triazol-1-yl)octyloxy]phenyl]benzoyl] benzotriazole 3-oxide

IR (KBr): 1776, 1600, 1193, 983 cm$^{-1}$

NMR (CDCl$_3$, δ): 1.2–2.0 (12H, m), 4.03 (2H, t, J=6.4Hz), 4.18 (2H, t, J=7.1Hz), 7.02 (2H, d, J=8.7Hz), 7.4–7.63 (3H, m), 7.63 (2H, d, J=8.7Hz), 7.79 (2H, d, J=8.3Hz), 7.95 (1H, s), 8.06 (1H, s), 8.12 (1H, d, J=7.7Hz), 8.32 (2H, d, J=8.3Hz)

APCI-MASS: m/z=511 (M$^+$+1)

Preparation 52

1-[2-Methyl-2-(4-octyloxyphenoxy)propionyl] benzotriazole 3-oxide

IR (Neat): 2927, 1810, 1504, 1047 cm$^{-1}$

Preparation 53

1-[2-(4-Octyloxyphenoxy)propionyl]benzotriazole 3-oxide

IR (KBr): 2954, 1812, 1513, 1232 cm$^{-1}$

Preparation 54

1-[(S)-2-tert-Butoxycarbonyl-1,2,3,4-tetrahydro-7-octyloxyisoquinolin-3-yl-carbonyl]benzotriazole 3-oxide IR (Neat): 2929, 1816, 1739, 1704, 1392 cm$^{-1}$

Preparation 55

Succinimido 4-(4-n-octyloxyphenyl)piperazine-1-carboxylate

IR (KBr): 2925, 1758, 1743, 1513, 1241 cm$^{-1}$

NMR (CDCl$_3$, δ): 0.89 (3H, t, J=6.8Hz), 1.2–1.5 (10H, m), 1.65–1.85 (2H, m), 2.83 (4H, s), 3.0–3.2 (2H, m), 3.6–3.85 (2H, m), 3.91 (2H, t, J=6.5Hz), 6.84 (2H, dd, J=8.5 and 2.7Hz), 6.90 (2H, dd, J=8.5 and 2.7Hz)

APCI-MASS: m/z=432 (M$^+$+1)

Preparation 56

(6-Heptyloxy-2-naphthyl)methylsuccinimido carbonate

IR (KBr): 1878, 1832, 1787, 1735, 1209 cm$^{-1}$

NMR (CDCl$_3$, δ): 0.90 (3H, t, J=6.2Hz), 1.2–1.6 (8H, m), 1.73–2.0 (2H, m), 2.83 (4H, s), 4.07 (2H, t, J=6.5Hz), 5.44 (2H, s), 7.13 (1H, d, J=2.4Hz), 7.17 (1H, dd, J=8.8 and 2.4Hz), 7.44 (1H, dd, J=8.4 and 1.6Hz), 7.67–7.85 (3H, m)

Preparation 57

1-(3,4-Dipentyloxypenzoyl)benzotriazole 3-oxide

IR (KBr): 2952, 1774, 1594, 1515, 1430, 1272, 1147, 1089 cm$^{-1}$

NMR (CDCl$_3$, δ): 0.9–1.1 (6H, m), 1.3–1.6 (8H, m), 1.8–2.1 (4H, m), 4.0–4.2 (4H, m), 6.99 (1H, d, J=8.5Hz), 7.4–7.6 (3H, m), 7.68 (1H, d J=2.0Hz), 7.92 (1H, dd, J=8.5 and 2.0Hz), 8.10 (1H, d, J=8.5Hz)

APCI-MASS: m/z=412 (M$^+$+1)

Preparation 58

1-(7-Octyloxycoumarin-3-yl-carbonyl)benzotriazole 3-oxide

IR (KBr): 2925, 1754, 1716, 1610, 1548, 1282, 1199, 1172, 1139, 1064, 781, 750 cm$^{-1}$

NMR (DMSO-d$_6$, δ): 0.86 (3H, t, J=7.8Hz), 1.2–1.5 (10H, m), 1.6–1.8 (2H, m), 4.11 (2H, t, J=6.5Hz), 6.9–7.1 (2H, m), 7.41 (1H, t, J=7.2Hz), 7.54 (1H, t, J=7.2Hz), 7.72 (1H, d, J=8.3Hz), 7.82 (1H, d, J=8.3Hz), 7.99 (1H, d, J=8.3Hz), 8.72 (1H, s)

APCI-MASS: m/z=436 (M$^+$+1)

Preparation 59

1-[4-(4-Pentyloxyphenyl)cinnamoyl]benzotriazole 3-oxide

IR (Nujol): 2854, 1778, 1708, 1620, 1597, 1494, 1459, 1434, 1377, 1350, 1250, 1188, 1138, 1086, 978 cm$^{-1}$

Preparation 60

1-(5-Octyloxybenzo[b]thiophen-2-yl-carbonyl) benzotriazole 3-oxide

IR (KBr): 2950, 1776, 1517, 1342, 1211, 1151 cm$^{-1}$

NMR (DMSO-d$_6$, δ): 0.86 (3H, t, J=6.7Hz), 1.2–1.5 (10H, m), 1.7–1.9 (2H, m), 4.01 (2H, t, J=6.4Hz), 7.13 (1H, dd, J=8.8 and 2.4Hz), 7.42 (1H, d, J=7.1Hz), 7.5–7.6 (3H, m), 7.72 (1H, d, J=8.4Hz), 7.89 (1H, d, J=8.8Hz), 7.9–8.1 (2H, m)

APCI-MASS: m/z=424 (M$^+$+1)

Preparation 61

1-(3-Methyl-5-octylbenzo[b]furan-2-yl-carbonyl) benzotriazole 3-oxide

IR (KBr): 1776, 1575, 1469, 1363, 1324, 1276, 1114, 1027 cm$^{-1}$

NMR (CDCl$_3$, δ): 0.89 (3H, t, J=6.7Hz), 1.2–1.5 (10H, m), 2.6–2.8 (2H, m), 2.71 (3H, s), 2.76 (2H, t, J=7.4Hz), 7.4–7.6 (6H, m), 8.12 (1H, s)

APCI-MASS: m/z=406 (M$^+$+1)

Preparation 62

1-(2-Nonylbenzoxazol-5-yl-carbonyl)benzotriazole 3-oxide

IR (KBr): 2980, 1783, 1623, 1573, 1276, 1151, 1091, 989 cm$^{-1}$

NMR (DMSO-d$_6$, δ): 0.84 (3H, t, J=6.8Hz), 1.1–1.4 (12H, m), 1.81 (2H, t, J=7.2Hz), 2.96 (3H, t, J=7.4Hz), 7.41 (1H, t, J=7.0Hz), 7.54 (1H, t, J=7.0Hz), 7.74 (2H, t, J=7.0Hz), 7.98 (2H, d, J=7.0Hz), 8.19 (1H, s)

APCI-MASS: m/z=407 (M$^+$+1)

Preparation 63

1-[2-(4-Hexyloxyphenyl)benzimidazole-5-yl-carbonyl]benzotriazole 3-oxide

IR (KBr): 3160, 2931, 2863, 1778, 1612, 1502, 1448, 1388, 1294, 1247, 1174, 1097, 1010, 732 cm$^{-1}$

NMR (DMSO-d$_6$, δ): 0.89 (3H, t, J=6.7Hz), 1.2–1.5 (6H, m), 1.7–1.8 (2H, m), 4.08 (2H, t, J=6.4Hz), 7.16 (2H, d, J=8.7Hz), 7.6–8.4 (9H, m), 8.3–8.6 (1H, br)

APCI-MASS: m/z=456 (M$^+$+1)

Preparation 64

1-[4-[4-(8-Methoxyoctyloxy)phenyl]benzoyl]benzotriazole-3-oxide

IR (KBr): 2931, 1793, 1770, 1600 cm$^{-1}$

NMR (CDCl$_3$, δ): 1.2–1.7 (10H, m) 1.7–1.93 (2H, m), 3.34 (3H, s), 3.38 (2H, t, J=6.4Hz), 4.03 (2H, t, J=6.5Hz), 7.03 (2H, d, J=8.8Hz), 7.4–7.7 (3H, m), 7.63 (2H, d, J=8.8Hz), 7.79 (2H, d, J=8.6Hz), 8.12 (1H, d, J=8.2Hz), 8.32 (2H, d, J=8.6Hz)

Preparation 65

1-[4-[4-(4-Hexyloxyphenyl)piperazin-1-yl]benzoyl]benzotriazole 3-oxide

IR (KBr): 1770, 1604, 1510, 1232, 1186 cm$^{-1}$

NMR (CDCl$_3$, δ): 0.91 (3H, t, J=6.6Hz), 1.2–1.6 (6H, m), 1.6–1.9 (2H, m), 3.1–3.3 (4H, m), 3.5–3.7 (4H, m), 3.93 (2H, t, J=6.5Hz), 6.87 (2H, d, J=9.2Hz), 6.96 (2H, d, J=9.2Hz), 7.00 (2H, d, J=9.0Hz), 7.3–7.7 (3H, m), 8.10 (1H, d, J=8.2Hz), 8.15 (2H, d, J=9.0Hz)

APCI-MASS: m/z=500 (M+H$^+$)

Preparation 66

1-[4-[5-(4-Pentyloxyphenyl)isoxazol-3-yl]benzoyl]benzotriazole 3-oxide

IR (KBr): 2950, 2837, 1774, 1616, 1508, 1452, 1251, 1006 cm$^{-1}$

NMR (CDCl$_3$, δ): 0.95 (3H, t, J=7.1Hz), 1.3–1.5 (4H, m), 1.8–2.0 (2H, m), 4.04 (2H, t, J=6.5Hz), 6.81 (1H, s), 7.0–7.1 (3H, m), 7.4–7.6 (3H, m), 7.80 (2H, d, J=8.8Hz), 8.0–8.2 (3H, m), 8.40 (2H, d, J=8.4Hz)

APCI-MASS: m/z=469 (M+H)$^+$

Preparation 67

To a suspension of 1-hydroxybenzotriazole (0.20 g) and 4-(4-pentylphenyl)cinnamic acid (0.40 g) in dichloromethane (12.0 ml) was added 1-ethyl-3-(3'-dimethylaminopropyl)carbodiimide hydrochloride (0.33 g) (WSCD.HCl), and the mixture was stirred for 12 hours at ambient temperature. The reaction mixture was diluted with dichloromethane, and washed with brine, and dried over magnesium sulfate. After magnesium sulfate was filtered off, evaporation of the filtrate and trituration with acetonitrile gave 1-[4-(4-Pentylphenyl)cinnamoyl]benzotriazole 3-oxide (0.24 g).

NMR (CDCl$_3$, δ): 0.91 (3H, t, J=6.6Hz), 1.20–1.50 (4H, m), 1.50–1.75 (2H, m), 2.66 (2H, t, J=8.0Hz), 7.20–8.25 (11H, m), 8.55 (1H, d, J=8.4Hz)

APCI-MASS: m/z=412 (M$^+$+1)

The following compounds (Preparations 68 to 73) were obtained according to a similar manner to that of Preparation 67.

Preparation 68

1-[3-[4-(4-Pentyloxyphenyl)phenyl]-2-propanoyl]benzotriazole 3-oxide

NMR (CDCl$_3$, δ): 0.90–1.05 (3H, m), 1.30–1.65 (4H, m), 1.70–1.95 (2H, m), 3.10–3.60 (4H, m), 3.90–4.10 (2H, m), 6.88–7.08 (2H, m), 7.20–8.50 (10H, m)

APCI-MASS: m/z=430 (M$^+$+1)

Preparation 69

1-[4-(4-Heptylphenyl)cinnamoyl]benzotriazole 3-oxide

NMR (CDCl$_3$, δ): 0.89 (3H, t, J=6.7Hz), 1.20–1.50 (8H, m), 1.50–1.80 (2H, m), 2.66 (2H, t, J=7.6Hz), 6.70–8.60 (12H, m)

APCI-MASS: m/z=440 (M$^+$+1)

Preparation 70

1-[3-[4-(4-Pentylphenyl)phenyl]-2-propanoyl]benzotriazole 3-oxide

NMR (CDCl$_3$, δ): 0.90 (3H, t, J=6.8Hz), 1.20–1.50 (4H, m), 1.50–1.76 (2H, m), 2.63 (2H, t, J=7.4Hz), 3.21 (2H, t, J=7.3Hz), 3.51 (2H, t, J=7.3Hz), 7.20–7.45 (4H, m), 7.45–7.70 (5H, m), 7.78 (1H, dt, J=1.0 and 7.2Hz), 8.00 (1H, d, J=8.2Hz), 8.42 (1H, d, J=8.4Hz)

APCI-MASS: m/z=414 (M$^+$+1)

Preparation 71

1-[3-(6-Heptyloxynaphthalen-2-yl)propanoyl]benzotriazole 3-oxide

NMR (CDCl$_3$, δ): 0.80–1.10 (3H, m), 1.20–1.70 (8H, m), 1.70–2.00 (2H, m), 3.10–3.70 (4H, m), 4.00–4.18 (2H, m), 6.80–8.50 (10H, m)

APCI-MASS: m/z=432 (M$^+$+1)

Preparation 72

1-[3-(6-Heptyloxynaphthalen-2-yl)propenoyl]benzotriazole 3-oxide

NMR (CDCl$_3$, δ): 0.90 (3H, t, J=6.5Hz), 1.20–1.65 (8H, m), 1.75–1.95 (2H, m), 4.10 (2H, d, J=6.5Hz), 6.75–8.62 (8H, m)

APCI-MASS: m/z=430 (M$^+$+1)

Preparation 73

1-(4-Hexylphenylbenzoyl)benzotriazole 3-oxide

NMR (CDCl$_3$, δ): 0.90 (3H, t, J=4.4Hz), 1.2–1.5 (6H, m), 1.6–1.8 (2H, m), 2.68 (2H, t, J=8.0Hz), 7.32 (2H, d, J=8.2Hz), 7.4–7.7 (5H, m), 7.81 (2H, d, J=6.6Hz), 8.10 (2H, d, J=8.1Hz), 8.32 (2H, d, J=7.6Hz)

APCI-MASS: m/z=400 (M$^+$+1)

Preparation 74

To a solution of 4-octyloxyphenol (1 g) in dimethylformamide (10 ml) and pyridine (0.364 ml) was added N,N'-disuccinimidylcarbonate (1.16 g). The mixture was stirred for 12 hours at ambient temperature. The reaction mixture was added to a mixture of water and ethyl acetate. The organic layer was taken, and dried over magnesium sulfate. The magnesium sulfate was filtered off, and the filtrate was evaporated under reduced pressure to give 4-Octyloxyphenylsuccinimidyl carbonate (0.59 g).

IR (KBr): 2927, 1876, 1832, 1735 cm$^{-1}$

NMR (CDCl$_3$, δ): 0.89 (3H, t, J=6.3Hz), 1.2–1.55 (10H, m), 1.67–1.87 (2H, m), 2.87 (4H, s), 3.94 (2H, t, J=6.5Hz), 6.89 (2H, d, J=9.2Hz), 7.17 (2H, d, J=9.2Hz)

APCI-MASS: m/z=364 (M$^+$+1)

The following compounds (Preparations 75 to 88) were obtained according to a similar manner to that of Preparation 1.

Preparation 75

Methyl 4-[4-(6-phenylpyridazin-3-yl-oxy)phenyl]benzoate

IR (KBr): 1708, 1427, 1280, 1197, 1112 cm$^{-1}$

NMR (CDCl$_3$, δ): 3.95 (3H, s), 7.2–7.7 (10H, m), 7.92 (1H, d, J=9.2Hz), 8.0–8.2 (4H, m)

APCI-MASS: m/z=383 (M+H)$^+$

Preparation 76

Methyl 4-[4-(5-bromopentyloxy)phenyl]benzoate

IR (KBr): 2946, 2871, 1716, 1602, 1294, 1199, 1112, 837 cm$^{-1}$

NMR (CDCl$_3$, δ): 1.7–2.0 (6H, m), 3.45 (2H, t, J=6.7Hz), 3.93 (3H, s), 4.02 (2H, t, J=6.1Hz), 6.97 (2H, d, J=8.7Hz), 7.56 (2H, d, J=8.7Hz), 7.61 (2H, d, J=8.3Hz), 8.07 (2H, d, J=8.3Hz)

APCI-MASS: m/z=378 (M+H)$^+$

Preparation 77

Methyl 4-[4-(5-phenoxypentyloxy)phenyl]benzoate

IR (KBr): 2944, 2931, 1720, 1600, 1492, 1197, 1110 cm$^{-1}$

NMR (CDCl$_3$, δ): 1.6–1.8 (2H, m), 1.8–2.0 (4H, m), 3.93 (3H, s), 4.00 (2H, t, J=6.3Hz), 4.04 (2H, t, J=6.3Hz), 6.9–7.1 (5H, m), 7.3–7.4 (2H, m), 7.56 (2H, d, J=8.7Hz), 7.62 (2H, d, J=8.3Hz), 8.07 (2H, d, J=8.3Hz)

APCI-MASS: m/z=391 (M+H)$^+$

Preparation 78

1-[2-(4-Cyclohexylphenylamino)ethyl]-2-oxazolidone hydrochloride

IR (KBr): 2923.6, 2852.2, 1747.2, 1683.6 cm$^{-1}$

NMR (DMSO-d$_6$, δ): 1.1–1.5 (6H, m), 1.6–1.9 (4H, m, 2.3–2.6 (1H, m), 3.3–3.5 (4H, m), 3.58 (2H, dd, J=9.4 and 7.4Hz), 4.22 (2H, dd, J=9.4 and 7.4 Hz), 7.1–7.4 (4H, m)

Preparation 79

Methyl 4-[4-(8-hydroxyoctyloxy)phenyl]benzoate

IR (KBr): 3250, 2933, 2856, 1724, 1602, 1436, 1292, 1199 cm$^{-1}$

NMR (CDCl$_3$, δ): 1.3–1.9 (12H, m), 3.6–3.8 (2H, br), 3.93 (3H, s), 4.00 (2H, t, J=6.7Hz), 4.82 (1H, s), 7.68 (2H, d, J=8.7Hz), 7.56 (2H, d, J=8.7Hz), 7.62 (2H, d, J=8.3Hz), 8.07 (2H, d, J=8.3Hz)

APCI-MASS: m/z=357 (M+H$^+$)

Preparation 80

Methyl 4-[4-(6-bromohexyloxy)phenyl]benzoate

IR (KBr): 2937, 2861, 1724, 1602, 1529, 1436, 1292, 1199, 1112 cm$^{-1}$

NMR (CDCl$_3$, δ): 1.5–2.0 (8H, m), 3.43 (2H, t, J=6.8Hz), 3.93 (3H, s), 4.02 (2H, t, J=6.3Hz), 6.98 (2H, d, J=8.8Hz), 7.56 (2H, d, J=8.8Hz), 7.62 (2H, d, J=8.4Hz), 8.07 (2H, d, J=8.4Hz)

APCI-MASS: m/z=391 (M+H$^+$)

Preparation 81

Methyl 4-[4-(5-Bromopentyloxy)phenyl]bromobenzene

IR (KBr): 2942, 2867, 1604, 1515, 1477, 1286 cm$^{-1}$

NMR (CDCl$_3$, δ): 1.5–2.0 (6H, m), 3.44 (2H, t, J=6.7Hz), 3.99 (2H, t, J=6.2Hz), 6.95 (2H, d, J=8.7Hz), 7.3–7.6 (6H, m)

APCI-MASS: m/z=399 (M+H$^+$)

Preparation 82

8-[4-(4-Methoxycarbonyloxy)phenoxy]octanoyl piperidine

IR (KBr): 2935, 2852, 1720, 1639, 1604, 1438, 1292 cm$^{-1}$

NMR (CDCl$_3$, δ): 1.3–1.9 (16H, m), 2.34 (2H, d, J=7.6Hz), 3.4–3.6 (4H, m), 3.93 (3H, s), 3.99 (2H, t, J=6.4Hz), 6.97 (2H, d, J=8.8Hz), 7.55 (2H, d, J=8.8Hz), 7.61 (2H, d, J=8.6Hz), 8.07 (2H, d J=8.6Hz)

APCI-MASS: m/z=438 (M+H$^+$)

Preparation 83

Methyl 6-[4-(4-n-heptyloxyphenyl)piperazin-1-yl]nicotinate

IR (KBr): 2933, 2859, 1726, 1608, 1513, 1430, 1280, 1245 cm$^{-1}$

NMR (CDCl$_3$, δ): 0.89 (3H, t, J=6.7Hz), 1.2–1.8 (10H, m), 3.17 (4H, t, J=4.9Hz), 3.8–4.0 (9H, m), 6.65 (1H, d, J=9.1Hz), 6.86 (2H, d, J=9.1Hz), 6.96 (2H, d, J=9.1Hz), 8.05 (1H, dd, J=9.1 and 2.3 Hz), 8.82 (1H, d, J=2.3Hz)

APCI-MASS: m/z=412 (M+H$^+$)

Preparation 84

Methyl 6-[4-[4-(8-bromooctyloxy)phenyl]piperazin-1-yl]nicotinate

IR (KBr): 2933, 2861, 1724, 1608, 1513, 1430, 1280 cm$^{-1}$

NMR (CDCl$_3$, δ): 1.2–2.0 (12H, m), 3.17 (4H, t, J=5.0Hz), 3.40 (2H, t, J=6.8Hz), 3.8–4.0 (9H, m), 6.64 (1H, d, J=9.0Hz), 6.85 (2H, d, J=9.1Hz), 6.96 (2H, d, J=9.1Hz), 8.05 (1H, dd, J=9.0 and 2.2Hz), 8.82 (1H, d, J=2.2Hz)

APCI-MASS: m/z=504 (M+H$^+$)

Preparation 85

4-[4-(7-Bromoheptyloxy)phenyl]bromobenzene

IR (KBr): 2935.1, 2856.1, 1604.5 cm$^{-1}$

NMR (CDCl$_3$, δ): 1.18–1.65 (6H, m), 1.70–2.02 (4H, m), 3.41 (2H, t, J=6.8Hz), 3.99 (2H, t, J=6.4Hz), 6.95 (2H, d, J=8.6Hz), 7.40 (2H, d, J=8.6Hz), 7.46 (2H, d, J=8.6Hz), 7.52 (2H, d, J=8.6Hz)

Preparation 86

4-[4-(8-Bromooctyloxy)phenyl]bromobenzene

NMR (CDCl$_3$, δ): 1.22–1.65 (8H, m), 1.65–1.95 (4H, m), 3.41 (2H, t, J=6.8Hz), 3.99 (2H, t, J=6.4Hz), 6.95 (2H, d,

J=8.6Hz), 7.40 (2H, d, J=8.6Hz), 7.46 (2H, d, J=8.6Hz), 7.52 (2H, d, J=8.6Hz)

Preparation 87

Methyl (E)-3-[4-[4-(5-hexenyloxy)phenyl]phenyl]acrylate

NMR (CDCl$_3$, δ): 1.50–1.72 (2H, m), 1.72–1.95 (2H, m), 2.05–2.14 (2H, m), 3.82 (3H, s), 4.01 (2H, t, J=6.3Hz), 4.95–5.10 (2H, m), 5.70–5.93 (1H, m), 6.46 (1H, d, J=16Hz), 6.97 (2H, d, J=8.7Hz), 7.54 (2H, d, J=8.7Hz), 7.58 (4H, s), 7.72 (1H, d, J=16Hz)

APCI-MASS: m/z=337 (M$^+$+1)

Preparation 88

4-Bromo-4'-(4-methylpentyloxy)biphenyl

IR (KBr): 2956.3, 2871.5, 1606.4 cm$^{-1}$

NMR (CDCl$_3$, δ): 0.93 (6H, d, J=6.6Hz), 1.25–1.45 (2H, m), 1.62 (1H, sept, J=6.6Hz), 1.72–1.93 (2H, m), 3.98 (2H, d, J=6.6Hz), 6.95 (2H, d, J=8.6Hz), 7.30–7.60 (6H, m)

APCI-MASS: m/z=332, 334 (M$^+$, M$^+$+2)

The following compounds (Preparations 89 to 90) were obtained according to a similar manner to that of Preparation 2.

Preparation 89

N-[4-[2-(4-Methylpentyl)-2,3-dihydro-4H-1,2,4-triazol-3-one-4-yl]phenyl]piperazine ditrifluoroacetate IR (KBr): 1668.1, 1519.6, 1203.4, 1176.4, 1130.1 cm$^{-1}$ NMR (DMSO-d$_6$, δ): 0.86 (6H, d, J=6.6Hz), 1.1–1.3 (2H, m), 1.4–1.8 (3H, m), 3.1–3.3 (4H, m), 3.3–3.5 (4H, m), 3.70 (2H, t, J=7.0Hz), 7.11 (2H, d, J=9.0Hz), 7.53 (2H, d, J=9.0Hz), 8.35 (1H, s), 8.90 (2H, s)

Preparation 90

1-(4-Phenylcyclohexyl)piperazine ditrifluoroacetate

IR (KBr): 1677.8, 1197.6, 1133.9 cm$^{-1}$

NMR (DMSO-d$_6$, δ): 1.4–1.8 (4H, m), 1.8–2.25 (4H, m), 2.4–2.7 (1H, m), 3.2–3.7 (9H, m), 4.54 (2H, br s), 7.0–7.4 (5H, m), 9.32 (1H, br s)

APCI-MASS: m/z=245 (M$^+$+H)

The following compounds (Preparations 91 to 103) were obtained according to a similar manner to that of Preparation 3.

Preparation 91

Methyl 6-[4-(4-octyloxyphenyl)piperazin-1-yl]nicotinate

IR (KBr): 2923, 1726, 1608, 1515, 1278, 1116 cm$^{-1}$

NMR (CDCl$_3$, δ): 0.88 (3H, t, J=6.8Hz), 1.2–1.5 (10H, m), 1.7–1.8 (2H, m), 3.1–3.2 (4H, m), 3.8–4.0 (9H, m), 6.64 (1H, d, J=9.0Hz), 6.8–7.0 (4H, m), 8.04 (1H, dd, J=9.0 and 2.4Hz), 8.81 (1H, d, J=2.4Hz)

APCI-MASS: m/z=426 (M+H$^+$)

Preparation 92

4-[4-[4-[2-(4-Methylpentyl)-2,3-dihydro-4H-1,2,4-triazol-3-one-4-yl]phenyl]piperazin-1-yl]benzonitrile IR (KBr): 2217.7, 1685.5 cm$^{-1}$ NMR (CDCl$_3$, δ): 0.90 (6H, d, J=6.6Hz), 1.2–1.4 (2H, m), 1.5–2.0 (3H, m), 3.3–3.4 (4H, m), 3.4–3.6 (4H, m), 3.83 (2H, t, J=7.4Hz), 6.92 (2H, d, J=9.0Hz), 7.01 (2H, d, J=9.0Hz) 7.43 (2H, d, J=9.0Hz), 7.54 (2H, d, J=9.0Hz), 7.62 (1H, s)

Preparation 93

3-Fluoro-4-[4-(4-methoxyphenyl)piperazin-1-yl]benzonitrile

IR (KBr): 2225.5, 1510.0, 1240.0 cm$^{-1}$

NMR (CDCl$_3$, δ): 3.1–3.55 (8H, m), 3.79 (3H, s), 6.7–7.1 (6H, m), 7.3–7.5 (1H, m)

Preparation 94

3-Chloro-4-[4-(4-n-hexyloxyphenyl)piperazin-1-yl]benzonitrile

IR (KBr): 2223.5, 1592.9, 1510.0, 1490.7, 1236.1 cm$^{-1}$

NMR (CDCl$_3$, δ): 0.90 (3H, t, J=6.7Hz), 1.3–1.6 (6H, m), 1.7–1.9 (2H, m), 3.2–3.4 (8H, m), 3.92 (2H, t, J=6.6Hz), 6.85 (2H, d, J=9.3Hz), 6.94 (2H, d, J=9.3Hz), 7.08 (1H, d, J=8.4Hz), 7.53 (1H, dd, J=8.4 and 1.9Hz), 7.64 (1H, d, J=1.9Hz)

APCI-MASS: m/z=398 (M$^+$+H)

Preparation 95

Ethyl 3-[4-(4-n-hexyloxyphenyl)piperazin-1-yl]-6-pyridazinecarboxylate

IR (KBr): 1729.8, 1587.1, 1511.9, 1245.8 cm$^{-1}$

NMR (CDCl$_3$, δ): 0.90 (3H, t, J=6.5Hz), 1.2–1.4 (6H, m), 1.44 (3H, t, J=7.1Hz), 1.65–1.85 (2H, m), 3.1–3.25 (4H, m), 3.8–4.0 (6H, m), 4.46 (2H, q, J=7.1Hz), 6.8–7.0 (5H, m), 7.91 (1H, d, J=9.6Hz)

APCI-MASS: m/z=413 (M$^+$+H)

Preparation 96

4-(4-Piperidinopiperidin-1-yl)benzonitrile

IR (KBr): 2217.7, 1602.6, 1511.9 cm$^{-1}$

NMR (CDCl$_3$, δ): 1.35–1.75 (8H, m), 1.92 (2H, d, J=12.9Hz), 2.3–2.6 (5H, m), 2.86 (2H, td, J=12.8 and 2.6Hz), 3.90 (2H, d, J=12.8Hz), 6.84 (2H, d, J=9.1Hz), 7.46 (2H, d, J=9.1Hz)

APCI-MASS: m/z=270 (M$^+$+H)

Preparation 97

5-[4-(4-n-Hexyloxyphenyl)piperazin-1-yl]picolinonitrile

IR (KBr): 2223.5, 1575.6, 1511.9, 1241.9 cm$^{-1}$

NMR (CDCl$_3$, δ): 0.90 (3H, t, J=6.5Hz), 1.2–1.55 (6H, m), 1.7–1.85 (2H, m), 3.22 (4H, t, J=5.1Hz), 3.52 (4H, t, J=5.1Hz), 3.92 (2H, t, J=6.5Hz), 6.86 (2H, d, J=9.4Hz), 6.93 (2H, d, J=9.4Hz), 7.13 (1H, dd, J=8.8 and 3.0Hz), 7.53 (1H, d, J=8.8Hz), 8.35 (1H, d, J=3.0Hz)

APCI-MASS: m/z=365 (M$^+$+H)

Preparation 98

4-[4-(4- Cyclohexylphenyl)piperazin-1-yl]benzonitrile

IR (KBr): 2219.7, 1606.4, 1513.8, 1238.1 cm$^{-1}$

NMR (CDCl$_3$, δ): 1.1–1.5 (6H, m), 1.65–2.0 (4H, m), 2.44 (1H, m), 3.30 (4H, t, J=5.1Hz), 3.46 (4H, t, J=5.1Hz), 6.90 (4H, d, J=8.9Hz), 7.14 (2H, d, J=8.9Hz), 7.52 (2H, d, J=8.9Hz)

APCI-MASS: m/z=346 (M$^+$+H)

Preparation 99

4-[4-(4-n-Hexylphenyl)piperazin-1-yl]benzonitrile

IR (KBr): 2925.5, 2850.3, 2213.9, 1604.5, 1513.8, 1234.2, 944.9 cm$^{-1}$

NMR (CDCl$_3$, δ): 0.88 (3H, t, J=6.4Hz), 1.2–1.45 (6H, m), 1.45–1.7 (2H, m), 2.54 (2H, t, J=7.6Hz), 3.2–3.4 (4H, m), 3.4–3.6 (4H, m), 6.89 (2H, d, J=8.5Hz), 6.91 (2H, d, J=8.9Hz), 7.11 (2H, d, J=8.5Hz), 7.52 (2H, d, J=8.9Hz)

Preparation 100

1-[2-(4-n-Hexylphenylamino)ethyl]-2-oxazolidone hydrochloride

IR (KBr): 2925.5, 2852.2, 1753.0, 1729.8, 1267.0 cm$^{-1}$

NMR (CDCl$_3$, δ): 0.85 (3H, t, J=6.5Hz), 1.1–1.4 (6H, m), 1.45–1.7 (2H, m), 2.56 (2H, t, J=7.6Hz), 3.3–3.53 (4H, m), 3.57 (2H, t, J=7.9Hz), 4.24 (2H, t, J=7.9Hz), 7.24 (4H, s)

APCI-MASS: m/z=291 (M$^+$+H)

Preparation 101

4-[4-(4-Phenylcyclohexyl)piperazin-1-yl]benzonitrile

IR (KBr): 2212.0, 1602.6, 1513.8, 1249.6 cm$^{-1}$

NMR (CDCl$_3$, δ): 1.3–1.8 (4H, m), 1.9–2.2 (4H, m), 2.3–2.6 (2H, m), 2.75 (4H, t, J=5.0Hz), 3.34 (4H, t, J=5.0Hz), 6.86 (2H, d, J=8.9Hz), 7.1–7.4 (5H, m), 7.49 (2H, d, J=8.9Hz)

APCI-MASS: m/z=346 (M$^+$+H)

Preparation 102

Methyl 6-[4-(4-hydroxyphenyl)piperazin-1-yl]nictinate

IR (KBr): 3411, 1691, 1602, 1510, 1432, 1249, 1147 cm$^{-1}$

NMR (DMSO$_6$, δ): 3.0–3.1 (4H, m), 3.7–3.9 (7H, m), 6.67 (2H, d, J=8.8Hz), 6.84 (2H, d, J=8.8Hz), 6.93 (1H, d, J=9.1Hz), 7.97 (1H, dd, J=2.4 and 9.1Hz), 8.66 (1H, d, J=2.4Hz), 8.88 (1H, s)

APCI-MASS: m/z=314 (M+H)$^+$

Preparation 103

1-n-Decylindole-5-carboxylic acid

IR (KBr): 2921, 2854, 1679, 1612, 1427, 1313, 1199 cm$^{-1}$

NMR (DMSO$_6$, δ): 0.84 (3H, t, J=6.8Hz), 1.1–1.3 (14H, m), 1.6–1.8 (2H, m), 4.19 (2H, t, J=6.9Hz), 6.57 (1H, s), 7.4–7.8 (3H, m), 8.23 (1H, s), 12.40 (1H, s)

APCI-MASS: m/z=302 (M+H$^+$)

The following compounds (Preparations 104 to 111) were obtained according to a similar manner to that of Preparation 10.

Preparation 104

(E)-Methyl 4-(4-n-butoxyphenyl)cinnamate

IR (KBr): 2958, 2939, 2873, 1720, 1637, 1498, 1313, 1195, 1170 cm$^{-1}$

NMR (CDCl$_3$, δ): 0.98 (3H, t, J=7.3Hz), 1.4–1.8 (4H, m), 3.81 (3H, s), 4.00 (2H, t, J=6.4Hz), 6.45 (1H, d, J=16.0Hz), 6.97 (2H, d, J=8.7Hz), 7.5–7.7 (6H, m), 7.72 (1H, d, J=16.0Hz)

APCI-MASS: m/z=311 (M+H$^+$)

Preparation 105

Methyl (E)-3-[4-[4-(4-methylpentyloxy)phenyl]phenyl]acrylate

IR (KBr): 2956.3, 2873.4, 1720.2, 1635.3, 1600.6 cm$^{-1}$

NMR (CDCl$_3$, δ): 0.93 (6H, d, J=6.5Hz), 1.28–1.50 (2H, m), 1.50–1.95 (3H, m), 3.82 (3H, s), 3.99 (2H, t, J=6.6Hz), 6.44 (1H, d, J=16.0Hz), 6.97 (2H, d, J=8.7Hz), 7.49–7.65 (6H, m), 7.71 (1H, d, J=16Hz)

APCI-MASS: m/z=339 (M$^+$+1)

Preparation 106

Methyl (E)-3-[4-[4-(6-fluorohexyloxy)phenyl]phenyl]acrylate

NMR (CDCl$_3$, δ): 1.23–2.00 (8H, m), 3.81 (3H, s), 4.01 (2H, t, J=6.4Hz), 4.47 (2H, dt, J=47.4 and 6.0Hz), 6.45 (1H, d, J=16.0Hz), 6.96 (2H, d, J=8.8Hz), 7.45–7.63 (6H, m), 7.72 (1H, d, J=16.0Hz)

APCI-MASS: m/z=357 (M$^+$+1)

Preparation 107

Methyl (E)-3-[4-[4-(6-methoxyhexyloxy)phenyl]phenyl]acrylate

APCI-MASS: m/z=369 (M$^+$)

Preparation 108

Methyl (E)-3-[4-[4-(8-methoxyoctyloxy)phenyl]phenyl]acrylate

IR (KBr): 2935.1, 2858.0, 1722.1, 1637.3, 1602.6 cm$^{-1}$

NMR (CDCl$_3$, δ): 1.30–1.70 (10H, m), 1.70–1.92 (2H, m), 3.33 (3H, s), 3.37 (2H, t, J=6.5Hz), 3.81 (3H, s), 4.00 (2H, t, J=6.5Hz), 6.45 (1H, d, J=16.0Hz), 6.97 (2H, d, J=8.8Hz), 7.46–7.78 (6H, m), 7.72 (1H, d, J=16.0Hz)

APCI-MASS: m/z=397 (M$^+$+1)

Preparation 109

Methyl (E)-3-[4-(8-hydroxyphenyl)phenyl]acrylate

IR (KBr): 3409.5, 1695.1 cm$^{-1}$

NMR (DMSO$_6$, δ): 3.73 (3H, s), 6.64 (1H, d, J=16Hz), 6.85 (2H, d, J=8.6Hz), 7.50–7.83 (5H, m)

APCI-MASS: m/z=255 (M$^+$+1)

Preparation 110

Methyl (E)-3-[4-[4-(7-methoxyheptyloxy)phenyl]phenyl]acrylate

NMR (CDCl$_3$, δ): 1.32–1.70 (8H, m), 1.70–1.92 (2H, m), 3.34 (3H, s), 3.38 (2H, t, J=6.4Hz), 3.81 (3H, s), 4.00 (2H, t, J=6.5Hz), 6.45 (1H, d, J=16.0Hz), 6.97 (2H, d, J=8.8Hz), 7.74–7.65 (6H, m), 7.70 (1H, d, J=16Hz)

APCI-MASS: m/z=383 (M⁺+1)

Preparation 111

Methyl (E)-3-[4-[4-(7-fluoroheptyloxy)phenyl]phenyl]acrylate (KBr): 2937.1, 2861.8, 1722.1, 1637.3, 1600.6 cm$^{-1}$ The following compound was obtained according to a similar manner to that of Preparation 20.

Preparation 112

Methyl 3-[4-(4-heptylphenyl)phenyl]propanoate

NMR (CDCl$_3$, δ): 0.88 (3H, t, J=6.5Hz), 1.15–1.50 (8H, m); 1.50–1.77 (2H, m), 2.52–2.73 (4H, m), 2.99 (2H, t, J=7.8Hz), 3.68 (3H, s), 7.18–7.35 (4H, m), 7.40–7.58 (4H, m)

APCI-MASS: m/z=339 (M⁺+1)

The following compounds (Preparation 113 to 164) were obtained according to a similar manner to that of Preparation 32.

Preparation 113

4-(4-Octylphenyl)-2,4-dihydro-3H-1,2,4-triazol-3-one-2-yl-acetic acid

IR (KBr): 2923.6, 1704.8, 1224.6 cm$^{-1}$

NMR (DMSO$_6$, δ): 0.85 (3H, t, J=6.7Hz), 1.1–1.4 (10H, m), 1.4–1.7 (2, H, m), 2.60 (2H, t, J=7.2Hz), 4.38 (2H, s), 7.32 (2H, d, J=8.5Hz), 7.58 (2H, d, J=8.5Hz), 8.43 (1H, s)

Preparation 114

1-Heptyl-4-(4-carboxyphenyl)pyrazole

IR (KBr): 3106, 2917, 1687, 1612, 1425, 1295, 1184, 952, 860, 773 cm$^{-1}$

NMR (DMSO$_6$, δ): 0.85 (3H, t, J=6.8Hz), 1.1–1.4 (8H, m), 1.7–1.9 (2H, m), 4.11 (2H, t, J=7.0Hz), 7.69 (2H, d, J=8.5Hz), 7.91 (2H, d, J=8.5Hz), 7.98 (1H, s), 8.32 (1H, s), 12.82 (1H, br)

APCI-MASS: m/z=287 (M+H⁺)

Preparation 115

6-[4-(4-Octyloxyphenyl)piperazin-1-yl]nicotinic acid

IR (KBr pelet): 2919, 2854, 1697, 1608, 1515, 1429, 1263, 1245, 1228 cm$^{-1}$

NMR (DMSO$_6$, δ): 0.86 (3H, t, J=6.7Hz), 1.1–1.5 (10H, m), 1.6–1.8 (2H, m), 3.0–3.2 (4H, m), 3.7–3.9 (4H, m), 3.88 (2H, t, J=6.4Hz), 6.7–7.0 (5H, m), 7.95 (1H, dd, J=9.0 and 1.1Hz), 8.64 (1H, d, J=1.1Hz)

APCI-MASS: m/z=412 (M+H⁺)

Preparation 116

2-(4-Hexyloxyphenyl)benzoxazole-5-carboxylic acid

IR (KBr): 2952, 1689, 1677, 1619, 1500, 1415, 1299, 1172, 1024 cm$^{-1}$

NMR (DMSO$_6$, δ): 0.89 (3H, t, J=6.7Hz), 1.2–1.5 (6H, m), 1.7–1.9 (2H, m), 4.09 (2H, t, J=6.5Hz), 7.16 (2H, d, J=8.8Hz), 7.84 (1H, d, J=8.5Hz), 8.01 (1H, dd, J=8.5 and 1.5Hz), 8.15 (2H, d, J=8.8Hz), 8.26 (1H, d, J=1.5Hz)

APCI-MASS: m/z=340 (M+H⁺)

Preparation 117

4-[4-(4-n-Butyloxyphenyl)phenyl]benzoic acid

IR (KBr): 2958, 2873, 1689, 1600, 1537, 1396 cm$^{-1}$

Preparation 118

6-(4-Heptyloxyphenyl)nicotinic acid

IR (KBr): 2858, 1699, 1674, 1589, 1425, 1180, 1016, 781 cm$^{-1}$

NMR (DMSO$_6$, δ): 0.87 (3H, t, J=6.7Hz), 1.2–1.5 (8H, m), 1.6–1.8 (2H, m), 4.04 (2H, t, J=6.4Hz), 7.06 (2H, d, J=8.9Hz), 8.03 (1H, d, J=8.2Hz), 8.13 (2H, d, J=8.9Hz), 8.27 (1H, dd, J=8.2 and 2.2Hz), 9.09 (1H, d, J=2.2Hz), 13.31 (1H, br)

APCI-MASS: m/z=314 (M+H⁺)

Preparation 119

5-(4-Octyloxyphenyl)isoxazole-3-carboxylic acid

IR (KBr pelet): 2923, 2852, 1704, 1612, 1440, 1272, 1178 cm$^{-1}$

NMR (DMSO$_6$, δ): 0.86 (3H, t, J=6.8Hz), 1.2–1.6 (10H, m), 1.6–1.9 (2H, m), 4.03 (2H, t, J=6.5Hz), 7.08 (2H, d, J=8.9Hz), 7.25 (1H, s), 7.86 (2H, d, J=8.9Hz)

APCI-MASS: m/z=318 (M+H⁺)

Preparation 120

2-(2-Octyloxypyridin-5-yl)benzoxazole-5-carboxylic acid

IR (KBr): 2954, 2923, 2854, 1697, 1683, 1625, 1488, 1290 cm$^{-1}$

NMR (DMSO$_6$, δ): 0.86 (3H, t, J=7.6Hz), 1.2–1.5 (10H, m), 1.7–1.8 (2H, m), 4.36 (2H, t, J=6.6Hz), 7.04 (1H, d, J=8.7Hz), 7.88 (1H, d, J=8.5Hz), 8.04 (1H, dd, J=8.5 and 1.6Hz), 8.29 (1H, d, J=1.6Hz), 8.43 (1H, dd, J=8.7 and 2.4Hz), 8.99 (1H, d, J=2.4Hz), 13.0–13.2 (1H, br)

APCI-MASS: m/z=369 (M+H⁺)

Preparation 121

2-[4-(4-Hexylphenyl)phenyl]benzoxazole-5-carboxylic acid

IR (KBr): 2923, 2854, 1683, 1411, 1299, 1054 cm$^{-1}$

APCI-MASS: m/z=400 (M+H⁺)

Preparation 122

6-[4-(4-n-Butyloxyphenyl)phenyl]nicotinic acid

IR (KBr): 3406, 2958, 1691, 1591, 1394, 1284, 1253 cm$^{-1}$

NMR (DMSO-d$_6$, δ): 0.94 (3H, t, J=7.3Hz), 1.4–1.8 (4H, m), 4.01 (2H, t, J=6.4Hz), 7.02 (2H, d, J=8.7Hz), 7.57 (2H, d, J=8.7Hz), 7.61 (2H, d, J=8.2Hz), 7.83 (2H, d, J=8.2Hz), 8.05 (1H, d, J=8.5Hz), 8.22 (1H, dd, J=8.5 and 1.6Hz), 9.14 (1H, d, J=1.6Hz)

APCI-MASS: m/z=348 (M+H⁺)

Preparation 123

4-[4-(5-Phenoxypentyloxy)phenyl]benzoic acid

NMR (DMSO-d$_6$, δ): 1.5–1.7 (2H, m), 1.7–1.9 (4H, m), 3.98 (2H, t, J=6.3Hz), 4.05 (2H, t, J=6.1Hz), 6.8–7.0 (3H, m), 7.05 (2H, d, J=8.6Hz), 7.25 (2H, t, J=8.2Hz), 7.68 (2H, d, J=8.5Hz), 7.75 (2H, d, J=8.2Hz), 7.98 (2H, d, J=8.2Hz), 12.8–13.0 (1H, br s)

APCI-MASS: m/z=375 (M−H)⁻

Preparation 124

4-[5-(4-Hexyloxyphenyl)-1,3,4-oxadiazol-2-yl] benzoic acid

IR (KBr): 2935, 2854, 1685, 1612, 1495, 1425, 1286, 1251 cm⁻¹

NMR (DMSO-$d_6$, δ): 0.89 (3H, t, J=6.7Hz), 1.2–1.5 (6H, m), 1.6–1.9 (3H, m), 4.12 (2H, t, J=6.4Hz), 7.19 (2H, d, J=8.7Hz), 8.08 (2H, d, J=8.7Hz), 8.18 (2H, d, J=8.4Hz), 8.24 (2H, d, J=8.4Hz)

APCI-MASS: m/z=367 (M+H)⁺

Preparation 125

4-[5-(4-Hexyloxyphenyl)-1,3,4-thiadiazol-2-yl] benzoic acid

IR (KBr): 2952, 2586, 1699, 1604, 1517, 1432, 1251, 1174 cm⁻¹

NMR (DMSO-$d_6$, δ): 0.89 (3H, t, J=6.7Hz), 1.3–1.9 (8H, m), 4.04 (2H, t, J=6.3Hz), 7.13 (2H, d, J=8.8Hz), 7.97 (2H, d, J=8.8Hz), 8.11 (4H, s)

APCI-MASS: m/z=383 (M+H)⁺

Preparation 126

5-(4-Octyloxyphenyl)-1-methylpyrazole-3-carboxyic acid

IR (KBr pelet): 2950, 2923, 1695, 1450, 1282, 1251, 956 cm⁻¹

NMR (DMSO$_6$, δ): 0.86 (3H, t, J=6.8Hz), 1.2–1.5 (10H, m), 1.6–1.8 (2H, m), 3.98 (2H, t, J=6.5Hz), 4.10 (3H, s), 6.95 (1H, d, J=8.8Hz), 7.18 (1H, s), 7.73 (2H, d, J=8.8Hz), 13.37 (1H, br)

APCI-MASS: m/z=331 (M+H⁺)

Preparation 127

4-[3-(4-n-Pentyloxyphenyl)pyrazol-5-yl]benzoic acid

IR (KBr): 3224, 2956, 1692, 1614, 1506, 1251 cm⁻¹

NMR (DMSO$_6$, δ): 0.91 (3H, t, J=6.9Hz), 1.3–1.5 (4H, m), 1.6–1.8 (2H, m), 4.00 (2H, t, J=6.5Hz), 7.02 (2H, d, J=8.8Hz), 7.19 (1H, s), 7.75 (2H, d, J=8.8Hz), 7.95 (2H, d, J=8.7Hz), 8.02 (2H, d, J=8.7Hz), 12.8–13.3 (2H, br)

APCI-MASS: m/z=351 (M+H⁺)

Preparation 128

5-[4-(4n-Butoxyphenyl)phenyl]furan-2-carboxylic acid

IR (KBr): 2958, 2873, 1679, 1487, 1253, 1166 cm⁻¹

NMR (DMSO$_6$, δ): 0.95 (3H, t, J=7.3Hz), 1.3–1.8 (4H, m), 4.02 (2H, t, J=6.3Hz), 7.03 (2H, d, J=8.6Hz), 7.17 (1H, d, J=3.6Hz), 7.33 (1H, d, J=3.6Hz), 7.66 (2H, d, J=8.6Hz), 7.74 (2H, d, J=8.4Hz), 7.86 (2H, d, J=8.4Hz), 13.1 (1H, br s)

APCI-MASS: m/z=337 (M+H)⁺

Preparation 129

3-(S)-Hydroxyhexadecanoic acid

IR (KBr): 1679.7, 1467.6, 1224.6 cm⁻¹

NMR (CDCl$_3$, δ): 0.88 (3H, t, J=6.4Hz), 1.1–1.7 (24H, m), 2.35–2.65 (2H, m), 4.03 (1H, m), 5.41 (1H, br s)

Preparation 130

6-[4-(4-n-Hexyloxyphenyl)piperazin-1-yl] pyridazine-3-carboxylic acid

IR (KBr): 1697.1, 1589.1, 1515.8, 1448.3 cm⁻¹

NMR (DMSO$_6$, δ): 0.87 (3H, t, J=6.4Hz), 1.2–1.5 (6H, m), 1.6–1.8 (2H, m), 3.0–3.2 (4H, m), 3.7–4.0 (6H, m), 6.83 (2H, d, J=9.0Hz), 6.95 (2H, d, J=9.0Hz), 7.36 (1H, d, J=9.6Hz), 7.86 (1H, d, J=9.6Hz), 11.68 (1H, s)

Preparation 131

4-[4-[1-(4-n-Hexyloxyphenyl)piperidin-4-yl] piperazin-1-yl]benzoic acid hydrochloride IR (KBr): 1699.0, 1608.3, 1513.8 cm⁻¹

NMR (DMSO$_6$, δ): 0.88 (3H, t, J=6.5Hz), 1.2–1.5 (6H, m), 1.6–1.8 (2H, m), 2.0–2.45 (3H, m), 3.2–3.8 (12H, m), 3.94 (2H, t, J=6.4Hz), 4.03 (2H, d, J=11Hz), 6.95 (2H, d, J=8.7Hz), 7.07 (2H, d, J=8.9Hz), 7.32 (2H, br s), 7.83 (2H, d, J=8.9Hz)

APCI-MASS: m/z=466 (M⁺+H)

Preparation 132

6-(8-Methoxyoctyloxy)-2-naphtholic acid

IR (KBr): 2937.1, 2854.1, 1677.8, 1211.1 cm⁻¹

NMR (DMSO$_6$, δ): 1.2–1.6 (10H, m), 1.7–1.9 (2H, m), 3.20 (3H, s), 3.29 (2H, t, J=6.5Hz), 4.11 (2H, t, J=6.4Hz), 7.23 (1H, dd, J=9.0 and 2.3Hz), 7.39 (1H, d, J=2.3Hz), 7.85 (1H, d, J=8.7Hz), 7.93 (1H, d, J=8.7Hz), 7.99 (1H, d, J=9.0Hz), 8.51 (1H, s), 12.9 (1H, s)

Preparation 133

Mixture of (E) and (Z)-3-[4-(4-Heptylphenyl)phenyl]-2-butenoic acid

NMR (CDCl$_3$, δ): 0.88 (3H, t, J=6.6Hz), 1.15–1.50 (8H, m), 1.52–1.75 (2H, m), 2.63 and 3.62 (total 3H, each s), 2.53–2.75 (2H, m), 6.24 and 5.68 (total 1H, each s), 7.19–7.35 (2H, m), 7.47–7.70 (6H, m)

APCI-MASS: m/z=337 (M⁺+1), 351 (methyl ester⁺+1)

Preparation 134

3-[4-(4-Heptylphenyl)phenyl]propanoic acid

NMR (CDCl$_3$, δ): 0.88 (3H, t, J=6.6Hz), 1.13–1.48 (8H, m), 1.48–1.75 (2H, m), 2.52–2.83 (4H, m), 3.00 (2H, t, J=7.8Hz), 7.15–7.35 (4H, m), 7.40–7.60 (4H, m)

APCI-MASS: m/z=323 (M⁺−1)

Preparation 135

4-(4-Heptylphenyl)benzoyl-carboxylic acid

NMR (CDCl$_3$, δ): 0.88 (3H, t, J=6.6Hz), 1.13–1.50 (8H, m), 1.50–1.75 (2H, m), 2.66 (2H, t, J=7.7Hz), 7.20–7.40 (2H, m), 7.50–7.66 (2H, m), 7.66–7.84 (2H, m), 8.40–8.60 (2H, m)

APCI-MASS: m/z=323 (M⁺−1)

Preparation 135

6-Hexylnaphthalene-2carboxylic acid

NMR (CDCl$_3$, δ): 0.89 (3H, t, J=6.8Hz), 1.15–1.53 (6H, m), 1.55–1.84 (2H, m), 2.80 (2H, t, J=7.6Hz), 7.42 (1H, dd,

J=1.7 and 8.4Hz), 7.67 (1H, s) 7.84 (1H, d, J=8.6Hz), 7.90 (1H, d, J=8.4Hz), 8.09 (1H, dd, J=1.7 and 8.6Hz), 8.68 (1H, s) p APCI-MASS: m/z=257 (M$^+$+1), 271 (methyl ester$^+$+1)

Preparation 137

3-(E)-[4-[4-(7-Methoxyheptyloxy)phenyl]phenyl] acrylic acid

NMR (DMSO$_6$, δ): 1.20–1.60 (8H, m), 1.60–1.83 (2H, m), 3.21 (3H, s), 3.25–3.60 (2H, m), 4.01 (2H, t, J=6.4Hz), 6.54 (1H, d, J=16.0Hz), 7.02 (2H, d, J=8.8Hz), 7.55–7.80 (7H, m)

APCI-MASS: m/z=369 (M$^+$+1)

Preparation 138

3-(E)-[4-[4-(8-Methoxyoctyloxy)phenyl]phenyl] acrylic acid

IR (KBr): 3037.3, 2933.2, 2858.0, 2551.4, 1706.7, 1677.8, 1629.6, 1602.6 cm$^{-1}$

NMR (DMSO$_6$, δ): 1.18–1.55 (10H, m), 1.65–1.83 (2H, m), 3.18–3.45 (5H, m), 4.01 (2H, t, J=6.5Hz), 6.53 (1H, d, J=16.0Hz), 7.02 (2H, d, J=8.8Hz), 7.50–8.80 (7H, m)

APCI-MASS: m/z=383 (M$^+$+1)

Preparation 139

3-(E)-[4-[4-(5-Hexenyloxy)phenyl]phenyl]acrylic acid

NMR (DMSO$_6$, δ): 1.42–1.63 (2H, m), 1.63–1.85 (2H, m), 2.00–2.20 (2H, m), 4.03 (2H, t, J=6.3Hz), 4.90–5.15 (2H, m), 5.68–5.97 (1H, m), 6.54 (1H, d, J=16Hz), 7.02 (2H, d, J=8.7Hz), 7.50–7.80 (7H, m)

APCI-MASS: m/z=323 (M$^+$+1)

Preparation 140

3-(E)-[4-[4-(4-Methylpentyloxy)phenyl]phenyl] acrylic acid

IR (KBr): 2956.3, 2869.6, 2713.4, 2599.6, 1689.3, 1627.6, 1602.6 cm$^{-1}$

NMR (DMSO$_6$, δ): 0.89 (6H, d, J=6.5Hz), 1.15–1.43 (2H, m), 1.48–1.90 (3H, m), 4.00 (2H, t, J=6.7Hz), 6.54 (1H, d, J=16Hz), 7.02 (2H, d, J=8.7Hz), 7.50–7.90 (7H, m)

APCI-MASS: m/z=325 (M$^+$+1)

Preparation 141

3-(E)-[4-[4-(6-Fluorohexyloxy)phenyl]phenyl] acrylic acid

NMR (CDCl$_3$, δ): 1.39–2.00 (8H, m), 4.01 (2H, t, J=6.5Hz) 4.47 (2H, dt, J=47.3 and 6.0Hz), 6.49 (1H, d, J=15.9Hz), 6.98 (2H, d, J=8.7Hz), 7.40–7.70 (6H, m), 7.81 (1H, d, J=15.9Hz)

APCI-MASS: m/z=343 (M$^+$+1)

Preparation 142

3-(E)-[4-[4-(6-Methoxyhexyloxy)phenyl]phenyl] acrylic acid

NMR (DMSO$_6$, δ): 1.22–1.63 (6H, m), 1.63–1.88 (2H, m), 3.21 (3H, s), 3.22–3.40 (2H, m), 4.00 (2H, t, J=6.5Hz), 6.54 (1H, d, J=15.8Hz), 7.02 (2H, d, J=8.7Hz), 7.50–7.84 (7H, m)

APCI-MASS: m/z=369 (methyl ester, M$^+$+1)

Preparation 143

4-[4-[8-(Tetrahydropyran-2-yl-oxy)octyloxy]phenyl] benzoic acid

IR (KBr): 2935, 1697, 1683, 1604, 1303, 1290, 1197 cm$^{-1}$

NMR (DMSO$_6$, δ): 1.2–1.8 (18H, m), 3.3–3.9 (4H, m), 4.01 (2H, t, J=6.3Hz), 4.5–4.6 (1H, m), 7.03 (2H, d, J=8.7Hz), 7.67 (2H, d, J=8.7Hz), 7.74 (2H, d, J=8.3Hz), 7.98 (2H, d, J=8.3Hz)

APCI-MASS: m/z=425 (M−H$^+$)

Preparation 144

4-[3-(4-n-Hexyloxyphenyl)pyrazol-5-yl]benzoic acrylic acid

IR (KBr): 2956, 2935, 1693, 1614, 1508, 1432, 1251, 1178 cm$^{-1}$

NMR (DMSO$_6$, δ): 0.89 (3H, t, J=6.4Hz), 1.2–1.5 (6H, m), 1.6–1.8 (2H, m), 4.00 (2H, t, J=6.4Hz), 7.02 (2H, d, J=8.7Hz), 7.12 (1H, s), 7.74 (2H, d, J=8.7Hz), 7.95 (2H, d, J=8.8Hz), 8.01 (2H, d, J=8.8Hz), 13.17 (1H, s)

APCI-MASS: m/z=365 (M+H$^+$)

Preparation 145

4-[4-[4-(6-Methoxyhexyloxy)phenyl]phenyl]benzoic acid

IR (KBr): 2939, 2861, 1685, 1602, 1430, 1286, 1128 cm$^{-1}$

NMR (DMSO$_6$, δ): 1.3–1.8 (8H, m), 3.21 (3H, s), 3.3–3.4 (2H, m), 4.01 (2H, t, J=6.5Hz), 7.04 (2H, d, J=8.6Hz), 7.66 (2H, d, J=8.6Hz), 7.7–7.9 (6H, m), 8.03 (2H, d, J=8.2Hz)

APCI-MASS: m/z=405 (M+H$^+$)

Preparation 146

4-[5-[4-(8-Methoxyoctyloxy)phenyl]-1,3,4-thiadiazol-2-yl]benzoic acid

IR (KBr): 2931, 2854, 1691, 1602, 1251 cm$^{-1}$

NMR (DMSO$_6$, δ): 1.2–2.0 (12H, m), 3.20 (3H, s), 3.29 (2H, t, J=6.4Hz), 4.04 (2H, d, J=6.4Hz), 7.13 (2H, t, J=8.8Hz), 7.9–8.2 (6H, m), 13.95 (1H, br)

APCI-MASS: m/z=441 (M+H$^+$)

Preparation 147

4-(4-n-Butoxyphenyl)cinnamic acid

IR (KBr): 2958, 2871, 1695, 1625, 1498, 1249 cm$^{-1}$

NMR (DMSO$_6$, δ): 0.94 (3H, t, J=7.3Hz), 1.44 (2H, tq, J=7.0 and 7.3Hz), 1.71 (2H, tt, J=7.0 and 6.4Hz), 4.01 (2H, t, J=6.4Hz), 6.54 (1H, d, J=16.0Hz), 7.02 (2H, d, J=8.7Hz), 7.6–7.9 (7H, m)

APCI-MASS: m/z=297 (M+H$^+$)

Preparation 148

4-[5-(4-Cyclohexylphenyl)-1,3,4-thiadiazol-2-yl] benzoic acid

IR (KBr): 2925, 2850, 1683, 1429, 1292 cm$^{-1}$

NMR (DMSO$_6$, δ): 1.1–1.5 (5H, m), 1.6–2.0 (5H, m), 2.4–2.6 (1H, m), 7.45 (2H, d, J=8.3Hz), 7.96 (2H, d, J=8.3Hz), 8.13 (4H, s)

APCI-MASS: m/z=365 (M+H$^+$)

Preparation 149

4-[5-[4-Piperidin-1-yl)phenyl]-1,3,4-thiadiazol-2-yl]benzoic acid

IR (KBr): 2931, 2854, 1685, 1604, 1415, 1238 cm$^{-1}$

NMR (DMSO$_6$, δ): 1.61 (6H, s), 3.31 (4H, s), 7.05 (2H, d, J=9.0Hz), 7.83 (2H, d, J=9.0Hz), 8.10 (4H, s)

APCI-MASS: m/z=366 (M+H)$^+$

Preparation 150

4-[5-[4-[4-n-Propyloxyphenyl)-phenyl]-1,3,4-oxadiazol-2-yl]benzoic acid

IR (KBr): 2939, 1689, 1606, 1488, 1429, 1290 cm$^{-1}$

NMR (DMSO$_6$, δ): 1.00 (3H, t, J=7.3Hz), 1.76 (2H, tq, J=6.5 and 7.3Hz), 4.00 (2H, t, J=6.5Hz), 7.07 (2H, d, J=8.8Hz), 7.70 (2H, d, J=8.5Hz), 7.78 (2H, d, J=8.8Hz), 7.90 (2H, d, J=8.5Hz), 8.0–8.4 (4H, m)

APCI-MASS: m/z=401 (M+H)$^+$

Preparation 151

4-(5-Nonyl-1,3,4-oxadiazol-2-yl)benzoic acid

IR (KBr): 2919, 2852, 1685, 1565, 1430, 1284 cm$^{-1}$

NMR (DMSO$_6$, δ): 0.84 (3H, t, J=6.5Hz), 1.2–1.5 (12H, m), 1.7–1.9 (2H, m), 2.94 (2H, t, J=7.4Hz), 8.0–8.2 (4H, m), 13.35 (1H, s)

APCI-MASS: m/z=317 (M+H$^+$)

Preparation 152

4-[3-(4-n-Hexyloxyphenyl)-1,2,4-oxadiazol-5-yl]benzoic acid

IR (KBr): 2942, 2869, 1695, 1421, 1251 cm$^{-1}$

NMR (DMSO$_6$, δ): 0.89 (3H, t, J=6.8Hz), 1.2–1.8 (8H, m), 4.06 (2H, t, J=6.5Hz), 7.13 (2H, d, J=8.9Hz), 8.03 (2H, d, J=8.9Hz), 8.17 (2H, d, J=8.5Hz), 8.28 (2H, d, J=8.5Hz)

APCI-MASS: m/z=367 (M+H)$^+$

Preparation 153

4-[4-[4-(5-Methoxypentyloxy)phenyl]phenyl]phenylacetic acid

IR (KBr): 2939, 2861, 1699, 1253, 1182, 1124 cm$^{-1}$

NMR (DMSO$_6$, δ): 1.4–1.9 (6H, m), 3.22 (3H, s), 3.39 (2H, t, J=6.2Hz), 3.61 (2H, s), 4.01 (2H, t, J=6.4Hz), 7.02 (2H, d, J=8.8Hz), 7.35 (2H, d, J=8.2Hz), 7.6–7.8 (8H, m)

APCI-MASS: m/z=405 (M+H$^+$)

Preparation 154

4-[5-(4-n-Octyloxyphenyl)-1,3,4-thiadiazol-2-yl]benzoic acid

IR (KBr): 2921, 2856, 1691, 1432, 1251 cm$^{-1}$

NMR (DMSO$_6$, δ): 0.87 (3H, t, J=6.7Hz), 1.2–1.5 (10H, m), 1.7–1.9 (2H, m), 4.07 (2H, t, J=6.5Hz), 7.13 (2H, d, J=8.9Hz), 7.97 (2H, d, J=8.9Hz), 8.12 (4H, s)

APCI-MASS: m/z=411 (M+H$^+$)

Preparation 155

4-[5-(4-Trans-n-pentylcyclohexyl)-1,3,4-thiadiazol-2-yl]benzoic acid

IR (KBr): 2919, 2848, 1677, 1430, 1294 cm$^{-1}$

NMR (DMSO$_6$, δ): 0.87 (3H, t, J=6.9Hz), 1.0–1.4 (11H, m), 1.5–1.6 (2H, m), 1.8–2.0 (2H, m), 2.1–2.3 (2H, m), 3.1–3.3 (1H, m), 8.07 (4H, s)

APCI-MASS: m/z=359 (M+H$^+$)

Preparation 156

4-[3-(4-n-Pentyloxyphenyl)isoxazol-5-yl]benzoic acid

IR (KBr): 2925, 2869, 1699, 1687, 1612, 1432, 1251, 1178 cm$^{-1}$

NMR (DMSO$_6$, δ): 0.91 (3H, t, J=6.9Hz), 1.2–1.5 (4H, m), 1.7–1.9 (2H, m), 4.04 (2H, t, J=6.5Hz), 7.09 (2H, d, J=8.8Hz), 7.69 (1H, s), 7.85 (2H, d), J=8.8Hz), 8.01 (2H, d, J=8.5Hz), 8.11 (2H, d, J=8.5Hz)

APCI-MASS: m/z=352 (M+H$^+$)

Preparation 157

4-[5-[4-(8-Methoxyoctyloxy)phenyl]-1,3,4-oxadiazol-2-yl]benzoic acid

IR (KBr): 2967, 2937, 2877, 1687, 1290 cm$^{-1}$

NMR (DMSO$_6$, δ): 1.2–1.6 (10H, m), 1.7–1.9 (2H, m), 3.20 (3H, s), 3.29 (2H, t, J=6.4Hz), 4.08 (2H, t, J=6.5Hz), 7.17 (2H, d, J=8.9Hz), 8.07 (2H, d, J=8.9Hz), 8.15 (2H, d, J=8.6Hz), 8.24 (2H, d, J=8.6Hz)

APCI-MASS: m/z=425 (M+H)$^+$

Preparation 158

4-[4-(6-Phenylpyridazin-3-yl-oxy)phenyl]benzoic acid

IR (KBr): 1700, 1687, 1608, 1427, 1284, 1186 cm$^{-1}$

NMR (DMSO$_6$, δ): 7.40 (2H, d, J=8.6Hz), 7.5–7.7 (4H, m), 7.7–7.9 (4H, m), 7.9–8.1 (4H, m), 8.35 (1H, d, J=9.2Hz), 12.99 (1H, br s)

APCI-MASS: m/z=369 (M+H)$^+$

Preparation 159

4-[5-(4-n-Octyloxyphenyl)-1,3,4-oxadiazol-2-yl]benzoic acid

IR (KBr): 2921, 2852, 1685, 1612, 1496, 1425, 1288, 1251 cm$^{-1}$

NMR (DMSO$_6$, δ): 0.87 (3H, t, J=6.7Hz), 1.2–1.5 (10H, m), 1.7–1.9 (2H, m), 4.08 (2H, t, J=6.4Hz), 7.17 (2H, d, J=8.7Hz), 8.07 (2H, d, J=8.7Hz), 8.15 (2H, d, J=8.5Hz), 8.24 (2H, d, J=8.5Hz), 13.36 (1H, br)

APCI-MASS: m/z=395 (M+H$^+$)

Preparation 160

4-[2-(4-n-Hexyloxyphenyl)pyrimidin-6-yl]benzoic acid

IR (KBr): 2944, 2863, 1697, 1585, 1415, 1386, 1253 cm$^{-1}$

NMR (DMSO$_6$, δ): 0.89 (3H, t, J=6.7Hz), 1.2–1.6 (6H, m), 1.7–1.9 (2H, m), 4.07 (2H, t, J=6.6Hz), 7.10 (2H, d, J=8.9Hz), 8.00 (1H, d, J=5.2Hz), 8.13 (2H, d, J=8.4Hz), 8.44 (2H, d, J=5.9Hz), 8.47 (2H, d, J=5.9Hz), 8.95 (1H, d, J=5.2Hz)

APCI-MASS: m/z=377 (M+H$^+$)

Preparation 161

4-[4-(7-Piperidinocarbonylheptyloxy)phenyl]benzoic acid

IR (KBr): 2933, 2858, 1697, 1677, 1637, 1604, 1429, 1249 cm$^{-1}$

NMR (DMSO$_6$, δ): 1.2–1.8 (16H, m), 2.26 (2H, t, J≦7.5Hz), 3.2–3.5 (4H, m), 4.01 (2H, t, J=6.4Hz), 7.03 (2H, d, J=8.8Hz), 7.67 (2H, d, J=8.8Hz), 7.74 (2H, d, J=8.4Hz) 7.98 (2H, d, J=8.4Hz)

APCI-MASS: m/z=424 (M+H$^+$)

Preparation 162
6-[4-(4-n-Heptyloxyphenyl)-piperazin-1-yl]nicotinic acid

IR (KBr): 2929, 2854, 1695, 1673, 1606, 1577, 1515, 1421 1245 cm$^{-1}$

NMR (DMSO$_6$, δ): 0.86 (3H, t, J=6.7Hz), 1.2–1.5 (8H, m), 1.6–1.8 (2H, m), 3.0–3.2 (4H, m), 3.6–3.8 (4H, m), 3.87 (2H, t, J=6.5Hz), 6.8–7.2 (5H, m), 7.95 (1H, dd, J=8.9 and 2.3 Hz), 8.62 (1H, d, J=2.3 Hz) APCI-MASS: m/z=398 (M+H$^+$)

Preparation 163
6-[4-[4-(8-Methoxyoctyloxy)phenyl]piperazin-1-yl]-nicotinic Acid IR (KBr): 2933, 856, 1697, 1672, 1605, 1511, 1421, 1245 cm$^{-1}$ NMR (DMSO-d$_6$, δ): 1.2–1.8 (12H, m), 3.08 (4H, t, J=5.0 Hz), 3.20 (3H, s), 3.28 (2H, t, J=6.5 Hz), 3.78 (4H, t, J=4.6 Hz), 3.87 (2H, t, J=6.4 Hz), 6.8–7.0 (5H, m), 7.95 (1H, dd, J=9.0 and 2.2 Hz), 8.65 (1H, d, J=2.2 Hz), 12.54 (1H, s) APCI-MASS: m/z=442 (M+H$^+$)

Preparation 164
4-[5-[4-(4-n-Propyloxyphenyl)phenyl]-1,3,4-thiadiazol-2-yl]benzoic Acid IR (KBr): 1685, 1537, 1423, 817 cm$^{-1}$ NMR (DMSO-d$_6$, δ): 1.00 (3H, t, J=6.7 Hz), 1.6–1.8 (2H, m), 4.00 (2H, t, J=6.6 Hz), 7.0–7.2 (2H, d, J=8.6 Hz), 7.6–8.1 (10H, m)

APCI-MASS: m/z=417 (M+H)$^+$

Preparation 165

To a solution of Ethyl 4-[5-(4-n-pentyloxyphenyl)-isoxazol-3-yl]benzoate (6.33 g) in ethanol (60 ml) and tetrahydrofuran (90 ml) was added 2N sodium hydroxide aqueous solution (12.5 ml) at 80° C. The mixture was refluxed for 1 hour and poured into ice-water. The suspension was adjusted to pH 2.0 with 1N HCl. The precipitate was collected by filtration, washed with water and dried to give 4-[5-(4-n-pentyloxyphenyl)isoxazol-3-yl]benzoic acid (5.80 g).

IR (KBr): 2939, 2867, 1681, 1614, 1429, 1255, 1178, 821 cm$^{-1}$ NMR (DMSO-d$_6$, δ): 0.91 (3H, t, J=7.1 Hz), 1.3–1.5 (4H, m), 1.6–1.8 (2H, m), 4.04 (2H, t, J=6.5 Hz), 7.11 (2H, d, J=8.9 Hz), 7.54 (1H, s), 7.85 (2H, d, J=8.9 Hz), 7.98 (2H, d, J=8.6 Hz), 8.11 (2H, d, J=8.6 Hz) APCI-MASS: m/z=352 (M+H)$^+$

The following compounds (Preparation 166 to 170) were obtained according to a similar manner to that of Preparation 40.

Preparation 166
5-[4-(4-n-Hexyloxphenyl)piperazin-1-yl]picolic Acid Trihydrochloride IR (KBr): 1689.3, 1577.5, 1511.9, 1241.9 cm$^{-1}$ NMR (DMSO-d$_6$, δ): 0.88 (3H, t, J=6.5 Hz), 1.15–1.5 (6H, m), 1.6–1.8 (2H, m), 3.1–3.25 (4H, m), 3.45–3.6 (4H, m), 3.89 (2H, t, J=6.4 Hz), 6.84 (2H, d, J=9.1 Hz), 6.97 (2H, d, J=9.1 Hz), 7.43 (1H, dd, J=8.8 and 3.0 Hz), 7.90 (1H, dd, J=8.8 and 0.7 Hz), 8.41 (1H, dd, J=3.0 and 0.7 Hz) APCI-MASS: m/z=384 (M$^+$+H)

Preparation 167
4-[4-(4-Phenylcyclohexyl)piperazin-1-yl]benzoic Acid Dihydrochloride IR (KBr): 1700.9, 1606.4, 1220.7, 1180.2 cm$^{-1}$ NMR (DMSO-d$_6$, δ): 1.4–1.85 (4H, m), 1.9–2.05 (2H, m), 2.2–2.4 (2H, m), 3.1–3.5 (6H, m), 3.5–3.7 (2H, m), 3.9–4.2 (2H, m), 7.06 (2H, d, J=8.8 Hz), 7.1–7.4 (5H, m), 7.83 (2H, d, J=8.8 Hz) APCI-MASS: m/z=365 (M$^+$+H)

Preparation 168
4-(4-Trans-n-pentylcyclohexyl)benzoic Acid

IR (KBr): 1681.6, 1423.2, 1290.1 cm$^{-1}$ NMR (CDCl$_3$, δ): 0.90 (3H, t, J=6.6 Hz), 1.0–1.6 (13H, m), 1.89 (4H, d, J=10 Hz), 2.54 (1H, t, J=12 Hz), 7.30 (2H, d, J=8.3 Hz), 8.03 (2H, d, J=8.3 Hz) APCI-MASS: m/z=274 (M$^+$+H)

Preparation 169
4-(4-Piperidinopiperidin-1yl)benzoic Acid

IR (KBr): 1710.6, 1403.9 cm$^{-1}$ NMR (DMSO-d$_6$, δ): 1.6–2.1 (8H, m), 2.17 (2H, d, J=12 Hz), 2.7–3.05 (4H, m), 3.2–3.5 (1H, m), 3.35 (2H, d, J=12 Hz), 4.05 (2H, d, J=13 Hz), 7.01 (2H, d, J=8.9 Hz), 7.77 (2H, d, J=8.9 Hz), 10.84 (1H, s) APCI-MASS: m/z=289 (M$^+$+H)

Preparation 170
3-Chloro-4-[4-(4-n-hexyloxyphenyl)piperazin-1-yl]benzoic Acid Dihydrochloride IR (KBr): 1712.5, 1598.7, 1513.8, 1251.6 cm$^{-1}$ NMR (DMSO-d$_6$, δ): 0.88 (3H, t, J=6.6 Hz), 1.2–1.5 (6H, m), 1.6–1.8 (2H, m), 3.4–3.6 (8H, m), 3.98 (2H, t, J=6.4 Hz), 7.02 (2H, d, J=9.0 Hz), 7.32 (1H, d, J=8.1 Hz), 7.60 (2H, d, J=9.0 Hz), 7.89 (1H, d, J=8.1 Hz), 8.02 (1H, s) APCI-MASS: m/z=417 (M$^+$+H)

The following compounds (Preparations 171 to 175) were obtained according to a similar manner to that of Preparation 41.

Preparation 171
Ethyl [4-(4-octylphenyl)-2,3-dihydro-4H-1,2,4-triazole-3-one-2yl]acetate IR (KBr): 1921.6, 1764.5, 1715, 1197.6 cm$^{-1}$ NMR (CDCl$_3$, δ): 0.88 (3H, t, J=6.7 Hz), 1.30 (3H, t, J=7.1 Hz), 1.2–1.4 (10H, m), 1.5–1.7 (2H, m), 2.63 (2H, t, J=7.9 Hz), 4.26 (2H, q, J=7.1 Hz), 4.64 (2H, s), 7.28 (2H, d, J=8.4 Hz), 7.44 (2H, d, J=8.4 Hz), 7.71 (1H, s)

Preparation 172
4-[4-(4-tert-Butoxycarbonylpiperazin-1-yl)phenyl]-2(4-methylpentyl)-2,3-dihydro-4H-1,2,4-triazol-3-one IR (KBr): 1687.4 cm$^{-1}$ NMR (CDCl$_3$, δ): 0.90 (6H, d, J=6.5 Hz), 1.1–1.4 (2H, m), 1.49 (9H, s), 1.4–1.9 (3H, m), 3.16 (4H, t, J=4.9 Hz), 3.59 (4H, t, J=4.9 Hz), 3.82 (2H, t, J=7.3 Hz), 6.98 (2H, d, J=9.0 Hz), 7.41 (2H, d, J=9.0 Hz), 7.61 (1H, s)

Preparation 173
Methyl 6-(8-bromooctyloxy)-2-naphthoate

IR (KBr): 2933.2, 2856.1, 1720.2, 1294, 1209.1 cm$^{-1}$ NMR (CDCl$_3$, δ): 1.3–1.6 (8H, m), 1.75–2.0 (4H, m), 3.42 (2H, t, J=6.8 Hz), 3.96 (3H, s), 4.09 (2H, t, J=6.5 Hz), 7.14 (1H, d, J=1.7 Hz), 7.19 (1H, dd, J=8.9 and 1.7 Hz, 7.73 (1H, d, J=8.7 Hz), 7.83 (1H, d, J=8.9 Hz), 8.01 (1H, dd, J=8.7 and 1.7 Hz), 8.51 (1H, d, J=1.7 Hz) APCI-MASS: m/z=393 (M$^+$+H)

Preparation 174
4-[4-(6-n-Propyloxyphenyl)phenyl]benzoic Acid

IR (KBr): 2937, 2858, 1695, 1683, 1604, 1430, 1290, 1247, 1195 cm$^{-1}$ NMR (DMSO-d$_6$, δ): 0.85 (3H, t, J=7.4

Hz), 1.3–1.9 (10H, m), 3.2–3.4 (4H, m), 4.01 (2H, t, J=6.3 Hz), 7.04 (2H, d, J=8.7 Hz), 7.67 (2H, d, J=8.7 Hz), 7.74 (2H, d, J=8.3 Hz), 7.98 (2H, d, J=8.3 Hz), 12.9 (1H, APCI-MASS: m/z=357 (M+H$^+$)

Preparation 175
4-[4-(6-Bromohexyloxy)phenyl]bromobenzene
NMR (CDCl$_3$, δ): 1.40–1.65 (4H, m), 1.70–2.00 (4H, m), 3.43 (2H, t, J=6.7 Hz), 4.00 (2H, t, J=6.4 Hz), 6.95 (2H, d, J=8.8 Hz), 7.30–7.60 (6H, m)

The following compounds (Preparations 176 to 180) were obtained according to a similar manner to that of Preparation 43.

Preparation 176
4-[4-(4-n-Pentyloxyphenyl)piperazin-1-yl]benzoic Acid Dihydrochloride
IR (KBr): 1668.1, 1602.6, 1510.0, 1228.4 cm$^{-1}$ NMR (DMSO-d$_6$, δ): 0.89 (3H, t, J=6.9 Hz), 1.2–1.5 (5H, m), 1.6–1.9 (2H, m), 3.0–3.2 (4H, m), 3.4–3.6 (4H, m), 3.88 (2H, t, J=6.4 Hz), 6.83 (2H, d, J=9 Hz), 6.9–7.1 (4H, m), 7.79 (2H, d, J=8.8 Hz), 12.32 (1H, s) APCI-MASS: m/z=369 (M+H$^+$)

Preparation 177
4-[4-(4-n-Heptyloxyphenyl)piperazin-1-yl]benzoic Acid Dihydrochloride
IR (KBr): 1666.2, 1600.6, 1511.9 cm$^{-1}$ NMR (CDCl$_3$, δ): 0.89 (3H, t, J=6.9 Hz), 1.2–2.0 (10H, m), 3.1–3.3 (4H, m), 3.4–3.6 (4H, m), 3.92 (2H, t, J=6.4 Hz), 6.8–7.1 (6H, m), 8.00 (2H, d, J=8.8 Hz)

Preparation 178
4-[4-[4-(4-Methylpentyloxy)phenyl]piperazin-1-yl]benzoic Acid Hydrochloride
IR (KBr): 1668.1, 1602.6, 1510.0, 1236.1 cm$^{-1}$ NMR (DMSO-d$_6$, δ): 0.89 (6H, d, J=6.5 Hz), 1.2–1.4 (2H, m), 1.4–1.8 (3H, m), 3.0–3.2 (4H, m), 3.3–3.5 (4H, m), 3.87 (2H, t, J=6.3 Hz), 6.83 (2H, d, J=9.0 Hz), 6.9–7.1 (4H, m), 7.79 (2H, d, J=8.8 Hz), 12.33 (1H, s) APCI-MASS: m/z=383 (M+H$^+$)

Preparation 179
4-[4-[4-(8-Bromooctyloxy)phenyl]piperazin-1-yl]benzoic Acid Dihydrochloride
IR (KBr): 1670.1, 1602.6, 1511.9, 1234.2 cm$^{-1}$ NMR (DMSO-d$_6$, δ): 1.2–1.5 (8H, m), 1.6–1.9 (4H, m), 3.0–3.2 (4H, m), 3.2–3.5 (4H, m), 3.52 (2H, t, J=6.7 Hz), 3.88 (2H, t, J=6.4 Hz), 6.83 (2H, d, J=9.1 Hz), 6.94 (2H, d, J=9.1 Hz), 7.02 (2H, d, J=8.9 Hz), 7.79 (2H, d, J=8.9 Hz)

Preparation 180
3-Fluoro-4-[4-(4-n-hexyloxyphenyl)piperazin-1yl]benzoic Acid Dihydrochloride
IR (KBr): 1673.9, 1511.9, 1240.0 cm$^{-1}$ NMR (DMSO-d$_6$, δ): 0.88 (3H, t, J=6.5 Hz), 1.2–1.5 (6H, m), 1.6–1.8 (2H, m), 3.0–3.5 (8H, m), 3.88 (2H, t, J=6.4 Hz), 6.7–7.2 (5H, m), 7.4–7.8 (2H, m), 12.82 (1H, s) APCI-MASS: m/z=401 (M$^+$+H)

The following compound was obtained according to a similar manner to that of Preparation 46.

Preparation 181
1-(4-Methoxycarbonylphenyl)-3-(4-n-hexyloxyphenyl)-propan-1,3-dione
IR KBr: 2956, 2927, 2856, 1722, 1511, 1284, 1108 cm$^{-1}$ NMR (CDCl$_3$, δ): 0.92 (3H, t, J=6.4 Hz), 1.2–2.0 (8H, m), 3.96 (3H, s), 4.04 (2H, t, J=6.5 Hz), 6.82 (1H, s), 6.97 (2H, d, J=8.7 Hz), 7.9–8.1 (4H, m), 8.14 (2H, d, J=8.3 Hz) APCI-MASS: m/z=383 (M+H$^+$)

The following compounds (Preparations 182 to 185) were obtained according to a similar manner to that of Preparation 47.

Preparation 182
Methyl 5-(4-octyloxyphenyl)-1-methylpyrazole-3-carboxylate
IR (KBr pelet): 2923, 1724, 1616, 1513, 1446, 1251, 1120 cm$^{-1}$ NMR (CDCl$_3$, δ): 0.89 (3H, t, J=6.8 Hz), 1.2–1.5 (10H, m), 1.7–1.9 (2H, m), 3.90 (3H, s), 3.98 (2H, t, J=6.6 Hz), 4.20 (3H, s), 6.92 (2H, d, J=8.9 Hz), 7.04 (1H, s), 7.89 (2H, d, J=8.9 Hz) APCI-MASS: m/z=345 (M+H$^+$)

Preparation 183
Methyl 4-[5-(4-n-pentyloxyphenyl)pyrazol-3-yl]benzoate
IR (KBr): 3236, 2952, 2873, 1716, 1616, 1508, 1276, 1174, 1106 cm$^{-1}$ NMR (CDCl$_3$, δ): 0.94 (3H, t, J=7.0 Hz), 1.3–1.5 (4H, m), 1.7–1.9 (2H, m), 3.92 (3H, s), 3.96 (2H, t, J=6.7 Hz), 6.78 (1H, s), 6.88 (2H, d, J=8.7 Hz), 7.55 (2H, d, J=8.7 Hz), 7.79 (2H, d, J=8.4 Hz), 8.02 (2H, d, J=8.4 Hz) APCI-MASS: m/s=365 (M+H$^+$)

Preparation 184
Methyl 5-(4-octyloxyphenyl)isoxazole-3-carboxylate
IR (KBr pelet): 2950, 2921, 1724, 1614, 1510, 1446, 1257, 1178, 1143, 1009 cm$^{-1}$ NMR (CDCl$_3$, δ): 0.89 (3H, t, J=6.8 Hz), 1.2–1.6 (10H, m), 1.7–1.9 (2H, m), 4.0–4.1 (5H, m), 6.80 (1H, s), 6.98 (2H, dd, J=6.9 and 2.1 Hz), 7.73 (2H, dd,, J=6.9 and 2.1 Hz) APCI-MASS: m/z=332 (M+H$^+$)

Preparation 185
Methyl 4-[3-(4n-hexyloxyphenyl)pyrazol-5-yl]benzoate
IR (KBr): 2952, 1716, 1616, 1508, 1276, 1106 cm$^{-1}$ NMR (CDCl$_3$, δ): 0.91 (3H, T, J=6.3 Hz), 1.2–1.6 (6H, m), 1.7–1.9 (2H, m), 3.8–4.0 (5H, m), 6.76 (1H, s), 6.86 (2H, d, J=8.8 Hz), 7.54 (2H, d, =8.8 Hz), 7.77 (2H, d, J=8.4 Hz), 8.00 (2H, d, J=8.4 Hz) APCI-MASS: m/z=379 (M+H$^+$)

Preparation 186
A suspension of 1-(4-n-Pentyloxyphenyl)-3-(4-ethoxycarbonylphenyl)-1-buten-3-one (74.43 g) and hydroxyamine hydrochloride (28.23 g) and potassium carbonate (56.11 g) in ethanol (400 ml) was refluxed for 4 hours. The mixture was diluted with ethyl acetate, washed with water (×2), brine and dried over magnesium sulfate. The solvents were removed under reduced pressure to give crude oxime. To a solution of crude oxime in dichloroethane (500 ml) was added activated-manganese (IV) oxide (200 g). The reaction mixture was refluxed for 2 hours and filtered. The residue was washed with dichloromethane. The solvents were removed under reduced pressure and the residue was triturated with acetonitrile. The solid was collected by filtration and dried to give the ethyl 4-[5-(4-n-Pentyloxyphenyl)isoxazol-3-yl]benzoate (21.07 g).

IR (KBr): 2945, 2872, 1717, 1615, 1508, 1280, 1108 cm$^{-1}$ NMR (CDCl$_3$, δ): 0.95 (3H, t, J=6.9 Hz), 1.3–1.9 (9H, m), 4.01 (2H, t, J=6.5 Hz), 4.41 (2H, q, J=7.1 Hz), 6.74 (1H, s), 6.99 (2H, d, J=8.8 Hz), 7.76 (2H, d, J=8.8 Hz), 7.93 (2H, d, J=8.4 Hz), 8.15 (2H, d, J=8.4 Hz) APCI-MASS: m/z=380 (M+H$^+$)

The following compounds (Preparations 187 to 190) were obtained according to a similar manner to that of Preparation 48.

Preparation 187
Methyl 6-[4-[4-(8-Methoxyoctyloxy)phenyl]piperazin-1-yl]nicotinate IR (KBr): 2933, 2858, 1722, 1608, 1513, 1432, 1405, 1278, 1245 cm$^{-1}$ NMR (CDCl$_3$, δ): 1.3–1.9 (12H, m), 3.16 (4H, t, J=5.0 Hz), 3.33 (3H, s), 3.36 (2H, t, J=6.5 Hz), 3.8–4.0 (9H, m), 6.64 (1H, d, J=9.1 Hz), 6.85 (2H, d, J=9.2 Hz), 6.93 (2H, d, J=9.2 Hz), 8.04 (1H, dd, J=9.1 and 2.2 Hz), 8.81 (1H, d, J=2.2 Hz) APCI-MASS: m/z=456 (M+H$^+$)

Preparation 188
4-[4-(5-methoxypentyloxy)phenyl]bromobenzene

IR (KBr): 2940, 2856, 1604, 1479, 1286, 1255, 1124 cm$^{-1}$ NMR (CDCl$_3$, δ): 1.5–1.9 (6H, m), 3.34 (3H, s), 3.41 (2H, t, J=6.1 Hz), 3.99 (2H, t, J=6.4 Hz), 6.95 (2H, d, J=8.7 Hz), 7.4–7.6 (6H, m) APCI-MASS: m/z=349 (M+H$^+$)

Preparation 189
Methyl 6-(8-methoxyoctyloxy)-2-naphthoate NMR (DMSO-d$_6$, δ): 1.2–1.6 (10H, m), 1.7–1.9 (2H, m), 3.20 (3H, s), 3.29 (2H, t, J=6.4 Hz), 3.89 (3H, s), 4.11 (2H, t, J=6.4 Hz), 7.24 (1H, dd, J=9.0 and 2.4 Hz), 7.40 (1H, d, J=2.4 Hz), 7.88 (1H, d, J=8.7 Hz), 7.94 (1H, dd, J=8.7 and 1.5 Hz), 8.03 (1H, d, J=9.0 Hz), 8.55 (1H, d, J=1.5 Hz)

Preparation 190
4-[4-[4-(8-Methoxyoctyloxy)phenyl]piperazin-1yl]benzoic Acid Dihydrochloride IR (KBr): 1668.1, 1602.6, 1511.9, 1236.1 cm$^{-1}$ NMR (DMSO-d$_6$, δ): 1.2–1.8 (12H, m), 3.05–3.2 (4H, m), 3.29 (2H, t, J=7.1 Hz), 3.33 (3H, s), 3.4–3.55 (4H, m), 3.88 (2H, t, J=6.4 Hz), 6.82 (2H, d, J=9.0 Hz), 6.94 (2H, d, J=9.0 Hz), 7.02 (2H, d, J=8.8 Hz), 7.79 (2H, d, J=8.8 Hz), 12.31 (1H, s)

The following compounds (Preparations 191 to 254) were obtained according to a similar manner to that of Preparation 49.

Preparation 191
1-[4-[4-[4-[2-(4-Methylpentyl)-2,3-dihydro-4H, 1,2,4-triazol-3-one-4-yl]phenyl]piperazin-1-yl]benzoyl]benzotriazole 3-oxide IR (KBr): 1766.5, 1693.2, 1600.6, 1519.6 cm$^{-1}$

Preparation 192
1-[4-(4-Octylphenyl)-2,3-dihydro-4H-1,2,4-triazol-3one-2-yl-acetyl]benzotriazole 3-oxide IR (KBr): 2921.6, 1753.0, 1720.0, 1423.2 cm$^{-1}$ NMR (CDCl$_3$, δ): 0.88 (3H, t, J=6.7 Hz), 1.2–1.4 (10H, m), 1.5–1.8 (2H, m), 2.65 (2H, t, J=7.5 Hz), 5.46 (2H, s), 7.30 (2H, d, J=8.5 Hz), 7.48 (2H, d, J=8.5 Hz), 7.62 (1H, t, J=8.3 Hz), 7.80 (1H, s), 7.82 (1H, t, J=8.3 Hz), 8.05 (1H, d, J=8.3 Hz), 8.37 (1H, d, J=8.3 Hz)

Preparation 193
1-[4-[4-[4-(7-Methoxyheptyloxy)phenyl]piperazin-1-yl]benzoyl]benzotriazole 3-oxide IR (KBr): 1783.8, 1600.6, 1511.9, 1232.3, 1184.1 cm$^{-1}$ NMR (CDCl$_3$, δ): 1.3–1.9 (10H, m), 3.2–3.3 (4H, m), 3.34 (3H, s), 3.38 (2H, t, J=6.4 Hz), 3.5–3.7 (4H, m), 3.92 (2H, t, J=6.5 Hz), 6.87 (2H, d, J=9.2 Hz), 6.95 (2H, d, J=9.2 Hz), 7.00 (2H, d, J=9.0 Hz), 7.3–7.6 (3H, m), 8.09 (1H, d, J=8.2 Hz), 8.15 (2H, d, J=9.0 Hz)

Preparation 194
1-[4-[4-(4-n-Heptyloxyphenyl)piperazin-1-yl]benzoyl]benzotriazole 3-oxide IR (KBr): 1783.8, 1600.6, 1511.9, 1230.4, 1184.1 cm$^{-1}$ NMR (CDCl$_3$, δ): 0.90 (3H, t, J=6.3 Hz), 1.2–1.6 (8H, m), 1.7–1.9 (2H, m), 3.2–3.3 (4H, m), 3.5–3.7 (4H, m), 3.93 (2H, t, J=6.5 Hz), 6.87 (2H, d, J=9.2 Hz), 6.95 (2H, d, J=9.2 Hz), 7.00 (2H, d, J=9.0 Hz), 7.3–7.7 (3H, m), 8.09 (1H, d, J=8.2 Hz), 8.15 (2H, d, J=9.0 Hz)

Preparation 195
1-[4-[4-[4-(4-Methylpentyloxy)phenyl]piperazin-1-yl]benzoyl]benzotriazole 3-oxide NMR (CDCl$_3$, δ): 0.92 (6H, d, J=6.6 Hz), 1.2–1.4 (2H, m), 1.5–1.9 (3H, m), 3.1–3.3 (4H, m), 3.5–3.7 (4H, m), 3.92 (2H, t, J=6.6 Hz), 6.87 (2H, d, J=9.3 Hz), 6.96 (2H, d, J=9.3 Hz), 7.01 (2H, d, J=9.0 Hz), 7.4–7.6 (3H, m), 8.10 (1H, d, J=8.2 Hz), 8.15 (2H, d, J=9.0 Hz)

Preparation 196
1-[4-[4-(4-n-Pentyloxyphenyl)piperazin-1-yl]benzoyl]benzotriazole 3-oxide IR (KBr): 1787.7, 1600.6, 1511.9, 1232.3, 1184.1 cm$^{-1}$ NMR (CDCl$_3$, δ): 0.93 (3H, t, J=6.9 Hz), 1.3–1.6 (4H, m), 1.7–1.9 (2H, m), 3.1–3.4 (4H, m), 3.5–3.8 (4H, m), 3.93 (2H, t, J=6.6 Hz), 6.87 (2H, d, J=9.2 Hz), 6.92 (2H, d, J=9.2 Hz), 7.01 (2H, d, J=9.1 Hz), 7.4–7.6 (3H, m), 8.10 (1H, d, J=8.2 Hz), 8.15 (2H, d, J=9.1 Hz)

Preparation 197
1-[4-[4-[8-(1H-Tetrazol-1-yl)octyloxy]phenyl]benzoyl]benzotriazole 3-oxide and 1-[4-[4-[8-(2H-tetrazol-2-yl)octyloxy]phenyl]benzoyl]benzotriazole 3-oxide IR (KBr): 1778.0, 1602.6, 1189.9, 981.6 cm$^{-1}$ NMR (CDCl$_3$, δ): 1.2–1.6 (8H, m), 1.7–1.9 (2H, m), 1.9–2.2 (2H, m), 4.02 (2H, t, J=6.4 Hz), 4.44 and 4.66 (2H, t, J=7.1 Hz), 7.02 (2H, d, J=8.8 Hz), 7.4–7.6 (3H, m), 7.63 (2H, d, J=8.8 Hz), 7.79 (2H, d, J=8.6 Hz), 8.12 (1H, d, J=8.2 Hz), 8.32 (2H, d, J=8.6 Hz), 8.51 and 8.60 (1H, s)

Preparation 198
1-[4-[4-[8-(2,6-Dimethylmorpholin-4-yl)octyloxy]phenyl]benzoyl]benzotriazole 3-oxide IR (KBr): 1778.0, 1600.6, 977.7 cm$^{-1}$ NMR (CDCl$_3$, δ): 1.18 (6H, d, J=6.3 Hz), 1.2–1.7 (10H, m), 1.7–2.0 (4H, m), 2.4–2.6 (2H, m), 2.9–3.2 (2H, m), 3.7–3.9 (2H, m), 4.01 (2H, t, J=6.5 Hz), 7.02 (2H, d, J=8.8 Hz), 7.4–7.7 (3H, m), 7.63 (2H, d, J=8.8 Hz), 7.79 (2H, d, J=8.5 Hz), 8.12 (1H, d, J=8.1 Hz), 8.32 (2H, d, J=8.5 Hz)

Preparation 199
1-[6-[4-(4-Octyloxyphenyl)piperazin-1-yl]nicotinoyl]benzotriazole 3-oxide IR (KBr pelet): 2922, 2854, 1766, 1602, 1513, 1417, 1234, 1025, 950, 813 cm$^{-1}$ NMR (CDCl$_3$, δ): 0.89 (3H, t, J=6.8 Hz), 1.2–1.5 (10H, m), 1.7–1.9 (2H, m), 3.1–3.3 (4H, m), 3.9–4.1 (6H, m), 6.75 (1H, d, J=9.2 Hz), 6.87 (2H, d, J=9.2 Hz), 6.95 (2H, d, J=9.2 Hz), 7.4–7.6 (3H, m), 8.10 (1H, d, J=8.1 Hz), 8.19 (1H, dd, J=9.2 and 2.4 Hz), 9.04 (1H, d, J=2.4 Hz) APCI-MASS: m/z=529 (M+H$^+$)

Preparation 200
1-[2-(4-Hexyloxyphenyl)benzoxazol-5-yl-carbonyl]benzotriazole 3-oxide IR (KBr): 2950, 1774, 1623, 1504, 1265, 1176 cm$^{-1}$ NMR (CDCl$_3$, δ): 0.93 (3H, t, J=6.9 Hz), 1.3–1.6 (6H, m), 1.8–2.0 (2H, m), 4.07 (2H, t, J=6.5 Hz), 7.06 (2H, d, J=8.9 Hz), 7.4–7.6 (3H, m), 7.75 (1H, d, J=8.6 Hz), 8.13 (1H, d, J=8.2 Hz), 8.2–8.4 (3H, m), 8.67 (1H, d, =1.6 Hz) APCI-MASS: m/z=457 (M+H$^+$)

Preparation 201
1-[4-[4-(4-n-Butyloxyphenyl)phenyl]benzoyl]benzotriazole 3-oxide IR (KBr): 2958, 2871, 1776, 1600, 1398, 1255, 1211, 1037 cm$^{-1}$ NMR (CDCl$_3$, δ): 1.00 (3H, t, J=7.2 Hz), 1.4–1.9 (4H, m), 4.03 (2H, t, J=6.4 Hz), 7.01 (2H, d, J=8.3 Hz), 7.4–7.8 (9H, m), 7.87 (2H, d, J=8.1 Hz), 8.12 (1H, d, J=8.4 Hz), 8.36 (2H, d, J=7.9 Hz) APCI-MASS: m/z=464 (M+H)$^+$

Preparation 202
1-[2-(4-Heptyloxyphenyl)pyridin-5-yl-carbonyl]benzotriazole 3-oxide IR (KBr): 2944, 2867, 1793, 1770, 1589, 1471, 1321, 1093 cm$^{-1}$ NMR (CDCl$_3$, δ): 0.91 (3H, t, J=6.7 Hz), 1.2–1.6 (8H, m), 1.7–1.9 (2H, m), 4.05 (2H, t, J=6.5 Hz), 7.04 (2H, d, J=8.0 Hz), 7.4–7.6 (3H, m), 7.91 (1H, d, J=8.5 Hz), 8.1–8.2 (3H, m), 8.51 (1H, dd, J=8.5 and 2.3 Hz), 9.47 (1H, d, J=2.3 Hz) APCI-MASS: m/z=431 (M+M$^+$)

Preparation 203
1-[2-(2-Octyloxypyridin-5-yl)benzoxazol-5-yl-carbonyl]benzotriazole 3-oxide IR (KBr pelet): 2925, 2854, 1787, 1623, 1479, 1263, 989 cm$^{-1}$ NMR (CDCl$_3$, δ): 0.89 (3H, t, J=6.8 Hz), 1.2–1.5 (10H, m), 1.8–1.9 (2H, m), 4.42 (2H, t, J=6.7 Hz), 6.91 (1H, d, J=8.7 Hz), 6.4–6.6 (3H, m), 7.79 (1H, d, J=8.6 Hz), 8.13 (1H, d, J=8.2 Hz), 8.32 (1H, dd, J=8.6 and 1.7 Hz), 8.41 (1H, dd, J=8.7 and 2.4 Hz), 8.70 (1H, d, J=1.4 Hz), 9.07 (1H, d, J=1.9 Hz) APCI-MASS: m/z=486 (M+H$^+$)

Preparation 204
1-[2-[4-(4-Hexylphenyl)phenyl]benzoxazol-5-yl-carbonyl]benzotriazole 3-oxide IR (KBr): 2927, 2854, 1785, 1621, 1490, 1261, 1166, 1052 cm$^{-1}$ NMR (CDCl$_3$, δ): 0.90 (3H, t, J=6.5 Hz), 1.2–1.8 (8H, m), 2.68 (2H, t, J=7.9 Hz), 7.31 (2H, d, J=8.2 Hz), 7.4–7.7 (5H, m), 7.79–7.81 (3H, m), 8.13 (1H, d, J=8.3 Hz), 8.3–8.4 (3H, m), 8.73 (1H, d, J=1.3 Hz) APCI-MASS: m/z=517 (M+H$^+$)

Preparation 205
1-[2-[4-(4-n-Butyloxyphenyl)phenyl]pyridin-5-yl-carbonyl]benzotriazole 3-oxide IR (KBr): 2956, 2933, 2871, 1774, 1650, 1591, 1471, 1251 cm$^{-1}$ NMR (CDCl$_3$, δ): 1.00 (3H, t, J=7.2 Hz), 1.5–1.9 (4H, m), 4.03 (2H, t, J=6.4 Hz), 7.02 (2H, d, J=8.6 Hz), 7.4–7.6 (3H, m), 7.54 (2H, d, J=7.3 Hz), 7.62 (2H, d, J=8.5 Hz), 8.02 (1H, d, J=8.3 Hz), 8.13 (1H, d, J=8.2 Hz), 8.21 (2H, d, J=7.9 Hz), 8.57 (1H, dd, J=8.3 and 2.0 Hz), 9.54 (1H, d, J=2.0 Hz) APCI-MASS: m/z=465 (M+H)$^+$

Preparation 206
1-[4-[4-(5-Phenoxypentyloxy)phenyl]benzoyl]benzotriazole 3-oxide IR (KBr): 2944, 2869, 1770, 1600, 1494, 1249, 1189 cm$^{-1}$ NMR (CDCl$_3$, δ): 1.6–1.8 (2H, m), 1.8–2.0 (4H, m), 4.01 (2H, t, J=6.3 Hz), 4.07 (2H, t, J=6.2 Hz), 6.91 (2H, d, J=8.9 Hz), 7.04 (2H, d, J=8.7 Hz), 7.3–7.6 (4H, m), 7.63 (2H, d, J=8.6 Hz), 7.78 (2H, d, J=8.4 Hz), 8.12 (1H, d, J=8.1 Hz), 8.32 (2H, d, J=8.4 Hz) APCI-MASS: m/z=494 (M+H)$^+$

Preparation 207
1-[4-[5-(4-Hexyloxyphenyl)-1,3,4-oxadiazol-2-yl]benzoyl]benzotriazole 3-oxide IR (KBr): 2956, 2921, 2856, 1778, 1612, 1496, 1261, 1232, 1025 cm$^{-1}$ NMR (CDCl$_3$, δ): 0.92 (3H, t, J=6.7 Hz), 1.3–1.6 (6H, m), 1.8–2.0 (2H, m), 4.05 (2H, t, J=6.5 Hz), 7.05 (2H, d, J=8.7 Hz), 7.4–7.6 (3H, m), 8.10 (2H, d, J=8.7 Hz), 8.13 (1H, d, J=7.4 Hz), 8.37 (2H, d, J=8.5 Hz), 8.45 (2H, d, J=8.5 Hz) APCI-MASS: m/z=494 (M+H)$^+$

Preparation 208
1-[4-[5-(4-n-Hexyloxyphenyl)-1,3,4-thiadiazol-2-yl]benzoyl]benzotriazole 3-oxide IR (KBr): 2952, 2873, 1774, 1602, 1261, 1230, 1176 cm$^{-1}$ NMR (CDCl$_3$, δ): 0.92 (3H, t, J=6.8 Hz), 1.3–2.0 (8H, m), 4.04 (2H, t, J=6.5 Hz), 7.02 (2H, d, J=8.7 Hz), 7.4–7.7 (3H, m), 7.98 (2H, d, J=8.7 Hz), 8.13 (1H, d, J=8.7 Hz), 8.25 (2H, d, J=8.3 Hz), 8.41 (2H, d, J=8.3 Hz) APCI-MASS: m/z=500 (M+H)$^+$

Preparation 209
1-[5-(4-Octyloxyphenyl)-1-methylpyrazol-3-yl-carbonyl]benzotriazole 3-oxide IR (KBr pelet): 2939, 2852, 1776, 1687, 1612, 1448, 1249, 995 cm$^{-1}$ NMR (CDCl$_3$, δ): 0.89 (3H, t, J=6.7 Hz), 1.3–1.5 (10H, m), 1.7–1.9 (2H, m), 4.01 (2H, t, J=6.5 Hz), 4.25 (3H, s), 6.97 (2H, d, J=6.8 Hz), 7.4–7.7 (4H, m), 7.78 (2H, d, J=6.8 Hz), 8.14 (1H, d, J=8.0 Hz) APCI-MASS: m/z=448 (M+H$^+$)

Preparation 210
1-[4-[5-(4-n-Pentyloxyphenyl)pyrazol-3-yl]benzoyl]benzotriazole 3-oxide IR (KBr): 3251, 2956, 2869, 1780, 1612, 1506, 1232, 985 cm$^{-1}$ NMR (CDCl$_3$, δ): 0.95 (3H, t, J=6.9 Hz), 1.3–1.6 (4H, m), 1.7–2.0 (2H, m), 4.01 (2H, t, J=6.6 Hz), 6.90 (1H, s), 6.99 (2H, d, J=8.7 Hz), 7.4–7.6 (5H, m), 8.0–8.2 (3H, m), 8.33 (2H, d, J=8.4 Hz) APCI-MASS: m/z=468 (M+H$^+$)

Preparation 211
1-[5-[4-(4-n-Butoxyphenyl)phenyl]furan-2-yl-carbonyl]benzotriazole 3-oxide IR (KBr): 2958, 2871, 1781, 1678, 1603, 1535, 1479, 1265 cm$^{-1}$ NMR (CDCl$_3$, δ): 1.00 (3H, t, J=7.3 Hz), 1.4–1.9 (4H, m), 4.02 (2H, t, J=6.4 Hz), 6.9–7.1 (3H, m), 7.4–8.2 (11H, m) APCI-MASS: m/z=351 (Methyl ester)

Preparation 212
1-(3-(S)-Hydroxy-2-benzylhexadecanoyl)benzotriazole 3-oxide

IR (Neat: 2854.1, 1814.7, 1459.8,, 742.5 cm$^{-1}$

Preparation 213
1-(3-(R)-Benzyloxycarboxylamino-18-methoxyoctadecanoyl)benzotriazole 3-oxide IR (KBr): 1805.0, 1729.8, 1695.1 cm$^{-1}$ NMR (DMSO-d$_6$, δ): 1.1–1.65 (30H, m), 3.20 (3H, s), 3.28 (2H, t, J=6.5 Hz), 4.01 (1H, m), 5.06 (2H, s), 7.32 (5H, m), 7.4–7.8 (3H, m), 8.12 (1H, d, J=7 Hz)

Preparation 214
1(3-(S)-Hydroxyhexadecanoyl)benzotriazole 3-oxide

IR (KBr): 1710.6, 1498.4, 1429.0, 771.4 cm$^{-1}$ NMR (CDCl$_3$, δ): 0.88 (3H, t, J=6.4 Hz), 1.2–1.7 (24H, m), 2.00 (1H, s), 3.1–3.5 (2H, m), 4.30 (1H, m), 7.59 (1H, t, J=7.8 Hz), 7.81 (1H, t, J=7.8 Hz), 8.02 (1H, d, J=8.3 Hz), 8.42 (1H, d, J=8.3 Hz)

Preparation 215
1-(3-Methyl-2-tridecenoyl)benzotriazole 3-oxide

IR (KBr): 2927.4, 1791.5, 1633.4, 1081.9 cm$^{-1}$ NMR (CDCl$_3$, δ): 0.89 (3H, t, J=6.3 Hz), 1.1–1.7 (20H, m, 2.25 (3H, s), 6.08 (1H, s), 7.3–7.6 (3H, m), 8.06 (1H, d, J=8.2 Hz)

Preparation 216
1-[4-[4-[4-(8-Methyloxyoctyloxy)phenyl]piperazin-1-yl]benzoyl]benzotriazole 3-oxide IR (KBr): 1780.0, 1600.6, 1511.9, 1234.2, 1184.1 cm$^{-1}$ NMR (CDCl$_3$, δ): 1.3–1.9 (12H, m), 3.24 (4H, t, J=5.0 Hz), 3.33 (3H, s), 3.37 (2H, t, J=6.8 Hz), 3.62 (4H, t, J=5.0 Hz), 3.92 (2H, t, J=6.5 Hz), 6.8–7.1 (6H, m), 7.35–7.65 (3H, m), 8.09 (1H, d, J=8.2 Hz), 8.15 (2H, d, J=9.0 Hz)

Preparation 217
1-[3-Fluoro-4-[4-(4-n-hexyloxyphenyl)piperazine-1-yl]benzoyl]benzotriazole 3-oxide IR (KBr): 1778.0 cm$^-$ Preparation 218
1-[3-Chloro-4-[4-(4-n-hexyloxyphenyl)piperazin-1-yl]benzoyl]benzotriazole 3-oxide IR (KBr): 1778.0, 1594.8, 1511.9, 1218.8 cm$^{-1}$ NMR (CDCl$_3$, δ): 0.91 (3H, t, J=6.5 Hz), 1.2–1.6 (6H, m), 1.6–1.9 (2H, m), 3.29 (4H, t, J=3.6 Hz), 3.44 (4H, t, J=3.6 Hz), 3.93 (2H, t, J=6.5 Hz), 6.87 (2H, d, J=9.2 Hz), 6.97 (2H, d, J=9.2 Hz), 7.19 (1H, d, J=8.6 Hz), 7.4–7.7 (3H, m), 8.10 (1H, d, J=6.4 Hz), 8.14 (1H, dd, J=8.6 and 2.1 Hz), 8.27 (1H, d, J=2.1 Hz) APCI-MASS: m/z=534 (M$^+$+H)

Preparation 219
1-[4-(4-Piperidinopiperidin-1-yl)benzoyl]benzotriazole 3-oxide

IR (KBr): 1758.8, 1602.6, 1186.0 cm$^{-1}$ NMR (CDCl$_3$, δ): 1.35–1.8 (8H, m), 1.96 (2H, d, J=13 Hz), 2.45–2.7 (5H, m), 2.97 (2H, td, J=12.8 and 2.6 Hz), 4.04 (2H, d, J=13 Hz), 6.93 (2H, d, J=9.2 Hz), 7.35–7.6 (3H, m), 8.1–8.4 (3H, m)

Preparation 220
1-[3-[4-(4-n-Hexyloxyphenyl)piperazin-1yl]pyridazin-6-yl-carbonyl]benzotriazole 3-oxide IR (KBr): 1787.7, 1585.2, 1511.9, 1240.0 cm$^{-1}$ Preparation 221
1-[5-[4-(4-n-Hexyloxyphenyl)piperazin-1-yl]picolinoyl]benzotriazole 3-oxide IR (KBr): 1766.5, 1575.6, 1511.9, 1232.3 cm$^{-1}$ NMR (CDCl$_3$, δ): 0.91 (3H, t, J=6.5 Hz), 1.2–1.6 (6H, m), 1.65–1.9 (2H, m), 3.27 (4H, t, J=5.1 Hz), 3.66 (4H, t, J=5.1 Hz), 3.93 (2H, t, J=6.5 Hz), 6.88 (2H, d, J=9.2 Hz), 6.95 (2H, d, J=9.2 Hz), 7.25 (1H, dd, J=7.6 and 2.9 Hz), 7.35–7.6 (3H, m), 8.09 (1H, d, J=8.2 Hz), 8.18 (1H, d, J=8.9 Hz), 8.52 (1H, d, J=2.9 Hz) APCI-MASS: m/z=501 (M$^+$+H)

Preparation 222
1-[4-[4-(4-Cyclohexylphenyl)piperazin-1-yl]benzoyl]benzotriazole 3-oxide IR (KBr): 1770.3, 1602.6, 1515.8, 1232.3, 1186.0 cm$^{-1}$ NMR (CDCl$_3$, δ): 1.15–1.5 (6H, m), 1.65–2.0 (4H, m), 2.45 (1H, m), 3.33 (4H, t, J=5.1 Hz), 3.62 (4H, t, J=5.1 Hz), 6.92 (2H, d, =8.7 Hz), 6.99 (2H, d, J=9.2 Hz), 7.16 (2H, d, J=8.7 Hz), 7.35–7.65 (3H, m), 8.09 (1H, d, J=8.21 Hz), 8.15 (2H, d, J=9.2 Hz)

Preparation 223
1-[4-[4-(4-n-Hexylphenyl)piperazin-1-yl]benzoyl]benzotriazole 3-oxide IR (KBr): 1768.4, 1602.6, 1515.8, 1230.4, 1184.1 cm$^{-1}$ NMR (CDCl$_3$, δ): 0.89 (3H, t, J=6.5 Hz), 1.2–1.45 (6H, m), 1.5–1.7 (2H, m), 2.55 (2H, t, J=7.6 Hz), 3.2–3.4 (4H, m), 3.5–3.7 (4H, m), 6.91 (2H, d, J=8.6 Hz), 7.00 (2H, d, J=9.1 Hz), 7.13 (2H, d, J=8.5 Hz), 7.35–7.6 (3H, m), 8.09 (1H, d, J=8.2 Hz), 8.15 (2H, d, J=9.1 Hz)

Preparation 224
1-[4-[4-(4-Phenylcyclohexyl)piperazin-1-yl]benzoyl]benzotriazole 3-oxide IR (KBr): 1780.0, 1762.6, 1602.6, 1234.2, 1182.2 cm$^{-1}$ NMR (CDCl$_3$, δ): 1.3–1.7 (4H, m), 1.95–2.15 (4H, m), 2.35–2.6 (2H, m), 2.79 (4H, t, J=5.0 Hz), 3.49 (4H, t, J=5.0 Hz), 6.95 (2H, d, J=9.0 Hz), 7.1–7.35 (5H, m), 7.35–7.6 (3H, m), 8.08 (1H, d, J=7.1 Hz), 8.12 (2H, d, J=9.0 Hz)

Preparation 225
1-[4-[4-[1-(4-n-Hexyloxyphenyl)piperidin-4-yl]piperazin-1-yl]benzoyl]benzotriazole 3-oxide IR (KBr): 1768.4, 1602.6, 1511.9, 1234.2 cm$^{-1}$ NMR (CDCl$_3$, δ): 0.90 (3H, t, J=6.5 Hz), 1.2–1.55 (6H, m), 1.6–1.9 (4H, m), 1.96 (2H, d, J=11 Hz), 2.44 (1H, m), 2.64 (2H, d, J=1.1 Hz), 2.77 (4H, t, J=5.0 Hz), 3.48 (4H, t, J=5.0 Hz), 3.59 (2H, d, J=11 Hz), 3.91 (2H, t, J=6.5 Hz), 6.7–7.05 (6H, m), 7.35–7.6 (3H, m), 8.08 (1H, d, J=6.9 Hz), 8.12 (2H, d, J=7.7 Hz)

Preparation 226
1-[4-(4-Trans-n-pentylcylcohexyl)benzoyl]benzotriazole 3-oxide

IR (KBr): 1799.3, 1778.0, 1608.3, 1228.4, 977.7 cm$^{-1}$ NMR (CDCl$_3$,δ): 0.91 (3H, t, J=6.6 Hz), 1.0–1.7 (13H, m), 1.93 (4H, d, J=9.8 Hz), 2.62 (1H, t, J=12 Hz), 7.35–7.6 (5H, m), 8.09 (1H, d, J=7.9 Hz), 8.19 (2H, d, J=8.4 Hz)

Preparation 227
1-[6-(8-Methoxyoctyloxy)-2-naphthoyl]benzotriazole 3-oxide

IR (KBr): 2931.3, 2856.1, 1778.0, 1623.8 cm$^{-1}$

Preparation 228
1-(E)-[3-[4-[4-(7-Fluoroheptyloxy)phenyl]phenyl]acryloyl]benzotriazole 3-oxide IR (KBr): 3070.1, 2935.1, 2859.9, 1700.9, 1619.9, 1596.8 cm$^{-1}$ NMR (CDCl$_3$, δ): 1.30–2.00 (10H, m), 4.02 (2H, t, J=6.4 Hz), 4.45 (2H, dt, J=47.5 and 6.2 Hz), 6.70–8.65 (14H, m)

Preparation 229
1-(6-Heptylnaphthalene-2-carbonyl)benzotriazole 3-oxide

NMR (DMSO-d$_6$, δ): 0.75–0.93 (3H, m), 1.10–1.45 (8H, m), 1.55–1.80 (2H, m), 2.68–2.90 (2H, m), 7.35–9.06 (10H, m) APCI-MASS: m/z=388 (M$^+$+1)

Preparation 230
1-(E)-[3-[4-[4-(8-Methoxyoctyloxy)phenyl]phenyl]acryloyl]benzotriazole 3-oxide Preparation 231
1-(E)-[3-[4-[4-(5-Hexenyloxy)phenyl]phenyl]acryloyl]benzotriazole 3-oxide IR (KBr): 3072.0, 3033.5, 2939.0, 2865.7, 1780.0, 1693.2, 1619.9, 1596.8 cm$^{-1}$ NMR (DMSO-d$_6$, δ): 1.43–1.66 (2H, m), 1.66–1.90 (2H, m), 2.02–2.23 (2H, m), 3.90–4.16 (2H, m), 4.90–5.13 (2H, m), 5.72–6.00 (1H, m), 6.93–8.30 (14H, m) APCI-MASS: m/z=337 (Methyl ester, M$^+$+1)

Preparation 232
1-(E)-[3-[4-[4-(4-Methylpentyloxy)phenyl]phenyl]acryloyl]benzotriazole 3-oxide IR (KBr): 3072.0, 3033.5, 2952.5, 2869.6, 1780.0, 1693.2, 1618.0, 1598.7 cm$^{-1}$ NMR (DMSO-d$_6$, δ); 0.90 (6H, d, J=6.5 Hz), 1.20–1.40 (2H, m), 1.50–1.90 (3H, m), 3.90–4.10 (2H, m), 6.40–8.30 (14H, m) APCI-MASS: m/z=442 (M$^+$+1)

Preparation 233
1-(E)-[3-[4-[4-(6-Fluorohexyloxy)phenyl]phenyl]acryloyl]benzotriazole 3-oxide IR (KBr): 3074.0, 3033.5, 2939.0, 2865.7, 1780.0, 1697.1, 1598.7 cm$^{-1}$ NMR (DMSO-d$_6$, δ): 1.25–1.83 (6H, m), 4.04 (2H, t, J=6.5 Hz), 4.45 (2H, dt, J=47.5 and 6.5 Hz), 6.9–8.3 (14H, m) APCI-MASS: m/z=460 (M$^+$+1)

Preparation 234
1-(E)-[3-[4-[4-(6-Methoxyhexyloxy)phenyl]phenyl]acryloyl]benzotriazole 3-oxide NMR (DMSO-d$_6$, δ): 1.30–1.65 (6H, m), 1.65–1.90 (2H, m), 3.22 (3H, s), 3.22–3.40 (2H, m), 4.02 (2H, t, J=6.5 Hz), 6.5–8.3 (14H, m)

Preparation 235
1-[4-[3-(4-n-Hexyloxyphenyl)pyrazol-5-yl]benzoyl]benzotriazole 3-oxide IR (KBr): 2935, 1780, 1610, 1506, 1249, 1232, 1178, 1087 cm$^{-1}$ NMR (CDCl$_3$, δ): 0.91 (3H, d, J=6.4 Hz), 1.2–1.6 (6H, m), 1.7–1.9 (2H, m), 3.98 (2H, t, J=6.5 Hz), 6.8–7.0 (3H, m), 7.4–7.6 (5H, m), 8.00 (2H, d, J=8.4 Hz), 8.10 (1H, d, J=8.1 Hz), 8.28 (1H, d, J=8.4 Hz) APCI-MASS: m/z=482 (M+H$^+$)

Preparation 236
1-[4-[4-[4-(6-Methoxyhexyloxy)phenyl]phenyl]benzoyl]benzotriazole 3-oxide IR (KBr): 2935, 2858, 1774, 1600, 1490, 1257, 1211 cm$^{-1}$ NMR (CDCl$_3$, δ): 1.4–1.9 (8H, m), 3.35 (3H, s), 3.40 (2H, t, J=6.3 Hz), 4.02 (21H, t, J=6.4 Hz), 7.00 (2H, d, J=8.7 Hz), 7.4–7.8 (7H, m), 7.87 (2H, d, J=8.4 Hz), 8.12 (1H, d, J=8.2 Hz), 8.36 (2H, d, J=8.4 Hz) APCI-MASS: m/z=522 (M+H$^+$)

Preparation 237
1-[4-[5-[4-(8-Methoxyoctyloxy)phenyl]-1,3,4-thiadiazol-2-yl]benzoyl]benzotriazole 3-oxide IR (KBr): 2929, 2854, 1776, 1602, 1469, 1255 cm$^{-1}$ NMR (CDCl$_3$, δ): 1.2–1.6 (10H, m), 1.7–1.9 (2H, m), 3.33 (3H, s), 3.37 (2H, d, J=6.4 Hz), 4.03 (2H, d, J=6.5 Hz), 7.00 (2H, d, J=8.9 Hz), 7.4–7.6 (3H, m), 7.97 (2H, d, J=8.9 Hz), 8.12 (1H, d, J=8.2 Hz), 8.23 (2H, d, J=8.7 Hz), 8.39 (2H, d, J=8.7 Hz) APCI-MASS: m/z=558 (M+H$^+$)

Preparation 238
1-[4-(4-n-Butoxyphenyl)cinnamoyl]benzotriazole 3-oxide

IR (KBr): 2952, 2867, 1778, 1598, 1496, 1249, 1186 cm$^{-1}$ NMR (CDCl$_3$, δ): 0.99 (3H, t, J=7.3 Hz), 1.55 (2H, tq, J=7.0 and 7.3 Hz), 1.78 (2H, tt, J=7.0 and 6.4 Hz), 4.02 (2H, t, J=6.4 Hz), 6.75 (1H, d, J=16.0 Hz), 7.00 (2H, d, J=8.7 Hz), 7.4–8.2 (9H, m) APCI-MASS: m/z=414 (M+H$^+$)

Preparation 239
1-[4-[5-(4-Cyclohexylphenyl)-1,3,4-thiadiazol-2-yl]benzoyl]benzotriazole 3-oxide IR (KBr): 2925, 2850, 1778, 1230, 989 cm$^{-1}$ NMR (CDCl$_3$, δ): 1.2–1.6 (5H, m), 1.7–2.0 (5H, m), 2.5–2.7 (1H, m), 7.37 (2H, d, J=8.3 Hz), 7.4–7.6 (3H, m), 7.97 (2H, d, J=8.3 Hz), 8.13 (1H, d, J=8.2 Hz), 8.26 (2H, d, J=8.6 Hz), 8.42 (2H, d, J=8.6 Hz) APCI-MASS: m/z=482 (M+H)$^+$

Preparation 240
1-[4-[5-[4-(4-n-Propyloxyphenyl)phenyl]-1,3,4-oxadiazol-2-yl]benzoyl]benzotriazole 3-oxide IR (KBr): 1778, 1604, 1488, 1249, 1232, 998 cm$^{-1}$ NMR (CDCl$_3$, δ): 1.07 (3H, t, J=7.4 Hz), 1.85 (2H, tq, J=6.5 and 7.4 Hz), 7.02 (2H, d, J=8.8 Hz), 7.4–7.7 (3H, m), 7.61 (2H, d, J=8.8 Hz), 7.75 (2H, d, J=8.5 Hz), 8.14 (1H, d, J=8.2 Hz), 8.22 (2H, d, J=8.5 Hz), 8.40 (2H, d, J=8.8 Hz), 8.48 (2H, d, J=8.8 Hz) APCI-MASS: m/z=518 (M+H)$^+$

Preparation 241
1-[4-(5-n-Nonyl-1,3,4-oxadiazol-2-yl)benzoyl]benzotriazole 3-oxide IR (KBr): 2919, 2850, 1780, 1565, 1415, 1251 cm$^{-1}$ NMR (CDCl$_3$, δ): 0.89 (3H, t, J=6.7 Hz), 1.2–1.6 (12H, m), 1.8–2.0 (2H, m), 2.98 (2H, t, J=7.7 Hz), 7.4–7.6 (3H, m), 8.12 (1H, d, J=9.0 Hz), 8.28 (2H, d, J=8.7 Hz), 8.42 (2H, d, J=8.7 Hz) APCI-MASS: m/z=434 (M+H$^+$)

Preparation 242
1-[4-[3-(4-n-Hexyloxyphenyl)-1,2,4-oxadiazol-5-yl]benzoyl]benzotriazole 3-oxide IR (KBr): 2946, 2869, 1780, 1251, 1230, 1001 cm$^{-1}$ NMR (CDCl$_3$, δ): 0.92 (3H, t, J=6.8 Hz), 1.3–1.6 (6H, m), 1.8–1.9 (2H, m), 4.04 (2H, t, J=6.5 Hz), 7.03 (2H, d, J=8.9 Hz), 7.4–7.6 (3H, m), 8.0–8.2 (3H, m), 8.46 (4H, s) APCI-MASS: m/z=484 (M+H$^+$)

Preparation 243
1-[4-[5-(4-n-Octyloxyphenyl)-1,3,4-thiadiazol-2-yl]benzoyl]benzotriazole 3-oxide IR (KBr): 2925, 2856, 1774, 1602, 1259, 1232, 989 cm$^{-1}$ NMR (CDCl$_3$, δ): 0.90 (3H, t, J=6.7 Hz), 1.1–1.6 (10H, m), 1.7–1.9 (2H, m), 4.04 (2H, t, J=6.5 Hz), 7.01 (2H, d, J=8.9 Hz), 7.4–7.6 (3H, m), 7.97 (2H, d, J=8.8 Hz), 8.12 (1H, d, J=8.2 Hz), 8.24 (2H, d, J=8.6 Hz), 8.40 (2H, d, J=8.6 Hz) APCI-MASS: m/z=528 (M+H$^+$)

Preparation 244
1-[4-[5-(4-Trans-n-pentylcyclohexyl)-1,3,4-thiadiazol-2-yl]benzoyl]benzotriazole 3-oxide IR (KBr): 2952, 2919, 2848, 1785, 1444, 1226, 991 cm$^{-1}$ NMR (CDCl$_3$, δ): 0.90 (3H, t, J=6.9 Hz), 1.0–1.7 (13H, m), 1.94 (2H, d, J=12.0 Hz), 2.27 (2H, d, J=12.0 Hz), 3.19 (1H, tt, J=12.0 and 3.6 Hz), 7.4–7.6 (3H, m), 8.12 (1H, d, J=8.0 Hz), 8.19 (2H, d, J=8.6 Hz), 8.38 (2H, d, J=8.6 Hz)

APCI-MASS: m/z=476 (M+H$^+$)

Preparation 245
1-[4-[3-(4-n-Pentyloxyphenyl)isoxazol-5-yl]benzoyl]benzotriazole 3-oxide IR (KBr): 2948, 2867, 1776, 1610, 1436, 1253, 1002 cm$^{-1}$ NMR (CDCl$_3$, δ): 0.95 (3H, t, J=7.1 Hz), 1.2–1.6 (4H, m), 1.7–1.9 (2H, m), 4.02 (2H, t, J=6.5 Hz), 7.0–7.1 (3H, m), 7.4–7.6 (3H, m), 7.81 (2H, d, J=8.8 Hz), 8.06 (2H, d, J=8.6 Hz), 8.12 (1H, d, J=8.0 Hz), 8.39 (2H, d, J=8.6 Hz)

APCI-MASS: m/z=469 (M+H$^+$)

Preparation 246
1-[4-[5-[4-(8-Methoxyoctyloxy)phenyl]-1,3,4-oxadiazol-2-yl]benzoyl]benzotriazole 3-oxide IR (KBr): 2923, 2854, 1787, 1608, 1494, 1255, 1228, 993 cm$^{-1}$ NMR (CDCl$_3$, δ): 1.2–1.6 (10H, m), 1.7–1.9 (2H, m), 3.34 (3H, s), 3.38 (2H, t, J=6.4 Hz), 4.05 (2H, t, J=6.5 Hz), 7.04 (2H, d, J=8.8 Hz), 7.4–7.6 (3H, s), 8.1–8.2 (3H, s), 8.36 (2H, d, J=8.7 Hz), 8.45 (2H, d, J=8.7 Hz)

APCI-MASS: m/z=542 (M+H$^+$)

Preparation 247

1-[4-[4-(6-Phenylpyridazin-3-yl-oxy)phenyl]benzoyl]benzotriazole 3-oxide

IR (KBr): 1783, 1604, 1423, 1284, 985 cm$^{-1}$

NMR (CDCl$_3$, δ): 7.2–8.2 (15H, m), 8.12 (2H, d, J=8.3 Hz), 8.36 (2H, d, J=8.4 Hz)

APCI-MASS: m/z=486 (M$^+$+1)

Preparation 248

1-[4-[5-(4-n-Octyloxyphenyl)-1,3,4-oxadiazol-2-yl]benzoyl]benzotriazole 3-oxide

IR (KBr): 2925, 2854, 1780, 1610, 1496, 1257, 1228, 1180 cm$^{-1}$

NMR (CDCl$_3$, δ): 0.89 (3H, t, J=6.8 Hz), 1.2–2.0 (12H, m), 4.05 (2H, t, J=6.5 Hz), 7.05 (2H, d, J=8.7 Hz), 7.4–7.6 (3H, m), 8.0–8.2 (3H, m), 8.37 (2H, d, J=8.6 Hz), 8.45 (2H, d, J=8.6 Hz)

APCI-MASS: m/z=512 (M+H$^+$)

Preparation 249

1-[4-[2-(4-n-Hexyloxyphenyl)pyrimidin-6-yl]benzoyl]benzotriazole 3-oxide

IR (KBr): 2948, 2861, 1780, 1552, 1413, 1378, 987 cm$^{-1}$

NMR (CDCl$_3$, δ): 0.92 (3H, t, J=6.8 Hz), 1.2–1.6 (6H, m), 1.8–2.0 (2H, m), 4.06 (2H, t, J=6.5 Hz), 7.04 (2H, d, J=9.0 Hz), 7.4–7.6 (3H, m), 7.64 (1H, d, J=5.2 Hz), 8.13 (1H, d, J=8.2 Hz), 8.44 (4H, s), 8.55 (2H, d, J=9.0 Hz), 8.90 (1H, d, J=5.2 Hz)

APCI-MASS: m/z=494 (M+H$^+$)

Preparation 250

1-[4-[4-[8-(2-Ethoxyethoxy)octyloxy]phenyl]benzoyl]benzotriazole 3-oxide

IR (KBr): 2933, 2861, 1778, 1598, 1247, 1186, 977 cm$^{-1}$

NMR (CDCl$_3$, δ): 1.22 (3H, t, J=7.0 Hz), 1.3–2.0 (14H, m), 3.4–3.6 (6H, m), 4.02 (2H, t, J=6.5 Hz), 7.02 (2H, d, J=8.8 Hz), 7.4–7.6 (3H, m), 7.62 (2H, d, J=8.8 Hz), 7.78 (2H, d, J=8.6 Hz), 8.10 (1H, d, J=8.9 Hz), 8.31 (2H, d, J=8.6 Hz)

APCI-MASS: m/z=532 (M+H$^+$)

Preparation 251

1-[4-[4-[7-(Piperidin-1-yl-carbonyl)heptyloxy]phenyl]benzoyl]benzotriazole 3-oxide IR (KBr): 2935, 2856, 1774, 1631, 1598, 1255, 1191 cm$^{-1}$ NMR (CDCl$_3$, δ): 1.3–2.0 (16H, m), 2.37 (2H, t, J=7.6 Hz), 3.48 (4H, s), 4.02 (2H, t, J=6.4 Hz), 7.02 (2H, d, J=8.6 Hz), 7.4–7.6 (3H, m), 7.63 (2H, d, J=8.6 Hz), 7.78 (2H, d, J=8.3 Hz), 8.11 (1H, d, J=8.1 Hz), 8.31 (2H, d, J=8.3 Hz)

APCI-MASS: m/z=541 (M+H$^+$)

Preparation 252

1-[6-[4-(4-n-Heptyloxyphenyl)piperazin-1-yl]nicotinoyl]benzotriazole 3-oxide

IR (KBr): 2929, 2856, 1762, 1604, 1510, 1240 cm$^{-1}$

NMR (CDCl$_3$, δ): 0.89 (3H, t, J=6.7 Hz), 1.2–1.9 (10H, m), 3.20 (4H, t, J=5.0 Hz), 3.8–4.0 (6H, m), 6.75 (1H, d, J=9.5 Hz), 6.86 (2H, d, J=9.3 Hz), 6.95 (2H, d, J=9.3 Hz), 7.3–7.6 (3H, m), 8.10 (1H, d, J=8.2 Hz), 8.19 (1H, dd, J=9.2 and 2.3 Hz), 9.05 (1H, d, J=2.3 Hz)

APCI-MASS: m/z=515 (M+H$^+$)

Preparation 253

1-[6-[4-[4-(8-Methoxyoctyloxy)phenyl]piperazin-1-yl]nicotinoyl]benzotriazole 3-oxide IR (KBr): 2929, 2854, 1766, 1602, 1510, 1419, 1234 cm$^{-1}$ NMR (CDCl$_3$, δ): 1.3–1.9 (12H, m), 3.2–3.3 (4H, m), 3.33 (3H, s), 3.36 (2H, t, J=6.4 Hz), 3.92 (2H, t, J=6.5 Hz), 4.0–4.2 (4H, m), 6.75 (1H, ,d, J=9.1 Hz), 6.87 (2H, d, J=8.9 Hz), 7.0–7.2 (2H, m), 7.4–7.6 (3H, m), 8.09 (1H, d, J=8.1 Hz), 8.20 (1H, dd, J=9.1 and 2.3 Hz), 9.05 (1H, d, J=2.3 Hz)

APCI-MASS: m/z=559 (M+H$^+$)

Preparation 254

1-[4-[5-[4-(4-n-Propyloxyphenyl)phenyl]-1,3,4-thiadiazol-2-yl]benzoyl]benzotriazole 3-oxide IR (KBr): 1774, 1600, 1234, 985 cm$^{-1}$ NMR (CDCl$_3$, δ): 1.07 (3H, t, J=7.3 Hz), 1.85 (2H, tq, J=6.5 and 7.3 Hz), 3.99 (2H, t, J=6.5 Hz), 7.01 (2H, d, J=8.7 Hz), 7.4–7.7 (5H, m), 7.72 (2H, d, J=8.7 Hz), 8.1–8.2 (2H, m), 8.28 (2H, d, J=8.6 Hz), 8.44 (2H, d, J=8.6 Hz)

APCI-MASS: m/z=534 (M+H)$^+$

The following compounds (Preparation 255 to 256) were obtained according to a similar manner to that of Preparation 32.

Preparation 255

6-Heptylnaphthalene-2-carboxylic acid

NMR (CDCl$_3$, δ): 0.88 (3H, t, J=6.6 Hz), 1.15–1.53 (8H, m), 1.58–1.88 (2H, m), 2.80 (2H, t, J=7.6 Hz), 7.42 (1H, dd, J=1.7 and 8.4 Hz), 7.67 (1H, s), 7.84 (1H, d, J=8.6 Hz), 7.90 (1H, d, J=8.4 Hz), 8.09 (1H, dd, J=1.7 and 8.6 Hz), 8.68 (1H, s)

APCI-MASS: m/z=271 (M$^+$+1), 285 (methyl ester$^+$–1)

Preparation 256

3-(E)-[4-[4-(7-Fluoroheptyloxy)phenyl]phenyl]acrylic acid

IR (KBr): 3037.3, 2935.1, 2861.8, 1679.7, 1633.4, 1600.6 cm$^{-1}$

NMR (DMSO-d$_6$, δ): 1.30–1.85 (10H, m), 4.01 (2H, t, J=6.4 Hz), 4.44 (2H, dt, J=47.6 and 6.1 Hz), 6.54 (1H, d, J=15.9 Hz), 7.02 (2H, d, J=8.7 Hz), 7.53–7.80 (7H, m)

Preparation 257

To a solution of 4-methylpentanol (3.0 ml) in pyridine (20 ml) were added in turn with p-toluenesulfonyl chloride (4.6 g) and 4-N,N-dimethylaminopyridine (1.5 g) at ambient temperature. After stirring at ambient temperature, the reaction mixture was taken up into a mixture of ethyl acetate (100 ml) and water (100 ml). The separated organic layer was washed in turn with hydrochloric acid(1N), water, aqueous sodium hydrogencarbonate, and brine, and dried over magnesium sulfate. Evaporation gave 1-p-Toluenesulfonyloxy-4-methylpentane (5.30 g).

NMR (CDCl$_3$, δ): 0.83 (6H, d, J=6.6 Hz), 1.48 (1H, sept, J=6.6 Hz), 1.50–1.70 (2H, m), 2.45 (3H, s), 4.00 (2H, t, J=6.6 Hz), 7.34 (2H, d, J=8.1 Hz), 7.79 (2H, d, J=8.1 Hz)

APCI-MASS: m/z=257 (M$^+$+1)

Preparation 258

To a solution of 4-bromo-4'-n-butyloxybiphenyl (3.05 g) in tetrahydrofuran (60 ml) was added 1.55M n-butyllithium in n-hexane (7.74 ml) at −60° C. over a period of 10 minutes.

The solution was stirred at −30° C. for 1.5 hours and cooled to −60° C. To the solution was added triisopropylborate (3.46 ml) over a period of 5 minutes, and the mixture was stirred for 1.5 hours without cooling. To the solution was added 1N hydrochloric acid (20 ml) and the solution was stirred for 30 minutes and extracted with ethyl acetate. The organic layer was separated and washed with water, brine and dried over magnesium sulfate. The solvents were removed under reduced pressure and the residue was triturated with n-hexane. The solid was collected by filtration and dried under reduced pressure to give 4-(4-n-Butyloxyphenyl)phenylboronic acid (2.31 g).

IR (KBr): 3398, 2956, 2919, 2871, 1604, 1531, 1392, 1257 cm$^{-1}$

NMR (DMSO-d$_6$, δ): 0.94 (3H, t, J=7.3 Hz), 1.4–1.8 (4H, m), 4.01 (2H, t, J=6.3 Hz), 7.01 (2H, d, J=8.7 Hz), 7.58 (2H, d, J=7.9 Hz), 7.62 (2H, d, J=8.7 Hz), 7.84 (2H, d, J=7.9 Hz), 8.03 (2H, s)

The following compounds (Preparation 259 to 260) were obtained according to a similar manner to that of Preparation 258.

Preparation 259

4-[4-(6-Methoxyphexyloxy)phenyl]phenylboronic acid

IR (KBr): 3448, 3392, 2937, 2861, 1606, 1529, 1346, 1288 cm$^{-1}$

NMR (DMSO-d$_6$, δ): 1.3–1.8 (8H, m), 3.21 (3H, s), 3.31 (2H, t, J=6.3 Hz), 3.99 (2H, t, J=6.4 Hz), 7.00 (2H, d, J=8.7 Hz), 7.5–7.7 (4H, m), 7.84 (2H, d, J=8.1 Hz), 8.03 (2H, s)

APCI-MASS: m/z=329 (M+H$^+$)

Preparation 260

4-[4-(5-Methoxypentyloxy)phenyl]phenylboronic acid

IR (KBr): 3473, 3369, 3330, 2935, 2863, 1604, 1531, 1338, 1251 cm$^{-1}$

NMR (DMSO-d$_6$, δ): 1.4–1.8 (6H, m), 3.22 (3H, s), 3.3–3.4 (2H, m), 3.99 (2H, ,t, J=6.4 Hz), 7.00 (2H, d, J=8.7 Hz), 7.58 (2H, d, J=8.0 Hz), 7.61 (2H, d, J=8.7 Hz), 7.84 (2H, d, J=8.0 Hz), 8.04 (2H, s)

APCI-MASS: m/z=315 (M+H$^+$)

Preparation 261

To a suspension of 4-Methoxycarbonylphenyl boronic acid (648 mg) and 4-iodo-1-heptylpyrazole (876 mg) and Pd(PPh$_3$)$_4$ (173 mg) in 1,2-dimethoxyethane (10 ml) was added 2M Na$_2$CO$_3$ aq. (3.6 ml). The reaction mixture was stirred at 80° C. for 2 hours under N$_2$ atmosphere, and poured into ice-water and extracted with ethyl acetate. The organic layer was washed with brine, and dried over MgSO$_4$. The solvent was removed under pressure. The residue was subjected to column-chromatography on silica gel 60 (Merk) and eluted with n-hexane/ethyl acetate (80:20). The fractions containing the object compound were combined and evaporated under reduced pressure to give 1-heptyl-4-(4-methoxycarbonylphenyl)pyrazole (0.20 g).

IR (KBr): 2952, 2920, 2848, 1712, 1610, 1288, 1114, 769 cm$^{-1}$

NMR (DMSO-d$_6$, δ): 0.85 (3H, t, J=6.7 Hz), 1.1–1.4 (8H, m), 1.7–1.9 (2H, m), 3.85 (3H, s), 4.11 (2H, t, J=7.0 Hz), 7.72 (2H, d, J=8.5 Hz), 7.93 (2H, d, J=8.5 Hz), 7.99 (1H, s), 8.34 (1H, s)

APCI-MASS: m/z=301 (M+H$^+$)

The following compounds (Preparations 262 to 268) were obtaining according to a similar manner to that of Preparation 261.

Preparation 262

Ethyl 4-[4-(4-n-butyloxyphenyl)phenyl]benzoate

IR (KBr): 2958, 2935, 2871, 1714, 1602, 1396, 1280, 1108 cm$^{-1}$

NMR (CDCl$_3$, δ): 0.99 (3H, t, J=7.3 Hz), 1.4–2.0 (7H, m), 4.02 (2H, t, J=6.4 Hz), 4.40 (2H, q, J=7.1 Hz), 6.98 (2H, d, J=6.8 Hz), 7.56 (2H, d, J=6.8 Hz), 7.66 (4H, s), 7.68 (2H, d, J=8.4 Hz), 8.12 (2H, d, J=8.4 Hz)

APCI-MASS: m/z=375 (M+H)$^+$

Preparation 263

Methyl 6-(4-heptyloxyphenyl)nicotinate

IR (KBr): 2954, 2859, 1724, 1597, 1288, 1251, 1116, 783 cm$^{-1}$

NMR (CDCl$_3$, δ): 0.90 (3H, t, J=6.6 Hz), 1.2–1.5 (8H, m), 1.7–1.9 (2H, m), 3.96 (3H, s), 4.03 (2H, t, J=6.5 Hz), 7.00 (2H, d, J=8.8 Hz), 7.75 (1H, d, J=8.4 Hz), 8.02 (1H, d, J=8.8 Hz), 8.30 (1H, dd, J=8.4 and 2.2 Hz), 9.23 (1H, d, J=2.2 Hz)

APCI-MASS: m/z=328 (M+H$^+$)

Preparation 265

Methyl 5-[4-(4-n-butyloxyphenyl)phenyl]furan 2-carboxylate

IR (KBr): 2958, 2933, 2873, 1716, 1483, 1303, 1139 cm$^{-1}$

NMR (CDCl$_3$, δ): 0.99 (3H, t, J=7.3 Hz), 1.5–1.9 (4H, m), 3.93 (3H, s), 4.01 (2H, t, J=6.4 Hz), 6.75 (1H, d, J=3.6 Hz), 6.98 (2H, d, J=8.7 Hz), 7.26 (1H, d, J=3.6 Hz), 7.56 (2H, d, J=8.4 Hz), 7.61 (2H, d, J=8.7 Hz), 7.83 (2H, d, J=8.4 Hz)

APCI-MASS: m/z=351 (M+H)$^+$ (2H, t, J=6.4 Hz), 4.01 (2H, t, J=6.4 Hz), 4.41 (2H, q, J=7.1 Hz), 6.98 (2H, d, J=8.7 Hz), 7.56 (2H, d, J=8.7 Hz), 7.6–7.8 (6H, m), 8.12 (2H, d, J=8.4 Hz)

APCI-MASS: m/z=433 (M+H$^+$)

Preparation 267

4-[4-[4-(5-Methoxypentyloxy)phenyl]phenyl]benzoic acid

IR (KBr): 2939, 2859, 1679, 1587, 1396, 1321, 1292, 1126 cm$^{-1}$

NMR (DMSO-d$_6$, δ): 1.3–1.8 (6H, m), 3.21 (3H, s), 3.2–3.4 (2H, m), 4.01 (2H, t, J=6.5 Hz), 7.04 (2H, d, J=8.6 Hz), 7.66 (2H, d, J=8.6 Hz), 7.7–7.9 (6H, m), 8.03 (2H, d, J=8.2 Hz)

APCI-MASS: m/z=391 (M+H$^+$)

Preparation 268

Methyl 4-[4-[4-(5-methoxypentyloxy)phenyl]phenyl] phenyl acetate

IR (KBr): 2937, 2863, 1739, 1604, 1492, 1255 cm$^{-1}$

NMR (CDCl$_3$, δ): 1.5–2.0 (6H, m), 3.34 (3H, s), 3.42 (2H, t, J=6.3 Hz), 3.68 (2H, s), 3.72 (3H, s), 4.02 (2H, t, J=6.4 Hz), 6.97 (2H, d, J=8.7 Hz), 7.36 (2H, d, J=8.2 Hz), 7.5–7.7 (8H, m)

APCI-MASS: m/z=419 (M+H$^+$)

Preparation 269

A solution of 3-[2-(4-Hexylphenylamino)ethyl]-2-oxo-oxazolidine hydrochloride (2.131 g) in 25% hydrobromic acid in acetic acid (13.04 ml) was stirred for 96 hours at ambient temperature. The reaction mixture was pulverized with diisopropyl ether. The precipitate was collected by filtration and added to ethanol (15 ml). The solution was refluxed for 5 hours and pulverized with diisopropyl ether. The precipitate was collected by filtration to give 1-(4-n-Hexylphenyl)piperazine dihydrobromide (2.413 g).

IR (KBr): 2921.6, 2711.4, 2485.5, 1452.1, 1012.4 cm$^{-1}$

NMR (DMSO-d$_6$, δ): 0.85 (3H, t, J=6.6 Hz), 1.1–1.4 (6H, m), 1.4–1.6 (2H, m), 2.49 (2H, t, J=8.4 Hz), 3.1–3.4 (8H, m), 6.54 (2H, s), 6.90 (2H, d, J=8.7 Hz), 7.08 (2H, d, J=8.7 Hz), 8.78 (1H, s)

APCI-MASS: m/z=247 (M$^+$+H)

The following compounds (Preparations 270 to 274) were obtained according to a similar manner to that of Preparation 269.

Preparation 270

4-[4-(4-n-Hexylphenyl)piperazin-1-yl]benzoic acid dihydrobromide

IR (KBr): 2956.3, 1691.3, 1664.3, 1602.6, 1232.3 cm$^{-1}$

NMR (DMSO-d$_6$, δ): 0.85 (3H, t, J=6.5 Hz), 1.2–1.4 (10H, m), 1.4–1.6 (2H, m), 2.51 (2H, t, J=7.4 Hz), 3.2–3.6 (8H, m), 7.0–7.2 (6H, m), 7.81 (2H, d, J=8.8 Hz)

APCI-MASS: m/z=367 (M$^+$+H)

Preparation 271

1-[4-Cyclohexylphenyl)piperazine dihydrobromide

IR (KBr): 2927.4, 1510.0, 1452.1 cm$^{-1}$

NMR (DMSO-d$_6$, δ): 1.1–1.5 (6H, m), 1.6–1.9 (4H, m), 2.41 (1H, m), 3.1–3.4 (8H, m), 6.91 (2H, d, J=8.7 Hz), 7.11 (2H, d, J=8.7 Hz), 8.78 (1H, s)

APCI-MASS: m/z=245 (M$^+$+H)

Preparation 272

4-[4-(4-Cyclohexylphenyl)piperazin-1-yl]benzoic acid dihydrobromide

IR (KBr): 1668.1, 1602.6, 1230.4, 1189.9 cm$^{-1}$

APCI-MASS: m/z=365 (M$^+$+H)

Preparation 273

3-Fluoro-4-[4-(4-hydroxyphenyl)piperazin-1-yl]benzoic acid dihydrobromide

IR (KBr): 1708.6, 1610.3 cm$^{-1}$

NMR (DMSO-d$_6$, δ): 3.2–3.6 (8H, m), 6.81 (2H, d, J=8.6 Hz), 7.0–7.4 (3H, m), 7.4–7.8 (2H, m)

APCI-MASS: m/z=317 (M$^+$+H)

Preparation 274

4-[4-(4-Hydroxyphenylpiperazin-1-yl]benzoic acid dihydrobromide

IR (KBr): 1670.1, 1604.5, 1226.5, 775.2 cm$^{-1}$

NMR (DMSO-d$_6$, δ): 3.0–3.2 (4H, m), 3.3–3.5 (4H, m), 6.68 (2H, d, J=8.8 Hz), 6.85 (2H, d, J=8.8 Hz), 7.02 (2H, d, J=8.8 Hz), 7.79 (2H, d, J=8.8 Hz), 8.86 (1H, s), 12.29 (1H, s)

APCI-MASS: m/z=299 (M+H$^+$)

Preparation 275

A mixture of 4-n-hexyloxyaniline (10 g), ethyl acrylate (56.1 ml), glacial acetic acid (19.25 ml), and cuprous chloride (1.02 g) was heated under reflux with stirring under nitrogen for 26 hours. A solution of the cold product in ether was shaken with water and then with aqueous ammonia. The organic layer was taken and dried over magnesium sulfate. The magnesium sulfate was filtered off, and filtrate was evaporated under reduced pressure. The residue was subjected to column chromatography on silica gel and eluted with hexane-ethyl acetate (9:1). The fractions containing the object compound were combined and evaporated under reduced pressure to give Ethyl 3-[N-(2-ethoxycarbonylethyl)-N-(4-hexyloxyphenyl)amino]propionate (15.756 g).

IR (Neat): 1733.7, 1513.8, 1241.9, 1182.2 cm$^{-1}$

NMR (CDCl$_3$, δ): 0.90 (3H, t, J=6.5 Hz), 1.2–1.55 (6H, m), 1.24 (6H, t, J=7.1 Hz), 1.65–1.85 (2H, m), 2.51 (4H, t, J=7.2 Hz), 3.53 (4H, t, J=7.2 Hz), 3.89 (2H, t, J=6.5 Hz), 4.12 (4H, q, J=7.1 Hz), 6.72 (2H, d, J=9.3 Hz), 6.83 (2H, d, J=9.3 Hz)

APCI-MASS: m/z=394 (M$^+$+H)

Preparation 276

A suspension of methyl 4-formylbenzoate (4.92 g) hydroxylamine hydrochloride (5.21 g) and sodium acetate (6.15 g) in ethanol (50 ml) was refluxed for 2 hours. The mixture was poured into water and extracted with ethyl acetate and the separated organic layer was washed with brine and dried over magnesium sulfate. The solvents were removed under reduced pressure to give 4-methoxycarbonylbenzaldehyde oxime (5.28 g).

IR (KBr): 3291, 1727, 1438, 1284, 1112 cm$^{-1}$

NMR (CDCl$_3$, δ): 3.93 (3H, s), 7.65 (2H, d, J=8.3 Hz), 8.10 (2H, d, J=8.3 Hz), 8.18 (1H, s), 8.27 (1H, s)

APCI-MASS: m/z=180

The following compound was obtained according to a similar manner to that of Preparation 276.

Preparation 277

N-Hydroxy-4-n-hexyloxybenzamidine

IR (KBr): 3446, 3349, 2937, 2865, 1650, 1610, 1519, 1392, 1253 cm$^{-1}$

NMR (DMSO-d$_6$, δ): 0.88 (3H, t, J=6.4 Hz), 1.2–1.8 (8H, m), 3.97 (2H, t, J=6.5 Hz), 5.70 (2H, s), 6.90 (2H, d, J=8.4 Hz), 7.58 (2H, d, J=8.4 Hz), 9.43 (1H, s)

APCI-MASS: m/z=237 (M+H)$^+$

Preparation 278

To a solution of 4-methoxycarbonylbenzaldehyde oxime (896 mg) in N,N-dimethylformamide (10 ml) was added 4N-hydrochloride acid in 1,4-dioxane (1.38 ml) and oxone® (1.69 g). The suspension was stirred at ambient temperature for 16 hours and poured into ice-water. The object compound was extracted with ethyl acetate and the organic layer was washed with brine, dried over magnesium sulfate. The solvents were removed under reduced pressure to give 4-Methoxycarbonylbenzaldehyde oxime chloride (1.05 g).

IR (KBr): 3390, 1710, 1436, 1405, 1284, 1232, 1116, 1016 cm$^{-1}$

NMR (CDCl$_3$, δ): 3.95 (3H, s), 8.93 (2H, d, J=8.3 Hz), 8.10 (2H, d, J=8.7 Hz), 8.39 (1H, s)

APCI-MASS: m/z=176 (M–H$^+$-HCl)

Preparation 279

A solution of Ethyl 4-oxo-1-(4-n-hexyloxyphenyl)piperidine-3-carboxylate (1.437 g) in 20% hydrochloric acid (7.2 ml) was refluxed for 2 hours, cooled, basified with 60% aqueous sodium hydroxide, and extracted with ethyl acetate.

The organic layer was taken and dried over magnesium sulfate. The magnesium sulfate was filtered off, and filtrate was evaporated under reduced pressure to give 1-(4-n-Hexyloxyphenyl)-4-piperidone (0.959 g).

IR (Neat): 2931.3, 1716.3, 1511.9, 1243.9, 825.4 cm$^{-1}$

NMR (CDCl$_3$, δ): 0.90 (3H, t, J=6.5 Hz), 1.2–1.6 (6H, m), 1.65–1.85 (2H, m), 2.57 (4H, t, J=6.1 Hz), 3.46 (4H, t, J=6.1 Hz), 3.92 (2H, t, J=6.5 Hz), 6.85 (2H, d, J=9.3 Hz), 6.95 (2H, d, J=9.3 Hz)

APCI-MASS: m/z=276 (M$^+$+H)

Preparation 280

A solution of 4-[4-(7-Bromoheptyloxy)phenyl] bromobenzene (0.25 g) in a solution of tetra n-butylammonium fluoride (tetrahydrofuran solution, 1M 2.9 ml) was heated to 50° C. for 2 hours. After cooling to ambient temperature, the solution was taken up into a mixture of ethyl acetate (20 ml) and water (20 ml). The separated organic layer was washed with water, brine, and dried over magnesium sulfate. Evaporation gave a residue which was chromatographed on silica gel (30 ml) eluting with a mixture of n-hexane and ethyl acetate (100:0–97:3, V/V). The fractions which contained the objective compound were collected and evaporated a residue which was triturated with n-hexane to give 4-[4-(7-Fluoroheptyloxy) phenyl]bromobenzene (104 mg).

IR (KBr): 2937.1, 2859.9, 1606.4 cm$^{-1}$

NMR (CDCl$_3$, δ): 1.20–1.90 (10H, m), 3.99 (2H, t, J=6.4 Hz), 4.45 (2H, dt, J=47.3 and 6.1 Hz), 6.95 (2H, d, J=6.7 Hz), 7.40 (2H, d, J=6.7 Hz), 7.47 (2H, d, J=6.7 Hz), 7.52 (2H, d, J=6.7 Hz)

The following compound was obtained according to a similar manner to that of Preparation 280.

Preparation 281

4-[4-(6-Fluorohexyloxy)phenyl]bromobenzene

NMR (CDCl$_3$, δ): 1.40–1.95 (8H, m), 4.01 (2H, t, J=6.4 Hz), 4.47 (2H, dt, J=47.5 and 6.0 Hz), 6.95 (2H, d, J=8.6 Hz), 7.35–7.59 (6H, m)

Preparation 282

A solution of 4-[4-(8-Bromooctyloxy)phenyl] bromobenzene (3.7 g) in a mixture of sodium methoxide (4.9M in methanol, 17 ml), N,N-dimethylformamide (20 ml) and tetrahydrofuran (8 ml) was heated to 80° C. for 3 hours. The reaction mixture was taken up into a mixture of ethyl acetate (200 ml) and water (100 ml). The separated organic layer was washed in turn with water, brine, dried over magnesium sulfate. Evaporation gave a residue which was subjected to column chromatography (silica gel, 100 ml) eluting with n-hexane to give 4-[4-(8-Methoxyoctyloxy) phenyl]bromobenzene (2.73 g).

IR (KBr): 2935.1, 2858.0, 1604.5 cm$^{-1}$

NMR (CDCl$_3$, δ): 1.25–1.70 (10H, m), 1.70–1.95 (2H, m), 3.33 (3H, s), 3.37 (2H, t, J=6.5 Hz), 3.99 (2H, t, J=6.5 Hz), 6.95 (2H, d, J=8.8 Hz), 7.35–7.66 (6H, m)

APCI-MASS: m/z=391 (M$^+$)

The following compounds (Preparations 283 to 284) were obtained according to a similar manner to that of Preparation 282.

Preparation 283

4-[4-(6-Methoxyhexyloxy)phenyl]bromobenzene

NMR (CDCl$_3$, δ): 1.50–1.70 (6H, m), 1.70–1.95 (2H, m), 3.34 (3H, s), 3.40 (2H, t, J=6.2 Hz), 3.99 (2H, t, J=6.5 Hz), 6.95 (2H, d, J=8.7 Hz), 7.30–7.60 (6H, m)

APCI-MASS: m/z=365 (M$^+$+2)

Preparation 284

4-[4-(7-Methoxyheptyloxy)phenyl]bromobenzene

IR (KBr): 2935.1, 2854.1, 1604.5 cm$^{-1}$

NMR (CDCl$_3$, δ): 1.25–1.70 (8H, m), 1.70–1.95 (2H, m), 3.33 (3H, s), 3.37 (2H, t, J=6.4 Hz), 3.98 (2H, t, J=6.5 Hz), 6.95 (2H, d, J=8.8 Hz), 7.35–7.56 (6H, m)

APCI-MASS: m/z=379 (M$^+$+2)

Preparation 285

N-(4-octylphenyl)-N'-aminourea, Formamidine acetate (12.76 g) and N-carbazoyl-4-octylaniline (6.458 g) in N,N-dimethylformamide (19.4 ml) were stirred at 150° C. for 6 hours. The reaction mixture was pulverized with water. The precipitate was collected by filtration and washed with water to give 4-(4-Octylphenyl)-2,3-dihydro-4H-1,2,4-triazol-3-one (4.27 g).

IR (KBr): 3214.8, 3085.5, 1704.8 cm$^{-1}$

NMR (CDCl$_3$, δ): 0.88 (3H, t, J=6.7 Hz), 1.2–1.5 (10H, m), 1.5–1.8 (2H, m), 2.64 (2H, t, J=7.9 Hz), 7.29 (2H, d, J=8.5 Hz), 7.43 (2H, d, J=8.5 Hz), 7.67 (1H, d, J=1.3 Hz), 10.31 (1H, s)

APCI-MASS: m/z=274 (M+H$^+$)

The following compound (Preparation 286) was obtained according to a similar manner to that of Preparation 285.

Preparation 286

4-[4-(4-tert-Butoxycarbonylpiperazin-1-yl)phenyl]-2,3-dihydro-4H-1,2,4-triazol-3-one IR (KBr): 3200, 1699.0, 918.0 cm$^{-1}$ NMR (CDCl$_3$, δ): 1.49 (9H, s), 3.17 (4H, t, J=4.9 Hz), 3.60 (4H, t, J=4.9 Hz), 7.00 (2H, d, J=9.0 Hz), 7.40 (2H, d, J=9.0 Hz), 7.63 (1H, s), 10.4 (1H, s)

APCI-MASS: m/z=346 (M+H$^+$)

Preparation 287

A mixture of Methyl 6-(1-heptynyl)naphthalene-2-carboxylate (4.51 g) and platinum oxide (0.4 g) in tetrahydrofuran was stirred under 3.5 atm pressure of hydrogen for 5 hours. The catalyst was filtered off and the filtlate was evaporated to give Methyl 6-heptylnaphthalene-2-carboxylate (4.40 g).

NMR (CDCl$_3$, δ): 0.88 (3H, t, J=6.6 Hz), 1.16–1.50 (8H, m), 1.50–1.80 (2H, m), 2.78 (2H, t, J=7.6 Hz), 3.97 (3H, s), 7.39 (1H, dd, J=17 and 8.4 Hz), 7.64 (1H, s), 7.79 (1H, d, J=8.6 Hz), 7.86 (1H, d, J=8.4 Hz), 8.02 (1H, dd, J=1.7 and 8.6 Hz), 8.57 (1H, s)

APCI-MASS: m/z=285 (M$^+$+1)

The following compound (Preparation 288) was obtained according to a similar manner to that of Preparation 287.

Preparation 288

Methyl 6-hexylnaphthalene-2-carboxylate

NMR (CDCl$_3$, δ): 0.88 (3H, t, J=6.8 Hz), 1.17–1.53 (6H, m), 1.60–1.82 (2H, m), 2.79 (2H, t, J=7.7 Hz), 3.97 (3H, s), 7.39 (1H, dd, J=1.7 and 8.4 Hz), 7.64 (1H, s), 7.80 (1H, d, J=8.6 Hz), 7.86 (1H, d, J=8.4 Hz), 8.03 (1H, dd, J=1.7 and 8.6 Hz), 8.57 (1H, s)

APCI-MASS: m/z=271 (M+1)

Preparation 289

To a stirred solution of Methyl 6-hydroxynaphthalene-2-carboxylate (3.0 g) in dichloromethane (40 ml) were added in turn diisopropylethylamine (3.9 ml) and triflic anhydride (3.0 ml) at −40° C. After stirring at −40° C. for 20 minutes, the mixture was taken up into a mixture of ethyl acetate and cold water. The organic layer was separated, washed with brine, dried over magnesium sulfate, and dried in vacuo. The residue was taken up into piperidine (20 ml) and to the solution were added 1-heptyne (4.0 ml) and tetrakis (triphenylphosphine)palladium(0) (0.5 g). After heating to 85° C. for 1 hour under nitrogen atmosphere, the reaction mixture was evaporated in vacuo. The residue was diluted with ethyl acetate, and the solution was washed in turn with hydrochloric acid and brine, dried over magnesium sulfate and evaporated in vacuo. The residue was chromatographed on silica gel (200 ml) eluting with a mixture of n-hexane and ethyl acetate (9:1, V/V) to give Methyl 6-(1-heptynyl) naphthalene-2-carboxylate (4.01 g).

NMR (CDCl$_3$, δ): 0.94 (3H, t, J=7.1 Hz), 1.30–1.70 (6H, m), 2.46 (2H, t, J=7.0 Hz), 3.97 (3H, s), 7.50 (1H, dd, J=1.7 and 8.6 Hz), 7.80 (1H, d, J=8.6 Hz), 7.86 (1H, d, J=8.6 Hz), 8.04 (1H, dd, J=1.7 and 8.6 Hz), 8.55 (1H, s)

APCI-MASS: m/z=281 (M$^+$+1)

The following compound was obtained according to a similar manner to that of Preparation 289.

Preparation 290

Methyl 6-(1-hexynyl)naphthalene-2-carboxylate

NMR (CDCl$_3$, δ): 0.97 (3H, t, J=7.1 Hz), 1.40–1.71 (4H, m), 2.47 (2H, t, J=6.8 Hz), 3.98 (3H, s), 7.50 (1H, dd, J=1.5 and 8.5 Hz), 7.79 (1H, d, J=8.6 Hz), 7.85 (1H, d, J=8.5 Hz), 7.92 (1H, s), 8.04 (1H, dd, J=1.7 and 8.6 Hz), 8.55 (1H, s)

APCI-MASS: m/z=267 (M$^+$+1)

Preparation 291

To a solution of 4-octylaniline (5 ml) in a mixture of pyridine (12.5 ml) and chloroform (40 ml) was added phenyl chloroformate (2.95 ml) and stirred for 1.5 hours at ambient temperature. The reaction mixture was added to a mixture of water and ethyl acetate. The organic layer was taken and dried over magnesium sulfate. The magnesium sulfate was filtered off, and the filtrate was evaporated under reduced pressure to give 4-Octyl-N-phenoxycarbonylaniline (4.51 g)

IR (KBr): 3318.9, 1714.4, 1234.2 cm$^{-1}$

NMR (CDCl$_3$, δ): 0.88 (3H, t, J=6.2 Hz), 1.2–1.4 (10H, m), 1.5–1.7 (2H, m), 2.57 (2H, t, J=7.3 Hz), 6.88 (1H, s), 7.1–7.5 (9H, m)

The following compounds (Preparation 292 to 299) were obtained according to a similar manner to that of Preparation 291.

Preparation 292

4-(4-tert-Butoxycarbonylpiperazin-1-yl)-N-phenoxycarbonylaniline

IR (KBr): 3309.2, 1743.3, 1658.5, 1197.6 cm$^{-1}$

NMR (CDCl$_3$, δ): 1.48 (9H, s), 3.08 (4H, t, J=5.3 Hz), 3.58 (4H, t, J=5.3 Hz), 6.87 (1H, s), 6.91 (2H, d, J=9 Hz), 7.1–7.5 (7H, m)

APCI-MASS: m/z=398 (M+H$^+$)

Preparation 293

1-(4-Cyclohexylbenzoyl)-2-(4-methoxycarbonylbenzoyl)-hydrazine

IR (KBr): 3236, 2852, 1726, 1679, 1637, 1278, 1110 cm$^{-1}$

NMR (DMSO-d$_6$, δ): 1.1–1.5 (5H, m), 1.6–2.0 (5H, m), 2.60 (1H, m), 3.90 (3H, s), 7.37 (2H, d, J=8.0 Hz), 7.85 (2H, d, J=8.0 Hz), 8.0–8.2 (4H, m), 10.48 (1H, s), 10.68 (1H, s)

APCI-MASS: m/z=381 (M+H)$^+$

Preparation 294

1-[4-(Piperidin-1-yl)benzoyl]-2-(4-methoxycarbonylbenzoyl]hydrazine

IR (KBr): 3500, 3286, 2941, 2854, 1712, 1689, 1650, 1606, 1286, 1242 cm$^{-1}$

NMR (DMSO-d$_6$, δ): 1.59 (6H, s), 3.33 (4H, s), 3.90 (3H, s), 6.97 (2H, d, J=8.8 Hz), 7.79 (2H, d, J=8.8 Hz), 8.02 (2H, d, J=8.4 Hz), 8.09 (2H, d, J=8.4 Hz), 10.23 (1H, s), 10.57 (1H, s)

APCI-MASS: m/z=382 (M+H)$^+$

Preparation 295

1-[4-(4-n-Propyloxyphenyl)benzoyl]-2-(4-methoxycarbonylbenzoyl]hydrazine

IR (KBr): 3230, 1724, 1679, 1654, 1280, 1108 cm$^{-1}$

NMR (DMSO-d$_6$, δ): 1.00 3H, d, J=7.5 Hz), 1.76 (2H, tq, J=6.5 and 7.5 Hz), 3.91 (3H, s), 7.05 (2H, d, J=8.7 Hz), 7.71 (2H, d, J=8.7 Hz), 7.79 (2H, d, J=8.5 Hz), 8.00 (2H, d, J=8.5 Hz), 8.05 (2H, d, J=8.6 Hz), 8.11 (2H, d, J=8.6 Hz), 10.60 (1H, s), 10.72 (1H, s)

APCI-MASS: m/z=433 (M+H)$^+$

Preparation 296

1-(4-Methoxycarbonylbenzoyl)-2-decanoylhydrazine

IR (KBr): 3220, 2919, 2850, 1724, 1643, 1600, 1567, 1479, 1284 cm$^{-1}$

NMR (DMSO-d$_6$, δ): 0.86 (3H, t, J=6.8 Hz), 1.2–1.7 (14H, m), 2.18 (2H, t, J=7.4 Hz), 3.89 (3H, s), 7.97 (2H, d, J=8.5 Hz), 8.06 (2H, d, J=8.5 Hz), 9.15 (1H, s), 10.49 (1H, s)

APCI-MASS: m/z=349 (M+H$^+$)

Preparation 297

1-(4-Methoxycarbonylbenzoyl)-2-(trans-4-n-pentylcyclohexylcarbonyl)hydrazine

IR (KBr): 3201, 2923, 2852, 1727, 1600, 1567, 1479, 1282 cm$^{-1}$

NMR (DMSO-d$_6$, δ): 0.86 (3H, t, J=6.9 Hz), 0.9–1.0 (2H, m), 1.1–1.5 (11H, m), 1.7–1.9 (4H, m), 2.20 (1H, m), 3.88 (3H, s), 7.97 (2H, d, J=8.6 Hz), 8.06 (2H, d, J=8.6 Hz), 9.85 (1H, s), 10.46 (1H, s)

APCI-MASS: m/z=375 (M+H$^+$)

Preparation 298

1-[4-(8-Methoxyoctyloxy)benzoyl]-2-(4-methoxycarbonylbenzoyl)hydrazine

IR (KBr): 3213, 2935, 2856, 1718, 1600, 1567, 1465, 1282 cm$^{-1}$

NMR (DMSO-d$_6$, δ): 1.2–1.8 (12H, m), 3.21 (3H, s), 3.29 (2H, t, J=6.4 Hz), 3.90 (3H, s), 4.04 (2H, t, J=6.5 Hz), 7.04

(2H, d, J=8.8 Hz), 7.90 (2H, d, J=8.8 Hz), 8.04 (2H, d, J=8.7 Hz), 8.10 (2H, d, J=8.7 Hz), 10.41 (1H, s), 10.64 (1H, s)

APCI-MASS: m/z=457 (M+H$^+$)

Preparation 299

1-(4-Octyloxybenzoyl)-2-(4-methoxycarbonylbenzoyl) hydrazine

IR (KBr): 3224, 2923, 2854, 1724, 1681, 1643, 1502, 1434, 1282, 1253, 1106 cm$^{-1}$

NMR (DMSO-d$_6$, δ): 0.86 (3H, t, J=6.8 Hz), 1.2–1.5 (10H, m), 1.6–1.8 (2H, m), 3.89 (3H, s), 4.04 (2H, t, J=6.3 Hz), 7.04 (2H, d, J=8.7 Hz), 7.90 (2H, d, J=8.7 Hz), 8.03 (2H, d, J=8.6 Hz), 8.10 (2H, d, J=8.6 Hz), 10.42 (1H, s), 10.64 (1H, s)

APCI-MASS: m/z=427 (M+H$^+$)

Preparation 300

A solution of Methyl 4-n-hexyloxybenzoate (2.00 g) and hydrazine hydrate (4.24 g) in ethanol (10 ml) was refluxed for 6 hours. After cooling, the reaction mixture was poured into water. The precipitate was collected by filtration, washed with water and dried over P$_2$O$_5$ under reduced pressure to give N-(4-n-hexyloxybenzoyl)hydrazine (1.96 g).

IR (KBr): 3311, 2954, 2869, 1623, 1253 cm$^{-1}$

NMR (DMSO-d$_6$, δ): 0.87 (3H, t, J=6.8 Hz), 1.2–1.5 (6H, m), 1.6–1.8 (2H, m), 4.00 (2H, t, J=6.5 Hz), 4.40 (2H, s), 6.95 (2H, d, J=8.6 Hz), 7.77 (2H, d, J=8.6 Hz), 9.59 (1H, s)

APCI-MASS: m/z=237 (M+H)$^+$

The following compounds (Preparation 301 to 308) were obtained according to a similar manner to that of Preparation 300.

Preparation 301

N-(4-Octylphenyl)-N'-aminourea

IR (KBr): 3309.2, 1683.6, 1554.3 cm$^{-1}$

NMR (DMSO-d$_6$, δ): 0.85 (3H, t, J=6.7 Hz), 1.1–1.4 (10H, m), 1.4–1.6 (2H, m), 2.48 (2H, t, J=8.9 Hz), 4.32 (2H, s), 7.03 (2H, d, J=8.4 Hz), 7.32 (1H, s), 7.38 (2H, d, J=8.4 Hz), 8.50 (1H, s)

Preparation 302

N-[4-(4-tert-Butoxycarbonylpiperazin-1-yl)phenyl]-N'-aminourea

IR (KBr): 3237.9, 1695.1, 1670.1, 1540.8, 1230.4 cm$^{-1}$

NMR (DMSO-d$_6$, δ): 1.42 (9H, s), 2.97 (4H, t, J=4.9 Hz), 3.44 (4H, t, J=4.9 Hz), 4.30 (2H, s), 6.85 (2H, d, J=9.0 Hz), 7.26 (1H, s), 7.36 (2H, d, J=9.0 Hz), 8.41 (1H, s)

Preparation 303

4-Cyclohexylbenzoylhydrazine

IR (KBr): 3318, 2925, 2852, 1625, 1606, 1527, 1326 cm$^{-1}$

NMR (DMSO-d$_6$, δ): 1.1–1.5 (5H, m), 1.6–2.0 (5H, m), 2.4–2.6 (1H, m), 4.44 (2H, s), 7.27 (2H, d, J=8.2 Hz), 7.73 (2H, d, J=8.2 Hz), 9.66 (1H, s)

APCI-MASS: m/z=219 (M+H)$^+$

Preparation 304

4-(Piperidin-1-yl)benzoylhydrazine

IR (KBr): 3263, 2852, 1612, 1504, 1245, 1124 cm$^{-1}$

NMR (DMSO-d$_6$, δ): 1.57 (6H, s), 3.25 (4H, s), 4.35 (2H, s), 6.90 (2H, d, J=9.0 Hz), 7.68 (2H, d, J=9.0 Hz), 9.44 (1H, s)

APCI-MASS: m/z=220 (M+H)$^+$

Preparation 305

4-(4-n-Propyloxyphenyl)benzoylhydrazine

IR (KBr): 3350, 3276, 1610, 1494, 1288, 978 cm$^{-1}$

NMR (DMSO-d$_3$, δ): 0.99 (3H, t, J=7.5 Hz), 1.75 (2H, tq, J=6.5 and 7.5 Hz), 3.98 (2H, t, J=6.5 Hz), 4.50 (2H, s), 7.03 (2H, d, J=8.8 Hz), 7.65 (2H, d, J=8.8 Hz), 7.69 (2H, d, J=8.4 Hz), 7.88 (2H, d, J=8.4 Hz), 9.79 (1H, s)

APCI-MASS: m/z=271 (M+H$^+$)

Preparation 306

4-Methoxycarbonylbenzoylhydrazine

IR (KBr): 3322, 3250, 3018, 1727, 1658, 1621, 1565, 1432, 1280, 1110 cm$^{-1}$

NMR (DMSO-d$_6$, δ): 3.87 (3H, s), 4.58 (2H, s), 7.93 (2H, dd, J=8.6 and 3.1 Hz), 7.02 (2H, dd, J=8.6 and 3.1 Hz), 9.97 (1H, s)

APCI-MASS: m/z=195 (M+H$^+$)

Preparation 307

Trans-4-n-pentylcyclohexylcarbonylhydrazine

IR (KBr): 3303, 3199, 2954, 2925, 2850, 1639, 1619, 1533, 1457 cm$^{-1}$

NMR (DMSO-d$_6$, δ): 0.8–1.0 (6H, m), 1.1–1.5 (10H, m), 1.6–2.2 (5H, m), 4.10 (2H, s), 8.85 (1H, s)

APCI-MASS: m/z=213 (M+H$^+$)

Preparation 308

4-(8-Methoxyoctyloxy)benzoylhydrazine

IR (KBr): 3309, 2937, 2852, 1606, 1494, 1253 cm$^{-1}$

NMR (DMSO-d$_6$, δ): 1.2–1.8 (12H, m), 3.20 (3H, s), 3.25 (2H, t, J=6.5 Hz), 3.99 (2H, t, J=6.5 Hz), 4.39 (2H, s). 6.95 (2H, d, J=8.8 Hz), 7.7 (2H, d, J=8.8 Hz), 9.58 (1H, s)

APCI-MASS: m/z=295 (M+H)$^+$

Preparation 309

To a stirred solution of 4-bromo-4'-n-heptylbiphenyl (2.71 g) in tetrahydrofuran (100 ml) was added dropwise a solution of n-butyllithium in a mixture of diethyl ether and n-hexane (1.6M, 5.1 ml) at −78° C. After stirring at −78° C. for 30 minutes, the resultant mixture was added to a solution of diethyl oxalate (3.4 ml) in tetrahydrofuran (50 ml) at −78° C. The resultant mixture was allowed to warm to 0° C. for about 1 hour, and to the mixture was added acetic acid (0.5 ml). Evaporation gave a residue which was taken up into a mixture of water and ethyl acetate. The organic layer was separated, washed with brine, dried over magnesium sulfate. Evaporation gave a residue which was chromatographed on silica gel (200 ml) eluting with a mixture of n-hexane and ethyl acetate (10:0–95:5, V/V) to give 1-Ethyl-2-(4-n-heptylphenyl)ethanedione (2.23 g).

NMR (CDCl$_3$, δ): 0.88 (3H, t, J=6.6 Hz), 1.10–1.50 (8H, m), 1.44 (3H, t, J=7.1 Hz), 1.50–1.80 (2H, m), 2.66 (2H, t, J=7.7 Hz), 4.47 (2H, q, J=7.1 Hz), 7.20–7.40 (2H, m), 7.50–7.64 (2H, m), 7.64–7.85 (2H, m), 8.00–8.20 (2H, m)

APCI-MASS: m/z=353 (M$^+$+1)

Preparation 310

To a suspension of sodium hydride (60% in oil, 0.37 g) in tetrahydrofuran (40 ml) was added by portions 4-acetyl-4'-n-heptylbiphenyl (2.50 g) at ambient temperature. After stirring at ambient temperature for 1 hour, to the solution was added triethyl phosphonoacetate (1.9 ml) and the mixture was heated to reflux for 5 hours. After cooling to ambient temperature, to the mixture was added acetic acid (0.53 ml) and evaporated. The residue was taken up into a mixture of water and ethyl acetate. The separated organic layer was washed with brine, dried over magnesium sulfate and evaporated. The residue was chromatographed on silica gel (200 ml) eluting with mixture of n-hexane and diisopropyl ether (99:1–20:1, V/V) to give Ethyl (E)-3-[4-(4-heptylphenyl)phenyl]-2-butenoate (2.19 g).

NMR (CDCl$_3$, δ): 0.88 (3H, t, J=6.6 Hz), 1.13–1.48 (8H, m), 1.48–1.78 (2H, m), 2.61 (3H, s), 2.65 (2H, t, J=7.4 Hz), 4.22 (2H, q, J=7.1 Hz), 6.20 (1H, t, J=2.7 Hz), 7.23–7.28 (2H, m), 7.50–7.63 (6H, m)

APCI-MASS: m/s=365 (M$^+$+1)

Preparation 311

To a solution of 4-bromo-4'-n-heptylbiphenyl (5.1 g) in tetrahydrofuran (60 ml) was added a solution of n-butyllithium in a mixture of n-hexane and diethyl ether (1.6M, 9.7 ml) at −60° C. After stirring at −60° C. for 30 minutes, to the mixture was added N,N-dimethylacetamide (4.3 ml) and the reaction mixture was allowed to warm to 0° C. The reaction mixture was taken up into a mixture of cold water and ethyl acetate, and the pH was adjusted to around 1 with 1N hydrochloric acid. The organic layer was separated, washed with brine, dried over magnesium sulfate and evaporated. The residue was chromatographed on silica gel (150 ml) eluting with a mixture of n-hexane and ethyl acetate (20:1, V/V) to give 4-Acetyl-4'-n-heptylbiphenyl (1.60 g).

NMR (CDCl$_3$, δ): 0.89 (3H, t, J=6.6 Hz), 1.05–1.48 (8H, m), 1.48–1.75 (2H, m), 2.65 (2H, t, J=7.6 Hz), 2.63 (3H, s), 7.20–7.31 (2H, m), 7.52–7.58 (2H, m), 7.65–7.70 (2H, m), 7.97–8.05 (2H, m)

APCI-MASS: m/z=295 (M+1)

Preparation 312

To a solution of Methyl 4-[4-(8-hydroxyoctyloxy)phenyl] benzoate (500 mg) and dihydropyran (141 mg) in dichloromethane (15 ml) was added p-toluenesulfonic acid (5 ml). The mixture was stirred at ambient temperature for 10 minutes and diluted with dichloromethane and washed with water and brine. The separated organic layer was dried over magnesium sulfate and evaporated under reduced pressure to give Methyl 4-[4-(8-tetrahydropyran-2-yl-oxyoctyloxy) phenyl]benzoate (616 mg).

IR (KBr): 2935, 2856, 1722, 1602, 1438, 1290, 1199 cm$^{-1}$

NMR (CDCl$_3$, δ): 1.3–2.0 (18H, m), 3.3–3.9 (4H, m), 3.93 (3H, s), 4.00 (2H, t, J=6.5 Hz), 4.5–4.6 (1H, m), 6.98 (2H, d, J=8.7 Hz), 7.56 (2H, d, J=8.7 Hz), 7.62 (2H, d, J=8.3 Hz), 8.07 (2H, d, J=8.3 Hz)

Preparation 313

To a solution of titanium(IV) chloride (11.6 g) in dichloromethane (100 ml) was added 4-n-Pentyloxyacetophenone (10.3 g) and Methyl 4-formylbenzoate (8.21 g) in dichloromethane (50 ml) dropwise at 0° C. To the mixture was added triethylamine (11.15 ml) in dichloromethane (30 ml). The mixture was stirred at 0° C. for 30 minutes and diluted with n-hexane. The organic layer was washed with water (four times), brine and dried over magnesium sulfate. The solvents were removed under reduced pressure and the residue was triturated with iso-propyl ether. The solid was collected by filtration and dried to give 1-(4-Methoxycarbonylphenyl)-3-(4-n-pentyloxyphenyl)-1-propen-3-one (4.02 g).

IR (KBr): 2950, 2910, 2863, 1718, 1654, 1606, 1274, 1176 cm$^{-1}$ NMR (CDCl$_3$, δ): 0.94 (3H, t, J=6.9 Hz), 1.3–1.6 (4H, m), 1.8–2.0 (2H, m), 3.93 (3H, s), 4.04 (2H, t, J=6.5 Hz), 6.97 (2H, d, J=8.8 Hz), 7.60 (1H, d, J=15.7 Hz), 7.68 (2H, d, J=8.4 Hz), 7.80 (1H, d, J=15.7 Hz), 8.0–8.2 (4H, m) APCI-MASS: m/z=353 (M+H$^+$)

Preparation 314

To a solution of titanium(IV) chloride (13.88 g) in dichloromethane (100 ml) was added Ethyl 4-acetylbenzoate (11.53 g) and 4-n-pentyloxybenzaldehyde (12.68 g) in dichloromethane (50 ml) was added dropwise at 0° C. To the mixture was added triethylamine (12.44 ml) in dichloromethane (30 ml). The mixture was stirred at 0° C. for 30 minutes and diluted with ethyl acetate. The organic layer was washed with water (four times) and brine and dried over magnesium sulfate. The solvents were removed under reduced pressure and the residue was triturated with n-hexane. The solid was collected by filtration and dried to give 1-(4-n-Pentyloxyphenyl)-3-(4-ethoxycarbonylphenyl)-1-propen-3-one (13.45 g).

IR (KBr): 2956, 2929, 2861, 1718, 1656, 1594, 1510, 1272 cm$^{-1}$ NMR (CDCl$_3$, δ): 0.94 (3H, t, J=7.1 Hz), 1.3–1.9 (9H, m), 4.01 (2H, t, J=6.5 Hz), 4.42 (2H, q, J=7.1 Hz), 6.93 (1H, d, J=8.7 Hz), 7.37 (1H, d, J=15.6 Hz), 7.60 (2H, d, J=8.7 Hz), 7.81 (1H, d, J=15.6 Hz), 8.03 (2H, d, J=8.5 Hz), 8.16 (2H, d, J=8.5 Hz) APCI-MASS: m/z=367 (M+H$^+$)

The following compound was obtained according to a similar manner to that of Preparation 314.

Preparation 315

Ethyl 4-oxo-1-(4-n-hexyloxyphenyl)piperidine-3-carboxylate

IR (Neat): 1664.3, 1511.9, 1243.9, 1216.9 cm$^{-1}$ NMR (CDCl$_3$, δ): 0.90 (3H, t, J=6.5 Hz), 1.2–1.5 (6H, m), 1.32 (3H, t, J=7.1 Hz), 1.65–1.85 (2H, m), 2.51 (2H, t, J=5.8 Hz), 3.31 (2H, t, J=5.8 Hz), 3.76 (2H, s), 3.91 (2H, t, J=6.5 Hz), 4.26 (2H, q, J=7.1 Hz), 6.84 (2H, d, J=9.2 Hz), 6.94 (2H, d, J=9.2 Hz), 12.06 (1H, s) APCI-MASS: m/z=348 (M$^+$+H)

Preparation 316

To a solution of 4-n-Hexyloxybenzoylhydrazine (1.96 g) and pyridine (0.74 ml) in tetrahydrofuran (20 ml) was added a solution of terephthalic acid monomethyl ester chloride (1.56 g) in tetrahydrofuran (15 ml) dropwise at 0° C. The reaction mixture was stirred at room temperature for 2 hours, and poured into water. The precipitate was collected by filtration and washed with acetonitrile. The residue was dried under reduced pressure to give 1-(4-n-Hexyloxybenzoyl)-2-(4-methoxycarbonylbenzoyl) hydrazine (2.99 g).

IR (KBr): 3230, 3023, 2954, 2858, 1724, 1681, 1643, 1280, 1251, 1105 cm$^{-1}$ NMR (DMSO-d$_6$, δ): 0.88 (3H, t, J=6.6 Hz), 1.2–1.5 (6H, m), 1.6–1.8 (2H, m), 3.90 (3H, s), 4.04 (2H, t, J=6.4 Hz), 7.04 (2H, d, J=8.7 Hz), 7.90 (2H, d, J=8.7 Hz), 8.03 (2H, d, J=8.4 Hz), 8.10(2H, d, J=8.4 Hz), 10.42 (1H, s), 10.65 (1H, s) APCI-MASS: m/z=399 M+H)$^+$

Preparation 317

A mixture of 1-(4-n-Hexyloxyphenyl)-4-piperidone (0.823 g), 1-(4-Ethoxycarbonylphenyl)piperazine (0.7 g), and titanium(IV) isopropoxide (1.11 ml) was stirred at room temperature. After 1 hour, the IR spectrum of the mixture showed no ketone band, and the viscous solution was diluted with absolute ethanol (3 ml). Sodium cyanoborohydride (0.121 g) was added, and the solution was stirred for 3 hours. Water (3 ml) was added with stirring, and the resulting in organic precipitate was filtered and washed with ethanol. The filtrate was extracted with ethyl acetate. The organic layer was taken and dried over magnesium sulfate. The magnesium sulfate was filtered off, and filtrate was evaporated under reduced pressure to give Ethyl 4-[4-[1-(4-n-hexyloxyphenyl)piperidin-4-yl]piperazin-1-yl]benzoate (331 mg).

IR (KBr): 1708.6, 1606.4, 1511.9, 1284.4, 1236.1 cm$^{-1}$ NMR (CDCl$_3$, δ): 0.90 (3H, t, J=6.5 Hz), 1.2–1.55 (6H, m), 1.37 (3H, t, J=7.1 Hz), 1.6–1.85 (4H, m), 1.95 (2H, d, J=12 Hz), 2.41 (1H, m), 2.62 (2H, d, J=11 Hz), 2.75 (4H, t, J=5.0 Hz), 3.35 (4H, t, J=5.0 Hz), 3.58 (2H, d, J=11 Hz), 3.90 (2H, t, J=6.5 Hz), 4.32 (2H, q, J=7.1 Hz), 6.7–7.0 (6H, m), 7.92 (2H, d, J=9.0 Hz) APCI-MASS: m/z=494 (M$^+$+H)

The following compound was obtained according to a similar manner to that of Preparation 317.

Preparation 318

1-tert-Butoxycarbonyl-4-(4-phenylcyclohexyl)piperazine

IR (KBr): 1697.1, 1245.8, 1170.6, 1124.3, 700 cm$^{-1}$ NMR (CDCl$_3$, δ): 1.2–1.65 (17H, m), 1.9–2.1 (4H, m), 2.3–2.6 (2H, m), 2.55 (4H, t, J=5.0 Hz), 3.44 (4H, t, J=5.0 Hz), 7.1–7.4 (5H, m) APCI-MASS: m/z=345 (M$^+$+H)

Preparation 319

To a suspension of 1-(N,N-dimethylamino)-2-(4-ethoxycarbonylbenzoyl)ethylene (0.742 g) and 4-n-hexyloxybenzamidine hydrochloride (0.847 g) in methanol (10 ml) was added 28% sodium methoxide in methanol (0.64 ml). The suspension was refluxed for 6 hours, and partitioned with ethyl acetate and water. The organic layer was washed with water and brine, dried over magnesium sulfate and evaporated under reduced pressure. The residue was triturated with acetonitrile, collected by filtration and dried under reduced pressure to give Methyl 4-[2-(4-n-hexyloxyphenyl)pyrimidin-6-yl]benzoate (0.61 g).

IR (KBr): 2931, 2861, 1722, 1606, 1588, 1251 cm$^{-1}$ NMR (CDCl$_3$, δ): 0.95 (3H, t, J=6.7 Hz), 1.2–1.6 (6H, m), 1.8–2.0 (2H, m), 3.97 (3H, s), 4.05 (2H, t, J=6.5 Hz), 7.02 (2H, d, J=8.8 Hz), 7.56 (1H, d, J=5.2 Hz), 8.18 (2H, d, J=8.6 Hz), 8.28 (2H, d, J=8.6 Hz), 8.52 (2H, d, J=8.8 Hz), 8.83 (1H, d, J=5.2 Hz) APCI-MASS: m/z=391 (M+H$^+$)

Preparation 320

A solution of 1-(4-Methoxycarbonylphenyl)-3-(4-n-pentyloxyphenyl)-1-propen-3-one (4.0 g) and hydroxyamine hydrochloride (3.93 g) in ethanol (40 ml) was refluxed for 4 hours. The mixture was diluted with ethyl acetate, and the organic layer was washed with water (×2), brine and dried over magnesium sulfate. The solvents were removed under reduced pressure to give crude oxime. To a solution of crude oxime in 1,2-dichloroethane (20 ml) was added activated-manganese(IV) oxide (10.0 g). The reaction mixture was refluxed for 2 hours and filtered. The residue was washed with dichloromethane. The solvents were removed under reduced pressure and the residue was triturated with acetonitrile. The solid was collected by filtration and dried to give Methyl 4-[3-(4-n-pentyloxyphenyl) isoxazol-5-yl]benzoate (0.98 g).

IR (KBr): 2940, 2871, 1720, 1612, 1278, 1249, 1178, 1108 cm$^{-1}$ NMR (DMSO-d$_6$, δ): 0.94 (3H, t, J=7.2 Hz), 1.2–1.6 (4H, m), 1.7–1.9 (2H, m), 3.95 (3H, s), 4.01 (2H, t, J=6.5 Hz), 6.87 (1H, s), 6.98 (2H, d, J=8.9 Hz), 7.79 (2H, d, J=8.9 Hz), 7.89 (2H, d, J=8.6 Hz), 8.15 (2H, d, J=8.6 Hz)

APCI-MASS: m/z=366 (M+H$^+$)

Preparation 321

To a solution of 4-Methoxycarbonylphenylhydroxyiminomethyl chloride (16.98 g) and 4-n-pentyloxyphenylacetylene (18.96 g) in tetrahydrofuran (170 ml) was added triethylamine (14.4 ml) in tetrahydrofuran (140 ml) over a period of 2 hours at 40° C. and the mixture was stirred at 40° C. for 30 minutes. The mixture was diluted with dichloromethane and washed with water and brine. The separated organic layer was dried over magnesium sulfate and evaporated under reduced pressure. The residue was triturated with acetonitrile. The precipitate was collected by filtration and dried to give Methyl 4-[5-(4-n-pentyloxyphenyl)isoxazol-3-yl]benzoate (24.56 g).

IR (KBr): 2942, 2873, 1716, 1616, 1508, 1280, 1108 cm$^{-1}$ NMR (CDCl$_3$, δ): 0.95 (3H, t, J=6.9 Hz), 1.3–1.6 (4H, m), 1.8–2.0 (2H, m), 3.95 (3H, s), 4.02 (2H, t, J=6.5 Hz), 6.74 (1H, s), 6.99 (2H, d, J=8.8 Hz), 7.76 (2H, d, J=8.8 Hz), 7.93 (2H, d, J=8.5 Hz), 8.14 (2H, d, J=8.5 Hz) APCI-MASS: m/z=366 (M+H$^+$)

Preparation 322

To a solution of N-Hydroxy-4-octyloxybenzamidine (1.89 g) in pyridine (10 ml) was added terephthalic acid monomethyl ester chloride (1.67 g) in tetrahydrofuran (15 ml) dropwise at 0° C. The mixture was stirred at room temperature for 15 minutes, and poured into water. The precipitate was collected by filtration, dried and dissolved in pyridine (10 ml). The solution was refluxed for 1 hour. The reaction mixture was diluted with ethyl acetate and washed with 1 N HCl, water and brine. The separated organic layer was dried over magnesium sulfate and the solvents were removed under reduced pressure. The residue was triturated with acetonitrile and collected by filtration. The solid was dried to give Methyl 4-[3-(4-n-hexyloxyphenyl)-1,2,4-oxadiazol-5-yl]benzoate (2.27 g).

IR (KBr): 2950, 2925, 2863, 1720, 1280, 1255 cm$^{-1}$ NMR (CDCl$_3$, δ): 0.92 (3H, t, J=6.6 Hz), 1.2–1.9 (8H, m), 3.97 (3H, s), 4.03 (2H, d, J=6.5 Hz), 7.00 (2H, d, J=8.9 Hz), 8.09 (2H, d, J=8.9 Hz), 8.20 (2H, d, J=6.6 Hz), 8.28 (2H, d, J=6.6 Hz) APCI-MASS m/z=381 (M+H)$^+$

Preparation 323

A suspension of 1-(4-n-Hexyloxybenzoyl)-2-(4-methoxycarbonylbenzoyl)hydrazine (1.00 g) in phosphorus oxychloride (5 ml) was refluxed for 1 hour. After cooling, the solution was concentrated under reduced pressure. The residue was poured into ice-water and extracted with dichloromethane. The organic layer was washed with water, brine and dried over magnesium sulfate. The solvents were removed under reduced pressure. The residue was triturated with acetonitrile, collected by filtration and dried under reduced pressure to give Methyl 4-[5-(4-n-hexyloxyphenyl)-1,3,4-oxadiazole-2-yl]benzoate (761 mg).

IR (KBr): 2954, 2854, 1724, 1612, 1494, 1280, 1249 cm$^{-1}$ NMR (CDCl$_3$, δ): 0.91 (3H, t, J=6.6 Hz), 1.3–1.6 (6H, m), 1.7–1.9 (2H, m), 3.96 (3H, s), 4.04 (2H, t, J=6.5 Hz), 7.02 (2H, d, J=8.6 Hz), 8.07 (2H, d, J=8.6 Hz), 8.19 (4H, m) APCI-MASS: m/z=381 (M+H)$^+$

The following compounds (Preparations 324 to 327) were obtained according to a similar manner to that of Preparation 323.

Preparation 324

Methyl 4-[5-[4-(4-n-propyloxyphenyl)phenyl]-1,3,4-oxadiazol-2-yl]benzoate

IR (KBr): 1720, 1614, 1496, 1280, 1103 cm$^{-1}$ NMR (CDCl$_3$, δ): 1.07 (3H, d, J=7.5 Hz), 1.84 (2H, tq, J=6.5 and 7.5 Hz), 3.98 (3H, s), 3.99 (2H, t, J=6.5 Hz), 7.01 (2H, d, J=8.8 Hz), 7.60 (2H, d, J=8.8 Hz), 7.73 (2H, d, J=8.5 Hz), 8.19 (2H, d, J=8.5 Hz), 8.22 (4H, s) APCI-MASS: m/z=415 (M+H$^+$)

Preparation 325

Methyl 4-[5-(n-nonyl)-1,3,4-oxadiazol-2-yl]benzoate

IR (KBr): 2915, 2848, 1724, 1569, 1436, 1413, 1278 cm$^{-1}$ NMR (CDCl$_3$, δ): 0.88 (3H, t, J=6.4 Hz), 1.2–1.6 (12H, m), 1.8–2.0 (2H, m), 2.94 (2H, t, J=7.6 Hz), 3.96 (3H, s), 8.11 (2H, d, J=8.8 Hz), 8.17 (2H, d, J=8.8 Hz) APCI-MASS: m/z=331 (M+H)$^+$

Preparation 326

Methyl 4-[5-[4-(8-methoxyoctyloxy)phenyl]-1,3,4-oxadiazol-2-yl]benzoate

IR (KBr): 2925, 2858, 1722, 1614, 1280, 1259 cm$^{-1}$ NMR (CDCl$_3$, δ): 1.3–1.9 (12H, m), 3.36 (3H, s), 3.37 (2H, t, J=6.4 Hz), 3.97 (3H, s), 4.04 (2H, t, J=6.5 Hz), 7.02 (2H, d, J=8.9 Hz), 8.07 (2H, d, J=8.9 Hz), 8.20 (4H, s) APCI-MASS: m/z=439 (M+H$^+$)

Preparation 327

Methyl 4-[5-(4-n-octyloxyphenyl)-1,3,4-oxadiazol-2-yl]benzoate

IR (KBr): 2923, 2856, 1722, 1614, 1496, 1282, 1103 cm$^{-1}$ NMR (CDCl$_3$, δ): 0.89 (3H, t, J=6.8 Hz), 1.2–1.6 (10H, m), 1.7–1.9 (2H, m), 3.97 (3H, s), 4.04 (2H, t, J=6.5 Hz), 7.03 (2H, d, J=8.7 Hz), 8.07 (2H, d, J=8.7 Hz), 8.19 (4H, m) APCI-MASS: m/z=409 (M+H$^+$)

Preparation 328

A suspension of 1-(4-Hexyloxybenzoyl)-2-(4-methoxycarbonylbenzoyl)hydrazine (1.0 g) and di-phosphorus pentasulfide (1.28 g) in tetrahydrofuran (15 ml) was stirred at room temperature for 3 hours. The mixture was diluted with water (30 ml), stirred for 30 minutes and extracted with dichloromethane. The organic layer was washed with brine, dried over magnesium sulfate and evaporated under reduced pressure. The residue was triturated with acetonitrile. The solid was collected by filtration and dried under reduced pressure to give Methyl 4-[5-(4-n-hexyloxyphenyl)-1,3,4-thiadiazol-2-yl]benzoate (816 mg).

IR (KBr): 2925, 2871, 1722, 1608, 1436, 1276, 1106 cm$^{-1}$ NMR (CDCl$_3$, δ): 0.92 (3H, t, J=6.6 Hz), 1.3–2.0 (8H, m), 3.96 (3H, s), 4.03 (2H, t, J=6.5 Hz), 6.99 (2H, d, J=8.6 Hz), 7.95 (2H, d, J=8.4 Hz), 8.16 (2H, d, J=8.4 Hz) APCI-MASS: m/z=397 (M+H)$^+$

The following compounds (Preparations 329 to 334) were obtained according to a similar manner to that of Preparation 328.

Preparation 329

Methyl 4-[5-[4-(8-methoxyoctyloxy)phenyl]-1,3,4-thiadiazol-2-yl]benzoate

IR (KBr): 3210, 2935, 2856, 1718, 1600, 1465, 1280, 1110 cm$^{-1}$ NMR (CDCl$_3$, δ): 1.3–1.6 (10H, m), 1.7–1.9 (2H, m), 3.33 (3H, s), 3.37 (2H, d, J=6.4 Hz), 3.96 (3H, s), 4.03 (2H, t, J=6.5 Hz), 6.99 (2H, d, J=8.9 Hz), 7.94 (2H, d, J=8.9 Hz), 8.07 (2H, d, J=8.6 Hz), 8.16 (2H, d, J=8.6 Hz) APCI-MASS: m/z=455 (M+H$^+$)

Preparation 330

Methyl 4-[5-(4-cyclohexylphenyl)-1,3,4-thiadiazol-2-yl]benzoate

IR (KBr): 2925, 2850, 1716, 1432, 1274, 1108, 997 cm$^{-1}$ NMR (CDCl$_3$, δ): 1.2–1.6 (5H, m), 1.7–2.0 (5H, m), 2.58 (1H, m), 3.96 (3H, s), 7.34 (2H, d, J=8.2 Hz), 7.93 (2H, d, J=8.2 Hz), 8.07 (2H, ,d, J=8.6 Hz), 8.16 (2H, d, J=8.6 Hz) APCI-MASS: m/z=379 (M+H$^+$)

Preparation 331

Methyl 4-[5-[4-(piperidin-1-yl)phenyl]-1,3,4-thiadiazol-2-yl]benzoate

IR (KBr): 2940, 2848, 1720, 1602, 1436, 1415, 1276, 1108 cm$^{-1}$ NMR (CDCl$_3$, δ): 1.68 (6H, br), 3.34 (4H, br), 3.96 (3H, s), 6.95 (2H, d, J=8.7 Hz), 7.88 (2H, d, J=8.7 Hz), 8.05 (2H, d, J=8.6 Hz), 8.16 (2H, d, J=8.6 Hz) APCI-MASS: m/z=380 (M+H$^+$)

Preparation 332

Methyl 4-[5-(4-n-octyloxyphenyl)-1,3,4-thiadiazol-2-yl]benzoate

IR (KBr): 2927, 2858, 1720, 1606, 1434, 1276, 1106 cm$^{-1}$ NMR (CDCl$_3$, δ): 0.89 (3H, t, J=6.8 Hz), 1.2–1.6 (10H, m), 1.7–1.9 (2H, m), 3.96 (3H, s), 4.03 (2H, t, J=6.5 Hz), 7.00 (2H, d, J=8.9 Hz), 7.95 (2H, d, J=8.9 Hz), 8.06 (2H, d, J=8.4 Hz), 8.16 (2H, d, J=8.4 Hz) APCI-MASS: m/z=425 (M+H$^+$)

Preparation 333

Methyl 4-[5-(4-trans-n-pentylcyclohexyl)-1,3,4-thiadiazol-2-yl]benzoate

IR (KBr): 2923, 2850, 1722, 1440, 1276, 1110 cm$^{-1}$ NMR (CDCl$_3$, δ): 0.89 (3H, t, J=6.9 Hz), 1.0–1.8 (13H, m), 1.92 (2H, d, J=13.4 Hz), 2.24 (2H, d, J=12.2 Hz), 3.15 (1H, tt, J=12.2 and 3.5 Hz), 3.95 (3H, s), 8.01 (2H, dd, J=8.6 and 2.0 Hz), 8.13 (2H, dd, J=8.6 and 2.0 Hz) APCI-MASS: m/z=373 (M+H$^+$)

Preparation 334

Methyl 4-[5-[4-(4-n-propyloxyphenyl)phenyl]-1,3,4-thiadiazol-2-yl]benzoate

IR (KBr): 1720, 1540, 1508, 1282 cm$^{-1}$ NMR (CDCl$_3$, δ): 1.07 (3H, t, J=7.5 Hz), 1.85 (2H, m), 3.9–4.1 (5H, m), 7.01 (2H, d, J=8.8 Hz), 7.59 (2H, d, J=8.8 Hz), 7.70 (2H, d, J=8.4 Hz), 8.07 (2H, d, J=8.4 Hz), 8.1–8.2 (4H, m) APCI-MASS: m/z=431 (M+H)$^+$

Preparation 335

To a suspension of 4-hexyloxybenzoic acid in oxalyl chloride (10 ml) and dichloromethane (10 ml) was added N,N-dimethylformamide (0.1 ml). The mixture was stirred at room temperature for 2 hours. The solvent was removed under reduced pressure to give crude 4-hexyloxybenzoyl chloride. To a suspension of Ethyl 3-amino-4- hydroxybenzoate (733 mg) and triethylamine (1.38 ml) and 4-dimethylaminopyridine (DMAP, 10 mg) in methylene chloride (10 ml) was added the solution of 4-hexyloxybenzoyl chloride obtained above in dichloromethane (5 ml) dropwise at 10° C. The reaction mixture was stirred at 10° C. for 1.5 hours and diluted with dichloromethane (20 ml). The solution was washed with $H_2O$ (20 ml), 1 N HCl aq. (20 ml×2), $H_2O$ (20 ml) and brine (20 ml) successively. The organic layer was dried over $MgSO_4$ and the solvent was removed under reduced pressure. To the residue was added toluene (15 ml) and p-toluenesulfonic acid (10 mg). The mixture was refluxed for 6 hours and the solvent was removed under reduced pressure. The residue was triturated with acetonitrile, and precipitate was collected with filtration and dried over $PO_5$ to give 2-(4-Hexyloxyphenyl)-5-ethoxycarbonylbenzoxazole (0.60 g).

IR (KBr): 2952, 2871, 1712, 1623, 1500, 1294, 1255 cm$^{-1}$ NMR (CDCl$_3$, δ): 0.92 (3H, t, J=6.6 Hz), 1.3–1.6 (9H, m), 1.7–1.9 (2H, m), 4.05 (2H, t, J=6.5 Hz), 4.42 (2H, q, J=7.1 Hz), 7.03 (2H, d, J=6.9 Hz), 7.57 (1H, d, J=8.6 Hz), 8.08 (1H, dd, J=8.6 and 1.7 Hz), 8.18 (2H, d, J=6.9 Hz), 8.43 (1H, d, J=1.7 Hz) APCI-MASS: m/z=368 (M+H$^+$)

The following compounds (Preparations 336 to 337) were obtained according to a similar manner to that of Preparation 335.

Preparation 336

5-Ethoxycarbonyl-2-(2-octyloxypyridin-5-yl)benzoxazole

IR (KBr): 2933, 2858, 1716, 1623, 1604, 1577, 1467, 1290, 1213, 1083 cm$^{-1}$ NMR (CDCl$_3$, δ): 0.89 (3H, t, J=6.7 Hz), 1.2–1.5 (10H, m), 1.43 (3H, t, J=7.1 Hz), 1.7–1.9 (2H, m), 4.3–4.5 (4H, m), 6.87 (1H, d, J=8.7 Hz), 7.60 (1H, d, J=8.6 Hz), 8.11 (1H, dd, J=8.6 and 1.6 Hz), 8.37 (1H, dd, J=8.8 and 2.4 Hz), 8.45 (1H, d, J=1.6 Hz), 9.03 (1H, d, J=2.4 Hz) APCI-MASS: m/z=397 (M+H$^+$)

Preparation 337

2-[4-(4-hexylphenyl)phenyl]-5-ethoxycarbonylbenzoxazole

IR (KBr): 2952, 2871, 1712, 1623, 1500, 1294, 1255, 1024 cm$^{-1}$ NMR (CDCl$_3$, δn): 0.90 (3H, t, J=6.6 Hz), 1.2–1.5 (6H, m), 1.44 (3H, t, J=7.1 Hz), 1.6–1.8 (2H, m), 2.67 (2H, t, J=7.3 Hz), 4.43 (2H, q, J=7.1 Hz), 7.27 (1H, d, J=3.7 Hz), 7.32 (1H, s), 7.5–7.7 (3H, m), 7.77 (2H, d, J=8.6 Hz), 8.12 (1H, dd, J=8.6 and 1.7 Hz), 8.32 (2H, d, J=8.5 Hz), 8.48 (1H, d, J=1.2 Hz) APCI-MASS: m/z=428 (M+H$^+$)

Preparation 338

A suspension of 4-[4-(8-bromooctyloxy)phenyl]benzoic acid (1 g) in 2,6-dimethylmorpholine (3.06 ml) was refluxed for 30 minutes. The reaction mixture was added to a mixture of water and ethyl acetate and adjusted to pH 2.0 with conc. HCl. The organic layer was taken and dried over magnesium sulfate. The magnesium sulfate was filtered off, and the filtrate was evaporated under reduced pressure to give 4-[4-[8-(2,6-dimethylmorpholin-4-yl)octyloxy]phenyl]benzoic acid hydrochloride (0.95 g).

IR (KBr): 2939.0, 1704.8, 1606.4, 1189.9 cm$^{-1}$ NMR (DMSO-d$_6$, δ): 1.12 (6H, d, J=6.3 Hz), 1.2–1.6 (10H, m), 1.6–1.9 (4H, m), 2.4–2.7 (2H, m), 2.9–3.1 (2H, m), 3.8–4.0 (2H, m), 4.02 (2H, t, J=6.3 Hz), 7.04 (2H, d, J=8.8 Hz), 7.68 (2H, d, J=8.8 Hz), 7.75 (2H, d, J=8.4 Hz), 7.99 (2H, d, J=8.4 Hz) APCI-MASS: m/z=440 (M+H$^+$)

Preparation 339

Sodium hydride (60% suspension in mineral oil, 108 mg) was added to ethoxyethanol (10 ml), and the solution was stirred at 60° C. for 20 minutes. To the solution was added Methyl 4-[4-(8-bromooctyloxy)phenyl]benzoate (1.26 g), and the reaction mixture was stirred at 70° C. for 2 hours. To the reaction mixture was added 10% sodium hydroxide aqueous solution (2.4 ml), and the solution was stirred at 70° C. for 1 hour. After cooling, the solution was adjusted to pH 2.0 with 1 N hydrochloric acid. The precipitate was collected by filtration, and dried to give 4-[4-[8-(2-Ethoxyethoxy)octyloxy]phenyl]benzoic acid (1.13 g).

IR (KBr): 2933, 2858, 1685, 1604, 1434, 1294, 1132 cm$^{-1}$ NMR (DMSO-d$_6$, δ): 1.09 (3H, t, J=7.0 Hz), 1.2–1.9 (14H, m), 3.2–3.6 (6H, m), 4.01 (2H, d, J=6.3 Hz), 7.04 (2H, d, J=8.8 Hz), 7.67 (2H, d, J=8.8 Hz), 7.74 (2H, d, J=8.5 Hz), 7.98 (2H, d, J=8.5 Hz) APCI-MASS: m/z=415 (M+H$^+$)

The following compound was obtained according to a similar manner to that of Preparation 300.

Preparation 340

4-n-Pentyloxybenzoylhydrazine

IR (KBr): 3182, 2937, 2869, 1645, 1618, 1571, 1251 cm$^{-1}$ NMR (DMSO-d$_6$, δ): 0.89 (3H, d, J=7.1 Hz), 1.2–1.8 (6H, m), 4.00 (2H, t, J=6.5 Hz), 4.41 (2H, s), 6.96 (2H, d, J=8.8 Hz), 7.78 (2H, d, J=8.8 Hz), 9.59 (1H, s) APCI-MASS: m/z=223 (M+H$^+$)

The following compound was obtained according to a similar manner to that of Preparation 291.

Preparation 341

1-(4-Methoxycarbonylbenzoyl)-2-(4-n-pentyloxybenzoyl)hydrazine

IR (KBr): 3234, 2956, 2931, 1724, 1683, 1643, 1610, 1284, 1253 cm$^{-1}$ NMR (DMSO-d$_6$, δ): 0.90 (3H, t, J=6.9 Hz), 1.2–1.5 (4H, m), 1.6–1.8 (2H, m), 3.90 (3H, s), 4.04 (2H, t, J=6.5 Hz), 7.04 (2H, d, J=8.8 Hz), 7.90 (2H, d, J=8.8 Hz), 8.03 (2H, d, J=8.7 Hz), 8.10 (2H, d, J=8.7 Hz), 10.42 (1H, s), 10.64 (1H, s) APCI-MASS: m/z=385 (M+H$^+$)

The following compound was obtained according to a similar manner to that of Preparation 328.

Preparation 342

Methyl 4-[5-(4-n-pentyloxyphenyl)thiadiazol-2-yl]benzoate

IR (KBr): 2940, 2871, 1720, 1606, 1438, 1280 cm$^{-1}$ NMR (CDCl$_3$, δ): 0.95 (3H, t, J=7.1 Hz), 1.3–1.6 (4H, m), 1.8–2.0 (2H, m), 3.96 (3H, s), 4.03 (2H, t, J=6.5 Hz), 6.99 (2H, d, J=8.8 Hz), 7.94 (2H, d, J=8.8 Hz), 8.06 (2H, d, J=8.7 Hz), 8.16 (2H, d, J=8.7 Hz) APCI-MASS: m/z=383 (M+H$^+$)

The following compound was obtained according to a similar manner to that of Preparation 32

Preparation 343

4-[5-(4-n-Pentyloxyphenyl)thiadiazol-2-yl]benzoic acid

IR (KBr): 2954, 2867, 1687, 1602, 1432, 1294, 1255 cm$^{-1}$ NMR (DMSO-d$_6$, δ): 0.91 (3H, t, J=7.0 Hz), 1.3–1.5 (4H, m), 1.7–1.9 (2H, m), 4.07 (2H, t, J=6.7 Hz), 7.13 (2H, d, J=8.8 Hz), 7.97 (2H, d, J=8.8 Hz), 8.07 (4H, s) APCI-MASS: m/z=369 (M+H$^+$)

The following compound was obtained according to a similar manner to that of Preparation 49.

Preparation 344

1-[4-[5-(4-n-Pentyloxyphenyl)thiadiazol-2-yl]benzoyl]benzotriazole 3-oxide

IR (KBr): 2948, 2873, 1770, 1602, 1257, 1232 cm$^{-1}$
NMR (CDCl$_3$, δ): 0.95 (3H, t, J=7.1 Hz), 1.3–1.6 (4H, m), 1.8–2.0 (2H, m), 4.04 (2H, t, J=6.5 Hz), 7.01 (2H, d, J=8.1 Hz), 7.4–7.7 (3H, m), 7.97 (2H, d, J=8.1 Hz), 8.12 (1H, d, J=8.2 Hz), 8.24 (2H, d, J=8.0 Hz), 8.40 (2H, d, J=8.0 Hz) APCI-MASS: m/z=486 (M+H$^+$)

Preparation 345

To a solution of 4-bromobenzaldehyde oxime chloride (647 mg) and 4-n-pentyloxy-phenylacetylene (650 mg) in tetrahydrofuran (7 ml) was added triethylamine (0.5 ml) in tetrahydrofuran (5 ml) dropwise at 40° C. The solution was stirred at 40° C. for 30 minutes, poured into water and extracted with ethyl acetate. The organic layer was washed with H$_2$O, brine and dried over magnesium sulfate. The solvents were removed under reduced pressure and the residue was triturated with acetonitrile. The precipitate was collected by filtration and dried to give 4-[5-(4-n-pentyloxyphenyl)isoxazol-3-yl]bromobenzene (0.59 g).

IR (KBr): 2948, 2867, 1612, 1430, 1255 cm$^{-1}$ NMR (CDCl$_3$, δ): 0.95 (3H, t, J=6.9 Hz), 1.3–1.6 (4H, m), 1.7–1.9 (2H, m), 4.01 (2H, t, J=6.5 Hz), 6.66 (1H, s), 6.98 (2H, d, J=8.8 Hz), 7.60 (2H, d, J=8.6 Hz), 7.7–7.9 (4H, m) APCI-MASS: m/z=388 (M+H$^+$)

Preparation 346

To a suspension of 4-[5-(4-n-pentyloxyphenyl)isoxazol-3-yl]bromobenzene (386 mg) in tetrahydrofuran (5 ml) was added 1.55 M n-butyllithium in hexane (0.84 ml) at −40° C. under N$_2$ stream and the solution was stirred for 1 hour at −40° C. To the solution was added crushed dryice (1 g) and the suspension was stirred for 1 hour at −40° C. The suspension was diluted with H$_2$O, and acidified with 1 N-hydrochloric acid. The precipitate was collected by filtration and dried to give 4-[5-(4-n-pentyloxyphenyl)isoxazol-3-yl]benzoic acid (312 mg).

IR (KBr): 2939, 2867, 1681, 1614, 1429, 1255, 1178, 821 cm$^{-1}$ NMR (DMSO-d$_6$, δ): 0.91 (3H, t, J=7.1 Hz), 1.3–1.5 (4H, m), 1.6–1.8 (2H, m), 4.04 (2H, t, J=6.5 Hz), 7.11 (2H, d, J=8.9 Hz), 7.54 (1H, s), 7.85 (2H, d, J=8.9 Hz), 7.98 (2H, d, J=8.6 Hz), 8.11 (2H, d, J=8.6 Hz) APCI-MASS: m/z=352 (M+H$^+$)

The Starting Compound in the following Examples 1 to 117 and The Object Compounds (1to (122) and (124) in the following Examples 1 to 122 and 124 are illustrated by chemical formulae as below.

The Starting Compound (the same in Examples 1 to 117)

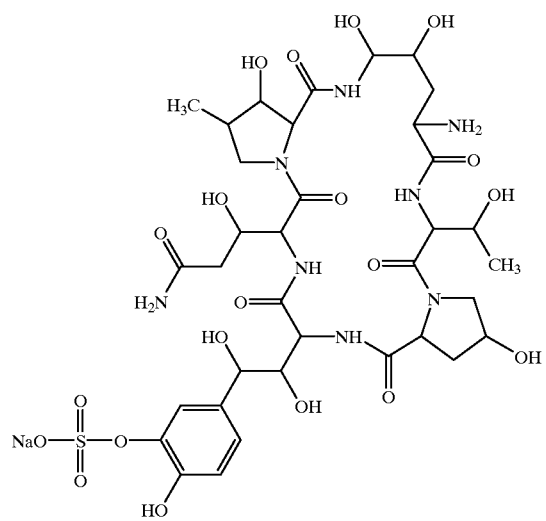

The Object Compounds (1) to (122) and (124)

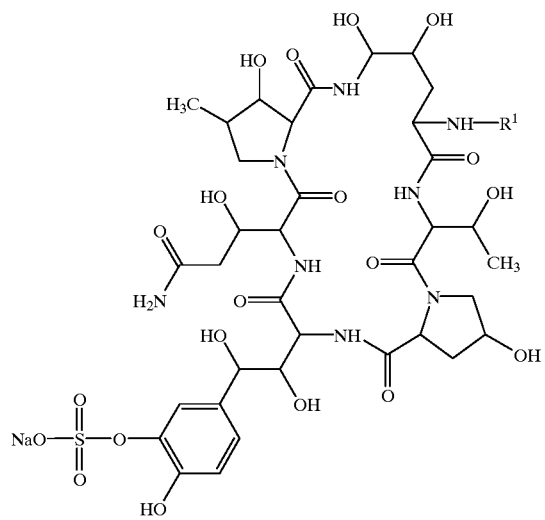

In the following Examples, The Object Compound (X) [e.g. The Object Compound (1)] means the object compound of Example (X) [e.g. Example (1)].

| Example No. | R$^1$ |
|---|---|
| 1 | —CO—[2-pyridyl]—CH$_2$—O—(CH$_2$)$_7$CH$_3$ |
| 2 | —CO—[C$_6$H$_4$]—N(piperazine)N—[C$_6$H$_4$]—O—(CH$_2$)$_7$CH$_3$ |

-continued
3 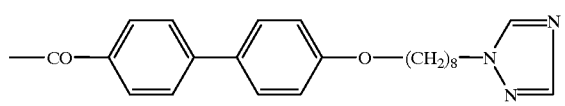
4 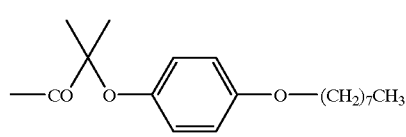
5 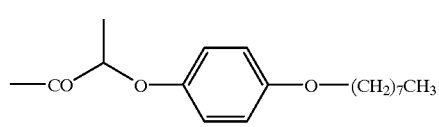
6 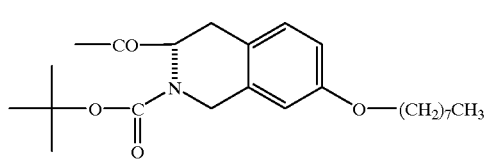
7 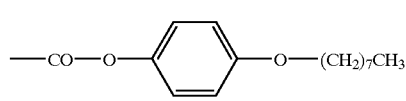
8 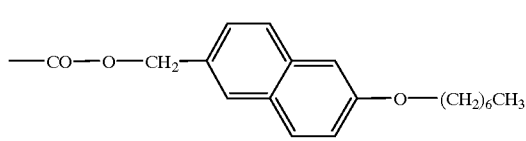
9 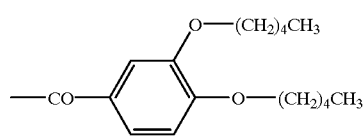
10 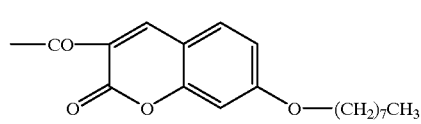
11 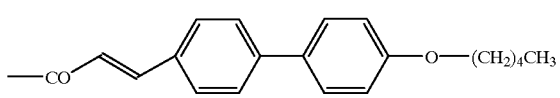
12 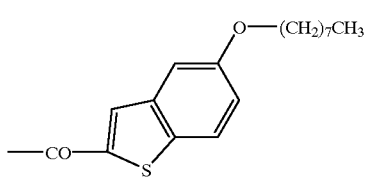
13 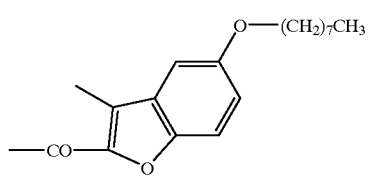

-continued

| # | Structure |
|---|---|
| 14 | —CO—⟨benzoxazole-5-yl⟩-2-(CH₂)₈CH₃ |
| 15 | —CO—⟨benzimidazole-5-yl⟩-2-(C₆H₄-O-(CH₂)₅CH₃) |
| 16 | —CO—CH₂CH₂—⟨biphenyl⟩—O—(CH₂)₄CH₃ |
| 17 | —CO—CH=CH—⟨biphenyl⟩—(CH₂)₆CH₃ |
| 18 | —CO—CH₂CH₂—⟨biphenyl⟩—(CH₂)₄CH₃ |
| 19 | —CO—CH=CH—⟨biphenyl⟩—(CH₂)₄CH₃ |
| 20 | —CO—CH₂CH₂—⟨naphthyl⟩—O—(CH₂)₆CH₃ |
| 21 | —CO—CH=CH—⟨naphthyl⟩—O—(CH₂)₆CH₃ |
| 22 | —CO—⟨biphenyl⟩—(CH₂)₅CH₃ |
| 23 | —CO—⟨C₆H₄⟩—N⟨piperazine⟩N—⟨C₆H₄⟩—O—(CH₂)₅CH₃ |
| 24 major product | —CO—⟨biphenyl⟩—O—(CH₂)₈OCH₃ |
| 24 minor product | —CO—⟨biphenyl⟩—O—(CH₂)₆—CH=CH₂ |

-continued
25 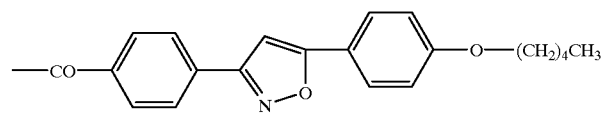
26 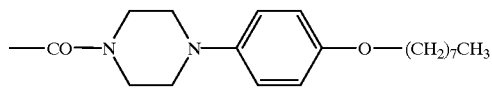
27 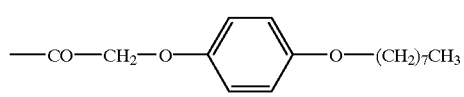
28 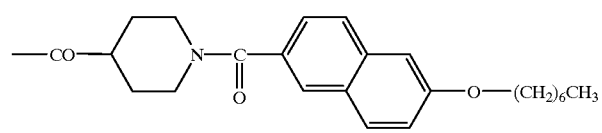
29 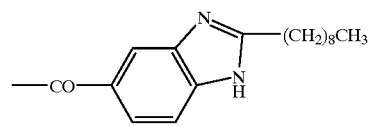
30 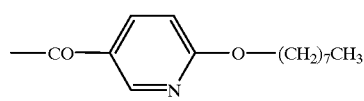
31 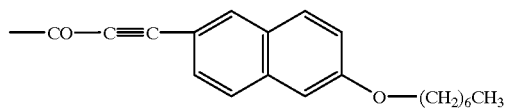
32 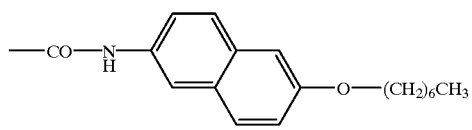
33 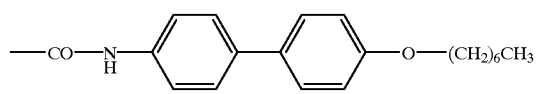
34 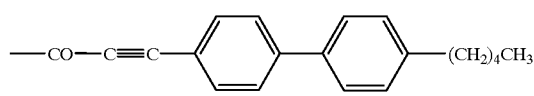
35 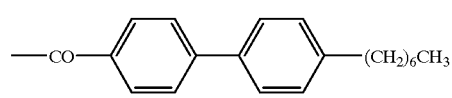
36 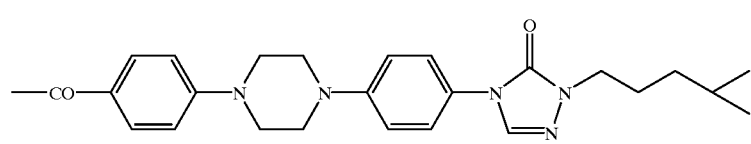

-continued
| | |
|---|---|
| 37 | 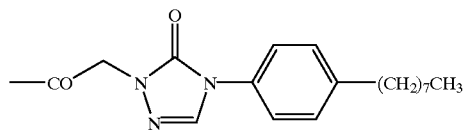 |
| 38 major product | 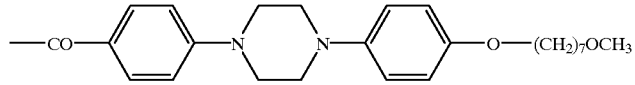 |
| 38 minor product | 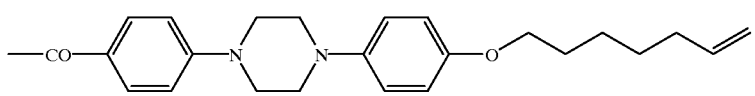 |
| 39 | 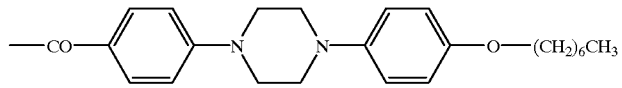 |
| 40 | 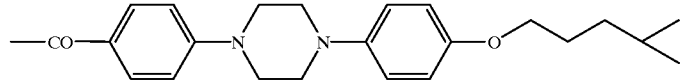 |
| 41 | 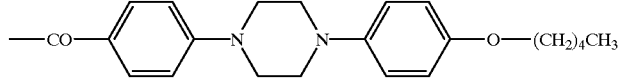 |
| 42 mixture product | 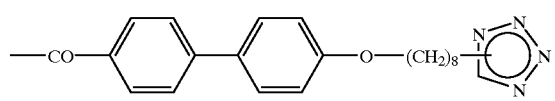 |
| 43 | 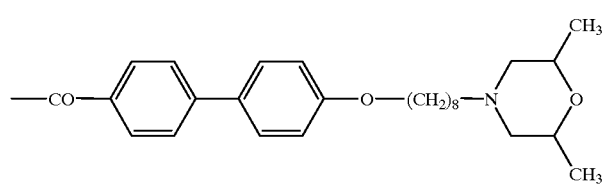 |
| 44 | 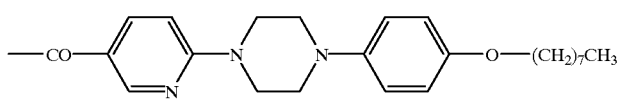 |
| 45 | 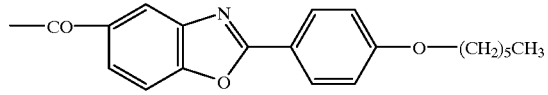 |
| 46 | 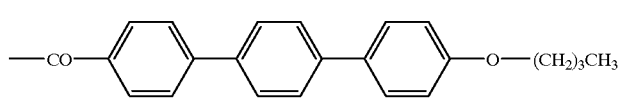 |
| 47 | 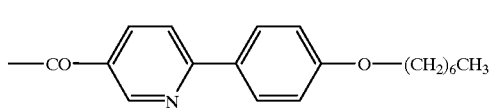 |
| 48 | 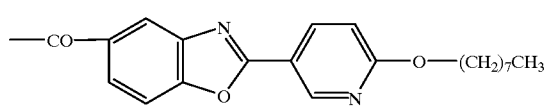 |

-continued
49 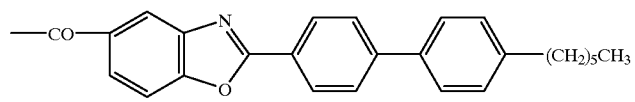
50 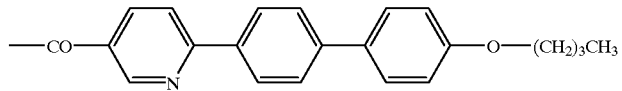
51 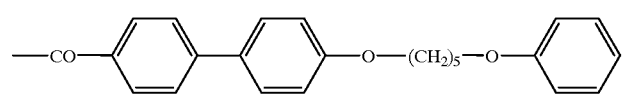
52 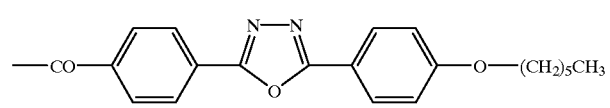
53 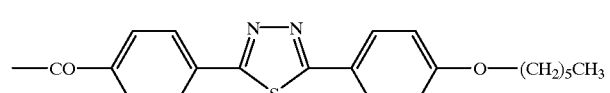
54 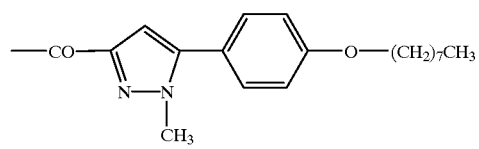
55 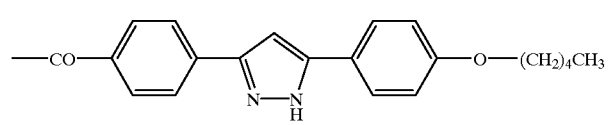
56 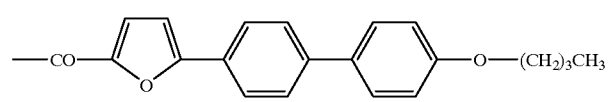
57 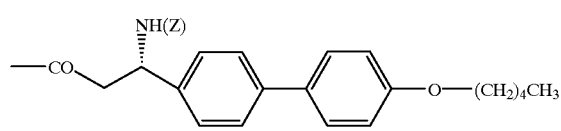
58 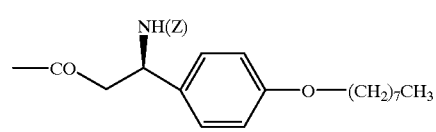
59 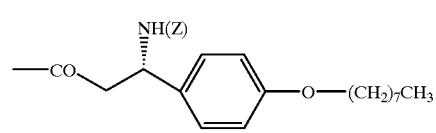
60 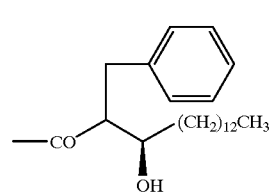

| | |
|---|---|
| 61 | 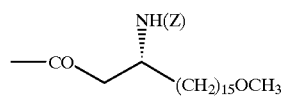 |
| 62 | 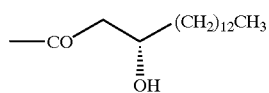 |
| 63 | 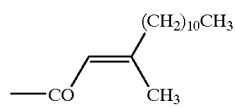 |
| 64 major product | 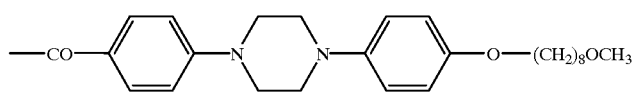 |
| 64 minor product | 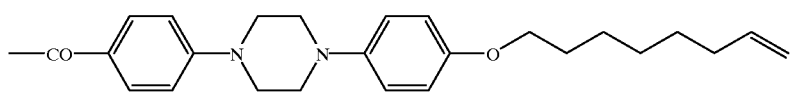 |
| 65 | 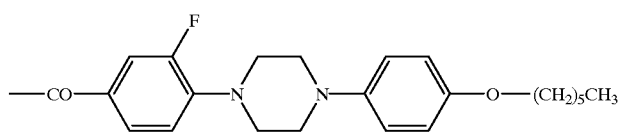 |
| 66 | 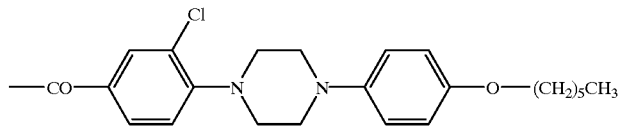 |
| 67 | 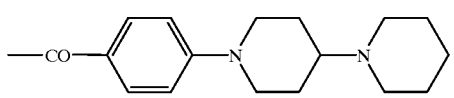 |
| 68 | 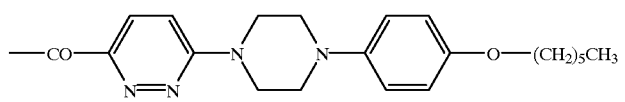 |
| 69 | 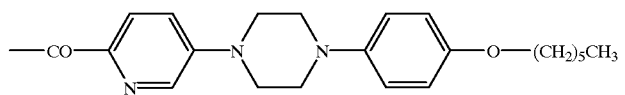 |
| 70 | 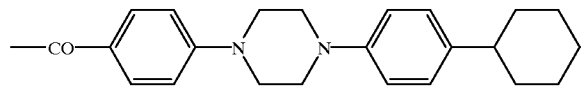 |
| 71 | 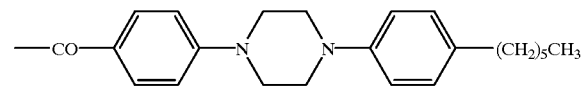 |
| 72 | 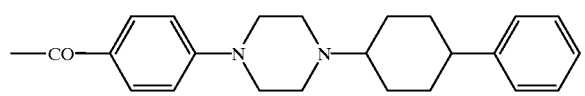 |

-continued
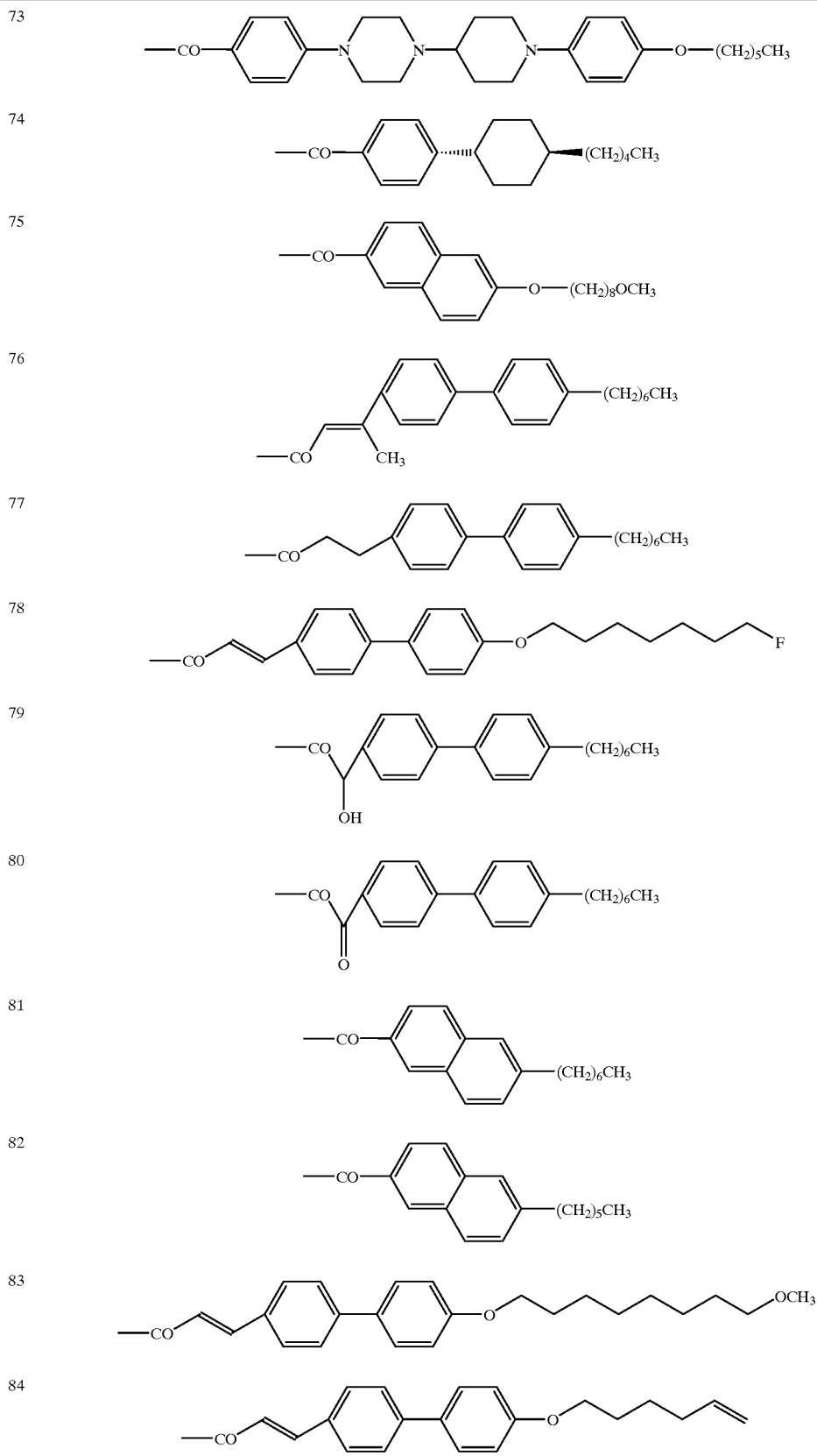

-continued
85 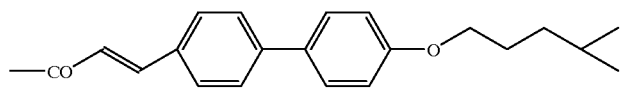
86 
87 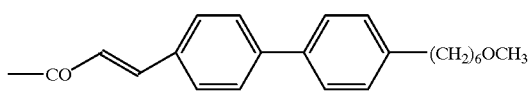
88 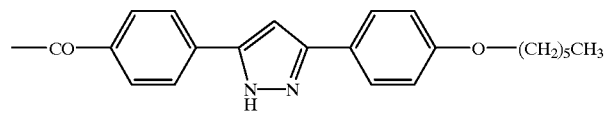
89 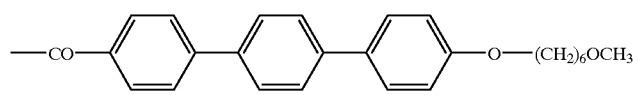
90 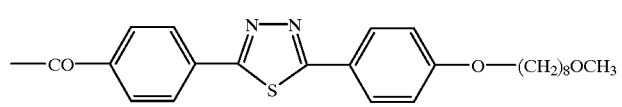
91 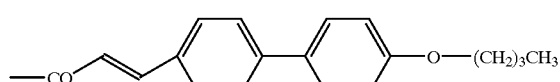
92 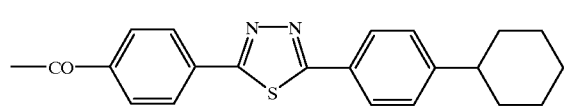
93 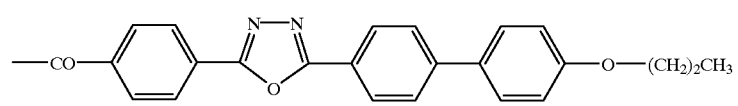
94 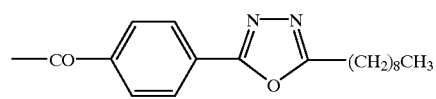
95 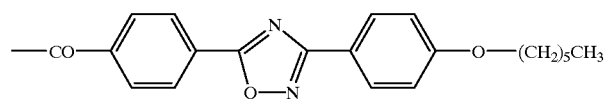
96 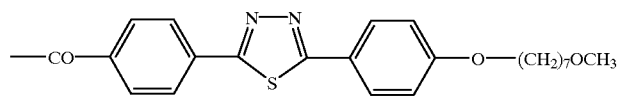
97 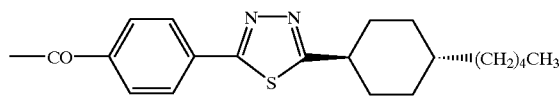

-continued
98 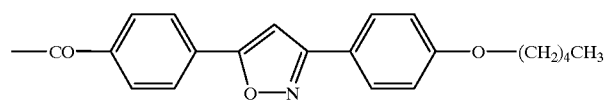
99 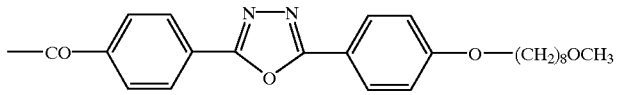
100 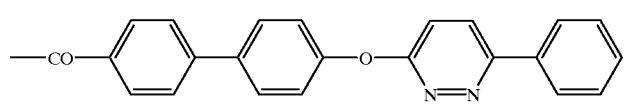
101 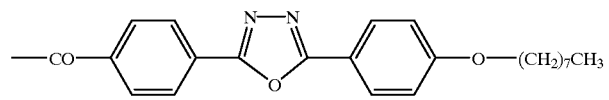
102 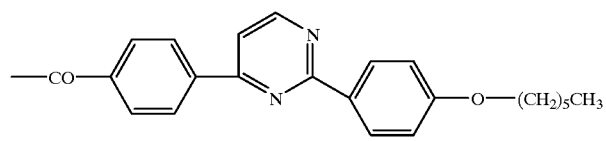
103 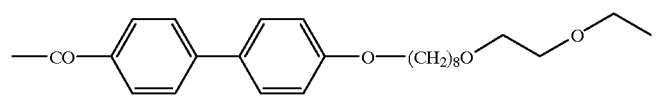
104 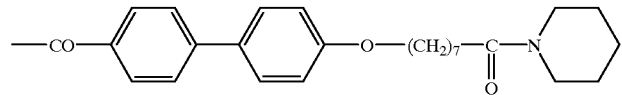
105 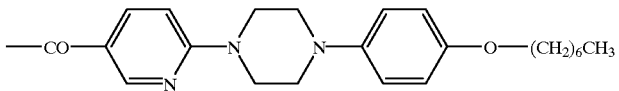
106 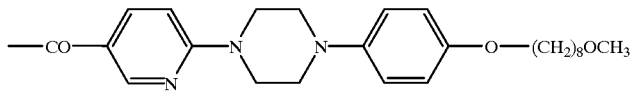
107 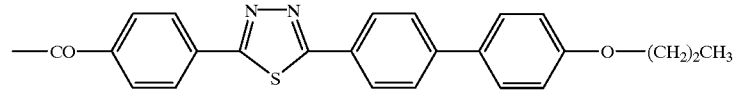
108 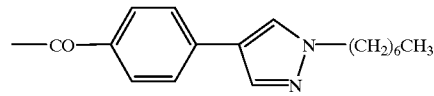
109 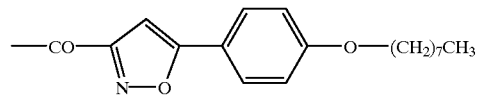
110 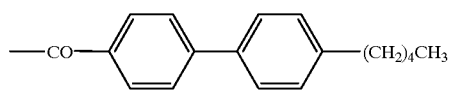

-continued
111 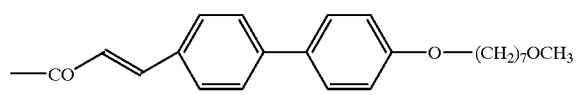
112 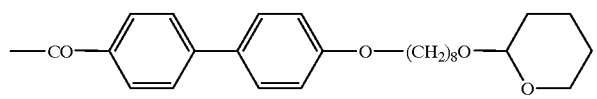
113 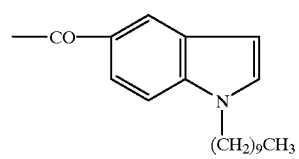
114 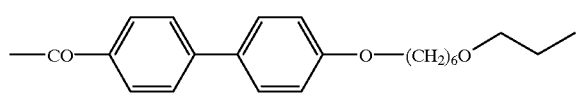
115 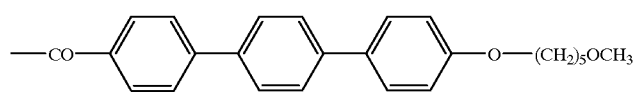
116 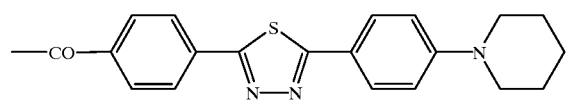
117 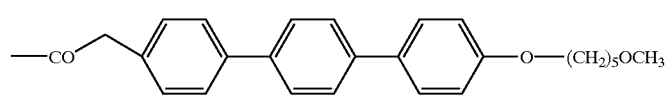
118 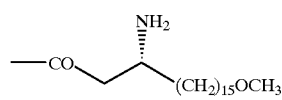
119 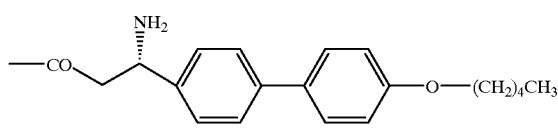
120 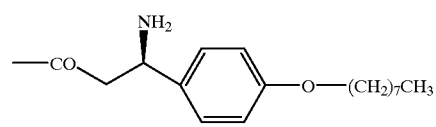
121 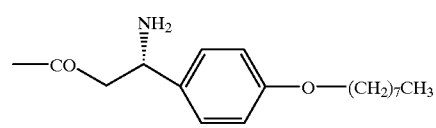
122 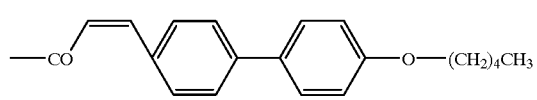

-continued

| Example No. | The Object Compound |
|---|---|
| 123 | 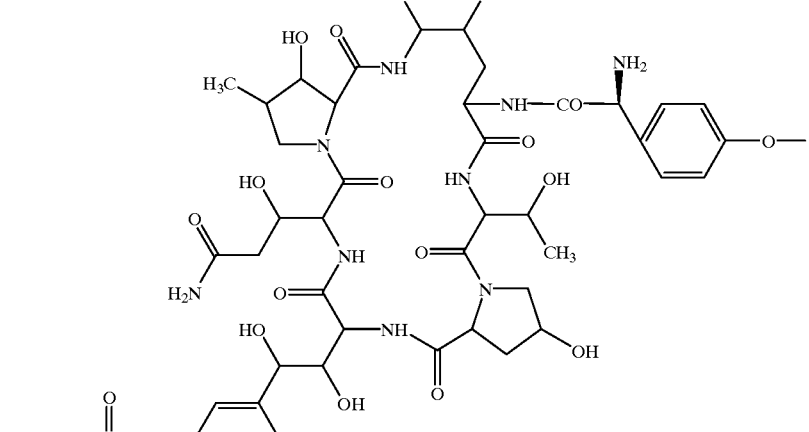 |

| Example No. | R |
|---|---|
| 124 | 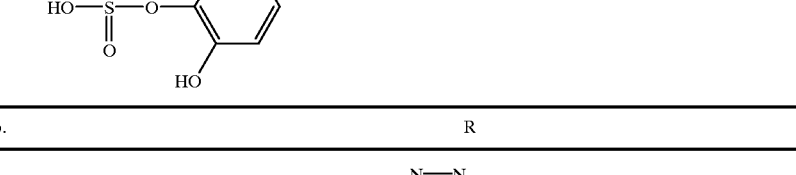 |

EXAMPLE 1

To a solution of the Starting Compound (1 g) and 1-(6-octyl-oxymethylpicolinoyl)benzotriazole 3-oxide (0.399 g) in N,N-dimethylformamide (10 ml) was added 4-(N,N-dimethylamino)pyridine (0.140 g), and stirred for 12 hours at ambient temperature. The reaction mixture was pulverized with ethyl acetate. The precipitate was collected by filtration, and dried under reduced pressure. The powder was dissolved in water, and subjected to column chromatography on ion exchange resin (DOWEX-50WX4 (Trademark: prepared by Dow Chemical)) eluting with water. The fractions containing the object compound were combined, and subjected to column chromatography on ODS (YMC-gel.ODS-AM.S-50) (Trademark: prepared by Yamamura Chemical Lab.) eluting with 50% methanol aqueous solution. The fractions containing the object compound were combined, and evaporated under reduced pressure to remove methanol. The residue was lyophilized to give The Object Compound (1).

IR (KRr): 3347, 1664, 1629, 1517 cm$^{-1}$

NMR (DMSO-d$_6$, δ): 0.86 (3H, t, J=6.7 Hz), 0.98 (3H, d, J=6.7 Hz), 1.09 (3H, d, J=6.0 Hz), 1.2–1.47 (10H, m), 1.47–1.67 (2H, m), 1.67–2.06 (3H, m), 2.06–2.5 (4H, m), 3.19 (1H, m), 3.53 (2H, t, J=6.4 Hz), 3.5–3.85 (2H, m), 3.85–4.7 (13H, m), 5.35 (11H, m), 5.56 (1H, d, J=5.7 Hz), 6.73 (1H, d, J=8.3 Hz), 6.83 (1H, d, J=8.3 Hz), 6.89 (1H, s), 7.05 (1H, s), 7.11 (1H, s), 7.32 (1H, m), 7.43 (1H, d, J=8.5 Hz), 7.63 (1H, d, J=7.3 Hz), 7.85–8.13 (4H, m), 8.66 (1H, d, J=7.8 Hz), 8.84 (1H, s)

FAB-MASS: m/z=1228 (M$^+$+Na)

Elemental Analysis Calcd. for C$_{50}$H$_{72}$N$_9$O$_{22}$SNa.6H$_2$O: C 45.49, H 6.44, H 9.59 Found: C 45.89, H 6.52, N 9.69

The Object Compounds (2) to (25) were obtained according to a similar manner to that of Example 1.

EXAMPLE 2

IR (KRr): 3353, 1666, 1510, 1236 cm$^{-1}$

NMR (DMSO-d$_6$, δ): 0.86 (3H, t, J=6.7 Hz), 0.96 (3H, d, J=6.7 Hz), 1.06 (3H, d, J=5.8 Hz), 1.2–1.5 (10H, m), 1.55–2.05 (5H, m), 2.11–2.7 (4H, m), 3.0–3.3 (5H, m), 3.3–3.5 (4H, m), 3.6–4.5 (15H, m), 4.6–5.6 (12H, m), 6.6–7.2 (10H, m), 7.2–7.5 (3H, m), 7.81 (2H, d, J=8.8 Hz), 8.05 (1H, d, J=8.7 Hz), 8.28 (1H, d, J=8.7 Hz), 8.41 (1H, d, J=6.7 Hz), 8.84 (1H, s)

FAB-MASS: m/z=1373 (M$^+$+Na)

Elemental Analysis Calcd. for C$_{60}$H$_{83}$N$_{10}$O$_{22}$SNa.4H$_2$O: C 50.63, H 6.44, H 9.84 Found: C 50.59, H 6.59, N 9.79

EXAMPLE 3

IR (KRr): 3350, 1664, 1627, 1047 cm$^{-1}$

NMR (DMSO-d$_6$, δ): 0.96 (3H, d, J=6.6 Hz), 1.08 (3H, d, J=5.7 Hz), 1.15–1.53 (8H, m), 1.55–2.1 (9H, m), 2.1–2.45 (3H, m), 2.5–2.7 (1H, m), 3.18 (1H, m), 3.6–3.83 (2H, m), 3.83–4.6 (17H, m), 4.7–5.4 (11H, m), 5.51 (1H, d, J=5.9 Hz), 6.73 (1H, d, J=8.2 Hz), 6.83 (1H, d, J=8.2 Hz), 6.85 (1H, s), 7.03 (2H, d, J=8.4 Hz), 7.05 (1H, s), 7.30 (1H, s), 7.2–7.5 (2H, m), 7.67 (2H, d, J=8.4 Hz), 7.71 (2H, d, J=7.4 Hz), 7.94 (1H, s), 7.96 (2H, d, J=7.4 Hz), 8.06 (1H, d, J=8.0 Hz), 8.25 (1H, d, J=6.7 Hz), 8.50 (1H, s), 8.74 (1H, d, J=6.7 Hz), 8.84 (1H, s)

FAB-MASS: m/z=1356 (M$^+$+Na)

Elemental Analysis Calcd. for C$_{58}$H$_{77}$N$_{11}$O$_{22}$SNa.4H$_2$O: C 49.53, H 6.02, N 10.95 Found: C 49.26, H 6.22, N 10.77

EXAMPLE 4

IR (KRr): 3350, 1660, 1631, 1047 cm$^{-1}$

NMR (DMSO-d$_6$, δ): 0.86 (3H, t, J=6.9 Hz), 0.97 (3H, d, J=6.6 Hz), 1.09 (3H, d, J=5.3 Hz), 1.2–1.5 (10H, m), 1.37 (6H, s), 1.55–2.0 (5H, m), 2.1–2.6 (4H, m), 3.16 (1H, m), 3.73 (2H, m), 3.89 (2H, t, J=6.3 Hz), 3.95–4.49 (11H, m), 5.68–5.21 (10H, m), 5.25 (1H, d, J=4.1 Hz), 5.53 (1H, d, J=5.7 Hz), 6.73 (1H, d, J=8.2 Hz), 6.75–6.85 (4H, m), 6.91 (1H, d, J=8.2 Hz), 7.05 (1H, s), 7.15 (1H, s), 7.3–7.5 (2H, m), 7.9–8.2 (3H, m), 8.84 (1H, s)

FAB-MASS: m/z=1271 (M$^+$+Na)

Elemental Analysis Calcd. for C$_{53}$H$_{77}$N$_8$O$_{23}$SNa.4H$_2$O: C 48.18, H 6.48, H 8.48 Found: C 48.04, H 6.51, N 8.38

EXAMPLE 5

IR (KRr): 1666, 1629, 1222 cm$^{-1}$

NMR (DMSO-d$_6$, δ): 0.85 (3H, t, J=6.6 Hz), 0.9–1.12 (6H, m), 1.12–1.52 (13H, m), 1.52–1.93 (5H, m), 2.08–2.55 (4H, m), 3.16 (1H, m), 3.6–5.3 (26H, m), 5.49+5.54 (1H, d, J=5.8 Hz, mixtures of diastereomer), 6.60–7.1 (7H, m), 7.04 (1H, s), 7.1 (1H, m), 7.2–7.5 (2H, m), 7.9–8.43 (3H, m), 8.83 (1H, s)

FAB-MASS: m/z=1257 (M$^+$+Na)

Elemental Analysis Calcd. for C$_{52}$H$_{75}$N$_8$O$_{23}$SNa.3H$_2$O: C 48.44, H 6.33, H 8.69 Found: C 48.16, H 6.51, N 8.53

EXAMPLE 6

IR (KBr): 3349, 1666, 1629, 1259 cm$^{-1}$

NMR (DMSO-d$_6$, δ): 0.86 (3H, t, J=6.7 Hz), 0.9 (3H, d, J=5.7 Hz), 0.96 (3H, d, J=6.7 Hz), 1.1–1.55 (19H, m), 1.55–2.0 (5H, m), 2.0–2.47 (4H, m), 2.65–3.25 (3H, m), 3.5–5.13 (27H, m), 5.17 (1H, d, J=3.2 Hz), 5.24 (1H, d, J=4.5 Hz), 5.38 (1H, d, J=5.9 Hz), 6.5–6.9 (5H, m), 6.9–7.1 (3H, m), 7.2–7.46 (2H, m), 7.7–8.1 (3H, m), 8.83 (1H, s)

FAB-MASS: m/z=1368 (M$^+$+Na)

Elemental Analysis Calcd. for C$_{58}$H$_{84}$N$_9$O$_{24}$SNa.5H$_2$O: C 48.50, H 6.60, H 8.78 Found: C 48.47, H 6.83, N 8.78

EXAMPLE 7

IR (KRr): 3350, 1666, 1502, 1199 cm$^{-1}$

NMR (DMSO-d$_6$, δ): 0.86 (3H, t, J=6.6 Hz), 0.97 (3H, d, J=6.7 Hz), 1.06 (3H, d, J=5.7 Hz), 1.2–1.5 (10H, m), 1.55–2.0 (5H, m), 2.1–2.6 (4H, m), 3.17 (1H, m), 3.7–4.5 (15H, m), 4.7–5.22 (10H, m), 5.24 (1H, d, J=4.4 Hz), 5.60 (1H, d, J=5.9 Hz), 6.68–7.03 (8H, m), 7.04 (1H, s), 7.2–7.42 (2H, m), 7.85–8.1 (3H, m), 8.83 (1H, s)

FAB-MASS: m/z=1229 (M$^+$+Na)

Elemental Analysis Calcd. for C$_{50}$H$_{71}$N$_8$O$_{23}$SNa.5H$_2$O: C 46.29, H 6.29, H 8.64 Found: C 46.39, H 6.05, N 8.72

EXAMPLE 8

IR (KRr): 3350, 1666, 1631, 1513 cm$^{-1}$

NMR (DMSO-d$_6$, δ): 0.88 (3H, t, J=6.2 Hz), 0.97 (3H, d, J=6.7 Hz), 1.04 (3H, d, J=5.7 Hz), 1.2–1.58 (8H, m), 1.58–2.0 (5H, m), 2.0–2.6 (4H, m), 3.17 (1H, m), 3.6–4.5 (15H, m), 4.63–5.33 (13H, m), 5.53 (1H, d, J=5.9 Hz), 6.73 (1H, d, J=8.2 Hz), 6.82 (1H, d, J=8.2 Hz), 6.84 (1H, s), 6.95–7.52 (7H, m), 7.66 (1H, d, J=7.6 Hz), 7.7–7.9 (3H, m), 8.05 (1H, d, J=9.1 Hz), 8.15 (1H, d, J=7.6 Hz), 8.85 (1H, s)

FAB-MASS: m/z=1279 (M$^+$+Na)

Elemental Analysis Calcd. for C$_{54}$H$_{73}$N$_8$O$_{23}$SNa.5H$_2$O: C 48.14, H 6.21, H 8.32 Found: C 48.43, H 6.28, N 8.30

EXAMPLE 9

IR (KRr): 3347, 2956, 1664, 1633, 1508, 1444, 1268, 1047 cm$^{-1}$

NMR (DMSO-d$_6$, δ): 0.9–1.1 (9H, m), 1.06 (3H, d, J=5.9 Hz), 1.3–1.5 (8H, m), 1.6–2.0 (7H, m), 2.1–2.4 (3H, m), 2.5–2.6 (1H, m), 3.1–3.3 (1H, m), 3.6–4.4 (17H, m), 4.7–5.0 (8H, m), 5.09 (1H, d, J=5.5 Hz), 5.16 (1H, d, J=3.1 Hz), 5.24 (1H, d, J=4.5 Hz), 6.73 (1H, d, J=8.2 Hz), 6.8–6.9 (2H, m), 6.98 (1H, d, J=8.3 Hz), 7.05 (1H, d, J=1.7 Hz), 7.3–7.6 (5H, m), 8.08 (1H, d, J=8.9 Hz), 8.25 (1H, d, J=8.4 Hz), 8.54 (1H, d, J=7.5 Hz), 8.93 (1H, s)

FAB-MASS: m/z=1257 (M$^+$+Na)

Elemental Analysis Calcd. for C$_{52}$H$_{75}$N$_8$O$_{23}$SNa.4H$_2$O: C 47.78, H 6.40, H 8.57 Found: C 47.88, H 6.71, N 8.53

EXAMPLE 10

IR (KRr): 3350, 2931, 1664, 1625, 1529, 1440, 1276, 1226, 1047 cm$^{-1}$

NMR (DMSO-d$_6$, δ): 0.86 (3H, t, J=6.8 Hz), 0.97 (3H, d, J=6.7 Hz), 1.12 (3H, d, J=5.9 Hz), 1.2–1.5 (10H, m), 1.6–2.1 (5H, m), 2.1–2.4 (4H, m), 3.1–3.3 (1H, m), 3.5–4.6 (15H, m), 4.7–5.0 (3H, m), 5.0–5.2 (7H, m), 5.27 (1H, d, J=4.4 Hz), 5.55 (1H, d, J=5.7 Hz), 6.73 (1H, d, J=8.2 Hz), 6.8–7.0 (2H, m), 7.0–7.2 (4H, m), 7.3–7.6 (2H, m), 7.90 (1H, d, J=8.8 Hz), 8.0–8.2 (2H, m), 8.8–8.9 (2H, m), 9.06 (1H, d, J=7.2 Hz)

FAB-MASS: m/z=1281 (M$^+$+Na)

Elemental Analysis Calcd. for C$_{53}$H$_{71}$N$_8$O$_{24}$SNa.5H$_2$O: C 47.18, H 6.05, H 8.30 Found: C 46.97, H 6.27, N 8.22

EXAMPLE 11

NMR (DMSO-D$_6$, δ): 0.87–1.05 (6H, m), 1.10 (3H, d, J=5.7 Hz), 1.3–1.5 (4H, m), 1.6–1.9 (5H, m), 2.2–2.5 (3H, m), 2.6 (1H, m), 3.1–3.2 (1H, m), 3.7–4.5 (15H, m), 4.8–5.1 (8H, m), 5.09 (1H, d, J=5.64 Hz), 5.16 (1H, d, J=3.2 Hz), 5.26 (1H, d, J=4.2 Hz), 5.52 (1H, d, J=6.0 Hz), 6.73 (2H, d, J=8.4 Hz), 6.8–6.9 (2H, m), 7.0–7.1 (3H, m), 7.2–7.4 (4H, m), 7.6–7.8 (6H, m), 8.11 (1H, d, J=8.4 Hz), 8.29 (1H, d, J=8.4 Hz), 8.51 (1H, d, J=7.7 Hz), 8.85 (1H, s)

FAB-MASS: m/z=1273 (M$^+$+Na)

Elemental Analysis Calcd. for C$_{55}$H$_{71}$N$_8$O$_{22}$SNa.4H$_2$O: C 49.92, H 6.02, H 8.47 Found: C 49.79, H 6.14, N 8.45

EXAMPLE 12

IR (KRr): 3330, 2929, 1670, 1629, 1533, 1440, 1280, 1226, 1045, 804 cm$^{-1}$

NMR (DMSO-d$_6$, δ): 0.86 (3H, t, J=6.7 Hz), 0.97 (3H, d, J=6.7 Hz), 1.08 (3H, d, J=5.9 Hz), 1.2–1.6 (10H, m), 1.6–2.0 (5H, m), 2.1–2.5 (4H, m), 3.1–3.3 (1H, m), 3.6–4.5 (15H, m), 4.8 (9H , m), 5.17 (1H, d, J=3.0 Hz), 5.25 (1H, d, J=4.5 Hz), 5.56 (1H, d, J=5.6 Hz), 6.73 (1H, d, J=8.2 Hz), 6.83 (1H, d, J=6.8 Hz), 7.1–7.2 (3H, m), 7.3–7.5 (3H, m), 7.85 (1H , d, J=8.8 Hz), 8.0–8.2 (3H, m), 8.84 (1H, s), 8.96 (1H, d, J=7.2 Hz)

FAB-MASS: m/z=1269 (M$^+$+Na)

Elemental Analysis Calcd. for C$_{52}$H$_{71}$N$_8$O$_{22}$S$_2$Na.4H$_2$O: C 47.34, H 6.04, H 8.49 Found: C 47.21, H 5.96, N 8.41

EXAMPLE 13

IR (KRr): 3345, 2927, 1664, 1629, 1515, 1442, 1274, 1047 cm$^{-1}$

NMR (DMSO-d$_6$, δ): 0.85 (3H, t, J=6.7 Hz), 0.97 (3H, d, J=6.7 Hz), 1.10 (3H, d, J=5.9 Hz), 1.2–1.4 (10H, m), 1.5–2.5

(8H, m), 2.46 (3H, s), 2.69 (2H, t, J=7.7 Hz), 3.1–3.4 (2H, m), 3.6–4.5 (17H, m), 4.8–5.2 (8H, m), 6.7–7.0 (3H, m), 7.05 (1H, d, J=1.7 Hz), 7.14 (1H, s), 7.3–7.6 (5H, m), 8.0–8.2 (2H, s), 8.47 (1H, d, J=7.0 Hz), 8.84 (1H, s)

FAB-MASS: m/z=1251 (M$^+$+Na)

Elemental Analysis Calcd. for $C_{53}H_{73}N_8O_{22}SNa.3H_2O$: C 49.61, H 6.21, H 8.73 Found: C 49.88, H 6.44, N 8.74

EXAMPLE 14

IR (KRr): 3340, 1672, 1627, 1542, 1513, 1440, 1268, 1045 cm$^{-1}$

NMR (DMSO-d$_6$, δ): 0.84 (3H, t, J=6.7 Hz), 0.94 (3H, d, J=6.7 Hz), 1.07 (3H, d, J=6.0 Hz), 1.2–1.4 (12H, m), 1.6–2.0 (5H, m), 2.1–2.4 (3H, m), 2.6 (1H, m), 2.96 (2H, t, J=7.4 Hz), 3.1–3.3 (1H, m), 3.6–4.5 (13H, m), 4.7–5.2 (11H, m), 5.50 (1H, d, J=5.7 Hz), 6.73 (1H, d, J=8.2 Hz), 6.8–6.9 (2H, m), 7.04 (1H, s), 7.2–7.5 (3H, m), 7.72 (1H, d, J=8.5 Hz), 7.91 (1H, d, J=8.4 Hz), 8.05 (1H, d, J=8.4 Hz), 8.2–8.4 (1H, m), 8.80 (1H, d, J=7.7 Hz), 8.83 (1H, s)

FAB-MASS: m/z=1252 (M$^+$+Na)

Elemental Analysis Calcd. for $C_{52}H_{72}N_9O_{22}SNa.6H_2O$: C 46.67, H 6.33, H 9.42 Found: C 46.72, H 6.53, N 9.45

EXAMPLE 15

IR (KRr): 3350, 2935, 1664, 1627, 1517, 1446, 1251, 1045 cm$^{-1}$

NMR (DMSO-d$_6$, δ): 0.90–1.1 (6H, m), 1.10 (3H, d, J=5.9 Hz), 1.2–1.4 (6H, m), 1.6–2.4 (8H, m), 2.6–2.7 (1H, m), 3.1–3.3 (1H, m), 3.7–4.5 (16H, m), 4.7–5.4 (11H, m), 5.51 (1H, d, J=5.6 Hz), 6.7–7.0 (3H, m), 7.0–7.6 (7H, m), 7.74 (1H, d, J=8.6 Hz), 8.0–8.4 (5H, m), 8.7–8.8 (1H, m), 8.84 (1H, s)

FAB-MASS: m/z=1301 (M$^+$+Na)

Elemental Analysis Calcd. for $C_{55}H_{71}N_{10}O_{22}SNa.6H_2O$: C 47.62, H 6.03, H 10.01 Found: C 47.65, H 6.03, N 10.03

EXAMPLE 16

IR (KRr): 3353, 1668, 1627, 1540, 1515, 1500 cm$^{-1}$

NMR (DMSO-d$_6$, δ): 0.80–1.00 (6H, m), 1.06 (3H, d, J=5.9 Hz), 1.20–1.53 (4H, m), 1.60–1.95 (5H, m), 2.00–2.65 (8H, m), 2.80 (2H, t, J=7.5 Hz), 3.05–3.45 (1H, m), 3.50–3.85 (2H, m), 3.90–4.48 (11H, m), 4.65–5.38 (11H, m), 5.47 (1H, d, J=6.0 Hz), 6.65–6.90 (2H, m), 6.90–7.10 (2H, m), 7.10–7.65 (11H, m), 7.90–8.25 (2H, m), 8.30 (1H, d, J=7.8 Hz), 8.84 (1H, s)

FAB-MASS: m/z=1275.3 (M$^+$+Na)

Elemental Analysis Calcd. for $C_{55}H_{73}N_8O_{22}SNa.3H_2O$: C 50.53, H 6.09, H 8.57 Found: C 50.48, H 6.39, N 8.57

EXAMPLE 17

IR (Nujol): 3351, 1656, 1623, 1538, 1515 cm$^{-1}$

NMR (DMSO-D$_6$, δ): 0.86 (3H, t, J=6.7 Hz), 0.96 (3H, d, J=6.7 Hz), 1.08 (3H, d, J=5.8 Hz), 1.15–1.40 (8H, m), 1.50–2.00 (5H, m), 2.10–2.48 (4H, m), 2.52–2.70 (2H, m), 3.05–3.28 (1H, m), 3.60–4.50 (13H, m), 4.70–5.20 (9H, m), 5.25 (1H, d, J=4.6 Hz), 5.52 (1H, d, J=6.0 Hz), 6.68–6.92 (4H, m), 7.04 (1H, d, J=1.0 Hz), 7.22–7.50 (5H, m), 7.55–7.82 (7H, m), 8.14 (1H, d, J=8.4 Hz), 8.31 (1H, d, J=8.4 Hz), 8.54 (1H, d, J=7.7 Hz), 8.84 (1H, s)

FAB-MASS: m/z=1285 (M$^+$+Na)

EXAMPLE 18

IR (Nujol): 3351, 1668, 1627, 1540, 1515 cm$^{-1}$

NMR (DMSO-D$_6$, δ): 0.87 (3H, t, J=6.8 Hz), 0.96 (3H, d, J=6.7 Hz), 1.06 (3H, d, J=5.8 Hz), 1.17–1.48 (4H, m), 1.50–1.95 (5H, m), 2.05–2.70 (8H, m), 2.70–2.95 (2H, m), 3.05–3.30 (1H, m), 3.60–3.90 (2H, m), 3.90–4.50 (11H, m), 4.65–5.10 (9H, m), 5.15 (1H, d, J=3.2 Hz), 5.23 (1, d, J=4.2 Hz), 5.48 (1H, d, J=6.0 Hz), 6.67–6.90 (3H, m), 7.03 (1H, d, J=1.5 Hz), 7.15–7.80 (11H, m), 8.00–8.20 (2H, m), 8.29 (1H, d, J=7.8 Hz), 8.84 (1H, s)

FAB-MASS: m/z=1259 (M$^+$+Na)

Elemental Analysis Calcd. for $C_{55}H_{73}N_8O_{21}SNa.6H_2O$: C 50.30, H 6.52, H 8.53 Found: C 50.42, H 6.50, N 8.45

EXAMPLE 19

IR (Nujol): 3351, 1668, 1652, 1623, 1540 cm$^{-1}$

NMR (DMSO-D$_6$, δ): 0.87 (3H, t, J=6.7 Hz), 0.96 (3H, d, J=6.7 Hz), 1.07 (3H, d, J=6.0 Hz), 1.25–1.45 (4H, m), 1.50–2.00 (5H, m), 2.05–2.48 (4H, m), 2.40–2.75 (2H, m), 3.60–4.50 (13H, m), 4.68–5.25 (10H, m), 5.27 (1H, d, J=4.5 Hz), 5.53 (1H, d, J=6.0 Hz), 6.67–6.98 (4H, m), 7.05 (1H, d, J=1.0 Hz), 7.22–7.58 (5H, m), 7.58–7.90 (7H, m), 8.16 (1H, d, J=9.0 Hz), 8.34 (1H, d, J=8.4 Hz), 8.57 (1H, d, J=7.7 Hz), 8.85 (1H, s)

FAB-MASS: m/z=1258 (M$^+$+Na)

Elemental Analysis Calcd. for $C_{55}H_{71}N_8O_{21}SNa.5H_2O$: C 49.84, H 6.15, H 8.45 Found: C 49.77, H 6.27, N 8.39

EXAMPLE 20

IR (Nujol): 3353, 1670, 1629, 1540, 1508 cm$^{-1}$

NMR (DMSO-D$_6$, δ): 0.88 (3H, t, J=6.5 Hz), 0.97 (3H, d, J=6.8 Hz), 1.04 (3H, d, J=5.9 Hz), 1.20–1.58 (8H, m), 1.60–1.96 (5H, m), 2.08–2.60 (6H, m), 2.70–3.00 (2H, m), 3.00–3.40 (1H, m), 3.60–3.85 (2H, m), 3.85–4.50 (13H, m), 4.50–5.60 (12H, m), 6.65–6.90 (3H, m), 7.00–7.15 (3H, m), 7.18–7.50 (4H, m), 7.59 (1H, s), 7.62–7.78 (2H, m), 7.95–8.20 (2H, m), 8.30 (1H, d, J=7.7 Hz), 8.83 (1H, s)

FAB-MASS: m/z=1277 (M$^+$+Na)

Elemental Analysis Calcd. for $C_{55}H_{75}N_8O_{22}SNa.4H_2O$: C 49.77, H 6.30, H 8.44 Found: C 49.67, H 6.31, N 8.40

EXAMPLE 21

IR (Nujol): 3351, 1654, 1623, 1538, 1515 cm$^{-1}$

NMR (DMSO-D$_6$, δ): 0.87 (3H, t, J=6.7 Hz), 0.97 (3H, d, J=6.7 Hz), 1.08 (3H, d, J=5.9 Hz), 1.20–1.58 (8H, m), 1.66–1.95 (5H, m), 2.10–2.60 (4H, m), 3.09–3.30 (1H, m), 3.58–4.60 (15H, m), 4.69–5.20 (10H, m), 5.24 (1H, d, J=4.5 Hz), 5.51 (1H, d, J=6.0 Hz), 6.68–6.95 (4H, m), 7.04 (1H, d, J=1.0 Hz), 7.10–7.73 (7H, m), 7.73–7.90 (2H, m), 7.98 (1H, d, J=1.9 Hz), 8.10 (1H, d, J=8.4 Hz), 8.32 (1H, d, J=8.4 Hz), 8.50 (1H, d, J=7.7 Hz), 8.84 (1H, s)

FAB-MASS: m/z=1275 (M$^+$+Na)

Elemental Analysis Calcd. for $C_{55}H_{73}N_8O_{22}SNa.5H_2O$: C 50.38, H 6.38, H 8.55 Found: C 49.98, H 6.37, N 8.41

EXAMPLE 22

IR (Nujol): 3340, 2931, 1664, 1627, 1531, 1444, 1278, 1047 cm$^{-1}$

NMR (DMSO-D$_6$, δ): 0.86 (3H, t, J=6.6 Hz), 0.96 (3H, d, J=6.8 Hz), 1.08 (3H, d, J=5.9 Hz), 1.2–1.4 (6H, m), 1.5–1.7 (2H, m), 1.7–2.1 (3H, m), 2.2–2.4 (3H, m), 2.6–2.7 (3H, m), 3.1–3.2 (1H, m), 3.7–4.6 (13H, m), 4.78 (1H, d, J=6.0 Hz), 4.8–5.1 (1H, m), 5.09 (1H, d, J=5.6 Hz), 5.16 (1H, d, J=3.2 Hz), 5.24 (1H, d, J=4.4 Hz), 5.52 (1H, d, J=6.0 Hz), 6.73 (1H, d, J=8.2 Hz), 6.83 (2H, d, J=8.3 Hz), 7.05 (1H, s), 7.3–7.5 (5H, m), 7.65 (2H, d, J=8.2 Hz), 7.74 (2H, d, J=8.4 Hz), 7.98 (2H, d, J=8.4 Hz), 8.11 (1H, d, J=8.4 Hz), 8.31 (1H, d, J=8.4 Hz), 8.79 (1H, d, J=7.7 Hz), 8.84 (1H, s)

FAB-MASS: m/z=1245 ($M^+$+Na)

Elemental Analysis Calcd. for $C_{54}H_{71}N_8O_{21}SNa.4H_2O$: C 50.07, H 6.15, H 8.65 Found: C 50.26, H 6.44, N 8.67

EXAMPLE 23

NMR (DMSO-$D_6$, δ): 0.91 (3H, t, J=6.7 Hz), 0.96 (3H, d, J=6.8 Hz), 1.05 (3H, d, J=5.6 Hz), 1.2–1.5 (6H, m), 1.6–2.1 (5H, m), 2.1–2.7 (5H, m), 3.0–3.5 (9H, m), 3.6–4.5 (15H, m), 4.6–5.6 (11H, m), 6.73 (1H, d, J=8.2 Hz), 6.8–6.9 (4H, m), 6.95 (2H, d, J=8.6 Hz), 7.02 (2H, d, J=9.2 Hz), 7.04 (1H, s), 7.2–7.5 (3H, m), 7.82 (2H, d, J=8.6 Hz), 8.06 (1H, d, J=8 Hz), 8.25 (1H, d, J=6.7 Hz), 8.43 (1H, d, J=6.7 Hz), 8.85 (1H, s)

IR (KBr): 3350, 1668, 1629, 1510 $cm^{-1}$

FAB-MASS: m/z=1345 (M+Na)

Elemental Analysis Calcd. for $C_{58}H_{79}N_{10}O_{22}SNa.6H_2O$: C 48.67, H 6.41, N 9.78 Found: C 48.80, H 6.46, N 9.82

EXAMPLE 24

Major product

IR (KBr): 3350, 1668, 1631, 1047 $cm^{-1}$

NMR (DMSO-$d_6$, δ): 0.96 (3H, d, J=6.7 Hz), 1.08 (3H, d, J=5.7 Hz), 1.2–1.6 (10H, m), 1.6–2.4 (8H, m), 2.5–2.7 (1H, m), 3.18 (1H, m), 3.21 (3H, s), 3.29 (2H, t, J=6.4 Hz), 3.6–3.83 (2H, m), 3.83–4.6 (13H, m), 4.7–5.4 (11H, m), 5.51 (1H, d, J=5.9 Hz), 6.73 (1H, d, J=8.2 Hz), 6.83 (1H, d, J=8.2 Hz), 6.85 (1H, s), 7.04 (2H, d, J=8.4 Hz), 7.06 (1H, s), 7.31 (1H, s), 7.2–7.5 (2H, m), 7.67 (2H, d, J=8.4 Hz), 7.71 (2H, d, J=8.4 Hz), 7.96 (2H, d, J=8.4 Hz), 8.06 (1H, d, J=8 Hz), 8.25 (1H, d, J=6.7 Hz), 8.74 (1H, d, J=6.7 Hz), 8.84 (1H, s)

FAB-MASS: m/z=1319 (M+Na)

Elemental Analysis Calcd. for $C_{57}H_{77}N_8O_{23}SNa.4H_2O$: C 49.99, H 6.26, N 8.18 Found: C 49.74, H 6.27, N 8.06

Minor Product

IR (KBr): 3350, 1668, 1631 $cm^{-1}$

NMR (DMSO-$d_6$, δ): 0.96 (3H, d, J=6.7 Hz), 1.08 (3H, d, J=5.7 Hz), 1.2–1.6 (6H, m), 1.6–2.1 (7H, m), 2.1–2.5 (3H, m), 2.5–2.7 (1H, m), 3.18 (1H, m), 3.6–3.8 (2H, m), 3.8–4.6 (13H, m), 4.6–5.2 (12H, m), 5.26 (1H, d, J=4.6 Hz), 5.53 (1H, d, J=5.8 Hz), 5.6–6.0 (1H, m), 6.73 (1H, d, J=8.2 Hz), 6.83 (1H, d, J=8.3 Hz), 6.85 (1H, s), 7.04 (2H, d, J=8.5 Hz), 7.06 (1H, s), 7.30 (1H, s), 7.2–7.5 (2H, m), 7.68 (2H, d, J=8.5 Hz), 7.72 (2H, d, J=8.5 Hz), 7.96 (2H, d, J=8.5 Hz), 8.06 (1H, d, J=8 Hz), 8.25 (1H, d, J=6.7 Hz), 8.74 (1H, d, J=6.7 Hz), 8.85 (1H, s)

FAB-MASS: m/z=1287 (M+Na)

Elemental Analysis Calcd. for $C_{56}H_{73}N_8NaO_{22}S.7H_2O$: C 48.34, H 6.30, H 8.05 Found: C 48.19, H 6.19, N 7.99

EXAMPLE 25

IR (KRr): 3350, 2935, 2873, 1668, 1629, 1538, 1506, 1437, 1257, 1049 $cm^{-1}$

NMR (DMSO-$d_6$, δ): 0.9–1.0 (6H, m), 1.08 (3H, d, J=5.7 Hz), 1.2–1.6 (4H, m), 1.6–2.0 (5H, m), 2.1–2.4 (3H, m), 2.5–2.6 (1H, m), 3.1–3.2 (1H, m), 3.6–4.6 (15H, m), 4.7–5.2 (10H, m), 5.26 (1H, d J=4.5 Hz), 5.55 (1H, d, J=5.9 Hz), 6.7–6.9 (3H, m), 7.0–7.6 (7H, m), 7.85 (2H, d, J=8.6 Hz), 7.9–8.2 (4H, m), 8.26 (1H, d, J=7.7 Hz), 8.8–9.0 (2H, m)

FAB-MASS: m/z=1314.3 $(M+Na)^+$

Elemental Analysis Calcd. for $C_{56}H_{70}N_9O_{23}NaS.7H_2O$: C 47.42, H 5.97, H 8.89 Found: C 47.33, H 5.85, N 8.73

EXAMPLE 26

To a solution of The Starting Compound (1 g) and succinimido 4-(4-octyloxyphenyl)piperazine-1-carboxylate (0.45 g) in N,N-dimethylformamide (10 mL) was added 4-dimethylaminopyridine (0.141 g), and stirred for 5 days at 50° C. The reaction mixture was pulverized with ethyl acetate. The precipitate was collected by filtration, and dried under reduced pressure. The powder was dissolved in water, and subjected to column chromatography on ion exchange resin (DOWEX-50WX4) eluting with water. The fractions containing the object compound were combined, and subjected to column chromatography on ODS (YMC-gel.ODS-AM.S-50) eluting with 50% acetonitrile aqueous solution. The fractions containing the object compound were combined, and evaporated under reduced pressure to remove acetonitrile. The residue was lyophilized to give crude The Object Compound (23). The powder of crude The Object Compound (23) was purified by preparative HPLC utilizing a $C_{18}\mu$ Bondapak resin (Waters Associates, Inc.) which was eluted with a solvent system comprised of (acetonitrile-pH 3 phosphate buffer=40:60) at a flow rate of 80 ml/minute using a Shimadzu LC-8A pump. The column was monitored by a UV detector set at 240 um. The fractions containing the object compound were combined, and evaporated under reduced pressure to remove acetonitrile. The residue was subjected to column chromatography on ion exchange resin (DOWEX-50WX4) eluting with water. The fractions containing the object compound were combined, and subjected to column chromatography on ODS (YMC-gel.ODS-AM.S-50) eluting with 50% acetonitrile aqueous solution. The fractions containing the object compound were combined, and evaporated under reduced pressure to remove acetonitrile. The residue was lyophilized to give The Object Compound (23) (60 mg).

IR (KBr): 3347, 1629, 1511, 1245 $cm^{-1}$

NMR (DMSO-$d_6$, δ): 0.86 (3H, t, J=6.7 Hz), 0.95 (3H, d, J=6.8 Hz), 1.06 (3H, d, J=5.9 Hz), 1.2–1.5 (10H, m), 1.55–1.92 (5H, m), 2.0–2.65 (4H, m), 2.8–3.05 (5H, m), 3.2–4.47 (17H, m), 4.6–5.6 (12H, m), 6.6–7.0 (7H, m), 7.03 (1H, s), 7.2–7.5 (3H, m), 7.9–8.3 (3H, m), 8.94 (1H, s)

FAB-MASS: m/z=1297 ($M^+$+Na)

Elemental Analysis Calcd. for $C_{54}H_{79}N_{10}O_{22}SNa.6H_2O.CH_3CN$: C 47.22, H 6.65, H 10.82 Found: C 47.58, H 7.05, N 10.85

EXAMPLE 27

To a suspension of 1-hydroxybenzotriazole (0.53 g) and 2-(4-octyloxyphenoxy)acetic acid (1 g) in dichloromethane (30 ml) was added 1-ethyl-3-(3'-dimethylaminopropyl) carbodiimide hydrochloride (WSCD.HCl) (0.886 g), and stirred for 3 hours at ambient temperature. The reaction mixture was added to water. The organic layer was taken, and dried over magnesium sulfate. The magnesium sulfate was filtered off, and the filtrate was evaporated under reduced pressure to give 1-[2-(4-octyloxyphenoxy)acetyl]benzotriazole 3-oxide (892 mg). To a solution of The Starting Compound (1.79 g) and 1-[2-(4-octyloxyphenoxy]benzotriazole 3-oxide (892 mg) in N,N-dimethylformamide (18 ml) was added 4-(N, N-dimethylamino)pyridine (0.297 g), and stirred for 12 hours at ambient temperature. The reaction mixture was pulverized with ethyl acetate. The precipitate was collected by filtration, and dried under reduced pressure. The powder was added to water, and subjected to ion-exchange column chromatography on DOWEX-50WX4, and eluted with water. The fractions containing the object compound were combined, and subjected to column chromatograph on ODS (YMC-gel.ODS-AM.S-50), and eluted with 50% methanol aqueous solution. The fractions containing the object compound were combined, and evaporated under reduced pressure to remove methanol. The residue was lyophilized to give The Object Compound (24) (1.75 g).

IR (KBr): 3350, 1666, 1629, 1228 cm$^{-1}$

NMR (DMSO-d$_6$, δ): 0.86 (3H, t, J=6.9 Hz), 0.95 (3H, d, J=6.7 Hz), 1.04 (3H, d, J=5.7 Hz), 1.15–1.5 (10H, m), 1.55–2.0 (5H, m), 2.05–2.5 (4H, m), 3.16 (1H, m), 3.72 (2H, m), 3.88 (3H, t, J=6.3 Hz), 4.41 (2H, s), 3.93–4.6 (11H, m), 4.69–5.25 (10H, m), 5.28 (1H, d, J=4.3 Hz), 5.57 (1H, d, J=5.7 Hz), 6.73 (1H, d, J=8.2 Hz), 6.8–7.0 (5H, m), 7.04 (1H, s), 7.09 (1H, s), 7.3–7.4 (2H, m), 7.92–8.17 (2H, m), 8.29 (1H, d, J=7.5 Hz), 8.84 (1H, s)

FAB-MASS: m/z=1243 (M$^+$+Na)

Elemental Analysis Calcd. for C$_{51}$H$_{73}$N$_8$O$_{23}$SNa.4H$_2$O: C 47.36, H 6.31, H 8.66 Found: C 47.22, H 6.44, N 8.37

The Object Compounds (28) to (31) were obtained according to a similar manner to that of Example 27.

EXAMPLE 28

IR (KBr): 3350, 2933, 1664, 1628, 1446, 1205, 1045 cm$^{-1}$

NMR (DMSO-d$_6$, δ): 0.81–1.1 (9H, m), 1.2–2.0 (19H, m), 2.1–2.3 (3H, m), 3.6–3.8 (4H, m), 3.9–4.4 (13H, m), 4.6–5.0 (8H, m), 5.07 (1H, d, J=5.6 Hz), 5.14 (1H, d, J=3.2 Hz), 5.23 (1H, d, J=4.3 Hz), 5.46 (1H, d, J=6.7 Hz), 6.7–6.9 (3H, m), 7.04 (1H, s), 7.2–7.5 (6H, m), 7.8–8.0 (3H, m), 8.05 (1H, d, J=8.4 Hz), 8.2–8.4 (2H, m), 8.83 (1H, s)

FAB-MASS: m/z=1360 (M$^+$+Na)

Elemental Analysis Calcd. for C$_{59}$H$_{80}$N$_9$O$_{23}$SNa.4H$_2$O: C 48.99, H 6.41, H 8.72 Found: C 48.92, H 6.37, N 8.64

EXAMPLE 29

IR (KBr): 3350, 2927, 1668, 1627, 1535, 1515, 1452, 1440, 1286, 1045 cm$^{-1}$

NMR (DMSO-d$_6$, δ): 0.83 (3H, t, J=6.7 Hz), 0.95 (3H, d, J=6.7 Hz), 1.07 (3H, d, J=5.9 Hz), 1.2–1.4 (12H, m), 1.6–2.0 (5H, m), 2.1–2.4 (3H, m), 2.6 (1H, m), 2.82 (2H, t, J=7.4 Hz), 3.1–3.2 (1H, m), 3.6–4.5 (13H, m), 4.7–5.2 (11H, m), 5.4–5.6 (1H, m), 6.72 (1H, d, J=8.2 Hz), 6.82 (2H, d, J=8.1 Hz), 7.03 (1H, s), 7.2–7.4 (3H, m), 7.47 (1H, d, J=8.5 Hz), 7.69 (1H, d, J=8.5 Hz), 8.1–8.2 (2H, m), 8.23 (1H, d, J=8.4 Hz), 8.62 (1H, d, J=7.8 Hz), 8.83 (1H, s)

FAB-MASS: m/z=1251 (M$^+$+Na)

Elemental Analysis Calcd. for C$_{52}$H$_{73}$N$_{10}$O$_{21}$SNa.5H$_2$O: C 47.34, H 6.34, H 10.61 Found: C 47.30, H 6.45, N 10.45

EXAMPLE 30

NMR (DMSO-d$_6$, δ): 0.86 (3H, t, J=6.8 Hz), 0.96 (3H, d, J=6.7 Hz), 1.05 (3H, d, J=5.8 Hz), 1.2–1.5 (10H, m), 1.6–2.0 (5H, m), 2.2–2.4 (3H, m), 2.5–2.6 (1H, m), 3.1–3.2 (1H, m), 3.7–4.5 (15H, m), 4.7–5.0 (8H, m), 5.10 (1H, d, J=5.6 Hz), 5.17 (1H, d, J=3.1 Hz), 5.26 (1H, d, J=4.5 Hz), 5.52 (1H, d, J=5.8 Hz), 6.73 (1H, d, J=8.2 Hz), 6.8–7.0 (3H, m), 7.04 (1H, s), 7.2–7.4 (3H, m), 8.0–8.3 (3H, m), 8.68 (1H, d, J=2.3 Hz), 8.7–8.8 (1H, m), 8.85 (1H, m)

FAB-MASS: m/z=1214 (M$^+$+Na)

Elemental Analysis Calcd. for C$_{49}$H$_{70}$N$_9$O$_{22}$SNa.4H$_2$O: C 46.55, H 6.22, H 9.97 Found: C 46.29, H 6.18, N 9.71

EXAMPLE 31

IR (Nujol): 3342, 2210, 1668, 1623 cm$^{-1}$

NMR (DMSO-D$_6$, δ): 0.88 (3H, t, J=6.7 Hz), 0.97 (3H, d, J=6.7 Hz), 1.08 (3H, d, J=6.7 Hz), 1.20–1.60 (8H, m), 1.60–2.00 (5H, m), 2.05–2.50 (4H, m), 3.05–3.30 (1H, m), 3.60–4.60 (15H, m), 4.65–5.18 (10H, m), 5.24 (1H, d, J=4.5 Hz), 5.58 (1H, d, J=6.0 Hz), 6.68–7.10 (4H, m), 7.15–7.65 (5H, m), 7.80–8.30 (6H, m), 8.84 (1H, s), 9.18 (1H, d, J=7.7 Hz)

FAB-MASS: m/z=1273.5 (M$^+$+Na)

EXAMPLE 32

To a solution of 6-heptyloxy-2-naphthoic acid (0.358 g) and triethylamine (0.174 ml) in N,N-dimethylformamide (10 ml) was added diphenylphophoryl azide (0.4 ml), and stirred for an hour at ambient temperature. Then, the reaction mixture was stirred for an hour at 100° C. After cooling, to the reaction mixture was added The Starting Compound (1 g) and 4-(N,N-dimethylamino)pyridine (0.140 g), and stirred for 10 hours at ambient temperature. The reaction mixture was pulverized with ethyl acetate. The precipitate was collected by filtration, and dried under reduced pressure. The powder was dissolved in water, and subjected to column chromatography on ion exchange resin (DOWEX-50WX4) eluting with water. The fractions containing the object compound were combined, and subjected to column chromatography on ODS (YMC-gel.ODS-AM.S-50) eluting with 50% acetonitrile aqueous solution. The fractions containing the object compound were combined, and evaporated under reduced pressure to remove acetonitrile. The residue was lyophilized to give The Object Compound (29) (0.832 g).

IR (KRr): 3350, 1664, 1629, 1546, 1240 cm$^{-1}$

NMR (DMSO-d$_6$, δ): 0.88 (3H, t, J=6.6 Hz), 0.97 (3H, d, J=6.7 Hz), 1.08 (3H, d, J=5.9 Hz), 1.2–1.55 (8H, m), 1.55–2.0 (5H, m), 2.1–2.5 (4H, m), 3.18 (1H, m), 3.6–3.8 (3H, m), 3.9–4.5 (13H, m), 4.7–4.95 (3H, m), 5.0–5.3 (7H, m), 5.59 (1H, d, J=5.8 Hz), 6.52 (1H, d, J=8.1 Hz), 6.73 (1H, d, J=8.2 Hz), 6.83 (1H, d, J=8.2 Hz), 6.90 (1H, s), 7.0–7.15 (3H, m), 7.20 (1H, s), 7.27–7.4 (3H, m), 7.6–7.7 (2H, m), 7.87 (1, s), 7.95–8.2 (2H, m), 8.69 (1H, s), 8.85 (1H, s)

FAB-MASS: m/z=1264 (M$^+$+Na)

Elemental Analysis Calcd. for C$_{53}$H$_{72}$N$_9$O$_{22}$SNa.5H$_2$O: C 47.78, H 6.20, H 9.46 Found: C 47.65, H 6.42, N 9.34

The Object Compound (33) was obtained according to a similar manner to that of Example 32.

EXAMPLE 33

IR (KRr): 3350, 1666, 1629, 1537, 1240 cm$^{-1}$

NMR (DMSO-d$_6$, δ): 0.87 (3H, t, J=6.7 Hz), 0.97 (3H, d, J=6.7 Hz), 1.09 (3H, d, J=5.8 Hz), 1.2–1.55 (8H, m), 1.55–2.0 (5H, m), 2.07–2.6 (4H, m), 3.18 (1H, m), 3.6–3.85 (3H, m), 3.9–4.5 (13H, m), 4.7–4.98 (3H, m), 5.0–5.3 (7H, m), 5.57 (1H, d, J=5.9 Hz), 6.50 (1H, d, J=8.1 Hz), 6.73 (1H, d, J=8.2 Hz), 6.82 (1H, dd, J=8.2 and 1.7 Hz), 6.87 (1H, s), 6.97 (2H, d, J=8.8 Hz), 7.05 (1H, d, J=1.7 Hz), 7.10 (1H, s), 7.23–7.43 (2H, m), 7.38 (2H, d, J=8.8 Hz), 7.50 (2H, d, J=8.8 Hz), 7.52 (2H, d, J=8.8 Hz), 8.0–8.15 (2H, m), 8.65 (1H, s), 8.84 (1H, s)

FAB-MASS: m/z=1290 (M$^+$+Na)

Elemental Analysis Calcd. for C$_{55}$H$_{74}$N$_9$O$_{22}$SNa.7H$_2$O: C 47.38, H 6.36, H 9.04 Found: C 47.67, H 6.53, N 9.03

EXAMPLE 34

A solution of The Starting Compound (2.45 g), 3-[4-(4-pentylphenyl)phenyl]propiolic acid (0.90 g), 1-ethyl-3-(3'- dimethylaminopropyl)carbodiimide hydrochloride (WSCD-HCl) (0.59 g) and triethylamine (0.43 ml) in N,N-dimethylformamide (50 ml) was stirred for 15 hours at ambient temperature. The reaction mixture was diluted with ethyl acetate, and the resultant precipitate was collected by filtration, and washed in turn with ethyl acetate and diisopropyl ether, and dried under reduced pressure. The powder was dissolved in water, and was subjected to column chromatography on ion exchange resin (DOWEX-50WX4 (Na form, 50 ml)) eluting with water. The fractions containing the object compound were combined, and subjected to reversed phase chromatography on ODS (YMC-gel.ODS-AM.S-50, 50 ml) eluting with (water:acetonitrile=10:0–7:3, V/V. The fractions containing the object compound were combined, and evaporated under reduced pressure to remove acetonitrile. The residue was lyophilized to give The Object Compound (31) (1.53 g).

IR (KRr): 3351, 2212, 1668, 1627 cm$^{-1}$

NMR (DMSO-d$_6$, δ): 0.87 (3H, t, J=6.5 Hz), 0.96 (3H, d, J=6.7 Hz), 1.08 (3H, d, J=5.8 Hz), 1.20–1.50 (4H, m), 1.50–2.00 (5H, m), 2.03–2.55 (4H, m), 2.62 (2H, t, J=7.5 Hz), 3.17 (1H, t, J=8.4 Hz), 3.55–4.57 (15H, m), 4.65–5.13 (9H, m), 5.16 (1H, d, J=3.2 Hz), 5.24 (1H, d, J=4.5 Hz), 5.58 (1H, d, J=5.8 Hz), 6.67–6.90 (3H, m), 6.93–7.10 (2H, m), 7.15–7.50 (4H, m), 7.50–7.90 (6H, m), 8.06 (1H, d, J=8.4 Hz), 8.15 (1H, d, J=7.7 Hz), 8.84 (1H, s), 9.19 (1H, d, J=7.1 Hz)

FAB-MASS: m/z=1255 (M$^+$+Na)

Elemental Analysis Calcd. for $C_{55}H_{69}N_8O_{21}SNa.4H_2O$: C 50.61, H 5.95, H 8.58 Found: C 50.47, H 6.00, N 8.54

EXAMPLE 35

To a suspension of 1-hydroxybenzotriazole (501 mg) and 4-(4-heptylphenyl)benzoic acid (1 g) in dichloromethane (30 ml) was added 1-ethyl-3-(3'-dimethylaminopropyl) carbodiimide hydrochloride (WSCD.HCl) (839 mg), and stirred for 3 hours at ambient temperature. The reaction mixture was added to water. The organic layer was separated, and dried over magnesium sulfate. The magnesium sulfate was filtered off, and the filtrate was evaporated under reduced pressure to give 1-[4-(4-heptylphenyl) benzoyl]benzotriazole 3-oxide. To a solution of The Starting Compound (2.49 g) and 1-[4-(4-heptylphenyl)benzoyl] benzotriazole 3-oxide in N,N-dimethylformamide (25 ml) was added 4-(N,N-dimethylamino)pyridine (381 mg), and stirred for 12 hours at ambient temperature. The reaction mixture was pulverized with ethyl acetate. The precipitate was collected by filtration, and dried under reduced pressure. The residue was dissolved in water, and subjected to column chromatography on ion exchange resin (DOWEX-5WX4) eluting with water. The fraction containing the object compound were combined, and subjected to column chromatography on ODSD (YMC-gel.ODS-AM.S-50) eluting with 30% acetonitrile aqueous solution. The fractions containing the object compound were combined, and evaporated under reduced pressure to remove acetonitrile. The residue was lyophilized to give The Object Compound (32) (1.99 g).

IR (Nujol): 3350, 2852, 1749, 1621, 1457, 1376, 1045 cm$^{-1}$

NMR (DMSO-D$_6$, δ): 0.86 (3H, t, J=6.7 Hz), 0.96 (3H, d, J=6.7 Hz), 1.08 (3H, d, J=5.9 Hz), 1.5–1.7 (2H, m), 1.7–2.2 (3H, m), 2.2–2.5 (3H, m), 2.6–2.8 (3H, m), 3.1–3.2 (1H, m), 3.7–4.6 (13H, m), 4.7–5.2 (8H, m), 5.12 (1H, d, J=5.5 Hz), 5.18 (1H, d, J=2.9 Hz), 5.27 (1H, d, J=4.4 Hz), 5.54 (1H, d, J=5.8 Hz), 6.7–6.9 (3H, m), 7.05 (1H, s), 7.2–7.4 (5H, m), 7.65 (2H, d, J=8.0 Hz), 7.74 (2H, d, J =8.3 Hz), 7.98 (2H, d, J=8.3 Hz), 8.11 (1H, d, J=8.7 Hz), 8.28 (1H, d, J=8.4 Hz), 8.78 (1H, d, J=7.3 Hz), 8.95 (1H, s)

FAB-MASS: m/z=1259 (M$^+$+Na)

Elemental Analysis Calcd. for $C_{55}H_{73}N_8O_{21}SNa.5H_2O$: C 49.77, H 6.30, H 8.44 Found: C 49.98, H 6.44, N 8.41

The Object Compounds (36) to (107) were obtained according to a similar manner to that of Example 1.

EXAMPLE 36

IR (KRr): 3350, 1675.8, 1629.6, 1515.8 cm$^{-1}$

NMR (DMSO-d$_6$, δ): 0.86 (6H, t, J=6.6 Hz), 0.96 (3H, d, J=6.6 Hz), 1.06 (3H, d, J=5.7 Hz), 1.1–1.3 (2H, m), 1.4–2.0 (6H, m), 2.0–2.7 (4H, m), 3.1–3.5 (9H, m), 3.66 (2H, t, J=7.3 Hz), 3.6–4.5 (13H, m), 4.7–5.6 (12H, m), 6.73 (1H, d, J=8.3 Hz), 6.82 (1H, d, J=8.3 Hz), 6.8–6.9 (1H, m), 7.02 (2H, d, J=9.0 Hz), 7.04 (1H, s), 7.11 (2H, d, J=9.0 Hz), 7.2–7.6 (3H, m), (7.50 (2H, d, J=9.0 Hz), 7.82 (2H, d, J=9.0 Hz), 8.1 (1H, d, J=8.5 Hz), 8.28 (1H, d, J=8.5 Hz), 8.33 (1H, s), 8.45 (1H, d, J=7.0 Hz), 8.84 (1H, s)

FAB-MASS: m/z=1412 (M+Na)

Elemental Analysis Calcd. for $C_{60}H_{80}N_{13}O_{22}SNa.9H_2O$: C 46.42, H 6.36, H 11.73 Found: C 46.64, H 6.43, N 11.62

EXAMPLE 37

IR (KRr): 3350, 1668.1, 1629.6, 1268.9 cm$^{-1}$

NMR (DMSO-d$_6$, δ): 0.85 (3H, t, J=6.6 Hz), 0.96 (3H, d, J=6.7 Hz), 1.07 (3H, d, J=5.9 Hz), 1.2–1.4 (10H, m), 1.4–2.0 (5H, m), 2.0–2.5 (4H, m), 2.61 (2H, t, J=7.2 Hz), 3.1–3.3 (1H, m), 3.6–4.5 (13H, m), 4.40 (2H, s), 4.6–5.3 (11H, m), 5.60 (1H, d, J=5.8 Hz), 6.73 (1H, d, J=8.2 Hz), 6.82 (1H, d, J=8.2 Hz), 6.6–6.9 (1H, m), 7.04 (1H, s), 7.0–7.1 (1H, m), 7.32 (2H, d, J=8.5 Hz), 7.2–7.5 (2H, m), 7.58 (2H, d, J=8.5 Hz), 7.93 (1H, d, J=7 Hz), 8.04 (1H, d, J=9.4 Hz), 8.41 (1H, s), 8.44 (1H, d, J=9.4 Hz), 8.84 (1H, s)

FAB-MASS: m/z=1294 (M+Na)

Elemental Analysis Calcd. for $C_{53}H_{74}N_{11}O_{22}SNa.7H_2O$: C 45.52, H 6.34, H 11.02 Found: C 45.57, H 6.27, N 10.93

EXAMPLE 38

Major product

IR (KBr): 3349.7, 1670.1, 1627.6, 1508.1 cm$^{-1}$

NMR (DMSO-d$_6$, δ): 0.96 (3H, d, J=6.6 Hz), 1.06 (3H, d, J=5.7 Hz), 1.2–1.6 (8H, m), 1.6–2.1 (5H, m), 2.1–2.7 (4H, m), 3.0–3.2 (5H, m), 3.21 (3H, s), 3.30 (2H, t, J=6.5 Hz), 3.3–3.5 (4H, m), 3.6–4.5 (15H, m), 4.7–5.3 (11H, m), 5.49 (1H, d, J=5.9 Hz), 6.73 (1H, d, J=8.3 Hz), 6.8–6.9 (4H, m), 6.95 (2H, d, J=9.2 Hz), 7.01 (2H, d, J=8.5 Hz), 7.04 (1H, s), 7.20 (1H, s), 7.2–7.5 (2H, m), 7.81 (2H, d, J=8.5 Hz), 8.09 (1H, d, J=8.7 Hz), 8.28 (1H, d, J=8.7 Hz), 8.45 (1H, d, J=6.7 Hz), 8.84 (1, s)

FAB-MASS: m/z=1389 (M+Na)

Elemental Analysis Calcd. for $C_{60}H_{83}N_{10}O_{23}SNa.8H_2O$: C 47.68, H 6.60, N 9.27 Found: C 49.83, H 6.72, N 9.27

Minor Product

IR (KBr): 3338.2, 1646.9, 1151.9 cm$^{-1}$

NMR (DMSO-d$_6$, δ): 0.96 (3H, d, J=6.7 Hz), 1.06 (3H, d, J=5.7 Hz), 1.3–1.6 (4H, m), 1.6–2.7 (11H, m), 3.0–3.2 (5H, m), 3.3–3.5 (4H, m), 3.6–4.5 (15H, m), 4.7–5.3 (13H, m), 5.48 (1H, d, J=5.9 Hz), 5.7–6.0 (1H, m), 6.73 (1H, d, J=8.2 Hz), 6.8–6.9 (4H, m), 6.94 (2H, d, J=9.3 Hz),7.01 (2H, d, J=8.6 Hz), 7.04 (1H, s), 7.2–7.5 (3H, m), 7.81 (2H, d, J=8.6 Hz), 8.06 (1H, d, J=8.7 Hz), 8.25 (1H, d, J=8.7 Hz), 8.42 (1H, d, J=6.7 Hz), 8.84 (1H, s) FAB-MASS: m/z=1357 (M+Na) Elemental Analysis Calcd. for $C_{59}H_{79}N_{10}O_{22}SNa.9H_2O$: C, 47.32; H, 6.53; N, 9.35. Found: C, 47.08; H, 6.66; N,9.25.

EXAMPLE 39

IR (KBr): 3350, 1670.1, 1631.5, 1510.0, 1234.2 cm$^{-1}$ NMR (DMSO-d$_6$, δ): 0.87 (3H, t, J=6.7 Hz), 0.96 (3H, d, J=6.7 Hz), 1.06 (3H, d, J=5.6 Hz), 1.2–1.5 (8H, m), 1.6–2.1 (5H, m), 2.1–2.7 (4H, m), 3.0–3.3 (5H, m), 3.3–3.5 (4H, m), 3.6–3.8 (2H, m), 3.88 (2H, d, J=6.4 Hz), 3.8–4.5 (11H, m), 4.7–5.1 (8H, m), 5.10 (1H, d, J=5.6 Hz), 5.16 (1H, d, J=3.1 Hz), 5.25 (1H, d, J=4.5 Hz), 5.48 (1H, d, J=5.9 Hz), 6.73 (1H, d, J=8.2 Hz), 6.8–6.9 (4H, m), 6.94 (2H, d, J=9.3 Hz), 7.01 (2H, d, J=8.7 Hz), 7.04 (1H, s), 7.2–7.5 (3H, m), 7.81 (2H, d, J=8.7 Hz), 8.06 (1H, d, J=8 Hz), 8.25 (1H, d, J=6.7 Hz), 8.43 (1H, d, J=6.7 Hz), 8.85 (1H, s) FAB-MASS: m/z=1359 (M+Na) Elemental Analysis Calcd. for $C_{59}H_{81}N_{10}O_{22}SNa.5H_2O$: C, 49.64; H, 6.43; N, 9.81. Found: C, 49.49; H, 6.54; N, 9.72.

EXAMPLE 40

IR (KBr): 3355.5, 1670.1, 1627.6, 1510.0 1236.1 cm$^{-1}$ NMR (DMSO-d$_6$, δ): 0.89 (6H, d, J=6.5 Hz), 0.96 (3H, d, J=6.7 Hz), 1.05 (3H, d, J=7.5 Hz),1.2–1.4 (2H, m), 1.5–2.1 (6H, m), 2.1–2.7 (4H, m), 3.0–3.6 (9H, m), 3.6–4.5 (15H, m), 4.5–5.4 (12H, m), 6.73 (1H, d, J=8.2 Hz), 6.8–6.9 (4H, m), 6.96 (2H, d, J=9.6 Hz), 7.02 (2H, d, J=8.7 Hz), 7.05 (1H, s), 7.2–7.5 (3H, m), 7.82 (2H, d, J=8.7 Hz), 8.08 (1H, d, J=8 Hz), 8.27 (1H, d, J=6.7 Hz), 8.46 (1H, d, J=6.7 Hz), 8.85 (1H, s) FAB-MASS: m/z=1345 (M+Na) Elemental Analysis Calcd. for $C_{58}H_{79}N_{10}O_{22}SNa.8H_2O$: C, 47.47; H, 6.52; N, 9.54. Found: C, 47.47, H, 6.54; N, 9.51.

EXAMPLE 41

IR (KBr): 3347.8, 1668.1, 1629.6, 1510.0, 1234.2 cm$^{-1}$ NMR (DMSO-d$_6$, δ): 0.89 (3H, t, J=7.0 Hz), 0.96 (3H, d, J=6.7 Hz), 1.05 (3H, d, J=5.8 Hz), 1.2–1.5 (4H, m), 1.6–2.1 (5H, m), 2.1–2.7 (4H, m), 3.0–3.6 (9H, m), 3.6–3.8 (1H, m), 3.8–4.5 (13H, m), 4.7–5.6 (12H, m), 6.73 (1H, d, J=8.2 Hz), 6.8–6.9 (4H, m), 6.96 (2H, d, J=8.7 Hz), 7.02 (2H, d, J=9.0 Hz), 7.04 (1H, s), 7.2–7.5 (3H, m), 7.82 (2H, d, J=8.7 Hz), 8.07 (1H, d, J=8 Hz), 8.27 (1H, d, J=6.7 Hz), 8.45 (1H, d, J=6.7 Hz), 8.85 (1H, s) FAB-MASS: m/z=1331 (M+Na) Elemental Analysis Calcd. for $C_{57}H_{77}N_{10}O_{22}SNa.6H_2O$: C, 48.30; H, 6.33; N, 9.88. Found: C, 48.20; H, 6.58; N, 10.03.

EXAMPLE 42

Mixture product

IR (KBr): 3344, 1670.1, 1631.5 cm$^{-1}$ NMR (DMSO-d$_6$, δ): 0.96 (3H, d, J=6.7 Hz), 1.08 (3H, d, J=5.9 Hz), 1.2–1.5 (8H, m), 1.6–2.1 (7H, m), 2.1–2.7 (4H, m), 3.1–3.3 (1H, m), 3.6–4.5 (15H, m), 4.45 and 4.70 (2H, t, J=7.1 Hz), 4.6–5.3 (11H, m), 5.52 (1H, d, J=5.9 Hz), 6.73 (1H, d, J=8.2 Hz), 6.83 (1H, d, J=8.2 Hz), 6.85 (1H, s), 7.03 (2H, d, J=8.6 Hz), 7.05 (1H, s), 7.2–7.5 (3H, m), 7.68 (2H, d, J=8.6 Hz), 7.71 (2H, d, J=8.4 Hz), 7.96 (2H, d, J=8.4 Hz), 8.12 (1H, d, J=8.5 Hz), 8.30 (1H, d, J=7.0 Hz) FAB-MASS: m/z=1357 (M+Na) Elemental Analysis Calcd. for $C_{57}H_{75}N_{12}O_{22}SNa.4H_2O$: C, 48.64; H, 5.94; N, 11.94. Found: C, 48.91; H, 5.88; N, 11.86.

EXAMPLE 43

IR (KBr): 3350, 1666.2, 1651.5 cm$^{-1}$ NMR (DMSO-d$_6$, δ): 0.96 (3H, d, J=6.7 Hz), 1.05 (6H, d, J=6.3 Hz), 1.06 (3H, d, J=5.7 Hz), 1.2–1.6 (10H, m), 1.6–2.1 (7H, m), 2.1–2.7 (6H, m), 2.8–3.0 (2H, m), 3.0–3.2 (1H, m), 3.4–3.7 (2H, m), 3.6–3.8 (2H, m), 3.8–4.5 (13H, m), 4.7–5.6 (12H, m), 6.73 (1H, d, J=8.2 Hz), 6.8–7.0 (2H, m), 7.03 (2H, d, J=8.7 Hz), 7.06 (1H, s), 7.2–7.5 (3H, m), 7.67 (2H, d, J=8.7 Hz), 7.71 (2H, d, J=8.4 Hz), 7.96 (2H, d, J=8.4 Hz), 8.04 (1H, d, J=8.5 Hz), 8.31 (1H, d, J=8.5 Hz), 8.73 (1H, d, J=7.0 Hz), 8.90 (1H, s) FAB-MASS: m/z=1402 (M+Na)

EXAMPLE 44

IR (KBr pelet): 3350, 2929, 2856, 1670, 1631, 1510, 1243, 1045 cm$^{-1}$ NMR (DMSO-d$_6$, δ): 0.86 (3H, t, J=6.8 Hz), 0.96 (3H, d, J=6.7 Hz), 1.06 (3H, d, J=5.7 Hz), 1.6–2.0 (5H, m), 2.2–2.5 (5H, m), 2.6–2.7 (1H, m), 3.0–3.3 (5H, m), 3.6–4.5 (19H, m) 4.77 (2H, d, J=5.9 Hz), 4.8–5.1 (6H, m), 5.10 (1H, d, J=5.6 Hz), 5.17 (1H, d, J=3.1 Hz), 5.25 (1H, d, J=4.5 Hz), 5.50 (1H, d, J=5.8 Hz), 6.7–7.0 (8H, m), 7.04 (1H, s), 7.2–7.4 (3H, m), 8.0–8.2 (2H, m), 8.26 (1H, d, J=8.0 Hz), 8.55 (1H, d, J=7.3 Hz), 8.67 (1H, d, J=1.2 Hz), 8.85 (1H, s) FAB-MASS: m/z=1374.3 (M+Na$^+$) Elemental Analysis Calcd. for $C_{59}H_{82}N_{11}O_{22}NaS.5.5H_2O$: C, 48.82; H, 6.46; N, 10.61. Found: C,48.89; H, 6.74; N, 10.50.

EXAMPLE 45

IR (KBr): 3350, 2935, 1668, 1623, 1538, 1257, 1174, 1047 cm$^{-1}$ NMR (DMSO-d$_6$, δ): 0.8–1.1 (6H, m), 1.09 (3H, d, J=5.7 Hz), 1.2–1.6 (6H, m), 1.7–2.1 (5H, m), 2.2–2.4 (3H, m), 2.5–2.6 (1H, m), 3.6–3.8 (2H, m), 3.8–4.6 (14H, m), 4.8–5.2 (7H, m), 5.18 (1H, d, J=3.1 Hz), 5.26 (1H, d, J=4.5 Hz), 5.54 (1H, d, J=5.8 Hz), 6.7–7.5 (9H, m), 7.82 (1H, d, J=8.5 Hz), 7.96 (1H, d, J=8.7 Hz), 8.1–8.4 (5H, m), 8.8–9.0 (2H, m) FAB-MASS: m/z=1302.6 (M+Na$^+$) Elemental Analysis Calcd. for $C_{55}H_{70}N_9O_{23}SNa.6H_2O$: C, 47.58; H, 5.95; N, 9.08. Found: C, 47.46; H, 6.04; N, 9.05.

EXAMPLE 46

IR (KBr): 3355, 2958, 1670, 1627, 1521, 1247, 1047 cm$^{-1}$ NMR (DMSO-d$_6$, δ): 0.9–1.0 (6H, m), 1.08 (3H, d, J=5.6 Hz), 1.4–1.6 (2H, m), 1.7–2.1 (5H, m), 2.1–2.4 (3H, m), 2.5–2.6 (1H, m), 3.1–3.3 (1H, m), 3.7–3.8 (2H, m), 3.9–4.6 (13H, m), 4.8–5.1 (8H, m), 5.11 (1H, d, J=5.6 Hz), 5.17 (1H, d, J=3.1 Hz), 5.26 (1H, d, J=4.5 Hz), 5.54 (1H, d, J=5.9 Hz), 6.7–6.9 (3H, m), 7.0–7.2 (3H, m), 7.3–7.5 (3H, m), 7.7–7.9 (8H, m), 8.02 (2H, d, J=8.4 Hz), 8.08 (1H, d, J=8.4 Hz), 8.32 (1H, d, J=7.7 Hz), 8.81 (1H, d, J=7.0 Hz), 8.85 (1H, s) FAB-MASS: m/z=1309.3 (M+Na)$^+$ Elemental Analysis Calcd. for $C_{58}H_{71}N_8O_{22}NaS.6H_2O$: C, 49.92; H, 6.00; N, 8.03. Found: C, 49.92; H, 5.97; N, 8.03.

EXAMPLE 47

IR (KBr): 3350, 2933, 1668, 1629, 1517, 1249, 1045 cm$^{-1}$ NMR (DMSO-d$_6$, δ): 0.88 (3H, t, J=6.7 Hz), 0.96 (3H, d, J=6.7 Hz), 1.08 (3H, d, J=5.8 Hz), 1.7–2.7 (8H, m), 3.1–3.3 (1H, m), 3.6–4.5 (16H, m), 4.7–5.2 (8H, m), 5.18 (1H, d, J=3.1 Hz), 5.27 (1H, d, J=4.5 Hz), 5.56 (1H, d, J=5.8 Hz), 6.7–7.0 (3H, m), 7.0–7.2 (3H, m), 7.2–7.5 (3H, m), 8.0–8.4 (6H, m), 8.85 (1H, s), 8.96 (1H, d, J=7.0 Hz), 9.07 (1H, s) FAB-MASS: m/z=1276.6 (M+Na$^+$) Elemental Analysis Calcd. for $C_{54}H_{72}N_9O_{22}NaS.5H_2O$: C, 48.25; H, 6.15; N, 9.38. Found: C, 48.10; H, 6.14; N, 9.30.

EXAMPLE 48

IR (KBr): 3350, 2931, 1668, 1629, 1537, 1049 cm$^{-1}$ NMR (DMSO-d$_6$, δ): 0.86 (3H, t, J=6.9 Hz), 0.9–1.5 (16H, m), 1.6–2.4 (8H, m), 2.5–2.7 (1H, m), 3.1–3.3 (1H, m), 3.5–5.6 (25H, m), 6.6–7.4 (8H, m), 7.8–8.4 (6H, m), 8.7–9.0 (2H, m), 9.00 (1H, d, J=2.4 Hz) FAB-MASS: m/z=1331.4 (M+Na$^+$) Elemental Analysis Calcd. for $C_{56}H_{73}N_{10}O_{23}NaS.8H_2O$: C, 46.28; H, 6.17; N, 9.64. Found: C, 46.50; H, 6.27; N, 9.65.

EXAMPLE 49

IR (KBr pelet): 3300, 2931, 1668, 1650, 1629, 1538, 1515, 1268, 1049 cm$^{-1}$ NMR (DMSO-d$_6$, δ): 0.87 (3H, t, J=6.6 Hz), 0.97 (3H, d, J=6.7 Hz), 1.10 (3H, d, J=5.6 Hz), 1.2–1.4 (6H, m), 1.5–1.7 (2H, m), 1.7–2.1 (3H, m), 2.1–2.4 (3H, m), 2.6–2.7 (3H, m), 3.1–3.2 (1H, m), 3.7–3.9 (2H, m), 3.9–4.5 (12H, m), 4.8–5.1 (7H, m), 5.11 (1H, d, J=5.5 Hz), 5.18 (1H, d, J=3.1 Hz), 5.27 (1H, d, J=4.5 Hz), 5.55 (1H, d, J=5.8 Hz), 6.7–7.0 (3H, m), 7.06 (1H, s), 7.3–7.5 (5H, m), 7.72 (2H, d, J=8.2 Hz), 7.9–8.2 (5H, m), 8.3–8.4 (4H, m), 8.9–9.0 (2H, m) FAB-MASS: m/z=1260.5 (M+Na$^+$) Elemental Analysis Calcd. for $C_{61}H_{74}N_9O_{22}SNa \cdot 6H_2O$: C, 50.58; H, 5.98; N, 8.70. Found: C, 50.34; H, 6.16; N, 8.55.

EXAMPLE 50

IR (KBr): 3369, 2958, 2935, 1670, 1629, 1525, 1473, 1247, 1047 cm$^{-1}$ NMR (DMSO-d$_6$, δ): 0.95 (3H, t, J=7.3 Hz), 0.97 (3H, d, J=6.7 Hz), 1.09 (3H, d, J=5.7 Hz), 1.3–1.6 (2H, m), 1.7–2.1 (5H, m), 2.1–2.4 (3H, m), 2.5–2.6 (1H, m), 3.1–3.3 (1H, m), 3.7–4.6 (15H, m), 4.7–5.1 (8H, m), 5.10 (1H, d, J=5.6 Hz), 5.18 (1H, d, J=3.1 Hz), 5.26 (1H, d, J=4.4 Hz), 5.56 (1H, d, J=5.7 Hz), 6.7–7.0 (3H, m), 7.1–7.2 (3H, m), 7.2–7.4 (3H, m), 7.70 (2H, d, J=8.6 Hz), 7.78 (2H, d, J=8.4 Hz), 8.1–8.4 (6H, m), 8.85 (1H, s), 8.99 (1H, d, J=7.0 Hz), 9.13 (1H, d, J=1.6 Hz) FAB-MASS: m/z=1310.1 (M+Na)$^+$ Elemental Analysis Calcd. for $C_{57}H_{70}N_9O_{22}NaS \cdot 7H_2O$: C, 47.20; H, 6.12; N, 8.69. Found: C, 47.42; H, 6.19; N, 8.92.

EXAMPLE 51

IR (KBr): 3351, 2937, 2875, 1670, 1627, 1533, 1245, 1047 cm$^{-1}$ NMR (DMSO-d$_6$, δ): 0.96 (3H, d, J=6.7 Hz), 1.08 (3H, d, J=5.7 Hz), 1.5–1.7 (2H, m), 1.7–2.1 (7H, m), 2.1–2.4 (3H, m), 2.5–2.6 (1H, m), 3.1–3.2 (1H, m), 3.7–3.8 (2H, m), 3.9–4.6 (15H, m), 4.7–4.9 (3H, m), 5.0–5.1 (5H, m), 5.10 (1H, d, J=5.6 Hz), 5.17 (1H, d, J=3.1 Hz), 5.26 (1H, d, J=4.5 Hz), 5.52 (1H, d, J=5.9 Hz), 6.7–7.1 (9H, m), 7.2–7.5 (5H, m), 7.68 (2H, d, J=8.2 Hz), 7.72 (2H, d, J=6.7 Hz), 7.96 (2H, d, J=8.2 Hz), 8.06 (1H, d, J=8.4 Hz), 8.28 (1H, d, J=7.7 Hz), 8.76 (1H, d, J=7.0 Hz), 8.85 (1H, s) FAB-MASS: m/z=1339.5 (M+Na$^+$) Elemental Analysis Calcd. for $C_{59}H_{73}N_8O_{23}NaS \cdot 7H_2O$: C, 49.09; H, 6.08; N, 7.76. Found: C, 49.04; H, 6.08; N, 7.82.

EXAMPLE 52

IR (KBr): 3350, 2954, 2937, 1670, 1631, 1440, 1257, 1047 cm$^{-1}$ NMR (DMSO-d$_6$, δ): 0.89 (3H, t, J=6.8 Hz), 0.97 (3H, d, J=6.7 Hz), 1.09 (2H, d, J=5.8 Hz), 1.2–1.5 (6H, m), 1.7–2.1 (5H, m), 2.1–2.4 (3H, m), 2.5–2.6 (1H, m), 3.1–3.2 (1H, m), 3.7–4.6 (15H, m), 4.7–5.3 (11H, m), 5.5–5.6 (1H, m), 6.7–6.9 (1H, m), 7.0–7.5 (6H, m), 8.0–8.4 (8H, m), 8.85 (1H, s), 8.96 (1H, d, J=7.0 Hz) APCI-MASS: m/z=1329.0 (M+Na)$^+$ Elemental Analysis Calcd. for $C_{56}H_{71}N_{10}O_{23}NaS \cdot 6H_2O$: C, 47.52; H, 5.91; N, 9.90. Found: C, 47.42; H, 6.05; N, 9.90.

EXAMPLE 53

IR (KBr): 3350, 2952, 1666, 1629, 1537, 1519, 1255 cm$^{-1}$ NMR (DMSO-d$_6$, δ): 0.89 (3H, t, J=6.7 Hz), 0.96 (3H, d, J=6.4 Hz), 1.08 (3H, d, J=5.6 Hz), 1.7–2.4 (8H, m), 2.5–2.6 (1H, m), 3.7–4.5 (15H, m), 4.7–5.1 (8H, m), 5.11 (1H, d, J=5.5 Hz), 5.17 (1H, d, J=3.1 Hz), 5.26 (1H, d, J=3.1 Hz), 5.56 (1H, d, J=5.7 Hz), 6.73 (1H, d, J=8.2 Hz), 6.7–7.0 (2H, m), 7.05 (1H, s), 7.13 (2H, d, J=8.7 Hz), 7.2–7.5 (3H, m), 7.97 (2H, d, J=8.7 Hz), 8.1–8.4 (6H, m), 8.85 (1H, s), 8.92 (1H, d, J=7.0 Hz) FAB-MASS: m/z=1345.3 (M+Na)$^+$ Elemental Analysis Calcd. for $C_{56}H_{71}N_{10}O_{22}S_2Na \cdot 8H_2O$: C, 45.84; H, 5.98, N, 9.55. Found: C, 45.87; H, 6.07; N, 9.55.

EXAMPLE 54

IR (KBr pelet): 3350, 2931, 1670, 1652, 1628, 1442, 1247, 1047 cm$^{-1}$ NMR (DMSO-d$_6$, δ): 0.86 (3H, t, J=6.6 Hz), 0.97 (3H, d, J=6.8 Hz), 1.12 (3H, d, J=6.8 Hz), 1.2–1.5 (10H, m), 1.7–2.0 (5H, m), 2.2–2.4 (3H, m), 2.5–2.6 (1H, m), 3.1–3.2 (1H, m), 3.72 (2H, br), 3.8–4.5 (17H, m), 4.7–5.2 (9H, m), 5.26 (1H, d, J=4.6 Hz), 5.57 (1H, d, J=5.7 Hz), 6.7–7.1 (7H, m), 7.3–7.5 (3H, m), 7.66 (2H, d, J=8.7 Hz), 8.10 (1H, d, J=7.6 Hz), 8.17 (1H, d, J=7.6 Hz), 8.76 (1H, d, J=7.0 Hz), 8.85 (1H, s) FAB-MASS: m/z=1293 (M+Na$^+$) Elemental Analysis Calcd. for $C_{54}H_{75}N_{10}O_{22}NaS \cdot 7H_2O$: C, 46.41; H, 6.42; N, 10.02. Found: C, 46.51; H, 6.43; N, 9.95.

EXAMPLE 55

IR (KBr): 3345, 2937, 1650, 1511, 1249, 1047, cm$^{-1}$ NMR (DMSO-d$_6$, δ): 0.91 (3H, t, J=7.0 Hz), 0.96 (3H, t, J=7.8 Hz), 1.09 (3H, d, J=6.8 Hz), 1.3–1.5 (4H, m), 1.6–2.1 (5H, m), 2.1–2.5 (3H, m), 2.5–2.6 (1H, m), 3.1–3.3 (1H, m), 3.7–3.9 (2H, m), 3.9–4.6 (13H, m), 4.79 (2H, d, J=5.9 Hz), 4.8–4.9 (1H, m), 4.9–5.2 (5H, m), 5.10 (1H, d, J=5.9 Hz), 5.17 (1H, d, J=3.1 Hz), 5.25 (1H, d, J=4.6 Hz), 5.53 (1H, d, J=5.9 Hz), 6.7–7.0 (3H, m), 7.0–7.2 (3H, m), 7.19 (1H, s), 7.3–7.5 (3H, m), 7.7–8.1 (6H, m), 8.08 (1H, d, J=10.0 Hz), 8.26 (1H, d, J=8.8 Hz), 8.77 (1H, m), 8.85 (1H, s), 13.32 (1H, s) FAB-MASS: m/z=1314.0 (M+Na)$^+$ Elemental Analysis Calcd. for $C_{56}H_{71}N_{10}O_{22}SNa \cdot 8H_2O$: C, 46.86; H, 6.11; N, 9.76. Found: C, 46.93; H, 5.87; N, 9.74.

EXAMPLE 56

IR (KBr): 3350, 2958, 2935, 2873, 1666, 1629, 1247, 1045 cm$^{-1}$ NMR (DMSO-d$_6$, δ): 0.9–1.1 (6H, m), 1.08 (3H, d, J=6.0 Hz), 1.4–1.6 (2H, m), 1.6–2.1 (5H, m), 2.1–2.4 (3H, m), 2.5–2.6 (1H, m), 3.1–3.3 (1H, m), 3.6–4.5 (15H, m), 4.7–5.1 (8H, m), 5.10 (1H, d, J=5.5 Hz), 5.17 (1H, d, J=2.9 Hz), 5.25 (1H, d, J=4.5Hz), 5.55 (1H, d, J=5.7 Hz), 6.7–6.9 (3H, m), 7.0–7.5 (8H, m), 7.68 (2H, d, J=8.9 Hz), 7.73 (2H, d, J=8.3 Hz), 8.01 (2H, d, J=8.3 Hz), 8.10 (1H, d, J=8.4 Hz), 8.26 (1H, d, J=7.7 Hz), 8.8–9.0 (2H, m) FAB-MASS: m/z=1299.5 (M+Na)$^+$ Elemental Analysis Calcd. for $C_{56}H_{69}N_8O_{23}NaS \cdot 6H_2O$: C, 48.55; H, 5.89; N, 8.09. Found: C, 48.52; H, 5.94; N, 8.07.

EXAMPLE 57

IR (KBr): 3355.5, 1662.3, 1629.6, 1267.0 cm$^{-1}$ NMR (DMSO-d$_6$, δ): 0.88 (3H, t, J=6.8 Hz), 0.93 (3H, d, J=8.4 Hz), 0.97 (3H, d, J=6.7 Hz), 1.2–1.5 (4H, m), 1.5–1.95 (5H, m), 2.1–2.45 (4H, m), 2.5–2.7 (4H, m), 3.17 (1H, m), 3.55–4.45 (14H, m), 4.6–5.3 (13H, m), 5.56 (1H, d, J=5.6 Hz), 6.72 (1H, d, J=8.1 Hz), 6.75 (1H, s), 6.77 (1H, d, J=8.1 Hz), 7.04 (1H, s), 7.10 (1H, s), 7.2–7.45 (10H, m), 7.53 (4H, d, J=6.6 Hz), 7.85 (1H, d, J=7 Hz), 7.92 (1H, d, J=7 Hz), 8.05 (1H, d, J=7 Hz), 8.22 (1H, d, J=7 Hz), 8.84 (1H, s) FAB-MASS: m/z=1408 (M+Na)

EXAMPLE 58

IR (KBr): 3347.8, 1664.3, 1631.5, 1245.8 cm$^{-1}$ NMR (DMSO-d$_6$, δ): 0.86 (3H, t, J=6.6 Hz), 0.96 (3H, d, J=6.6 Hz), 1.04 (3H, d, J=5.7 Hz), 1.15–2.6 (21H, m), 3.16 (1H, m), 3.5–4.5 (16H, m), 4.6–5.4 (13H, m), 5.47 (1H, d, J=5.7 Hz), 6.73 (1H, d, J=8.2 Hz) 6.78–6.85 (4H, m), 7.05 (1H, s), 7.10 (1H, s), 7.18 (2H, d, J=8.6 Hz), 7.25–7.45 (6H, m), 7.72 (1H, d, J=7 Hz), 7.91 (1H, d, J=7 Hz), 8.05 (1H, d, J=9.3 Hz), 8.20 (1H, d, J=7 Hz), 8.85 (1H, s) FAB-MASS: m/z=1390 (M+Na) Elemental Analysis Calcd. for $C_{60}H_{82}N_9O_{24}SNa.5H_2O$: C, 49.41; H, 6.36; N, 8.64. Found: C, 49.77; H, 6.71; N, 8.71.

EXAMPLE 59

IR (KBr): 3353.6, 1670.1, 1627.6, 1247.7 cm$^{-1}$ NMR (DMSO-d$_6$, δ): 0.86 (3H, t, J=6.5 Hz), 0.97 (3H, d, J=6.8 Hz), 1.01 (3H, d, J=5.4 Hz), 1.1–1.55 (12H, m), 1.55–1.95 (5H, m), 2.05–4.7 (4H, m), 3.16 (1H, m), 3.5–4.5 (16H, m), 4.6–5.3 (13H, m), 5.55 (1H, d, J=5.6Hz), 6.7–6.9 (5H, m), 7.05 (1H, s), 7.1 (1H, s), 7.15 (1H, d, J=8.5 Hz), 7.25–7.5 (6H, m), 7.73 (1H, d, J=8.4 Hz), 7.92 (1H, d, J=7 Hz), 8.08 (1H, d, J=8.4 Hz), 8.18 (1H, d, J=7 Hz), 8.84 (1H, s) FAB-MASS: m/z=1390 (M+Na)

EXAMPLE 60

NMR (DMSO-d$_6$, δ): 0.85 (3H, t, J=6.6 Hz), 0.96 (3H, d, J=6.6 Hz), 1.05 (3H, d, J=5.6 Hz), 1.1–1.5 (22H, m), 1.5–2.5 (9H, m), 2.5–3.5 (4H, m), 3.5–4.45 (14H, m), 4.45–5.45 (12H, m), 6.72 (1H, d, J=8.2 Hz), 6.79 (1H, s), 6.81 (1H, d, J=8.2 Hz), 7.04 (1H, s), 7.05–7.5 (8H, m), 7.9–8.3 (3H, m), 8.84 (1H, s) FAB-MASS: m/z=1325 (M+Na) Elemental Analysis Calcd. for $C_{58}H_{89}N_8O_{22}SNa.6H_2O$: C, 49.35; H, 7.14; N, 7.94. Found: C, 49.33; H, 7.04; N, 7.87.

EXAMPLE 61

IR (KBr): 3400, 1668.1, 1629.6, 1270.0 cm$^{-1}$ NMR (DMSO-d$_6$, δ): 0.96 (3H, d, J=6.8 Hz), 1.06 (3H, d, J=5.7 Hz), 1.1–2.0 (33H, m), 2.1–2.5 (4H, m), 3.20 (3H, s), 3.28 (2H, t, J=6.5 Hz), 3.1–3.3 (1H, m), 3.6–4.45 (14H, m), 4.6–5.3 (13H, m), 5.49 (1H, d, J=6.1 Hz), 6.70 (1H, s), 6.72 (1H, d, J=8.2 Hz), 6.80 (1H, d, J=8.2 Hz), 7.03 (1H, s), 7.0–7.1 (1H, m), 7.15 (1H, s), 7.2–7.45 (6H, m), 8.0–8.3 (3H, m), 8.83 (1H, s) FAB-MASS: m/z=1426 (M+Na) Elemental Analysis Calcd. for $C_{62}H_{94}N_9O_{24}SNa.5H_2O$: C, 49.82; H, 7.01; N, 8.43. Found: C, 49.86; H, 7.31; N, 8.40.

EXAMPLE 62

IR (KBr): 3355.5, 1668.1, 1629.6, 1274.7 cm$^{-1}$ NMR (DMSO-d$_6$, δ): 0.85 (3H, t, J=6.5 Hz), 0.96 (3H, d, J=6.7 Hz), 1.04 (3H, d, J=5.9 Hz), 1.1–2.6 (34H, m), 3.2 (1H, m), 3.6–4.55 (14H, m), 4.7–5.3 (11H, m), 5.47 (1H, d, J=5.9 Hz), 6.72 (1H, d, J=8.1 Hz), 6.79 (1H, s), 6.81 (1H, d, J=8.1 Hz), 7.05 (1H, s), 7.11 (1H, s), 7.2–7.5 (2H, m), 8.0–8.15 (2H, m), 8.20 (1H, d, J=8.0 Hz), 8.84 (1H, s) FAB-MASS: m/z=1235 (M+Na) Elemental Analysis Calcd. for $C_{51}H_{81}N_8O_{22}SNa.7H_2O$: C, 45.73; H, 7.15; N, 8.37. Found: C, 45.55; H, 7.24; N, 8.23.

EXAMPLE 63

IR (KBr): 3353.6, 1664.3, 1627.6 cm$^{-1}$ NMR (DMSO-d$_6$, δ): 0.86 (3H, t, J=6.6 Hz), 0.95 (3H, d, J=6.7 Hz), 1.04 (3H, d, J=5.7 Hz), 1.2–2.7 (30H, m), 3.16 (1H, m), 3.6–4.5 (13H, m), 4.7–5.3 (11H, m), 5.51 (1H, d, J=6.0 Hz), 5.74 (1H, s), 6.72 (1H, d, J=8.2 Hz), 6.75 (1H, s), 6.77 (1H, d, J=8.2 Hz), 7.05 (1H, s), 7.2–7.5 (3H, m), 8.0–8.3 (3H, m), 8.85 (1H, s) FAB-MASS: m/z=1204 (M+Na) Elemental Analysis Calcd. for $C_{50}H_{77}N_8O_{21}SNa.5H_2O$: C, 47.24; H, 6.90; N, 8.81. Found: C, 46.98; H, 7.12; N, 8.72.

EXAMPLE 64

Major Product
IR (KBr): 3400, 1675.8, 1631.5, 1511.9, 1234.2 cm$^{-1}$ NMR (DMSO-d$_6$, δ): 0.96 (3H, d, J=6.6 Hz), 1.05 (3H, d, J=5.8 Hz), 1.2–1.6 (10H, m), 1.6–2.1 (5H, m), 2.1–2.7 (4H, m), 3.05–3.2 (4H, m), 3.20 (3H, s), 3.29 (2H, t, J=6.4 Hz), 3.3–3.5 (5H, m), 3.6–4.5 (15H, m), 4.7–5.3 (11H, m), 5.50 (1H, d, J=5.8 Hz), 6.73 (1H, d, J=8.2 Hz), 6.8–7.1 (9H, m), 7.2–7.5 (3H, m), 7.81 (2H, d, J=8.6 Hz), 8.08 (1H, d, J=8.2 Hz), 8.24 (1H, d, J=7 Hz), 8.44 (1H, d, J=7 Hz), 8.84 (1H, s) FAB-MASS: m/z=1403 (M+Na) Elemental Analysis Calcd. for $C_{61}H_{85}N_{10}O_{23}SNa.9H_2O$: C, 47.47; H, 6.73; N, 9.07. Found: C, 47.43; H, 7.06; N, 9.03.

Minor Product
IR (KBr): 3350, 1668.1, 1631.5, 1511.9, 1234.2 cm$^{-1}$ NMR (DMSO-d$_6$, δ): 0.96 (3H, d, J=6.6 Hz), 1.07 (3H, d, J=5.8 Hz), 1.2–1.5 (6H, m), 1.55–2.1 (7H, m), 2.1–2.65 (4H, m), 3.0–3.6 (9H, m), 3.7–4.5 (15H, m), 4.7–5.6 (14H, m), 5.7–6.0 (1H, m), 6.72 (1H, d, J=8.0 Hz), 6.75–7.1 (9H, m), 7.25–7.5 (3H, m), 7.81 (2H, d, J=8.3 Hz), 8.08 (1H, d, J=8.2 Hz), 8.25 (1H, d, J=7 Hz), 8.45 (1H, d, J=7 Hz), 8.85 (1H, s) FAB-MASS: m/z=1371 (M+Na) Elemental Analysis Calcd. for $C_{60}H_{81}N_{10}O_{22}SNa.8H_2O$: C, 48.25; H, 6.55; N, 9.38. Found: C, 48.10; H, 6.81; N, 9.40.

EXAMPLE 65

IR (KBr): 3450, 1668.1, 1635.3 cm$^{-1}$ NMR (DMSO-d$_6$, δ): 0.88 (3H, t, J=6.5 Hz), 0.96 (3H, d, J=6.7 Hz), 1.06 (3H, d, J=6 Hz), 1.2–1.5 (6H, m), 1.6–2.1 (5H, m), 2.1–2.7 (4H, m), 3.1–3.4 (9H, m), 3.6–4.5 (15H, m), 4.7–5.3 (11H, m), 5.49 (1H, d, J=5.8 Hz), 6.73 (1H, d, J=8.2 Hz), 6.8–7.0 (2H, m), 6.83 (2H, d, J=9.0 Hz), 6.94 (2H, d, J=9.0 Hz), 7.04 (1H, s), 7.12 (1H, t, J=8.4 Hz), 7.2–7.5 (3H, m), 7.65–7.8 (2H, m), 8.09 (1H, d, J=8.4 Hz), 8.25 (1H, d, J=7 Hz), 8.63 (1H, d, J=7 Hz), 8.84 (1H, s) FAB-MASS: m/z=1363 (M+Na) Elemental Analysis Calcd. for $C_{58}H_{78}FN_{10}O_{22}SNa.5H_2O$: C, 48.67; N, 6.20; N, 9.79. Found: C, 48.83; H, 6.15; N, 9.74.

EXAMPLE 66

IR (KBr): 3400, 1668.1, 1635.3, 1510.0, 1240.0 cm$^{-1}$ NMR (DMSO-d$_6$, δ): 0.88 (3H, t, J=6.6 Hz), 1.2–1.5 (6H, m), 1.5–2.05 (5H, m), 2.1–2.65 (4H, m), 3.1–3.3 (9H, m), 3.6–4.5 (15H, m), 4.7–5.3 (11H, m), 5.51 (1H, d, J=5.8 Hz), 6.73 (1H, d, J=8.2 Hz), 6.8–6.9 (4H, m), 6.94 (2H, d, J=9.2 Hz), 7.04 (1H, s), 7.24 (1H, d, J=8.5 Hz), 7.15–7.5 (3H, m), 7.86 (1H, dd, J=8.6 and 2.1 Hz), 8.02 (1H, d, J=2.1 Hz), 8.04 (1H, d, J=8.4 Hz), 8.23 (1H, d, J=7 Hz), 8.70 (1H, d, J=7 Hz), 8.84 (1H, s) FAB-MASS: m/z=1379 (M+Na) Elemental Analysis Calcd. for $C_{58}H_{78}ClN_{10}O_{22}SNa.6H_2O$: C, 47.52; H, 6.19; N, 9.55. Found: C, 47.78; H, 6.23; N, 9.55.

EXAMPLE 67

IR (KBr): 3400, 1670 cm$^{-1}$ NMR (DMSO-d$_6$, δ): 0.96 (3H, d, J=6.7 Hz), 1.05 (3H, d, J=5.7 Hz), 1.4–2.65 (17H, m), 2.65–3.6 (8H, m), 3.6–4.5 (15H, m), 4.6–5.3 (11H, m), 5.44 (1H, d, J=6.0 Hz), 6.73 (1H, d, J=8.2 Hz), 6.81 (1H, s), 6.83 (1H, d, J=8.2 Hz), 6.98 (2H, d, J=8.9 Hz), 7.05 (1H, s), 7.2–7.5 (3H, m), 7.80 (2H, d, J=8.9 Hz), 8.05 (1H, d, J=8.4 Hz), 8.26 (1H, d, J=7 Hz), 8.39 (1H, d, J=7 Hz), 8.84 (1H, s) FAB-MASS: m/z=1229 (M+Na) Elemental Analysis Calcd. for $C_{52}H_{74}N_{10}O_{21}S.5H_2O$: C, 48.14; H, 6.53; N, 10.80. Found: C, 48.29; H, 6.33; N, 10.95.

EXAMPLE 68

IR (KBr): 3400, 1652.7, 1635.3, 1511.9, 1241.9 cm$^{-1}$ NMR (DMSO-d$_6$, δ): 0.88 (3H, t, J=6.6 Hz), 0.97 (3H, d, J=6.7 Hz), 1.09 (3H, d, J=5.7 Hz), 1.2–1.5 (6H, m), 1.6–2.0 (5H, m), 2.1–2.6 (4H, m), 3.0–3.3 (5H, m), 3.6–4.6 (19H, m), 4.7–5.3 (11H, m), 5.53 (1H, d, J=5.6 Hz), 6.73 (1H, d, J=8.2 Hz), 6.75–7.0 (2H, m), 6.83 (2H, d, J=9.2 Hz), 6.95

(2H, d, J=9.2 Hz), 7.05 (1H, s), 7.12 (1H, s), 7.25–7.5 (2H, m), 7.42 (1H, d, J=9.5 Hz), 7.84 (1H, d, J=9.5 Hz), 7.9–8.1 (2H, m), 8.71 (1H, d, J=7 Hz), 8.84 (1H, s) FAB-MASS: m/z=1347 (M+Na) Elemental Analysis Calcd. for $C_{56}H_{77}N_{12}O_{22}SNa \cdot 7H_2O$: C, 46.34; H, 6.32; N, 11.58. Found: C, 46,38, H, 6.18; N, 11.36.

EXAMPLE 69

NMR (DMSO-$d_6$, δ): 0.88 (3H, t, J=6.6 Hz), 0.97 (3H, d, J=6.7 Hz), 1.08 (3H, d, J=5.8 Hz), 1.2–1.5 (6H, m), 1.6–2.05 (5H, m), 2.1–2.6 (4H, m), 3.0–3.3 (5H, m), 3.4–3.55 (4H, m), 3.7–4.6 (15H, m), 4.7–5.3 (11H, m), 5.52 (1H, d, J=5.8 Hz), 6.73 (1H, d, J=8.1 Hz), 6.8–6.95 (2H, m), 6.83 (2H, d, J=9.3 Hz), 6.95 (2H, d, J=9.3 Hz), 7.05 (1H, s), 7.14 (1H, s), 7.3–7.6 (3H, m), 7.84 (1H, d, J=8.6 Hz), 7.95–8.1 (2H, m), 8.40 (1H, s), 8.42 (1H, d, J=7 Hz), 8.84 (1H, s) FAB-MASS: m/z=1346 (M+Na) Elemental Analysis Calcd. for $C_{57}H_{78}N_{11}O_{22}SNa \cdot 5H_2O$: C, 48.40; H, 6.27; N, 10.89. Found: C, 48.32, H, 6.44; N, 10.86.

EXAMPLE 70

IR (KBr): 3400, 1668.1, 1629.6, 1511.9 $cm^{-1}$ NMR (DMSO-$d_6$, δ): 0.96 (3H, d, J=6.7 Hz), 1.06 (3H, d, J=5.7 Hz), 1.15–1.5 (6H, m), 1.6–2.0 (7H, m), 2.1–2.65 (5H, m), 3.1–3.5 (9H, m), 3.6–4.5(13H, m), 4.7–5.3 (11H, m), 5.46 (1H, d, J=5.9 Hz), 6.73 (1H, d, J=8.2 Hz), 6.81 (1H, s), 6.84 (1H, d, J=8.2 Hz), 6.91 (2H, d, J=8.7 Hz), 6.95–7.05 (3H, m), 7.09 (2H, d, J=8.7 Hz), 7.25–7.5 (3H, m), 7.81 (2 H, d, J=8.8 Hz), 8.09 (1H, d, J=7 Hz), 8.25 (1H, d, J=7 Hz), 8.04 (1H, d, J=7 Hz), 8.84 (1H, s) FAB-MASS: m/z=1327 (M+Na) Elemental Analysis Calcd. for $C_{58}H_{77}N_{10}O_{21}SNa \cdot 5H_2O$: C, 49.92; H, 6.28; N, 10.03. Found: C, 49.75; H, 6.41; N, 10.25.

EXAMPLE 71

IR (KBr): 3350, 1668.1, 1629.6, 1511.9, 1232.3 $cm^{-1}$ NMR (DMSO-$d_6$, δ): 0.85 (3H, t, J=6.5 Hz), 0.96 (3H, d, J=6.7 Hz), 1.06 (3H, d, J=6.0 Hz), 1.2–1.4 (6H, m), 1.4–1.6 (2H, m), 1.7–2.1 (3H, m), 2.1–2.7 (6H, m), 3.1–3.5 (9H, m), 3.72 (2H, m), 3.8–4.5 (11H, m), 4.7–5.3 (11H, m), 5.47 (1H, d, J=5.9 Hz), 6.73 (1H, d, J=8.2 Hz), 6.8–6.9 (2H, m), 6.91 (2H, d, J=8.6 Hz), 6.95–7.15 (5H, m), 7.25–7.5 (3H, m), 7.81 (2H, d, J=8.8 Hz), 8.09 (1H, d, J=8.4 Hz), 8.26 (1H, d, J=7 Hz), 8.40 (1H, d, J=7 Hz), 8.84 (1H, s) FAB-MASS: m/z=1329 (M+Na) Elemental Analysis Calcd. for $C_{58}H_{79}N_{10}NaO_{21}S \cdot 6H_2O$: C, 49.22; H, 6.48; N, 9.90. Found: C, 49.33; H, 6.67; N, 9.89.

EXAMPLE 72

IR (KBr): 3450, 1668.1, 1631.5, 1240.0 $cm^{-1}$ NMR (DMSO-$d_6$, δ): 0.96 (3H, d, J=6.6 Hz), 1.05 (3H, d, J=5.6 Hz), 1.3–1.7 (4H, m), 1.7–2.1 (7H, m), 2.1–2.73 (6H, m), 2.75–3.05 (4H, m), 3.05–4.5 (18H, m), 4.7–5.5 (12H, m), 6.72 (1H, d, J=8.3 Hz), 6.77–6.9 (2H, m), 6.96 (2H, d, J=8.6 Hz), 7.05 (1H, s), 7.1–7.5 (8H, m), 7.80 (2H, d, J=8.6 Hz), 8.06 (1H, d, J=8.4 Hz), 8.28 (1H, d, J=7 Hz), 8.41 (1H, d, J=7 Hz), 8.84 (1H, s) FAB-MASS: m/z=1305 (M+Na) Elemental Analysis Calcd. for $C_{58}H_{78}N_{10}O_{21}S \cdot 8H_2O$: C, 48.80; H, 6.64; N, 9.81. Found: C, 48.88; H, 6.50; N, 9.81.

EXAMPLE 73

IR (KBr): 1673.9, 1646.9, 1510.0, 1238.1 $cm^{-1}$ NMR (DMSO-$d_6$, δ): 0.87 (3H, t, J=6.4 Hz), 0.96 (3H, d, J=6.6 Hz), 1.05 (3H, d, J=5.6 Hz), 1.2–1.6 (6H, m), 1.5–2.0 (9H, m), 2.1–2.8 (11H, m), 3.1–3.4 (5H, m), 3.4–4.5 (17H, m), 4.6–5.5 (12H, m), 6.6–7.0 (9H, m), 7.04 (1H, s), 7.2–7.5 (3H, m), 7.78 (2H, d, J=8.7 Hz), 8.05 (1H, d, J=8.4 Hz), 8.24 (1H, d, J=7 Hz), 8.39 (1H, d, J=7 Hz), 8.84 (1H, s) FAB-MASS: m/z=1326 ($M^+$—$SO_3Na$) Elemental Analysis Calcd. for $C_{63}H_{89}N_{11}O_{22}S \cdot 9H_2O$ C, 48.92; H, 6.97; N, 9.96. Found: C, 48.77; H, 6.73; N, 9.94.

EXAMPLE 74

IR (KBr): 3450, 1670.1, 1631.5, 1280.5 $cm^{-1}$ NMR (DMSO-$d_6$, δ): 0.87 (3H, t, J=7.0 Hz), 0.96 (3H, t, J=6.8 Hz), 1.05 (3H, d, J=5.6 Hz), 1.1–1.65 (13H, m), 1.65–2.1 (7H, m), 2.1–2.65 (5H, m), 3.17 (1H, m), 3.6–4.5 (13H, m), 4.7–5.3 (11H, m), 5.49 (1H, d, J=5.9 Hz), 6.72 (1H, d, J=8.2 ), 6.82 (1H, d, J=8.2 Hz), 6.84 (1H, s), 7.04 (1H, s), 7.29 (2H, d, J=8.3 Hz), 7.2–7.5 (3H, m), 7.80 (2H, d, J=8.3 Hz), 8.10 (1H, d, J=8.4 Hz), 8.26 (1H, d, J=7 Hz), 8.65 (1H, d, J=7 Hz), 8.84 (1H, s) FAB-Mass: m/z=1237 (M+Na) Elemental Analysis Calcd. for $C_{53}H_{75}N_8O_{21}SNa \cdot 6H_2O$: C, 48.10; H, 6.63; N, 8.47. Found: C, 48.26; H, 6.62; N, 8.46.

EXAMPLE 75

IR (KBr): 3400, 1670.1, 1627.6, 1272.8 $cm^{-1}$ NMR (DMSO-$d_6$, δ): 0.96 (3H, d, J=3.3 Hz), 1.08 (3H, d, J=7.5 Hz), 1.2–1.6 (10H, m), 1.6–2.1 (5H, m), 2.1–2.7 (4H, m), 3.0–3.3 (1H, m), 3.20 (3H, s), 3.29 (2H, t, J=6.4 Hz), 3.73 (2H, m), 3.9–4.6 (13H, m), 4.7–5.3 (11H, m), 5.53 (1H, d, J=5.8 Hz), 6.73 (1H, d, J=8.3 Hz), 6.83 (1H, d, J=8.3 Hz), 6.91 (1H, s), 7.05 (1H, s), 7.23 (1H, dd, J=9.0 and 2.3 Hz), 7.3–7.5 (4H, m), 7.8–8.0 (3H, m), 8.09 (1H, d, J=8.4 Hz), 8.33 (1H, d, J=7 Hz), 8.44 (1H, s), 8.80 (1H, d, J=7 Hz), 8.85 (1H, s) FAB-MASS: m/z=1293 (M+Na) Elemental Analysis Calcd. for $C_{55}H_{75}N_8O_{23}SNa \cdot 6H_2O$: C, 47.89; H, 6.36; N, 8.12. Found: C, 47.81; H, 6.26; N, 8.05.

EXAMPLE 76

IR (KBr): 3361.3, 1668.1, 1635.3, 1627.6 $cm^{-1}$ NMR (DMSO-$d_6$, δ): 0.86 (3H, t, J=6.7 Hz), 0.96 (3H, d, J=6.7 Hz), 1.09 (3H, d, J=5.8 Hz), 1.19–1.25 (8H, m), 1.25–2.00 (5H, m), 2.02–2.53 (4H, m), 2.44 (3H, s), 2.61 (2H, t, J=7.6 Hz), 3.05–3.27 (1H, m), 3.55–4.50 (13H, m), 4.65–5.65 (12H, m), 6.42 (1H, s), 6.65–6.95 (3H, m), 7.05 (1H, d, J=0.4 Hz), 7.13–7.50 (5H, m), 7.50–7.88 (6H, m), 8.10 (1H, d, J=9.0 Hz), 8.25 (1H, d, J=8.4 Hz), 8.40 (1H, d, J=7.0 Hz), 8.85 (1H, s) FAB-MASS: m/z=1299.3 (M+Na-1) Elemental Analysis Calcd. for $C_{58}H_{77}N_8NaO_{21}S \cdot 5H_2O$: C, 50.94; H, 6.41; N, 8.19. Found: C, 50.99; H, 6.40; N, 8.15.

EXAMPLE 77

IR (Nujol): 3351.7, 1670.1, 1652.7, 1623.8 $cm^{-1}$ NMR (DMSO-$d_6$, δ): 0.86 (3H, t, J=6.7 Hz), 0.96 (3H, d, J=6.7 Hz), 1.06 (3H, d, J=5.8 Hz), 1.13–1.45 (8H, m), 1.47–1.96 (5H, m), 2.06–2.66 (4H, m), 2.81 (2H, t, J=7.6 Hz), 3.04–3.30 (1H, m), 3.53–4.50 (13H, m), 4.53–5.70 (12H, m), 6.64–6.88 (3H, m), 7.04 (1H, d, J=0.4 Hz), 7.13–7.60 (11H, m), 8.10 (1H, d, J=9.0 Hz), 8.18 (1H, d, J=8.4 Hz), 8.30 (1H, d, J=7.0 Hz), 8.85 (1H, s) FAB-MASS: m/z=1287.4 (M+Na-1) Elemental Analysis Calcd. for $C_{57}H_{77}N_8NaO_{21}S \cdot 5H_2O$: C, 50.51; H, 6.46; N, 8.27. Found: C, 50.84; H, 6.60; N, 8.33.

EXAMPLE 78

IR (KBr): 3361.3, 1683.6, 1670.1, 1662.3, 1652.7, 1646.9, 1635.3, 1627.6, 1623.8 $cm^{-1}$ NMR (DMSO-$d_6$, δ): 0.97 (3H, d, J=6.7 Hz), 1.07 (3H, d, J=5.6 Hz), 1.28–2.00 (13H, m), 2.08–2.60 (4H, m), 3.07–3.30 (1H, m), 3.60–4.66

(17H, m), 4.66–5.12 (9H, m), 5.11 (1H, d, J=3.1 Hz), 5.25 (1H, d, J=4.6 Hz), 5.52 (1H, d, J=6.0 Hz), 6.62–6.95 (4H, m), 6.95–7.15 (3H, m), 7.20–7.50 (3H, m), 7.50–7.85 (7H, m), 8.12 (1H, d, J=8.4 Hz), 8.35 (1H, d, J=7.7 Hz), 8.53 (1H, d, J=7.0 Hz), 8.85 (1H, s) FAB-MASS: m/z=1319.7 (M+Na−1) Elemental Analysis Calcd. for $C_{57}H_{74}N_8NaO_{22}SF.8H_2O$: C, 47.49; H, 6.29; N, 7.77. Found: C, 47.79; H, 6.16; N, 7.93.

EXAMPLE 79

IR (KBr): 3354.9, 1668.1, 1662.3, 1654.6, 1646.9, 1627.6 cm$^{-1}$ NMR (DMSO-d$_6$, δ): 0.85 (3H, t, J=6.7 Hz), 0.90–1.10 (6H, m), 1.10–1.40 (8H, m), 1.48–1.95 (5H, m), 2.05–2.46 (4H, m), 2.60 (2H, t, J=7.6 Hz), 3.07–3.23 (1H, m), 3.55–4.45 (14H, m), 4.67–5.32 (11H, m), 5.48–5.63 (1H, m), 6.22 (1H, , J=5.3 Hz), 6.65–6.89 (3H, m), 6.97–7.15 (2H, m), 7.20–7.68 (10H, m), 7.85–8.20 (3H, m), 8.84 (1H, s) FAB-MASS: m/z=1289.4 (M+Na−1) Elemental Analysis Calcd. for $C_{56}H_{75}N_8NaO_{22}S.3H_2O$: C, 50.90; H, 6.18; N, 8.48. Found: C, 50.80; H, 6.44; N, 8.29.

EXAMPLE 80

IR (KBr): 3361.3, 1664.3, 1631.5, 1600.6 cm$^{-1}$ NMR (DMSO-d$_6$, δ): 0.86 (3H, t, J=6.7 Hz), 0.98 (3H, d, J=6.7 Hz), 1.16 (3H, t, J=5.9 Hz), 1.20–1.45 (8H, m), 1.50–1.70 (2H, m), 1.70–2.05 (3H, m), 2.10–2.57 (4H, m), 2.63 (2H, t, J=7.6 Hz), 3.10–3.30 (1H, m), 3.68–4.50 (13H, m), 4.78–5.32 (11H, m), 5.66 (1H, d, J=5.7 Hz), 6.68–7.02 (3H, m), 7.04 (1H, d, J=0.4 Hz), 7.25–7.48 (4H, m), 7.60–8.08 (7H, m), 8.10 (1H, d, J=8.4 Hz), 8.28 (1H, d, J=7.7 Hz), 8.85 (1H, s), 9.30 (1H, d, J=7.1 Hz) FAB-MASS: m/z=1287.5 (M+Na−1) Elemental Analysis Calcd. for $C_{55}H_{73}N_8NaO_{22}S.3H_2O$: C, 50.53; H, 6.09; N, 8.57. Found: C, 50.66; H, 6.01; N, 8.22.

EXAMPLE 81

IR (KBr): 3349.7, 1668.1, 1627.6 cm$^{-1}$ NMR (DMSO-d$_6$, δ): 0.85 (3H, t, J=6.7 Hz), 0.96 (3H, d, J=6.7 Hz), 1.09 (3H, d, J=5.8 Hz), 1.18–1.48(8H, m), 1.50–2.10 (5H, m), 2.10–2.45 (3H, m), 2.50–2.65 (1H, m), 2.77 (2H, t, J=7.6 Hz), 3.05–3.25 (1H, m), 3.60–4.65 (13H, m), 4.67–5.60 (12H, m), 6.65–6.97 (3H, m), 7.05 (1H, d, J=0.4 Hz), 7.21–7.43 (4H, m), 7.76 (1H, s), 7.83–8.05 (3H, m), 8.10 (1H, d, J=9.0 Hz), 8.29 (1H, d, J=8.4 Hz), 8.48 (1H, s), 8.64–9.03 (2H, m) FAB-MASS: m/z=1233.0 (M+Na−1) Elemental Analysis Calcd. for $C_{53}H_{71}N_8NaO_{20}S.3H_2O$: C, 50.96; H, 6.22; N, 8.96. Found: C, 50.62; H, 6.40; N, 8.92.

EXAMPLE 82

IR (KBr): 3361.3, 1670.1, 1627.6 cm$^{-1}$ NMR (DMSO-d$_6$, δ): 0.88 (3H, t, J=6.7 Hz), 0.96 (3H, d, J=6.7 Hz), 1.09 (3H, d, J=5.9 Hz), 1.18–1.43 (6H, m), 1.50–2.10 (5H, m), 2.10–2.69 (4H, m), 2.77 (2H, t, J=7.6 Hz), 3.07–3.29 (1H, m), 3.60–4.62 (13H, m), 4.69–5.23 (10H, m), 5.27 (1H, d, J=4.5 Hz), 5.55 (1H, d, J=5.9 Hz), 6.68–7.00 (3H, m), 7.05 (1H, d, J=0.4 Hz), 7.25–7.53 (4H, m), 7.76 (1H, s), 7.84–8.05 (3H, m), 8.13 (1H, d, J=8.4 Hz), 8.33 (1H, d, J=7.7 Hz), 8.48 (1H, s), 8.73–9.00 (2H, m) FAB-MASS: m/z=1219.4 (M+Na−1) Elemental Analysis Calcd. for $C_{52}H_{69}N_8NaO_{21}S.5H_2O$: C, 48.51; H, 6.19; N, 8.71. Found: C, 48.67; H, 6.34; N, 8.74.

EXAMPLE 83

IR (KBr): 3357.5, 1668.1, 1627.6 cm$^{-1}$ NMR (DMSO-d$_6$, δ): 0.97 (3H, d, J=6.7 Hz), 1.07 (3H, d, J=6.0 Hz), 1.20–1.62 (10H, m), 1.62–2.00 (5H, m), 2.10–2.65 (4H, m), 3.20 (3H, s), 3.08–3.45 (1H, m), 3.28 (2H, t, J=6.5 Hz), 3.53–4.50 (15H, m), 4.68–5.13 (9H, m), 5.17 (1H, d, J=3.1 Hz), 5.25 (1H, d, J=4.4 Hz), 5.53 (1H, d, J=6.0 Hz), 6.68–6.95 (4H, m), 6.95–7.11 (3H, m), 7.20–7.52 (3H, m), 7.55–7.95 (7H, m), 8.13 (1H, d, J=8.4 Hz), 8.30 (1H, d, J=7.7 Hz), 8.52 (1H, d, J=7.0 Hz), 8.85 (1H, s) FAB-MASS: m/z=1345.2 (M+Na−1) Elemental Analysis Calcd. for $C_{59}H_{79}N_8NaO_{23}S.8H_2O$: C, 48.29; H, 6.53; N, 7.64. Found: C, 48.44; H, 6.58; N, 7.75.

EXAMPLE 84

IR (KBr): 3353.6, 1662.3, 1627.6 cm$^{-1}$ NMR (DMSO-d$_6$, δ): 0.96 (3H, d, J=6.7 Hz), 1.07 (3H, d, J=5.5 Hz), 1.40–1.65 (2H, m), 1.65–2.00 (5H, m), 2.00–2.67 (6H, m), 3.08–3.30 (1H, m), 3.50–4.50 (15H, m), 4.68–5.13 (11H, m), 5.18 (1H, d, J=3.1 Hz), 5.26 (1H, d, J=4.5 Hz), 5.53 (1H, d, J=6.0 Hz), 5.70–6.00 (1H, m), 6.63–6.95 (4H, m), 6.95–7.13 (3H, m), 7.20–7.52 (3H, m), 7.52–7.95 (7H, m), 8.12 (1H, d, J=8.4 Hz), 8.31 (1H, d, J=7.7 Hz), 8.53 (1H, d, J=7.0 Hz), 8.85 (1H, s) FAB-MASS: m/z=1285.4 (M+Na−1) Elemental Analysis Calcd. for $C_{56}H_{71}N_8O_{22}SNa.8H_2O$: C, 47.79; H, 6.23; N, 7.96. Found: C, 47.59; H, 6.32; N, 8.06.

EXAMPLE 85

IR (KBr): 3363.2, 1670.1, 1627.6 cm$^{-1}$ NMR (DMSO-d$_6$, δ): 0.89 (6H, d, J=6.5 Hz), 0.96 (3H, d, J=6.7 Hz), 1.07 (3H, d, J=5.7 Hz), 1.22–1.41 (2H, m), 1.50–1.97 (6H, m), 2.11–2.65 (4H, m), 3.10–3.30 (1H, m), 3.60–4.50 (15H, m), 4.70–5.08 (8H, m), 5.10 (1H, d, J=5.6 Hz), 5.16 (1H, d, J=3.1 Hz), 5.25 (1H, d, J=4.5 Hz), 5.50 (1H, d, J=5.9 Hz), 6.65–6.92 (4H, m), 6.92–7.12 (3H, m), 7.21–7.50 (3H, m), 7.52–7.90 (7H, m), 8.12 (1H, d, J=8.4 Hz), 8.30 (1H, d, J=7.7 Hz), 8.56 (1H, d, J=7.0 Hz), 8.85 (1H, s) FAB-MASS: m/z=1287.6 (M+Na−1) Elemental Analysis Calcd. for $C_{56}H_{73}N_8NaO_{22}S.6.5H_2O$: C, 48.66; H, 6.27; N, 8.11. Found: C, 48.67; H, 6.32; N, 8.20.

EXAMPLE 86

IR (KBr): 3361.3, 1683.6, 1670.1, 1654.6, 1635.3, 1623.8 cm$^{-1}$ NMR (DMSO-d$_6$, δ): 0.97 (3H, d, J=6.7 Hz), 1.07 (3H, d, J=5.6 Hz), 1.30–2.00 (11H, m), 2.10–2.70 (4H, m), 3.05–3.15 (1H, m), 3.55–4.70 (17H, m), 4.70–5.11 (9H, m), 5.16 (1H, d, J=3.1 Hz), 5.25 (1H, d, J=4.5 Hz), 5.52 (1H, d, J=6.0 Hz), 6.65–6.95 (4H, m), 6.95–7.10 (3H, m), 7.10–7.50 (3H, m), 7.50–7.85 (7H, m), 8.12 (1H, d, J=8.4 Hz), 8.30 (1H, d, J=8.3 Hz), 8.52 (1H, d, J=7.0 Hz), 8.85 (1H, s) FAB-MASS: m/z=1305.2 (M+Na−1) Elemental Analysis Calcd. for $C_{56}N_{72}N_8NaO_{22}SF.6H_2O$: C, 48.34; H, 6.09; N, 8.05. Found: C, 48.47; H, 6.29; N, 7.95.

EXAMPLE 87

IR (KBr): 3359.4, 1668.1, 1654.6, 1625.7 cm$^{-1}$ NMR (DMSO-d$_6$, δ): 0.97 (3H, d, J=6.7 Hz), 1.07 (3H, d, J=6.0 Hz), 1.22–1.62 (6H, m), 1.62–2.00 (5H, m), 2.10–2.65 (4H, m), 3.20 (3H, s), 3.05–3.40 (1H, m), 3.31 (2H, t, J=6.5 Hz), 3.60–4.55 (15H, m), 4.65–5.13 (9H, m), 5.16 (1H, d, J=3.1 Hz), 5.26 (1H, d, J=4.4 Hz), 5.53 (1H, d, J=6.0 Hz), 6.68–6.95 (4H, m), 6.95–7.20 (3H, m), 7.20–7.58 (3H, m), 7.58–7.90 (7H, m), 8.13 (1H, d, J=8.4 Hz), 8.32 (1H, d, J=7.7 Hz), 8.53 (1H, d, J=7.0 Hz), 8.85 (1H, s) FAB-MASS: m/z=1317.6 (M+Na−1) Elemental Analysis Calcd. for $C_{57}H_{75}N_8NaO_{23}S.7H_2O$: C, 48.16; H, 6.31; N, 7.88. Found: C, 48.21; H, 6.60; N, 7.78.

EXAMPLE 88

IR (KBr): 3350, 2954, 1668, 1629, 1538, 1511, 1454, 1249 cm$^{-1}$ NMR (DMSO-d$_6$, δ): 0.88 (3H, t, J=7.1 Hz), 0.96

(3H, d, J=7.5 Hz), 1.08 (2H, d, J=5.7 Hz), 1.2–1.5 (6H, m), 1.6–2.4 (8H, m), 2.6–2.7 (1H, m), 3.1–3.3 (1H, m), 3.6–4.5 (19H, m), 4.7–5.3 (8H, m), 6.73 (1H, d, J=8.2 Hz), 6.8–7.1 (5H, m), 7.19 (1H, s), 7.3–7.5 (3H, m), 7.75 (2H, d, J=8.7 Hz), 7.8–8.0 (4H, m), 8.08 (1H, d, J=8.9 Hz), 8.30 (1H, d, J=7.7 Hz), 8.7–9.0 (3H, m) FAB-MASS: m/z=1327 (M+Na$^+$)

Elemental Analysis Calcd. for $C_{57}H_{73}N_{10}O_{22}NaS.9H_2O$: C 46.65, H 6.25, N 9.54 Found: C 46.95, H 6.22, N 9.55

EXAMPLE 89

IR (KBr): 3376, 2931, 2858, 1662, 1631, 1521, 1444, 1245, 1047 cm$^{-1}$

NMR (DMSO-d$_6$, δ): 0.97 (3H, d, J=6.7Hz), 1.09 (3H, d, J=5.9Hz), 1.3–1.6 (6H, m), 1.7–2.1 (5H, m), 2.2–2.4 (3H, m), 2.5–2.6 (1H, m), 3.21 (3H, s), 3.2–3.4 (3H, m), 3.6–4.5 (16H, m), 4.79 (2H, d, J=6.0Hz), 4.9–5.2 (5H, m), 5.10 (1H, d, J=3.6Hz), 5.18 (1H, d, J=3.1Hz), 5.26 (1H, d, J=4.5Hz), 5.53 (1H, d, J=6.0Hz), 6.73 (1H, d, J=8.2Hz), 6.8–7.0 (2H, m), 7.0–7.2 (3H, m), 7.3–7.5 (3H, m), 7.6–7.9 (8H, m), 8.01 (2H, d, J=8.4Hz), 8.12 (1H, d, J=8.4Hz), 8.31 (1H, d, J=7.7Hz), 8.79 (1H, d, J=7.0Hz), 8.85 (1H, s)

FAB-MASS: m/z=1367 (M+Na$^+$)

Elemental Analysis Calcd. for $C_{61}H_{77}N_8O_{23}NaS.6.5H_2O$: C 50.10, H 6.20, N 7.66 Found: C 50.09, H 6.17, N 7.62

EXAMPLE 90

IR (KBr): 3363, 2937, 2869, 1646, 1444, 1255 cm$^{-1}$

NMR (DMSO-d$_6$, δ): 0.97 (3H, d, J=6.7Hz), 1.08 (3H, d, J=5.7Hz), 1.2–1.6 (10H, m), 1.7–2.1 (5H, m), 2.1–2.4 (3H, m), 2.5–2.7 (1H, m), 3.20 (3H, s), 3.2–3.4 (1H, m), 3.6–4.6 (16H, m), 4.7–5.2 (8H, m), 5.16 (1H, d, J=3.1Hz), 5.24 (1H, d, J=4.5Hz), 5.54 (1H, d, J=5.8Hz), 6.73 (1H, d, J=8.2Hz), 6.8–7.0 (2H, m), 7.1–7.4 (6H, m), 7.97 (2H, d, J=8.8Hz), 8.0–8.4 (6H, m), 8.84 (1H, s), 8.92 (1H, d, J=7.0Hz)

FAB-MASS: m/z=1403.6 (M+Na$^+$)

Elemental Analysis Calcd. for $C_{59}H_{77}N_{10}O_{23}NaS_2.6H_2O$: C 47.58, H 6.02, N 9.40 Found: C 47.72, H 6.12, N 9.42

EXAMPLE 91

IR (KBr): 3350, 1668, 1654, 1625, 1537, 1521, 1245, 1047 cm$^{-1}$

NMR (DMSO-d$_6$, δ): 0.9–1.1 (6H, m), 1.07 (3H, d, J=5.7Hz), 1.4–2.0 (7H, m), 2.2–2.5 (3H, m), 2.5–2.6 (1H, m), 3.1–3.3 (1H, m), 3.6–4.5 (16H, m), 4.7–5.1 (7H, m), 5.09 (1H, d, J=5.6Hz), 5.16 (1H, d, J=3.1Hz), 5.25 (1H, d, J=4.4Hz), 5.53 (1H, d, J=6.0Hz), 6.73 (1H, d, J=8.4Hz), 6.8–7.2 (6H, m) 7.2–7.5 (4H, m), 7.5–7.8 (6H, m), 8.11 (1H, d, J=8.4Hz), 8.32 (1H, d, J=7.7Hz), 8.54 (1H, d, J=7.0Hz), 8.84 (1H, s)

FAB-MASS: m/z=1259 (M+Na$^+$)

Elemental Analysis Calcd. for $C_{54}H_{69}N_8O_{22}NaS.8H_2O$: C 46.95, H 6.20, N 8.11 Found: C 47.20, H 6.23, N 8.28

EXAMPLE 92

IR (KBr): 3359, 2929, 2852, 1668, 1650, 1631, 1538, 1515 cm$^{-1}$

NMR (DMSO-d$_6$, δ): 0.96 (3H, J=6.7Hz), 1.09 (3H, d, J=6.1Hz), 1.2–1.6 (5H, m), 1.6–2.5 (10H, m), 2.5–2.6 (1H, m), 3.18 (1H, m), 3.7–4.5 (15H, m), 4.8–5.2 (8H, m), 5.17 (1H, d, J=3.1Hz), 5.26 (1H, d, J=4.5Hz), 5.55 (1H, d, J=5.9Hz), 6.73 (1H, d, J=8.1Hz), 6.81 (1H, s), 6.85 (1H, s), 7.05 (1H, s), 7.2–7.4 (3H, m), 7.45 (2H, d, J=8.2Hz), 7.96 (2H, d, J=8.2Hz), 8.0–8.2 (4H, s), 8.2–8.3 (1H, m), 8.85 (1H, s), 8.9–9.0 (1H, d, J=7.0Hz)

FAB-MASS: m/z=1327.5 (M+Na$^+$)

Elemental Analysis Calcd. for $C_{56}H_{69}N_{10}O_{21}S_2Na.6H_2O$: C 47.59, H 5.78, N 9.91

EXAMPLE 93

IR (KBr): 3350, 1654, 1629, 1517, 1249, 1047 cm$^{-1}$

NMR (DMSO-d$_6$, δ): 0.9–1.1 (6H, m), 1.11 (3H, d, J=5.9Hz), 1.6–2.0 (5H, s), 2.1–2.4 (3H, s), 2.6–2.7 (1H, m), 3.1–3.3 (1H, m), 3.6–4.5 (16H, m), 4.7–5.2 (7H, m), 5.10 (1H, d, J=5.6Hz), 5.17 (1H, d, J=3.1Hz), 5.25 (1H, d, J=4.5Hz), 5.55 (1H, d, J=5.7Hz), 6.7–6.9 (3H, m), 7.0–7.5 (6H, m), 7.74 (2H, d, J=8.8Hz), 7.91 (2H, d, J=8.5Hz), 8.1–8.4 (8H, m), 8.84 (1H, s), 8.97 (1H, d, J=7.0Hz)

FAB-MASS: m/z=1363.5 (M+Na$^+$)

Elemental Analysis Calcd. for $C_{59}H_{69}N_{10}O_{23}SNa.5H_2O$: C 49.51, H 5.56, N 9.79 Found: C 49.39, H 5.63, N 9.77

EXAMPLE 94

IR (KBr): 3355, 2929, 2856, 1664, 1631, 1519, 1440, 1282 cm$^{-1}$

NMR (DMSO-d$_6$, δ): 0.84 (3H, t, J=6.7Hz), 0.96 (3H, d, J=6.7Hz), 1.07 (3H, t, J=5.8Hz), 1.2–1.5 (12H, m), 1.7–2.0 (5H, m), 2.2–2.4 (3H, m), 2.5–2.7 (1H, m), 2.94 (2H, t, J=7.4Hz), 3.1–3.3 (1H, m), 3.6–4.6 (14H, m), 4.8–5.2 (7H, m), 5.10 (1H, d, J=3.6Hz), 5.17 (1H, d, J=3.1Hz), 5.26 (1H, d, J=4.5Hz), 5.55 (1H, d, J=5.9Hz), 6.73 (1H, d, J=8.2Hz), 6.8–7.0 (2H, m), 7.0–7.5 (4H, m), 8.0–8.2 (5H, m), 8.27 (1H, d, J=7.7Hz), 8.85 (1H, s), 8.93 (1H, d, J=7.0Hz)

FAB-MASS: m/z=1279 (M+Na$^+$)

Elemental Analysis Calcd. for $C_{53}H_{73}N_{10}O_{22}SNa.5.5H_2O$: C 46.93, H 6.24, N 10.33 Found: C 46.93, H 6.46, N 10.31

EXAMPLE 95

IR (KBr): 3363, 1673, 1648, 1538, 1253 cm$^{-1}$

NMR (DMSO-d$_6$, δ): 0.92 (3H, t, J=6.8Hz), 0.97 (3H, d, J=6.8Hz), 1.10 (3H, d, J=5.8Hz), 1.2–1.5 (6H, m), 1.7–2.1 (5H, m), 2.1–2.4 (3H, m), 2.5–2.6 (1H, m), 3.1–3.3 (1H, m), 3.6–4.5 (16H, m), 4.7–5.1 (9H, m), 5.16 (1H, d, J=3.1Hz), 5.24 (1H, d, J=4.5Hz), 5.54 (1H, d, J=5.8Hz), 6.73 (1H, d, J=8.2Hz), 6.8–7.4 (8H, m), 8.04 (2H, d, J=8.8Hz), 8.13 (2H, d, J=8.6Hz), 8.2–8.4 (4H, m), 8.84 (1H, s), 8.98 (1H, d, J=7.0Hz)

FAB-MASS: m/z=1329.6 (M+Na$^+$)

Elemental Analysis Calcd. for $C_{56}H_{71}N_{10}O_{23}SNa.7H_2O$: C 46.92, H 5.97, N 9.77 Found: C 46.86, H 5.99, N 9.77

EXAMPLE 96

IR (KBr): 3355, 2929, 1666, 1648, 1631, 1515, 1442, 1047 cm$^{-1}$

NMR (DMSO-d$_6$, δ): 0.87 (3H, t, J=6.7Hz), 0.97 (3H, d, J=6.7Hz), 1.10 (3H, d, J=5.8Hz), 1.2–1.5 (10H, m), 1.7–2.1 (5H, m), 2.1–2.4 (3H, m), 2.5–2.6 (1H, m), 3.1–3.3 (1H, m), 3.6–4.6 (16H, m), 4.79 (2H, d, J=5.9Hz), 4.8–5.2 (5H, m), 5.09 (1H, d, J=5.5Hz), 5.16 (1H, d, J=3.1Hz), 5.23 (1H, d, J=4.5Hz), 5.53 (1H, d, J=5.9Hz), 6.73 (1H, d, J=8.0Hz), 6.8–6.9 (2H, m), 7.0–7.5 (6H, m), 7.97 (2H, d, J=8.8Hz), 8.0–8.3 (6H, m), 8.83 (1H, s), 8.88 (1H, d, J=7.0Hz)

FAB-MASS: m/z=1373.5 (M+Na$^+$)

Elemental Analysis Calcd. for $C_{58}H_{75}N_{10}O_{22}S_2Na.6H_2O$: C 47.73, H 6.01, N 9.60 Found: C 47.57, H 5.92, N 9.53

EXAMPLE 97

IR (KBr): 3361, 2925, 2852, 1668, 1650, 1631, 1538, 1452, 1049 cm$^{-1}$

NMR (DMSO-d$_6$, δ): 0.87 (3H, t, J=6.9Hz), 0.96 (3H, d, J=6.7Hz), 1.08 (3H, d, J=5.7Hz), 1.2–1.4 (11H, m), 1.4–1.6 (2H, m), 1.7–2.1 (5H, m), 2.1–2.5 (5H, m), 2.5–2.6 (1H, m), 3.1–3.3 (2H, m), 3.7–4.5 (14H, m), 4.7–5.0 (7H, m), 5.09 (1H, d, J=5.6Hz), 5.16 (1H, d, J=3.1Hz), 5.25 (1H, d, J=4.5Hz), 5.54 (1H, d, J=5.8Hz), 6.73 (1H, d, J=8.2Hz), 6.8–7.0 (2H, d), 7.04 (1H, s), 7.2–7.5 (3H, m), 8.03 (4H, s), 8.0–8.3 (2H, m), 8.84 (1H, s), 8.95 (1H, d, J=7.0Hz)

FAB-MASS: m/z=1321.9 (M+Na)$^+$

Elemental Analysis Calcd. for $C_{55}H_{75}N_{10}O_{21}S_2Na.5H_2O$: C 47.54, H 6.17, N 10.08 Found: C 47.38, H 6.12, N 9.98

EXAMPLE 98

IR (KBr): 3374, 2937, 2875, 1658, 1629, 1531, 1436, 1255, 1047 cm$^{-1}$

NMR (DMSO-d$_6$, δ): 0.9–1.11 (6H, m), 1.09 (3H, d, J=5.7Hz), 1.2–1.5 (4H, m), 1.7–2.1 (5H, m), 2.2–2.5 (3H, m), 2.6–2.7 (1H, m), 3.2–3.3 (1H, m), 3.6–4.5 (16H, m), 4.80 (2H, d, J=5.8Hz), 4.8–5.2 (5H, m), 5.10 (1H, d, J=5.5Hz), 5.17 (1H, d, J=3.0Hz), 5.24 (1H, d, J=4.5Hz), 5.53 (1H, d, J=5.8Hz), 6.73 (1H, d, J=8.2Hz), 6.8–7.0 (2H, m), 7.06 (1H, s), 7.10 (2H, d, J=8.9Hz), 7.2–7.5 (3H, m), 7.68 (1H, s), 7.86 (2H, d, J=8.8Hz), 8.0–8.4 (6H, m), 8.84 (1H, s), 8.90 (1H, d, J=7.0Hz)

FAB-MASS: m/z=1314 (M+Na$^+$)

Elemental Analysis Calcd. for $C_{56}H_{70}N_9O_{23}NaS.6H_2O$: C 48.03, H 5.90, N 9.00 Found: C 47.92, H 5.83, N 8.88

EXAMPLE 99

IR (KBr): 3345, 1646, 1633, 1531, 1257 cm$^{-1}$

NMR (DMSO-d$_6$, δ): 0.97 (3H, d, J=6.7Hz), 1.11 (3H, d, J=5.7Hz), 1.2–1.6 (10H, m), 1.7–2.5 (8H, m), 2.6–2.7 (1H, m), 3.21 (3H, s), 3.3–3.4 (1H, m), 3.7–4.6 (16H, m), 4.8–5.2 (8H, m), 5.16 (1H, d, J=3.1Hz), 5.24 (1H, d, J=4.5Hz), 5.55 (1H, d, J=5.7Hz), 6.7–6.9 (3H, m), 7.0–7.5 (6H, m), 8.0–8.3 (8H, m), 8.84 (1H, s), 8.96 (1H, d, J=7.0Hz)

FAB-MASS: m/z=1387.7 (M+Na$^+$)

Elemental Analysis Calcd. for $C_{59}H_{77}N_{10}O_{24}NaS.6H_2O$: C 48.09, H 6.09, N 9.51 Found: C 47.81, H 5.83, N 9.38

EXAMPLE 100

IR (KBr): 3357, 1668, 1631, 1429, 1284, 1047 cm$^{-1}$

NMR (DMSO-d$_6$, δ): 0.97 (3H, d, J=6.7Hz), 1.09 (3H, d, J=5.8Hz), 1.8–2.4 (6H, m), 2.5–2.6 (1H, m), 3.1–3.2 (1H, m), 3.7–4.6 (14H, m), 4.7–5.2 (7H, m), 5.10 (1H, d, J=5.5Hz), 5.17 (1H, d, J=3.1Hz), 5.24 (1H, d, J=5.5Hz), 5.53 (1H, d, J=5.8Hz), 6.75 (1H, d, J=8.2Hz), 6.8–6.9 (2H, m), 7.05 (1H, s), 7.3–7.6 (9H, m), 7.8–7.9 (4H, m), 8.0–8.2 (5H, m), 8.2–8.3 (1H, m), 8.34 (1H, d, J=9.3Hz), 8.7–8.8 (1H, m), 8.85 (1H, s)

FAB-MASS: m/z=1332.7 (M+Na$^+$)

Elemental Analysis Calcd. for $C_{58}H_{65}N_{10}O_{22}SNa.8H_2O$: C 47.93, H 5.62, N 9.64 Found: C 47.83, H 5.53, N 9.56

EXAMPLE 101

IR (KBr): 3353, 2929, 2856, 1666, 1631, 1612, 1496, 1440, 1259 cm$^{-1}$

NMR (DMSO-d$_6$, δ): 0.87 (3H, t, J=6.6Hz), 0.97 (3H, d, J=6.5Hz), 1.09 (3H, d, J=5.9Hz), 1.2–1.5 (10H, m), 1.7–2.1 (5H, m), 2.2–2.5 (3H, m), 2.6–2.7 (1H, m), 3.1–3.2 (1H, m), 3.6–4.5 (16H, m), 4.7–5.0 (3H, m), 5.0–5.2 (5H, m), 5.10 (1H, d, J=3.1Hz), 5.26 (1H, d, J=4.2Hz), 5.56 (1H, d, J=5.5Hz), 6.73 (1H, d, J=8.1Hz), 6.8–7.0 (2H, m), 7.05 (1H, s), 7.1–7.5 (5H, m), 8.0–84 (8H, m), 8.85 (1H, s), 8.95 (1H, d, J=7.0Hz)

FAB-MASS: m/z=1357.3 (M+Na$^+$)

Elemental Analysis Calcd. for $C_{58}H_{75}N_{10}O_{23}NaS.7H_2O$: C 47.67, H 6.14, N 9.58 Found: C 47.63, H 6.42, N 9.52

EXAMPLE 102

IR (KBr): 3361, 1670, 1648, 1633, 1540, 1519, 1249 cm$^{-1}$

NMR (DMSO-d$_6$, δ): 0.89 (3H, t, J=7.0Hz), 0.97 (3H, d, J=6.8Hz), 1.10 (3H, d, J=5.7Hz), 1.2–1.5 (6H, m), 1.6–2.4 (8H, m), 2.5–2.7 (1H, m), 3.1–3.3 (1H, m), 3.6–4.5 (16H, m), 4.80 (2H, d, J=5.8Hz), 4.8–5.2 (5H, m), 5.10 (1H, d, J=5.4Hz), 5.18 (1H, d, J=3.1Hz), 5.25 (1H, d, J=4.3Hz), 5.55 (1H, d, J=5.7Hz), 6.73 (1H, d, J=8.2Hz), 6.8–7.0 (2H, m), 7.0–7.5 (6H, m), 8.02 (1H, d, J=5.3Hz), 8.0–8.4 (4H, m), 8.42 (2H, d, J=8.4Hz), 8.48 (2H, d, J=8.9Hz), 8.8–9.0 (3H, m)

FAB-MASS: m/z=1339.3 (M+Na$^+$)

Elemental Analysis Calcd. for $C_{58}H_{73}N_{10}O_{22}SNa.6H_2O$: C 48.87, H 6.01, N 9.83 Found: C 49.16, H 5.92, N 9.86

EXAMPLE 103

IR (KBr): 3350, 2971, 2859, 1672, 1629, 1537, 1442, 1247, 1047 cm$^{-1}$

NMR (DMSO-d$_6$, δ): 0.96 (3H, d, J≦6.8Hz), 1.0–1.2 (6H, m), 1.2–1.6 (12H, m), 1.7–2.5 (8H, m), 2.5–2.6 (1H, m), 3.2–3.6 (7H, m), 3.7–4.5 (16H, m), 4.76 (2H, d, J=5.6Hz), 4.8–5.1 (5H, m), 5.09 (1H, d, J=5.5Hz), 5.16 (1H, d, J=3.1Hz), 5.23 (1H, d, J=5.5Hz), 5.51 (1H, d, J=5.9Hz), 6.73 (1H, d, J=8.2Hz), 6.8–6.9 (2H, m), 7.0–7.1 (3H, m), 7.3–7.5 (3H, m), 7.67 (2H, d, J=6.9Hz), 7.71 (2H, d, J=6.9Hz), 7.95 (2H, d, J=8.4Hz), 8.05 (1H, d, J=7.0Hz), 8.23 (1H, d, J=7.7Hz), 8.70 (1H, d, J=7.0Hz), 8.84 (1H, s)

FAB-MASS: m/z=1377.1 (M+Na$^+$)

Elemental Analysis Calcd. for $C_{60}H_{83}N_8O_{24}NaS.5H_2O$: C 49.86, H 6.49, N 7.75 Found: C 49.74, H 6.73, N 7.68

EXAMPLE 104

IR (KBr): 3349, 2937, 2858, 1672, 1629, 1537, 1444, 1249, 1047 cm$^{-1}$

NMR (DMSO-d$_6$, δ): 0.96 (3H, d, J=6.7Hz), 1.08 (3H, d, J=5.6Hz), 1.2–1.7 (14H, m), 1.7–2.1 (5H, m), 2.1–2.4 (5H, m), 2.5–2.6 (1H, m), 3.1–3.2 (1H, m), 3.4–3.6 (4H, m), 3.7–4.5 (16H, m), 4.77 (2H, d, J=5.7Hz), 4.8–5.2 (5H, m), 5.09 (1H, d, J=5.6Hz), 5.16 (1H, d, J=3.1Hz), 5.24 (1H, d, J=4.5Hz), 5.51 (1H, d, J=5.8Hz), 6.73 (1H, d, J=8.2Hz), 6.8–6.9 (2H, m), 7.0–7.1 (3H, m), 7.3–7.5 (3H, m), 7.6–7.8 (4H, m), 7.96 (2H, d, J=8.4Hz), 8.10 (1H, d, J=8.4Hz), 8.24 (1H, d, J=7.7Hz), 8.71 (1H, d, J=7.0Hz), 8.89 (1H, s)

FAB-MASS: m/z=1386.5 (M+Na$^+$)

Elemental Analysis Calcd. for $C_{61}H_{82}N_9O_{23}NaS.6H_2O$: C 49.76, H 6.43, N 8.56 Found: C 49.99, H 6.39, N 8.52

EXAMPLE 105

IR (KBr): 3350, 2933, 2856, 1664, 1631, 1604, 1511, 1450, 1243, 1045 cm$^{-1}$

NMR (DMSO-d$_6$, δ): 0.86 (3H, t, J=6.7Hz), 0.96 (3H, d, J=6.5Hz), 1.05 (3H, d, J=5.7Hz), 1.2–1.5 (8H, m), 1.6–2.0 (5H, m), 2.1–2.4 (3H, m), 2.5–2.6 (1H, m), 3.0–3.3 (5H, m), 3.6–4.4 (20H, m), 4.7–5.1 (7H, m), 5.10 (1H, d, J=5.5Hz), 5.16 (1H, d, J=3.1Hz), 5.27 (1H, d, J=4.5Hz), 5.51 (1H, d, J=6.0Hz), 6.7–7.1 (9H, m), 7.2–7.5 (3H, m), 8.0–8.2 (2H, m), 8.2–8.4 (1H, m), 8.4–8.6 (1H, m), 8.66 (1H, d, J=2.2Hz), 8.85 (1H, s)

FAB-MASS: m/z=1360 (M+Na$^+$)

Elemental Analysis Calcd. for $C_{58}H_{80}N_{11}O_{22}SNa.6H_2O$: C 48.16, H 6.41, N 10.65 Found: C 47.91, H 6.31, N 10.56

EXAMPLE 106

IR (KBr): 3369, 3345, 2935, 1672, 1629, 1511, 1245, 1047 cm$^{-1}$

NMR (DMSO-d$_6$, δ): 0.96 (3H, d, J=6.7Hz), 1.06 (3H, d, J=5.8Hz), 1.3–1.6 (10H, m), 1.6–2.0 (5H, m), 2.1–2.4 (3H, m), 2.5–2.6 (1H, m), 3.20 (3H, s), 3.28 (2H, t, J=6.4Hz), 3.1–3.4 (5H, m), 3.7–4.5 (20H, m), 4.7–5.1 (7H, m), 5.08 (1H, d, J=5.5Hz), 5.15 (1H, d, J=3.1Hz), 5.23 (1H, d, J=4.5Hz), 5.48 (1H, d, J=5.8Hz), 6.73 (1H, d, J=8.2Hz), 6.82 (2H, d, J=9.1Hz), 6.94 (2H, d, J=9.1Hz), 6.9–7.0 (1H, m), 7.04 (1H, s), 7.3–7.5 (3H, m), 8.0–8.1 (2H, m), 8.27 (1H, d, J=7.7Hz), 8.49 (1H, d, J=7.0Hz), 8.66 (1H, d, J=2.2Hz), 8.84 (1H, s)

FAB-MASS: m/z=1404 (M+Na$^+$)

EXAMPLE 107

IR (KBr): 3357, 1647, 1631, 1537, 1444, 1249, 1049 cm$^{-1}$

NMR (DMSO-d$_6$, δ): 0.9–1.1 (6H, m), 1.09 (3H, d, J=5.9Hz), 1.6–2.4 (8H, m), 2.4–2.5 (1H, m), 3.1–3.3 (1H, m), 3.6–4.5 (16H, m), 4.8–5.2 (7H, m), 5.10 (1H, d, J=5.6Hz), 5.17 (1H, d, J=3.1Hz), 5.25 (1H, d, J=4.5Hz), 5.55 (1H, d, J=5.9Hz), 6.73 (1H, d, J=8.2Hz), 6.8–7.0 (2H, m), 7.0–7.6 (6H, m), 7.73 (2H, d, J=8.7Hz), 7.86 (2H, d, J=8.5Hz), 8.0–8.3 (8H, m), 8.84 (1H, s), 8.9–9.0 (1H, m)

FAB-MASS: m/z=1379.4 (M+Na)$^+$

Elemental Analysis Calcd. for $C_{59}H_{69}N_{10}O_{22}S_2Na.6H_2O$: C 48.36, H 5.57, N 9.56 Found: C 48.18, H 5.60, N 9.36

The Object Compounds (108) to (117) were obtained according to a similar manner to that of Example 27.

EXAMPLE 108

IR (KBr): 3350, 2933, 1670, 1627, 1521, 1436, 1272, 1047 cm$^{-1}$

NMR (DMSO-d$_6$, δ): 0.85 (3H, t, J=6.7Hz), 0.92 (3H, d, J=6.7Hz), 1.1–1.4 (11H, m), 1.7–2.4 (9H, m), 3.1–3.2 (1H, m), 3.5–5.4 (27H, m), 6.6–7.2 (8H, m), 7.5–7.8 (3H, m), 7.8–8.0 (3H, m), 8.1–8.8 (3H, m)

FAB-MASS: m/z=1249.4 (M+Na$^+$)

Elemental Analysis Calcd. for $C_{52}H_{71}N_{10}O_{21}NaS.7H_2O$: C 46.15, H 6.33, N 10.35 Found: C 46.12, H 6.35, N 10.24

EXAMPLE 109

IR (Kbr pelet): 3361, 2933, 2856, 1670, 1652, 1616, 1540, 1508, 1448, 1261, 1047 cm$^{-1}$ NMR (DMSO-d$_6$, δ): 0.86 (3H, d, J=6.6Hz), 0.97 (3H, d, J=6.8Hz), 1.12 (3H, d, J=6.8Hz), 1.2–1.5 (10H, m), 1.7–2.0 (5H, m), 2.2–2.6 (4H, m), 3.1–3.2 (1H, m), 3.7–4.4 (16H, m), 4.8–5.3 (10H, m), 5.59 (1H, d, J=6.0Hz), 6.7–6.9 (3H, m), 7.0–7.4 (7H, m), 7.8–8.2 (4H, m), 8.8–9.0 (2H, m)

FAB-MASS: m/z=1280.3 (M+Na$^+$)

Elemental Analysis Calcd. for $C_{54}H_{72}N_9O_{23}NaS.7H_2O$: C 46.45, H 6.21, N 9.03 Found: C 46.68, H 6.44, N 9.03

EXAMPLE 110

IR (KBr): 3350, 2931, 1670, 1627, 1540, 1436, 1276, 1047 cm$^{-1}$

NMR (DMSO-d$_6$, δ): 0.87 (3H, t, J=6.8Hz), 0.93 (2H, d, J=8.8Hz), 1.08 (2H, d, J=5.9Hz), 1.2–1.4 (4H, m), 1.5–1.7 (2H, m), 1.7–2.1 (3H, m), 2.1–2.4 (3H, m), 2.6–2.7 (3H, m), 3.1–3.3 (1H, m), 3.6–4.5 (17H, m), 4.7–5.4 (8H, m), 6.73 (1H, d, J=8.2Hz), 6.83 (2H, d, J=8.2Hz, 7.0–7.1 (1H, m), 7.2–7.5 (5H, m), 7.65 (2H, d, J=8.2Hz), 7.74 (2H, d, J=8.4Hz), 7.98 (2H, d, J=8.4Hz), 8.08 (1H, d, J=8.5Hz), 8.25 (1H, d, J=8.5Hz), 8.74 (1H, d, J=7.6Hz), 8.7–9.0 (1H, br)

FAB-MASS: m/z=1231.2 (M+Na$^+$)

Elemental Analysis Calcd. for $C_{53}H_{69}N_8O_{21}NaS.3H_2O$: C 50.39, H 5.98, N 8.87 Found: C 50.34, H 6.25, N 8.90

EXAMPLE 111

IR (KBr): 3353.6, 1670.1, 1652.7, 1623.8 cm$^{-1}$

NMR (DMSO-d$_6$, δ): 0.96 (3H, d, J=6.7Hz), 1.07 (3H, d, J=5.6Hz), 1.0–1.62 (8H, m), 1.62–2.00 (5H, m), 2.10–2.65 (4H, m), 3.20 (3H, s), 3.08–3.40 (1H, m), 3.30 (2H, t, J=6.5Hz), 3.53–4.50 (15H, m), 4.68–5.13 (9H, m), 5.16 (1H, d, J=2.9Hz), 5.26 (1H, d, J=4.5Hz), 5.53 (1H, d, J=5.9Hz), 6.68–6.95 (4H, m), 6.95–7.11 (3H, m), 7.20–7.52 (3H, m), 7.55–7.95 (7H, m), 8.13 (1H, d, J=8.4Hz), 8.31 (1H, d, J=7.7Hz), 8.53 (1H, d, J=7.0Hz), 8.85 (1H, s)

FAB-MASS: m/z=1331.5 (M+Na−1)

Elemental Analysis Calcd. for $C_{58}H_{77}N_8NaO_{23}S.6H_2O$: C 49.15, H 6.33, N 7.91 Found: C 49.07, H 6.53, N 7.84

EXAMPLE 112

IR (KBr): 3350, 2937, 1673, 1646, 1631, 1538, 1519, 1456, 1247, 1049 cm$^{-1}$

NMR (DMSO-d$_6$, δ): 0.97 (3H, d, J=6.6Hz), 1.07 (3H, d, J=5.7Hz), 1.3–2.4 (25H, m), 2.5–2.6 (1H, m), 3.2–3.4 (1H, m), 3.5–4.6 (20H, m), 4.8–5.7 (11H, m), 6.73 (1H, d, J=8.0Hz), 6.9–7.0 (2H, m), 7.0–7.2 (3H, m), 7.3–7.6 (3H, m), 7.74 (2H, d, J=8.5Hz), 7.77 (2H, d, J=8.3Hz), 8.02 (2H, d, J=8.3Hz), 8.13 (1H, d, J=8.4Hz), 8.30 (1H, d, J=7.7Hz), 8.77 (1H, d, J=7.0Hz), 8.85 (1H, s)

FAB-MASS: m/z=1389 (M+Na$^+$)

Elemental Analysis Calcd. for $C_{61}H_{83}N_8O_{24}NaS.7H_2O$: C 49.06, H 6.55, N 7.50 Found: C 49.03, H 6.54, N 7.56

EXAMPLE 113

NMR (DMSO-d$_6$, δ): 0.84 (3H, t, J=6.7Hz), 0.96 (3H, d, J=6.7Hz), 1.07 (3H, d, J=5.9Hz), 1.1–1.3 (14H, m), 1.7–2.1 (5H, m), 2.2–2.5 (3H, m), 2.6–2.7 (1H, m), 3.1–3.3 (1H, m), 3.7–4.5 (16H, m), 4.7–5.1 (7H, m), 5.10 (1H, d, J=5.5Hz), 5.16 (1H, d, J=3.1Hz), 5.25 (1H, d, J=4.5Hz), 5.49 (1H, d, J=5.7Hz), 6.53 (1H, d, J=3.1Hz), 6.73 (1H, d, J=8.2Hz), 6.8–6.9 (2H, m), 7.05 (1H, m), 7.31 (1H, d, J=8.1Hz), 7.4–7.6 (4H, m), 7.70 (1H, d, J=6.7Hz), 8.08 (1H, d, J=8.4Hz), 8.18 (1H, s), 8.31 (1H, d, J=7.7Hz), 8.57 (1H, d, J=7.0Hz), 8.85 (1H, s)

FAB-MASS: m/z=1264 (M+Na$^+$)

Elemental Analysis Calcd. for $C_{54}H_{76}N_9O_{21}NaS.6H_2O$: C 48.03, H 6.57, N 9.34 Found: C 48.02, H 6.61, N 9.28

EXAMPLE 114

IR (KBr): 3350, 2937, 1668, 1631, 1537, 1247, 1047 cm$^{-1}$

NMR (DMSO-d$_6$, δ): 0.85 (3H, t, J=7.4Hz), 0.96 (3H, d, J=6.5Hz), 1.07 (3H, d, J=5.7Hz), 1.3–1.7 (7H, m), 1.7–2.1

(5H, m), 2.2–2.4 (3H, m), 2.6–2.7 (1H, m), 3.0–3.8 (16H, m), 3.8–4.6 (11H, m), 4.7–5.3 (6H, m), 6.73 (1H, d, J=8.2Hz), 6.8–7.0 (2H, m), 7.0–7.2 (3H, m), 7.3–7.5 (3H, m), 7.6–7.8 (4H, m), 7.96 (2H, d, J=8.3Hz), 8.11 (1H, d, J=8.2Hz), 8.26 (1H, d, J=7.6Hz), 8.6–9.0 (2H, m)

FAB-MASS: m/z=1319.4 (M+Na$^+$)

Elemental Analysis Calcd. for $C_{57}H_{77}N_8O_{23}NaS.8H_2O$: C 47.50, H 6.50, N 7.77 Found: C 47.72, H 6.85, N 7.85

EXAMPLE 115

IR (KBr): 3350, 1666, 1631, 1546, 1276, 1247 cm$^{-1}$

NMR (DMSO-d$_6$, δ): 0.97 (3H, d, J=7.5Hz), 1.08 (3H, d, J=5.7Hz), 1.4–1.6 (4H, m), 1.6–2.1 (5H, m), 2.1–2.4 (3H, m), 2.5–2.6 (1H, m), 3.1–3.3 (1H, m), 3.23 (3H, s), 3.3–3.5 (2H, m), 3.7–4.5 (16H, m), 4.79 (2H, d, J=6.2Hz), 4.8–5.1 (5H, m), 5.11 (1H, d, J=5.6Hz), 5.18 (1H, d, J=3.1Hz), 5.26 (1H, d, J=4.4Hz), 5.54 (1H, d, J=5.7Hz), 6.73 (1H, d, J=8.1Hz), 6.8–7.0 (2H, m), 7.0–7.1 (3H, m), 7.3–7.5 (3H, m), 7.6–7.9 (8H, m), 8.01 (2H, d, J=8.4Hz), 8.08 (1H, d, J=8.4Hz), 8.32 (1H, d, J=7.7Hz), 8.80 (1H, d, J=7.0Hz), 8.85 (1H, s)

FAB-MASS: m/z=1353.9 (M+Na$^+$)

Elemental Analysis Calcd. for $C_{60}H_{75}N_8O_{23}NaS.9.5H_2O$: C 47.96, H 6.31, N 7.46 Found: C 47.97, H 6.25, N 7.41

EXAMPLE 116

IR (KBr): 3450, 2935, 1675, 1650, 1540, 1513, 1454, 1047 cm$^{-1}$

NMR (DMSO-d$_6$, δ): 0.97 (3H, d, J=6.7Hz), 1.09 (3H, d, J=5.9Hz), 1.60 (6H, s), 1.7–2.4 (6H, m), 2.5–2.6 (1H, m), 3.1–3.6 (5H, m), 3.7–4.5 (14H, m), 4.7–5.0 (3H, m), 5.0–5.2 (4H, m), 5.11 (1H, d, J=5.5Hz), 5.18 (1H, d, J=3.1Hz), 5.26 (1H, d, J=4.5Hz), 5.56 (1H, d, J=6.0Hz), 6.8–7.5 (9H, m), 7.84 (2H, d, J=8.8Hz), 8.0–8.4 (6H, m), 8.85 (1H, s), 8.91 (1H, d, J=7.0Hz)

FAB-MASS: m/z=1328 (M+Na)$^+$

Elemental Analysis Calcd. for $C_{55}H_{68}N_{11}O_{21}S_2Na.8H_2O$: C 45.55, H 5.84, N 10.62 Found: C 45.62, H 5.70, N 10.54

EXAMPLE 117

IR (KBr): 3350, 2939, 1664, 1627, 1531, 1446, 1249, 1049 cm$^{-1}$

NMR (DMSO-d$_6$, δ): 0.8–1.0 (6H, m), 1.4–1.9 (9H, m), 2.0–2.5 (4H, m), 3.1–3.2 (1H, m), 3.22 (3H, s), 3.3–3.4 (2H, m), 3.51 (2H, s), 3.6–4.4 (16H, m), 4.7–5.2 (7H, m), 5.07 (1H, d, J=5.6Hz), 5.17 (1H, d, J=3.1Hz), 5.23 (1H, d, J=4.5Hz), 5.54 (1H, d, J=5.9Hz), 6.7–6.8 (3H, m), 7.0–7.4 (8H, m), 7.5–7.7 (4H, m), 7.70 (4H, s), 8.1–8.2 (2H, m), 8.51 (1H, d, J=7.0Hz), 8.83 (1H, s)

FAB-MASS: m/z=1367.6 (*M+Na*$^+$)

Elemental Analysis Calcd. for $C_{61}H_{77}N_8O_{23}SNa.6.5H_2O$: C 50.01, H 6.20, N 7.66 Found: C 50,30, H 6.50, N 7.75

EXAMPLE 118

To a solution of The Object Compound (61) (0.25 g) in methanol (50 ml) was added dry 10% palladium on carbon (0.2 g) and stirred for 6 hours under hydrogen atmosphere. The palladium on carbon was filtered off, and the filtrate was evaporated under reduced pressure to give Object Compound 118 (179 mg).

IR (KBr): 3400, 1668.1, 1627.6 cm$^{-1}$

NMR (DMSO-d$_6$, δ): 0.92 (3H, d, J=6.7Hz), 1.1–2.45 (40H, m), 3.20 (3H, s), 3.28 (2H, t, J=6.5Hz), 3.0–3.4 (1H, m), 3.5–4.7 (14H, m), 4.95–5.5 (12H, m), 6.55 (1H, d, J=8.4Hz), 6.84 (1H, s), 6.86 (1H, d, J=8.4Hz), 7.0–7.3 (4H, m), 7.9–8.3 (4H, m)

FAB-MASS: m/z=1292 (M+Na)

Elemental Analysis Calcd. for $C_{54}H_{88}N_9O_{22}SNa.5H_2O$: C 47.67, H 7.26, N 9.26 Found: C 47.72, H 7.35, N 8.95

The Object Compounds (119) to (121) were obtained according to a similar manner to that of Example 118.

EXAMPLE 119

NMR (DMSO-d$_6$, δ): 0.87 (3H, t, J=6.6Hz), 1.00 (3H, d, J=7.3Hz), 1.03 (3H, d, J=6.0Hz), 1.2–1.5 (4H, m), 1.5–2.0 (5H, m), 2.1–2.7 (8H, m), 3.17 (1H, m), 3.6–4.5 (14H, m), 4.65–5.7 (12H, m), 6.72 (1H, d, J=8.1Hz), 6.75 (1H, s), 6.80 (1H, d, J=8.1Hz), 7.05 (1H, s), 7.1–7.7 (15H, m), 8.0–8.6 (4H, m), 8.85 (1H, s)

FAB-MASS: m/z=1274 (M+Na)

Elemental Analysis Calcd. for $C_{55}H_{74}N_9O_{21}SNa.7H_2O$: C 47.93, N 6.43, N 9.15 Found: C 48.12, N 6.56, N 9.03

EXAMPLE 120

IR (KBr): 3355.5, 1672.0 1629.6 cm$^{-1}$

NMR (DMSO-d$_6$, δ): 0.86 (3H, t, J=6.6Hz), 0.98 (3H, d, J=6.5Hz), 1.03 (3H, d, J=6.0Hz), 1.2–2.6 (21H, m), 3.18 (1H, m), 3.6–4.5 (16H, m), 4.65–5.55 (12H, m), 6.6–7.5 (10H, m), 8.0–8.6 (4H, m), 8.89 (1H, s) FAB-MASS: m/z=1256 (M+Na)

EXAMPLE 121

IR (KBr): 3357.5, 1660.4, 1629.6, 1249.6 cm$^{31\ 1}$

NMR (DMSO-d$_6$, δ): 0.86 (3H, t, J=6.6Hz), 0.96 (3H, d, J=6.8Hz), 1.03 (3H, d, J=6.0Hz), 1.1–1.5 (12H, m), 1.6–2.0 (5H, m), 2.0–2.5 (4H, m), 3.07 (1H, m), 3.5–4.5 (16H, m), 4.6–5.6 (12H, m), 6.72 (1H, d, J=8.1Hz), 6.7–6.9 (4H, m), 7.04 (1H, s), 7.16 (1H, s), 7.1–7.5 (2H, m), 7.25 (2H, d, J=8.6Hz), 8.0–8.2 (3H, m), 8.46 (1H, d, J=7Hz), 8.84 (1H, s)

FAB-MASS: m/z=1256 (M+Na)

Elemental Analysis Calcd. for $C_{52}H_{76}N_9O_{22}SNa.7H_2O$: C 45.91, H 6.67, N 9.27 Found: C 45.98, H 6.67, N 9.10

EXAMPLE 122

A solution of Object Compound (11) (795 mg) in water (16 ml) was left for 240 hours. The solution was subjected to column chromatography on ODS (YMC-gel ODS-AMS50) and eluted with 25% CH$_3$CN/H$_2$O. The fractions containing Object Compound were combined and the acetonitrile was removed under reduced pressure. The residue was lyophilized to give Object Compound (123) (38 mg).

IR (KBr): 3361, 2956, 2875, 1668, 1627, 1521, 1249, 1047 cm$^{-1}$

NMR (DMSO-d$_6$, δ): 0.8–1.5 (19H, m), 1.6–2.4 (13H, m), 3.1–3.2 (1H, m), 3.5–4.1 (12H, m), 4.1–4.7 (10H, m), 4.9–5.6 (5H, m), 5.98 (1H, d, J=10.6Hz), 6.36 (1H, d, J=10.6Hz), 6.7–7.3 (12H, m), 7.4–8.0 (7H, m)

FAB-MASS: m/z=1273.1 (M+Na$^+$)

Elemental Analysis Calcd. for $C_{55}H_{71}N_8O_{22}NaS.11H_2O$: C 45.58, H 6.47, N 7.73 Found: C 45.83, H 6.26, N 7.75

The Object Compound (123) was obtained according to a similar manner to that of Example 118.

EXAMPLE 123

IR (KBr): 3349.7, 1670.1, 1627.6 cm$^{-1}$

NMR (DMSO-d$_6$, δ): 0.87 (3H, t, J=7.2Hz), 0.96 (3H, d, J=6.7Hz), 1.13 (3H, d, J=5.7Hz), 1.18–1.55 (10H, m), 1.58–2.08 (5H, m), 2.08–2.90 (4H, m), 2.90–3.30 (2H, m), 3.60–4.50 (17H, m), 4.70–5.70 (12H, m), 6.65–7.60 (11H, m), 7.80 (2H, br s), 7.95–8.23 (2H, m), 8.75 (1H, d, J=7.0Hz), 8.85 (1H, s)

FAB-MASS: m/z=1114.4 (M-SO$_4$-2)

Elemental Analysis Calcd. for C$_{52}$H$_{77}$N$_9$O$_{21}$S.6H$_2$O: C 47.88, H 6.88, N 9.66 Found: C 47.60, H 6.74, N 9.53

The following compound (124) was obtained according to a similar manner to that of Example 1.

EXAMPLE 124

IR (KBr): 3324, 2937, 2873, 1664, 1629, 1442, 1257 cm$^{-1}$

NMR (DMSO-d$_6$, δ): 0.91 (3H, t, J=7.1Hz), 0.96 (3H, d, J=6.7Hz), 1.09 (3H, d, J=5.7Hz), 1.3–1.5 (4H, m), 1.7–2.6 (9H, m), 3.1–3.3 (1H, m), 3.7–4.6 (16H, m), 4.7–5.1 (7H, m), 5.11 (1H, d, J=5.6Hz), 5.17 (1H, d, J=3.1Hz), 5.26 (1H, d, J=4.5Hz), 5.55 (1H, d, J=5.8Hz), 6.7–6.9 (3H, m), 7.0–7.6 (6H, m), 7.97 (2H, d, J=8.8Hz), 8.0–8.4 (6H, m), 8.85 (1H, s), 8.92 (1H, d, J=7.0Hz)

FAB-MASS: m/z=1331 (M+Na$^+$)

Elemental Analysis Calcd. for C$_{55}$H$_{69}$N$_{10}$O$_{22}$NaS$_2$: C 45.45, H 5.89, N 9.64 Found: C 45.71, H 5.68, N 9.60

What is claimed is:

1. A polypeptide compound of the following general formula (I):

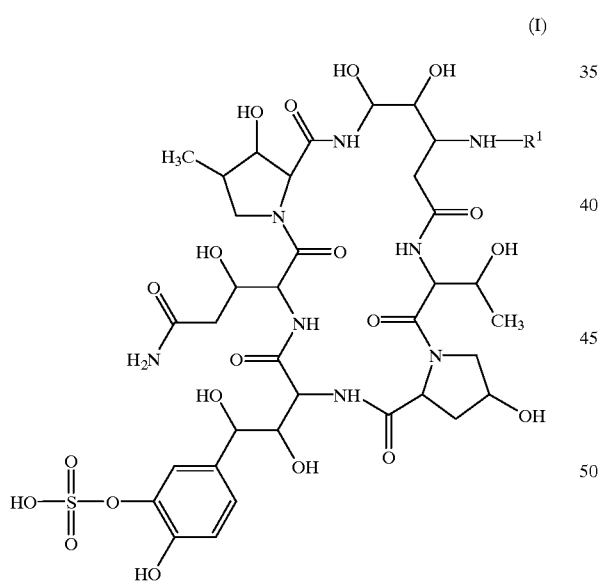

(I)

wherein R$^1$ is benzoyl substituted with isoxazolyl which has phenyl having lower alkoxy, or a salt thereof.

2. A compound of claim 1, wherein R$^1$ is

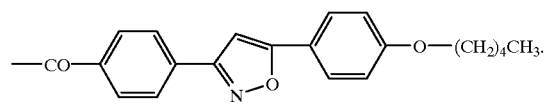

3. A process for the preparation of a polypeptide compound of the formula (I):

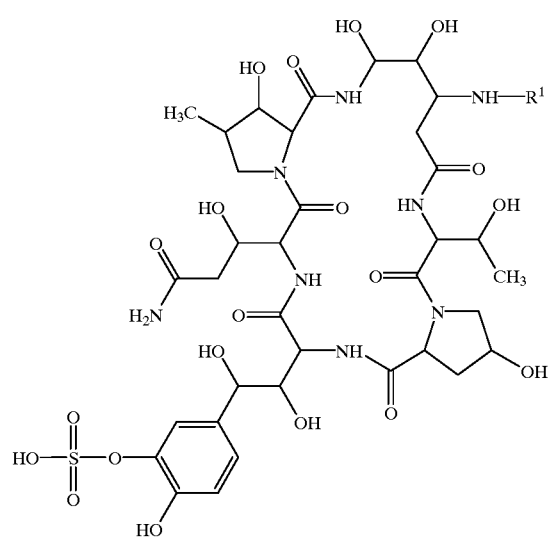

(I)

wherein R$^1$ is benzoyl substituted with isoxazolyl which has phenyl having lower alkoxy, or a salt thereof, said process comprising:

1) reacting a compound of the formula (II):

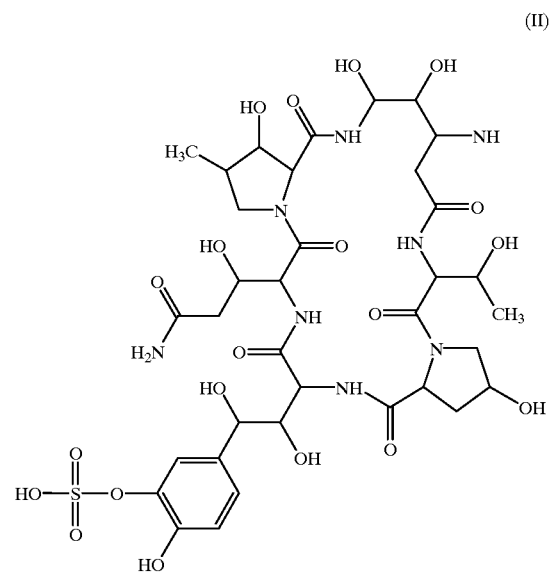

(II)

or its reactive derivative at the amino group or a salt thereof, with a compound of formula (III):

(III)

or its reactive derivative at the carboxy group or a salt thereof, wherein R$^1$ is defined above, to give a compound of formula (I).

4. A pharmaceutical composition which comprises, as an active ingredient, a compound of claim 1, or a pharmaceutically acceptable salt thereof in admixture with a pharmaceutically acceptable carrier or excipient.

5. A method for the therapeutic treatment of infectious diseases caused by pathogenic microorganisms, comprising administering an effective amount of a compound of claim 1 or a pharmaceutically acceptable salt thereof, to a human being or animal.

* * * * *

UNITED STATES PATENT AND TRADEMARK OFFICE
CERTIFICATE OF CORRECTION

PATENT NO. : 6,107,458

DATED : August 22, 2000

INVENTOR(S): Hidenori OHKI et al.

It is certified that an error appears in the above-identified patent and that said Letters Patent is hereby corrected as shown below:

On the title page, item [30], the Foreign Application Priority Data is erroneously listed. It should be:

--[30] Foreign Application Priority Data

Oct. 7, 1994   [GB]   United Kingdom..........9420425
Apr. 28, 1995   [GB]   United Kingdom..........9508745--

Signed and Sealed this

Twenty-ninth Day of May, 2001

*Attest:*

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO. : 6,107,458
DATED : August 22, 2000
INVENTOR(S) : Hidenori Ohki et al.

Page 1 of 2

It is certified that error appears in the above-identified patent and that said Letters Patent is hereby corrected as shown below:

Column 137,
Lines 34-54, formula (I):

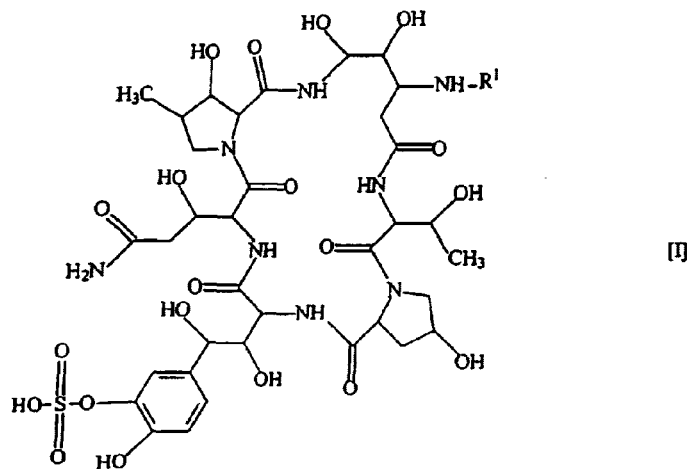

should read

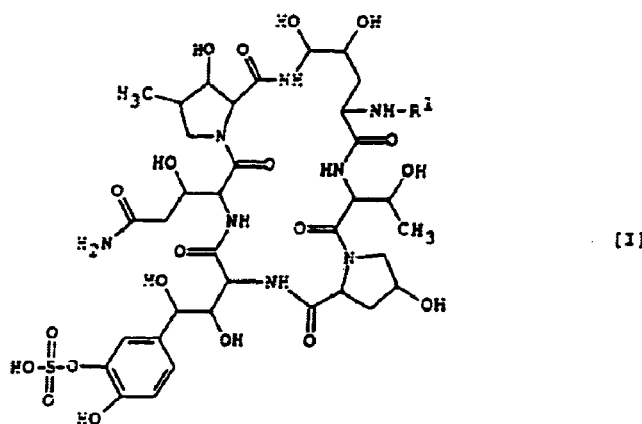

Column 138,
Lines 1-23, formula (I):

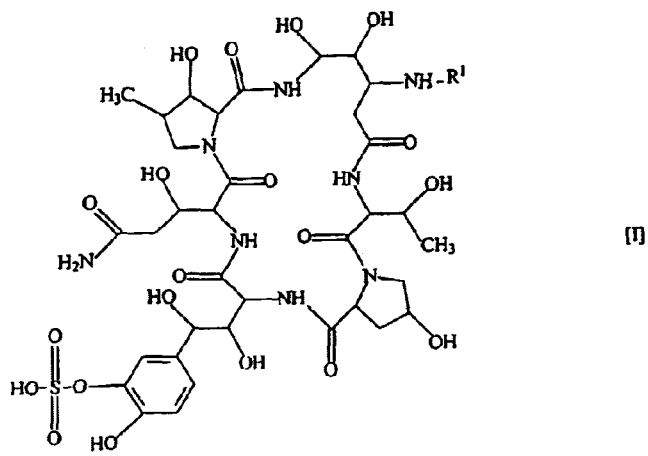

UNITED STATES PATENT AND TRADEMARK OFFICE
CERTIFICATE OF CORRECTION

PATENT NO. : 6,107,458
DATED : August 22, 2000
INVENTOR(S) : Hidenori Ohki et al.

It is certified that error appears in the above-identified patent and that said Letters Patent is hereby corrected as shown below:

Column 138 (cont'd),
should read

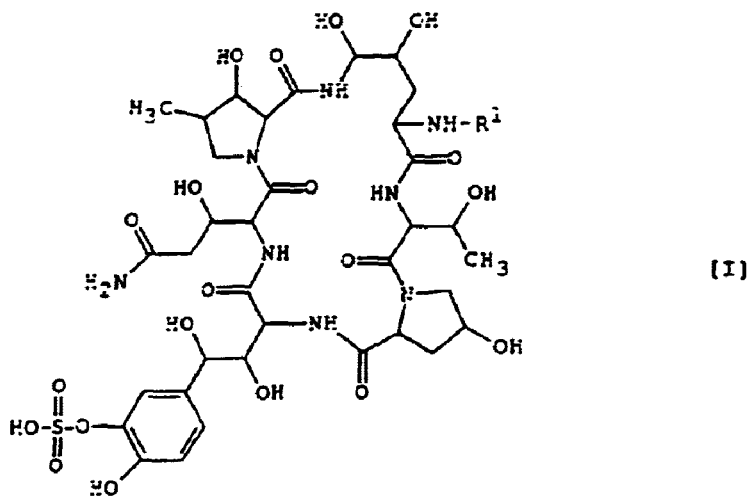

Signed and Sealed this

Twenty-seventh Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,107,458
APPLICATION NO. : 08/809723
DATED : August 22, 2000
INVENTOR(S) : Hidenori Ohki et al.

It is certified that error appears in the above-identified patent and that said Letters Patent is hereby corrected as shown below:

Column 137,
Lines 34-54, formula (I):

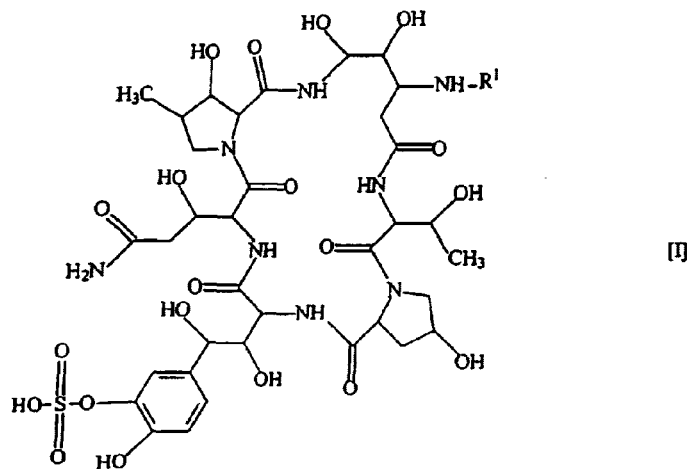

should read

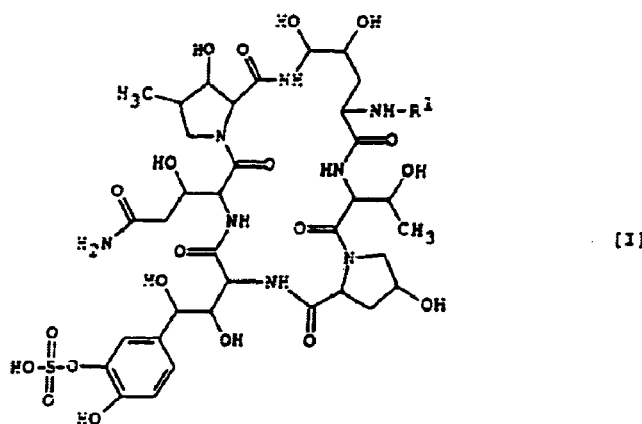

Column 138,
Lines 1-23, formula (I):

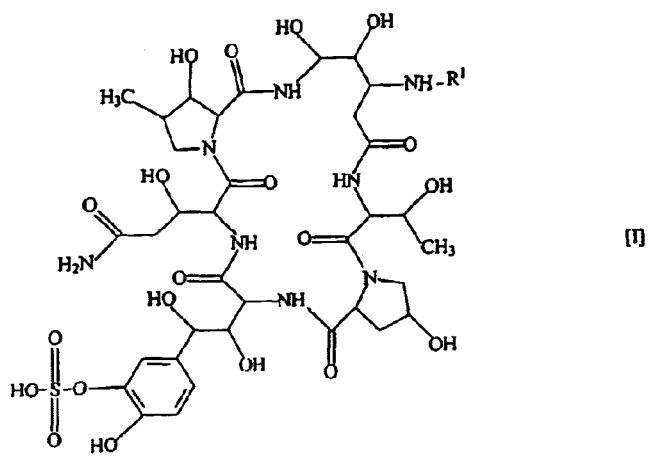

UNITED STATES PATENT AND TRADEMARK OFFICE
CERTIFICATE OF CORRECTION

PATENT NO. : 6,107,458  
APPLICATION NO. : 08/809723  
DATED : August 22, 2000  
INVENTOR(S) : Hidenori Ohki et al.

Page 2 of 3

It is certified that error appears in the above-identified patent and that said Letters Patent is hereby corrected as shown below:

Column 138 (cont'd),
should read

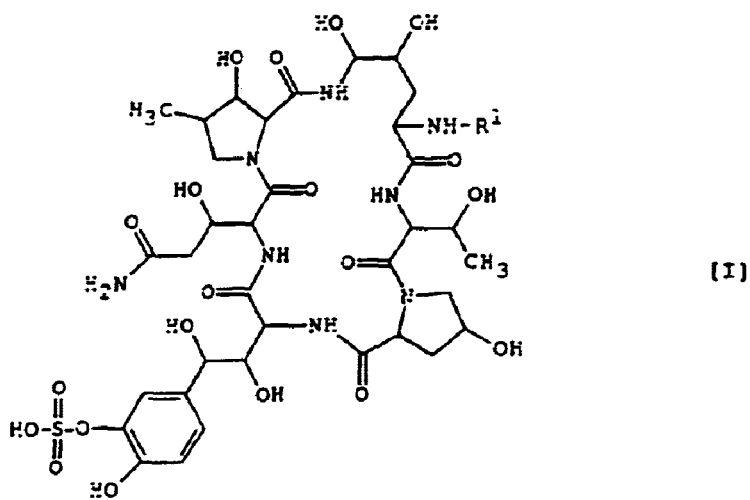

Column 138, lines 28-49, Claim 3, formula (II):

"

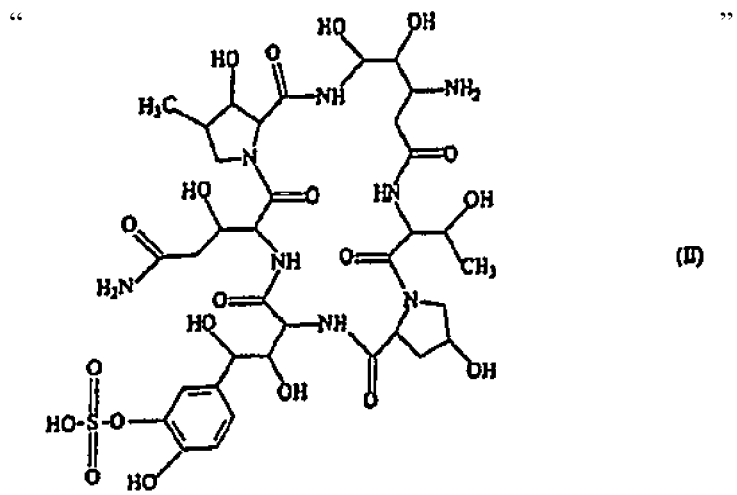

"

UNITED STATES PATENT AND TRADEMARK OFFICE
CERTIFICATE OF CORRECTION

PATENT NO. : 6,107,458
APPLICATION NO. : 08/809723
DATED : August 22, 2000
INVENTOR(S) : Hidenori Ohki et al.

It is certified that error appears in the above-identified patent and that said Letters Patent is hereby corrected as shown below:

should read

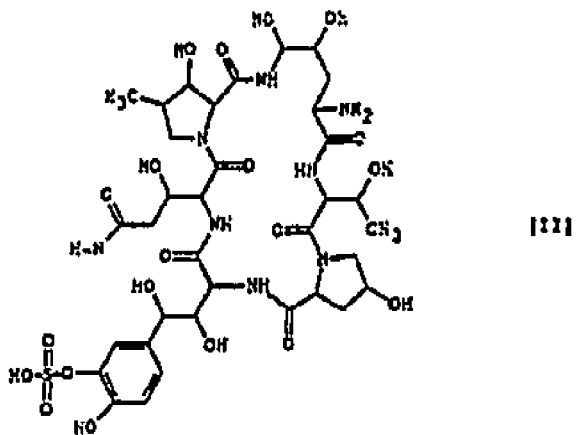

[II]

This certificate supersedes Certificate of Correction issued September 27, 2005.

Signed and Sealed this

Twenty-seventh Day of February, 2007

JON W. DUDAS
*Director of the United States Patent and Trademark Office*